United States Patent
Gartner et al.

(10) Patent No.: US 10,760,046 B2
(45) Date of Patent: Sep. 1, 2020

(54) METHODS OF PATTERNING CELLS ON A SURFACE OF A SUBSTRATE AND PROGRAMMED ASSEMBLY OF THREE-DIMENSIONAL LIVING TISSUES

(71) Applicant: The Regents of the University of California, Oakland, CA (US)

(72) Inventors: Zev Jordan Gartner, San Francisco, CA (US); Jennifer S. Liu, San Francisco, CA (US); Noel Youngho Jee, San Francisco, CA (US); Michael E. Todhunter, San Francisco, CA (US)

(73) Assignee: The Regents of the University of California, Oakland, CA (US)

( * ) Notice: Subject to any disclaimer, the term of this patent is extended or adjusted under 35 U.S.C. 154(b) by 196 days.

(21) Appl. No.: 14/441,453

(22) PCT Filed: Nov. 5, 2013

(86) PCT No.: PCT/US2013/068542
§ 371 (c)(1),
(2) Date: May 7, 2015

(87) PCT Pub. No.: WO2014/071388
PCT Pub. Date: May 8, 2014

(65) Prior Publication Data
US 2016/0010054 A1 Jan. 14, 2016

Related U.S. Application Data

(60) Provisional application No. 61/772,694, filed on Nov. 5, 2012, provisional application No. 61/786,124, filed on Mar. 14, 2013.

(51) Int. Cl.
| | | |
|---|---|---|
| *C12Q 1/68* | (2018.01) | |
| *G01N 33/53* | (2006.01) | |
| *C12N 5/00* | (2006.01) | |
| *C12N 11/06* | (2006.01) | |
| *C12N 11/00* | (2006.01) | |
| *C12N 5/07* | (2010.01) | |

(52) U.S. Cl.
CPC ............ *C12N 5/0068* (2013.01); *C12N 11/00* (2013.01); *C12N 11/06* (2013.01); *B01J 2219/0063* (2013.01); *B01J 2219/00612* (2013.01); *B01J 2219/00617* (2013.01); *B01J 2219/00626* (2013.01); *B01J 2219/00659* (2013.01); *B01J 2219/00722* (2013.01); *B01J 2219/00743* (2013.01); *C12N 2533/00* (2013.01); *C12N 2535/10* (2013.01)

(58) Field of Classification Search
None
See application file for complete search history.

(56) References Cited

U.S. PATENT DOCUMENTS

2002/0136709 A1* 9/2002 Zahner ................. C12N 5/0696
424/93.21

FOREIGN PATENT DOCUMENTS

| WO | 2012/155110 | 11/2012 |
|---|---|---|
| WO | 2013/067203 | 5/2013 |

OTHER PUBLICATIONS

"Mammal," (Wikipedia.com; accessed Sep. 22, 2011).*
"Murinae," (Wikipedia.com, accessed Mar. 18, 2013).*
"Bird," (Wikipedia.com, accessed Nov. 21, 2016).*
"Fish," (Wikipedia.com, accessed Nov. 2, 2014).*
"Mammal," Wikipedia.com; accessed Sep. 22, 2011. (Year: 2011).*
"Murinae," Wikipedia.com, accessed Mar. 18, 2013. (Year: 2013).*
"Bird", Wikipedia.com, accessed Nov. 21, 2016. (Year: 2016).*
"Fish," Wikipedia.com, accessed Nov. 2, 2014. (Year: 2014).*
Chanson et al. (2011) "Self-organization is a dynamic and lineage-intrinsic property of mammary epithelial cells" PNAS 108(8):3264-3269.
Hsiao et al. (2009) "Direct cell surface modification with DNA for the capture of primary cells and the investigation of myotube formation on defined patterns" 25:6985-6991.
Liu and Gartner (2012) "Directing the assembly of spatially organized multicomponent tissues from the bottom up" Trends Cell Biol 22:683-691.
Liu et al. (2012) "Programmed cell-to-cell variability in Ras activity triggers emergent behaviors during mammary epithelial morphogenesis" Cell Reports 2:1461-1470.
Needleman and Wunsch (1970) "A general method applicable to the search for similarities in the amino acid sequence of two proteins" Journal of molecular biology 48(3):443-453.
Onoe et al. (2012) "Cellular microfabrication: observing intercellular interactions using lithographically-defined DNA capture sequences" Langmuir 28:8120-8126.
Selden et al. (2011) "Chemically programmed cell adhesion with membrane-anchored oligonucleotides" Journal of the American Chemical Society 134(2):765-768.
Gartner and Bertozzi (2009) "Programmed assembly of 3-dimensional microtissues with defined cellular connectivity" PNAS 106(12):4606-4610.
Rago et al. (2009) "Encapsulated Arrays of Self-Assembled Microtissues: An Alternative to Spherical Microcapsules" Tissue Engineering 15(2):387-395.

\* cited by examiner

*Primary Examiner* — Bradley L. Sisson
(74) *Attorney, Agent, or Firm* — Edward J. Baba; Shweta Chandra; Bozicevic, Field & Francis LLP

(57) ABSTRACT

The present disclosure provides methods of patterning cells on a surface of a substrate. The methods include disposing a pattern of nucleic acids on a surface of a substrate, and contacting the patterned nucleic acids under hybridization conditions with a first suspension of cells, where cells of the first suspension include cell surface-attached nucleic acids complementary to the patterned nucleic acids, and where the cell surface-attached nucleic acids hybridize to the patterned nucleic acids to pattern the cells on the surface of the substrate. Systems and kits for practicing the methods are also provided.

20 Claims, 77 Drawing Sheets

Specification includes a Sequence Listing.

FACS plots for sorting luminal and myoepithelial HMEC unstained

FACS plots for sorting luminal and myoepithelial HMEC CD10-APC/Muc1-FITC

FACS plots for sorting luminal and myoepithelial HMEC Gates for LEP and MEP 10X phase 20X phase LEP/MEP 40X phase LEP/MEP FIG. 7A
FIG. 7B
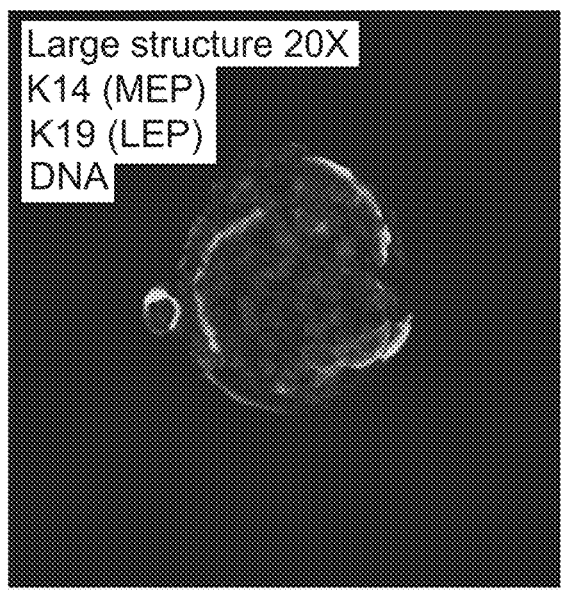
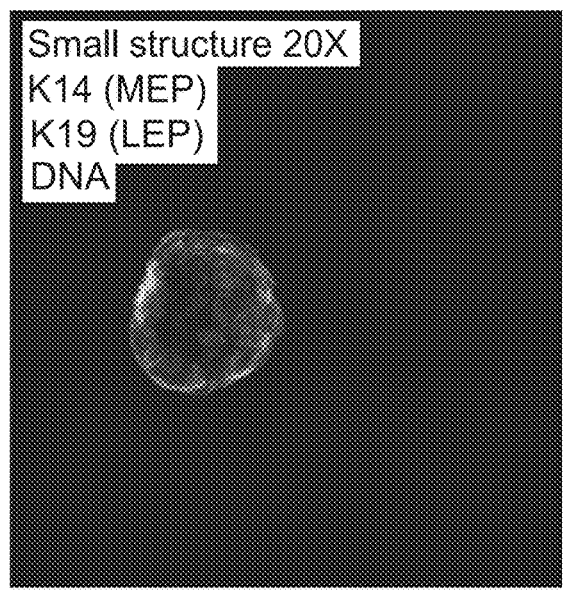
FIG. 7C
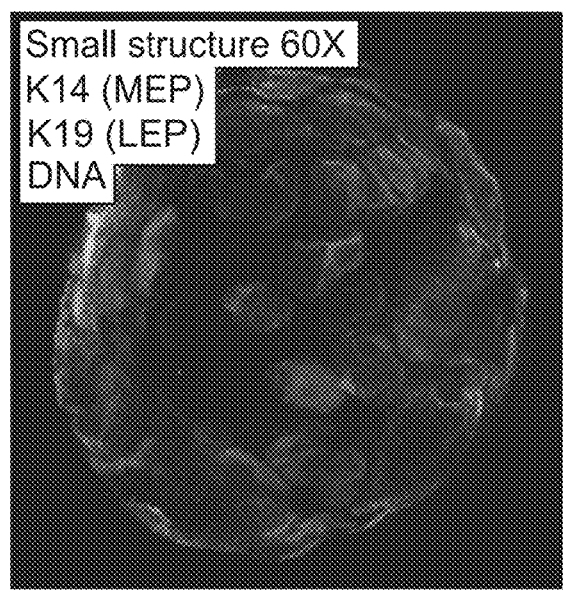

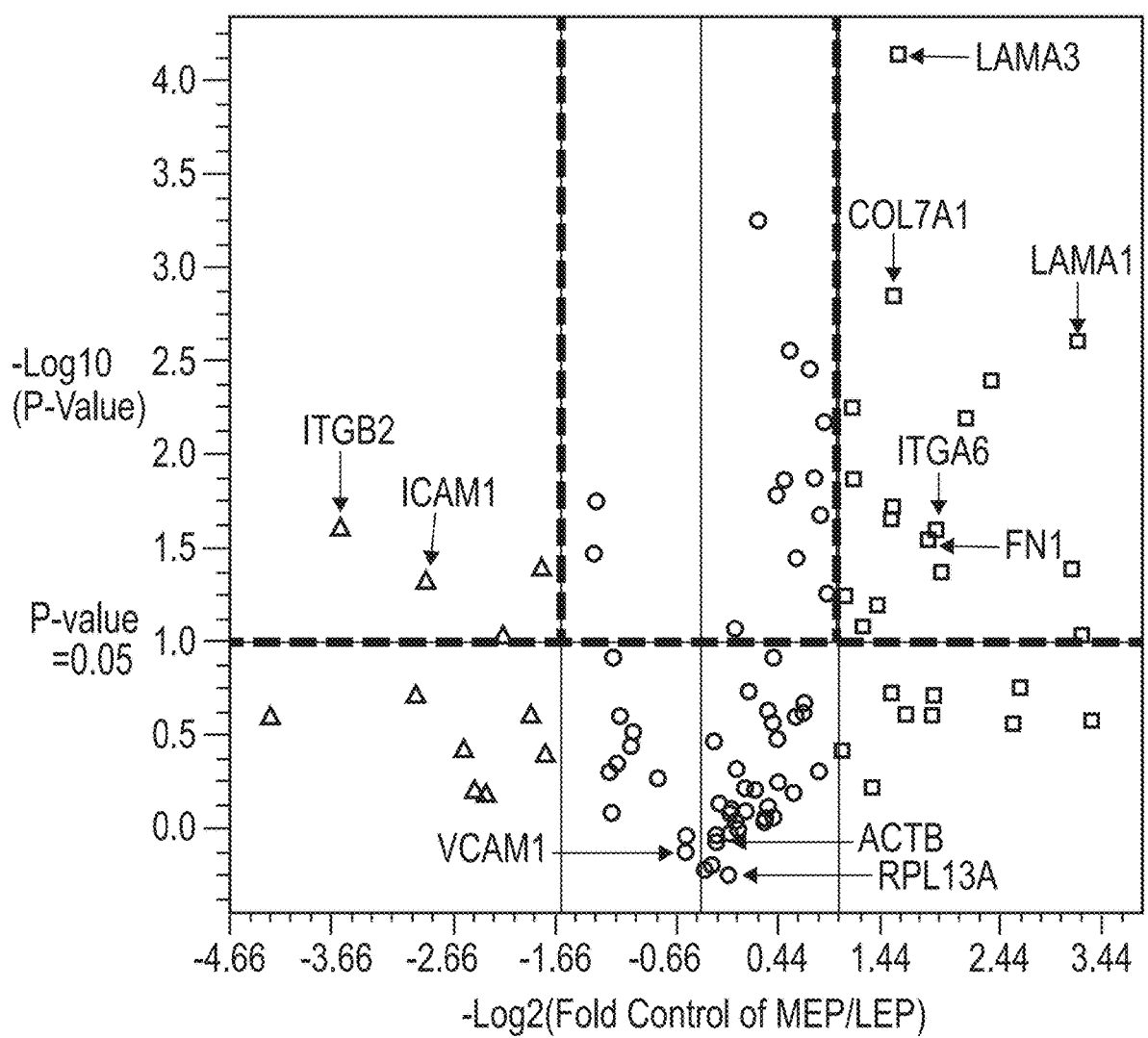

FIG. 8C

| GENE | Fold Reg | P-Value |
|---|---|---|
| MMP3 | 20.58 | 0.045848 |
| LAMA1 | 19.9 | 0.001156 |
| MMP1 | 18.9 | 0.020323 |
| COL7A1 | 10.07 | 0.001856 |
| ITGA4 | 8.36 | 0.002981 |
| THBS2 | 6.8 | 0.020468 |
| ITGA6 | 6.5 | 0.012699 |
| FN1 | 6.28 | 0.014437 |
| LAMA3 | 4.85 | 0.000031 |
| SPARC | 4.63 | 0.000653 |
| ITGA1 | 4.6 | 0.009826 |
| KAL1 | 4.5 | 0.010793 |
| COL6A1 | 3.96 | 0.031306 |
| ITGA3 | 3.62 | 0.041596 |
| COL5A1 | 3.34 | 0.006622 |
| ITGA2 | 3.27 | 0.002634 |
| ITGB4 | 3.06 | 0.02833 |
| MMP7 | -17.26 | 0.011632 |
| ITGB2 | -8.72 | 0.023136 |
| MMP15 | -4.73 | 0.045259 |
| ICAM1 | -3.43 | 0.019627 |

| GENE | Fold Reg | P-Value |
|---|---|---|
| COL11A1 | 23.18 | 0.138137 |
| MMP13 | 11.52 | 0.138647 |
| COL16A1 | 6.22 | 0.133479 |
| TIMP1 | 6.36 | 0.099112 |
| ITGB3 | 3.02 | 0.201825 |
| CD44 | 2.14 | 0.017713 |
| VCAN | 1.96 | 0.006662 |
| ECM1 | 2.06 | 0.001285 |
| ITGB1 | 1.6 | 0.000247 |
| LAMA2 | 1.77 | 0.060047 |
| LAMB1 | 2.38 | 0.001648 |
| LAMB3 | 2.68 | 0.003246 |
| TNC | 2.61 | 0.010367 |
| VTN | 2.16 | 0.125593 |
| CDH1 | 1.1 | 0.180546 |
| NCAM1 | -9.56 | 0.095578 |
| TGFBI | -2.28 | 0.008675 |
| TIMP2 | -2.3 | 0.016754 |
| VCAM1 | -1.11 | 0.595206 |
| RPL13A | 1.26 | 0.945848 |
| HPRT1 | 1.17 | 0.393554 |
| B2M | -1.91 | 0.126736 |
| GAPDH | 1.47 | 0.09394 |
| ACTB | 1.11 | 0.634511 |

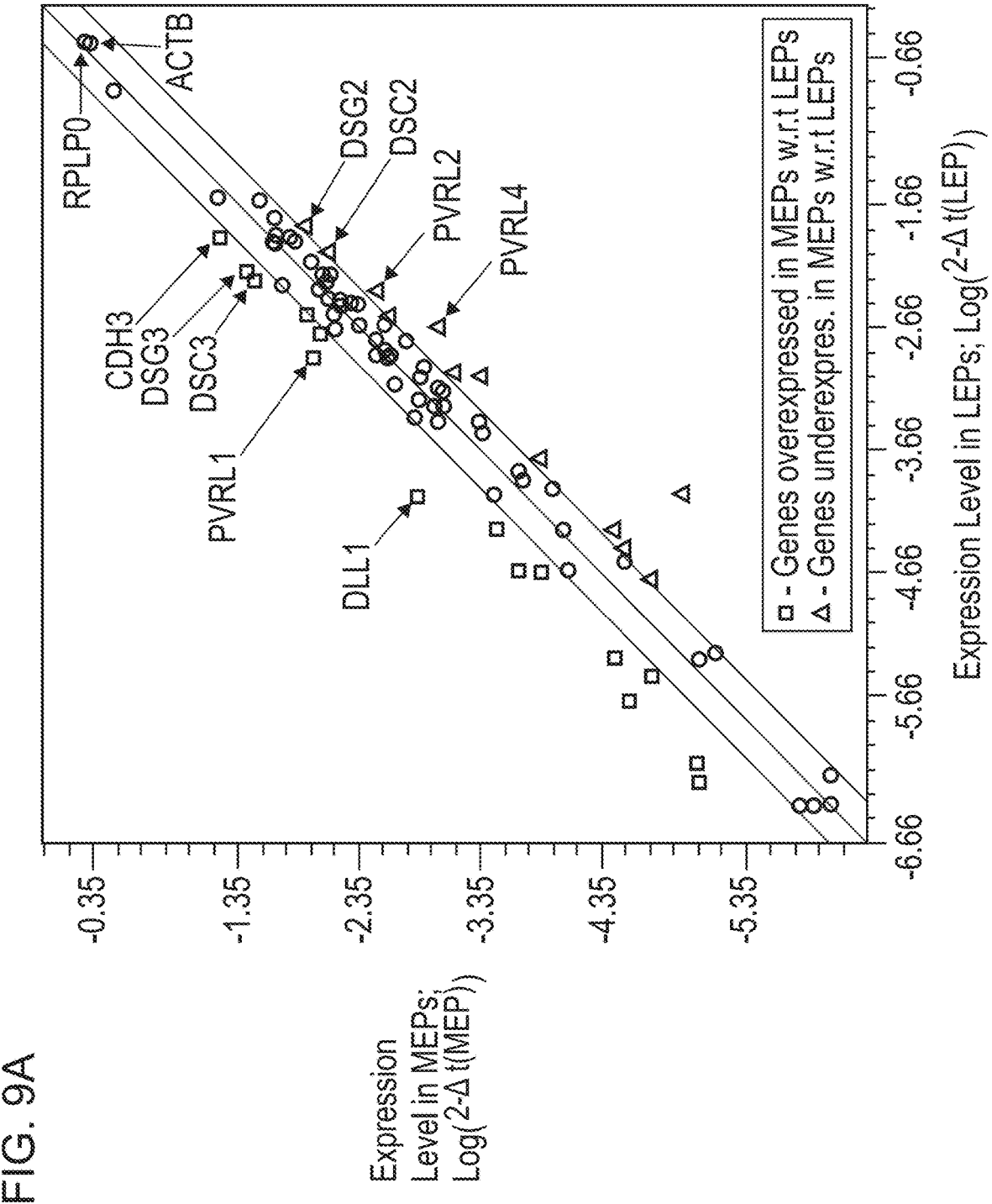

FIG. 9C

| GENE | Fold Reg | P-Value |
|---|---|---|
| DLL1 | 7.1376 | 0.009465 |
| CTNNA3 | 7.085 | 0.017444 |
| P2RX6 | 5.4168 | 0.029744 |
| PVRL1 | 4.3714 | 0.004773 |
| PVRL3 | 4.3302 | 0.013716 |
| DOCK4 | 3.7041 | 0.005895 |
| DSC1 | 2.9617 | 0.000481 |
| DSC3 | 2.9095 | 0.000445 |
| DSG3 | 2.8431 | 0.000684 |
| CDH3 | 2.537 | 0.020976 |
| DSG4 | 2.4219 | 0.001867 |
| PKP1 | 2.255 | 0.005657 |
| FLNA | 2.0187 | 0.00554 |
| CDH2 | -17.1788 | 0.000043 |
| MAPRE2 | -3.8368 | 0.004983 |
| PVRL4 | -3.3766 | 0.000044 |
| PVRL2 | -2.5301 | 0.006147 |
| MLLT4 | -2.4098 | 0.002287 |
| BAIAP2 | -2.3678 | 0.000015 |
| DNM1 | -2.1688 | 0.017836 |
| DSG2 | -2.1261 | 0.001182 |
| DSC2 | -2.0584 | 0.001646 |
| TJP1 | -2.0133 | 0.016625 |
| ARVCF | -2.0049 | 0.016034 |
| CDH1 | -1.094 | 0.108166 |
| HPRT1 | -1.1428 | 0.718387 |
| ACTB | -1.1855 | 0.080876 |
| GAPDH | 1.3017 | 0.023373 |
| RPLP0 | -1.098 | 0.132623 |

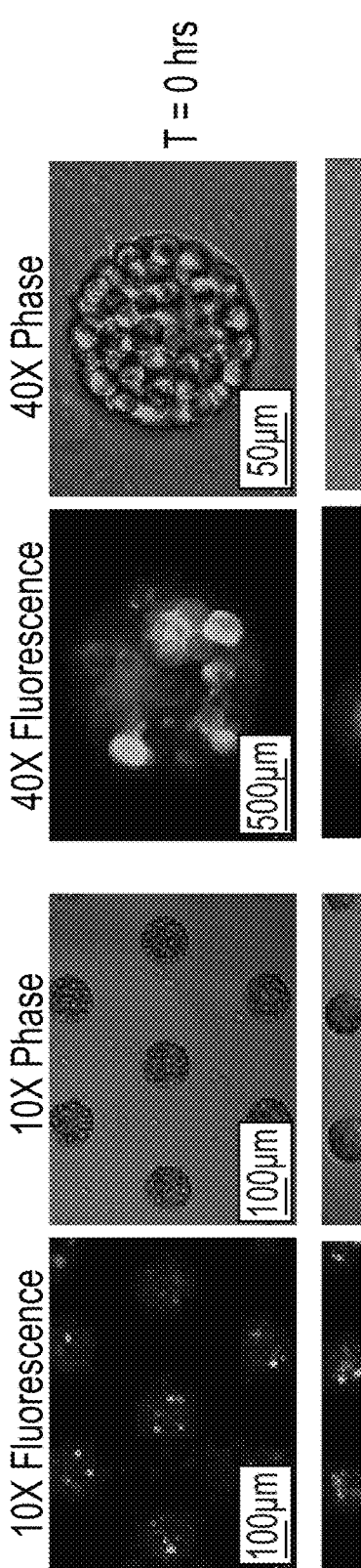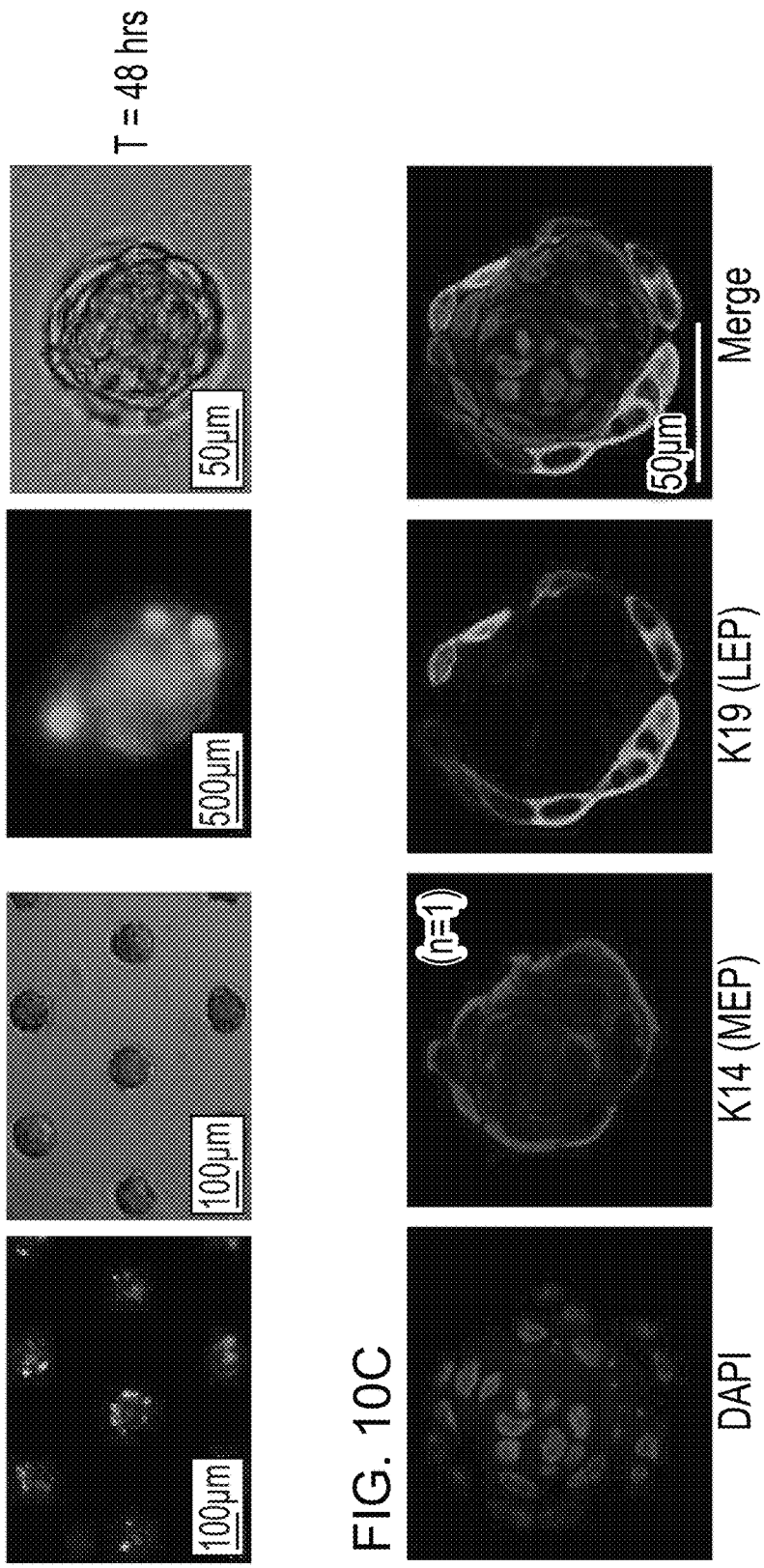

12μm  16μm  20μm  24μm

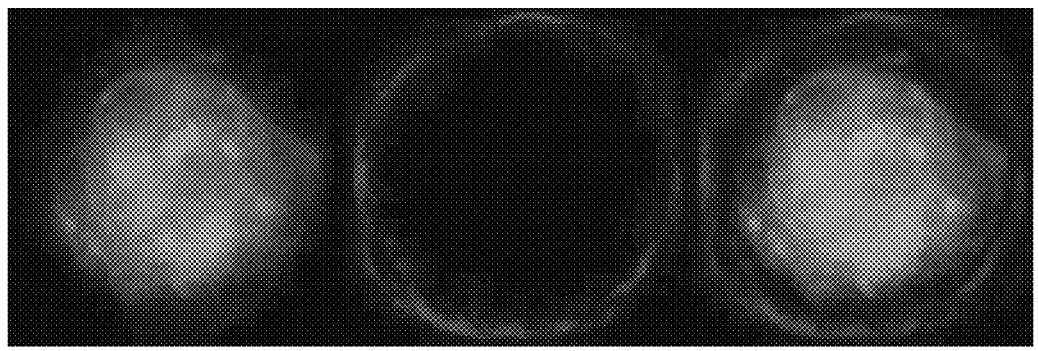
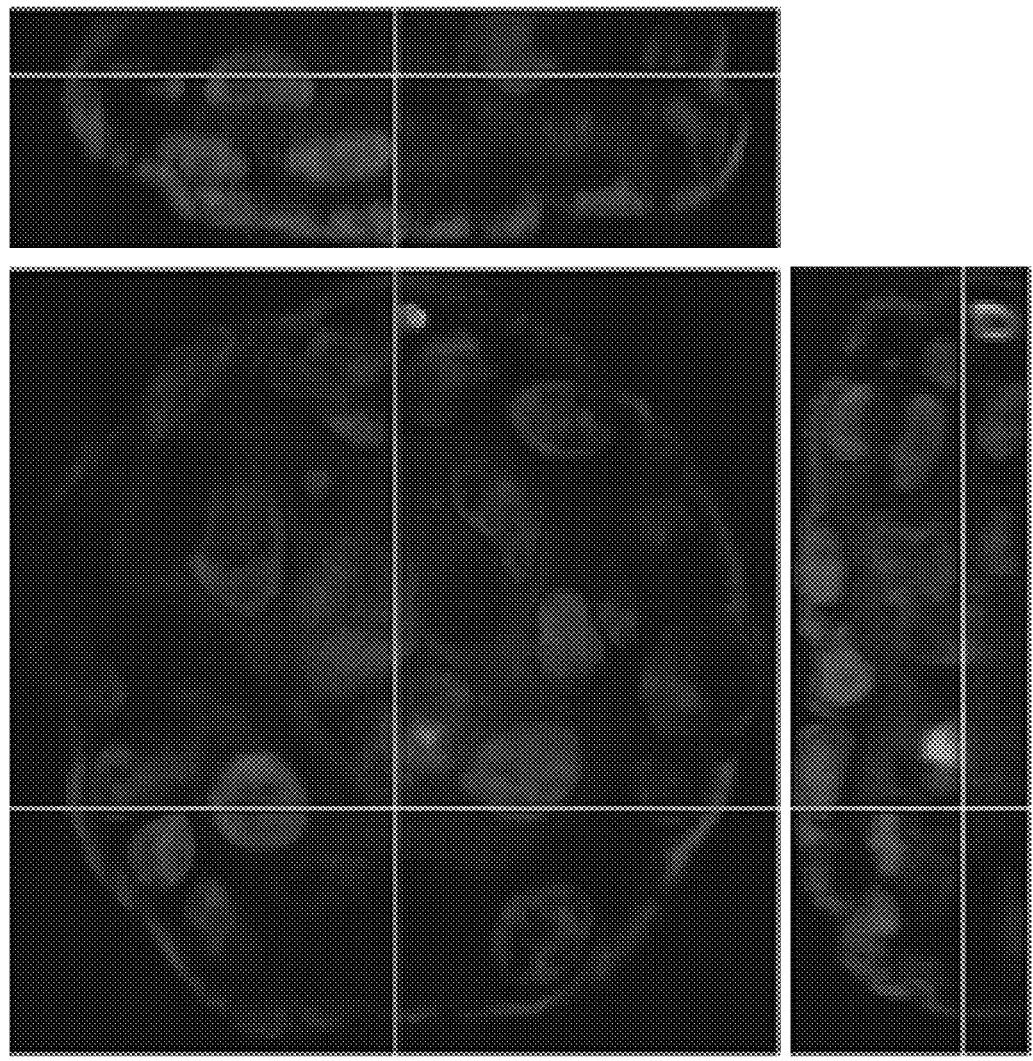

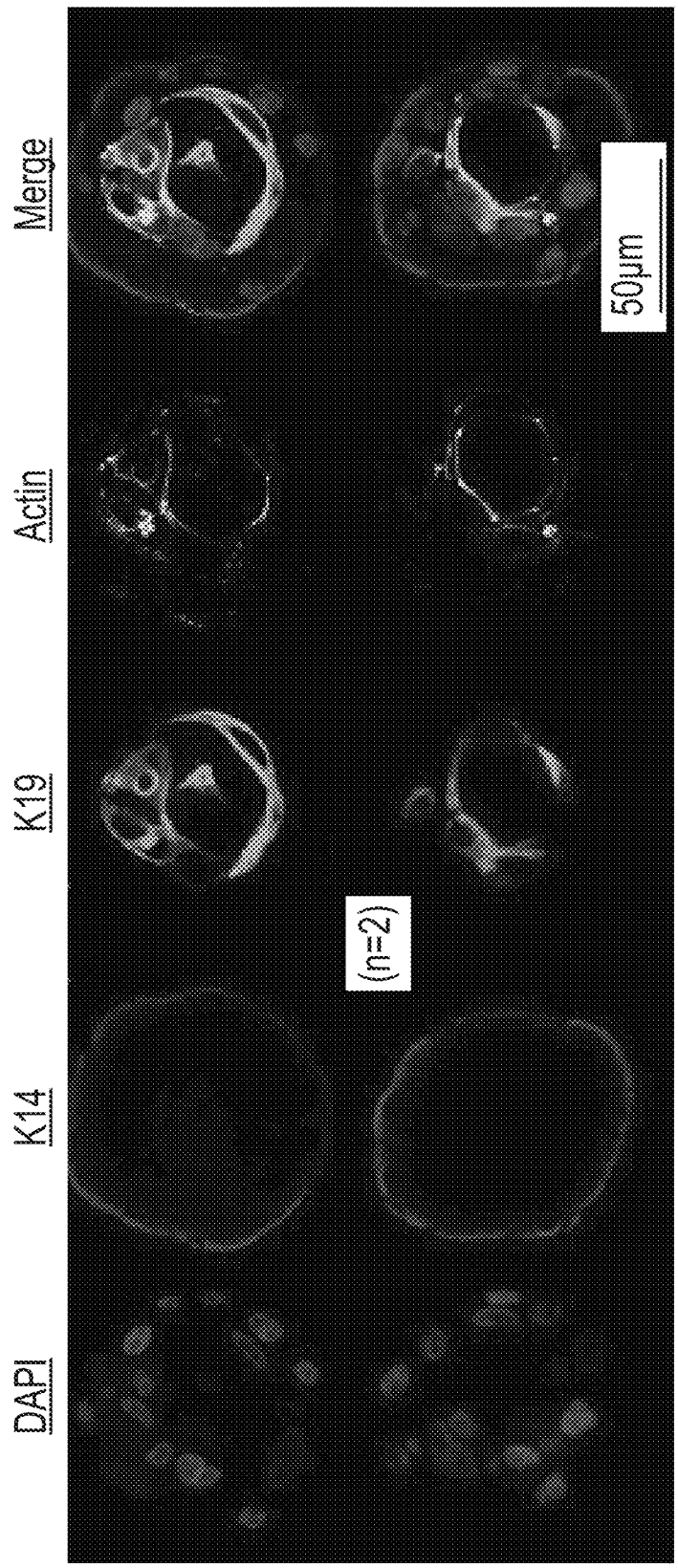

FIG. 27B
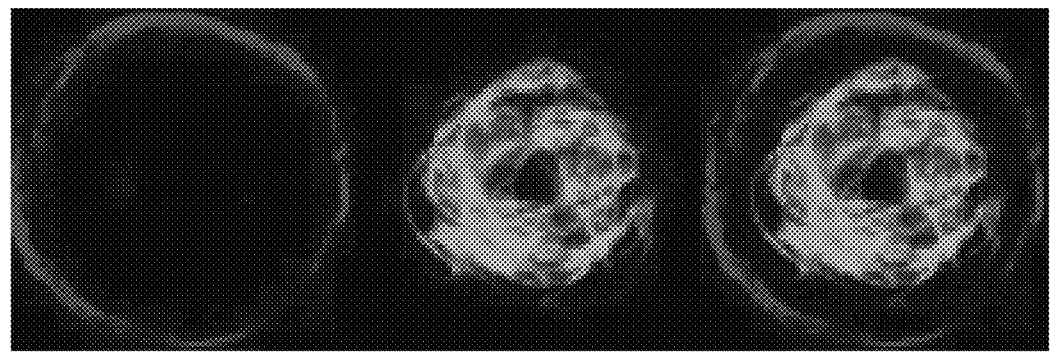
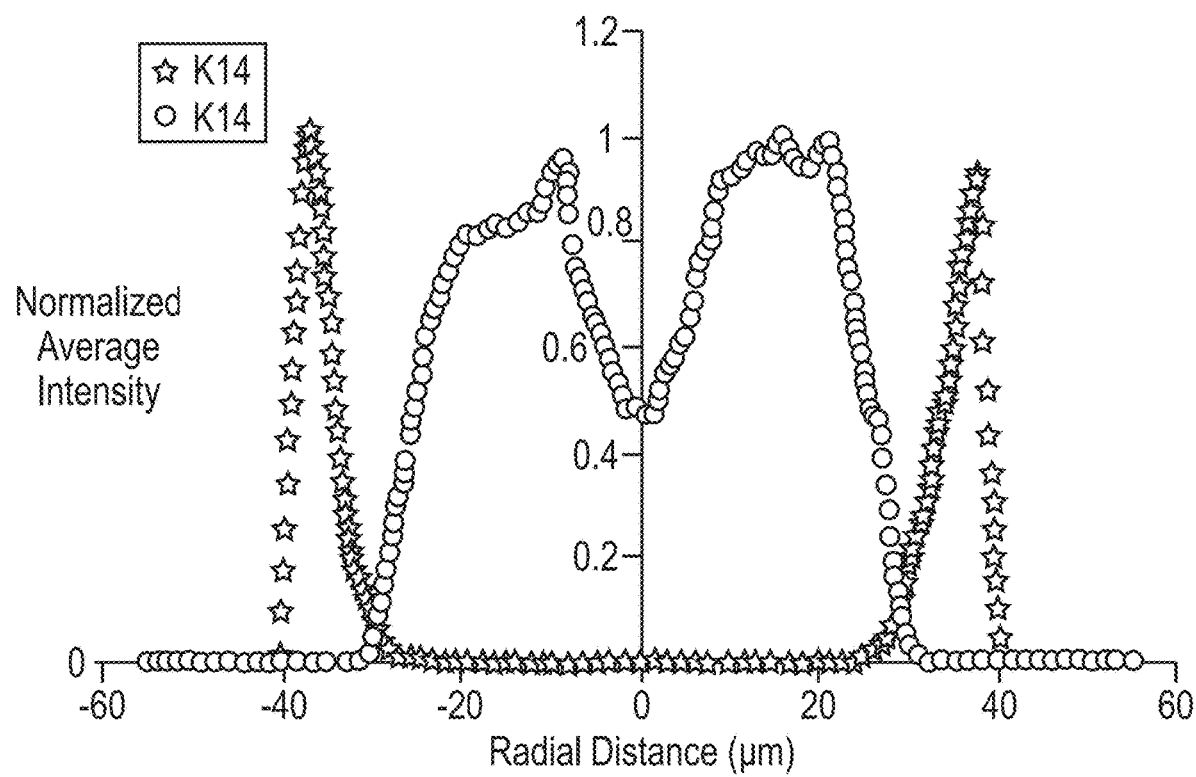

1 LEP / HMEC cluster

FIG. 29A
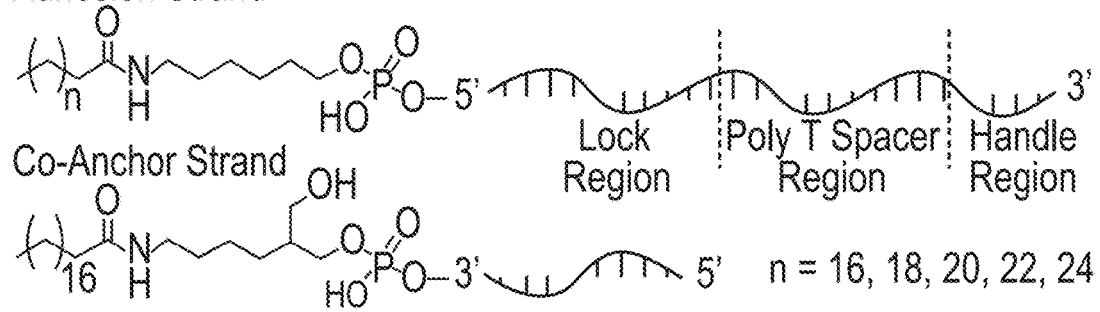
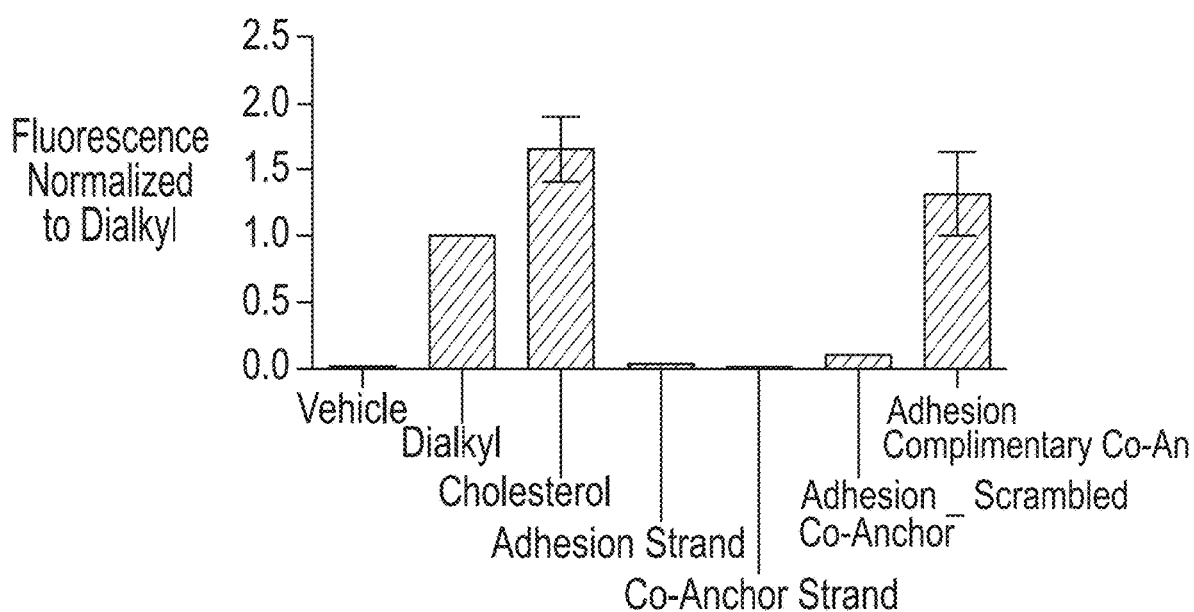
FIG. 29B
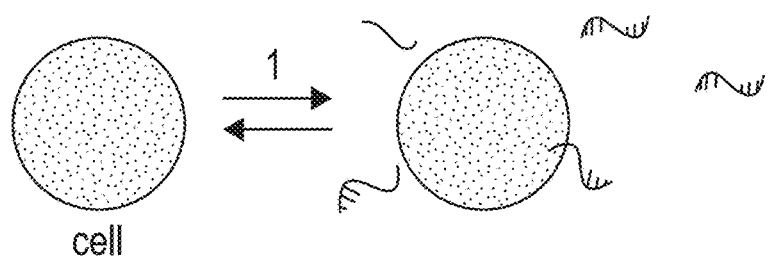

FIG. 31
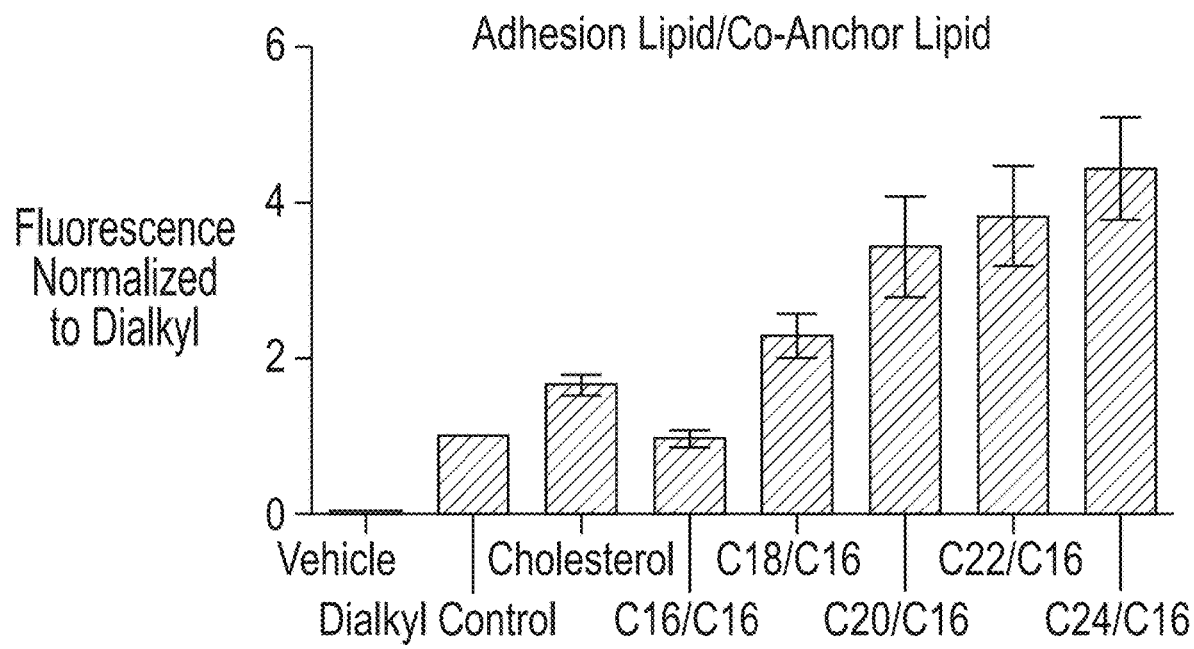
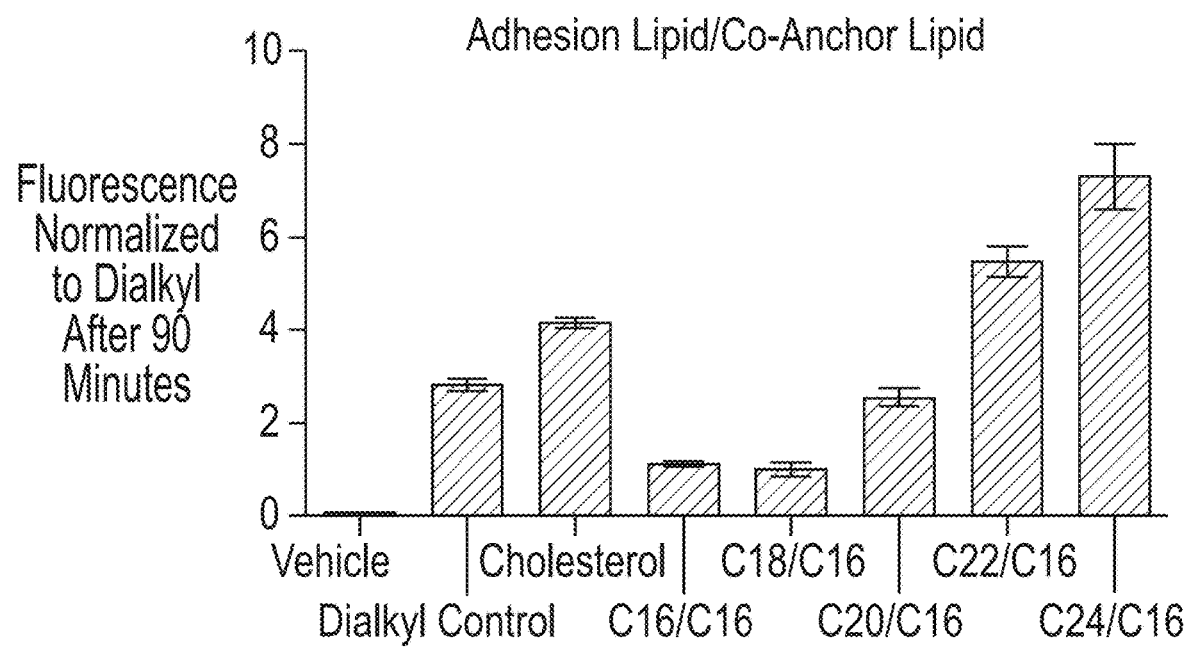

FIG. 32A
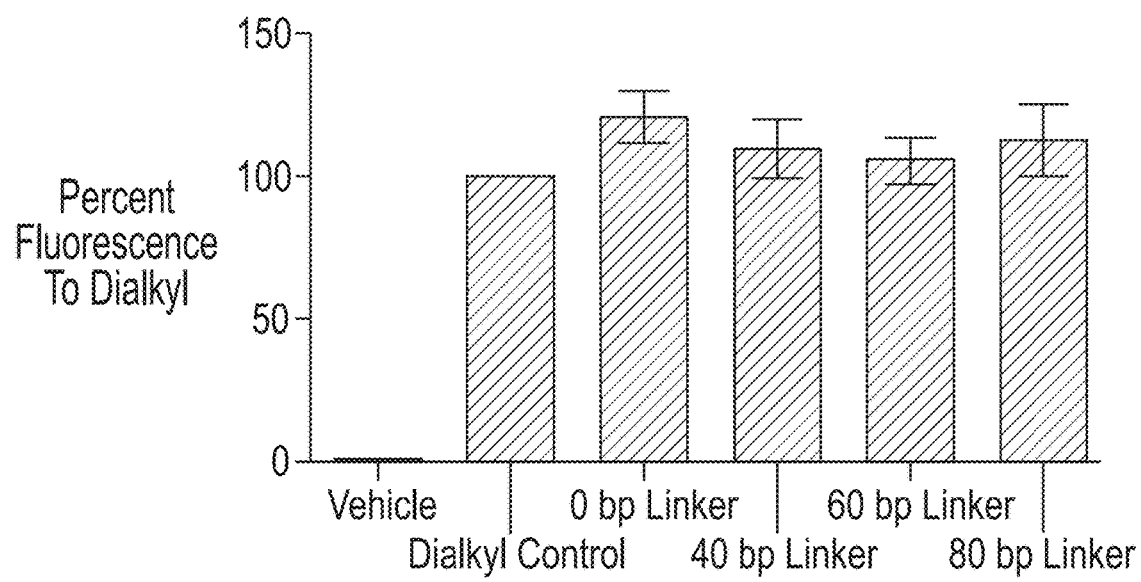
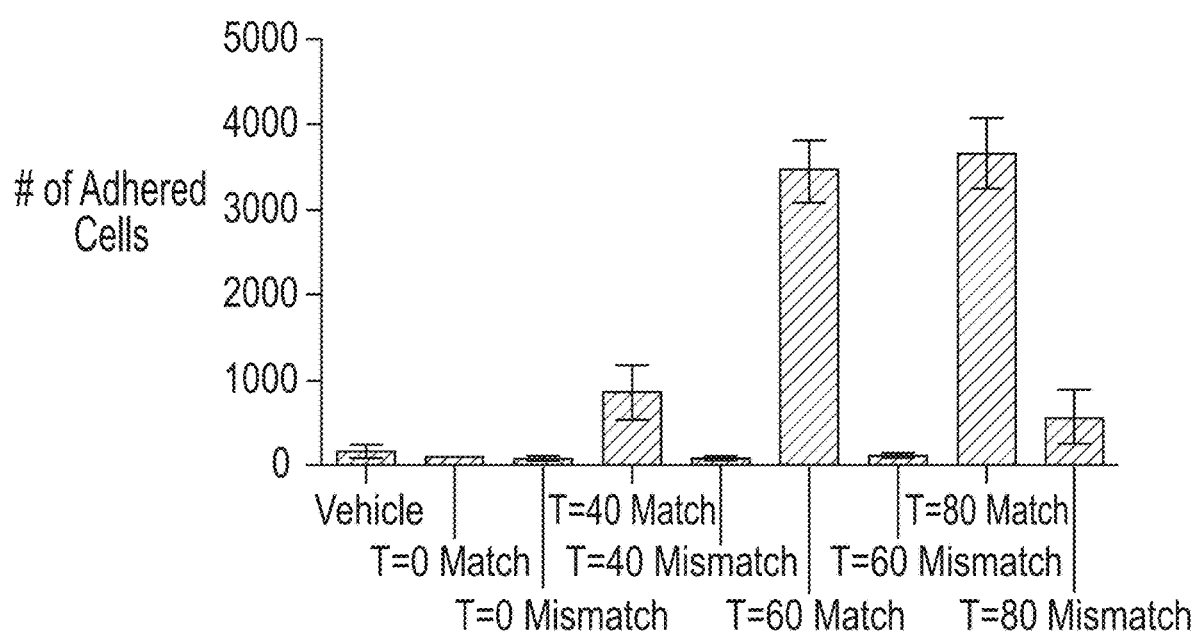

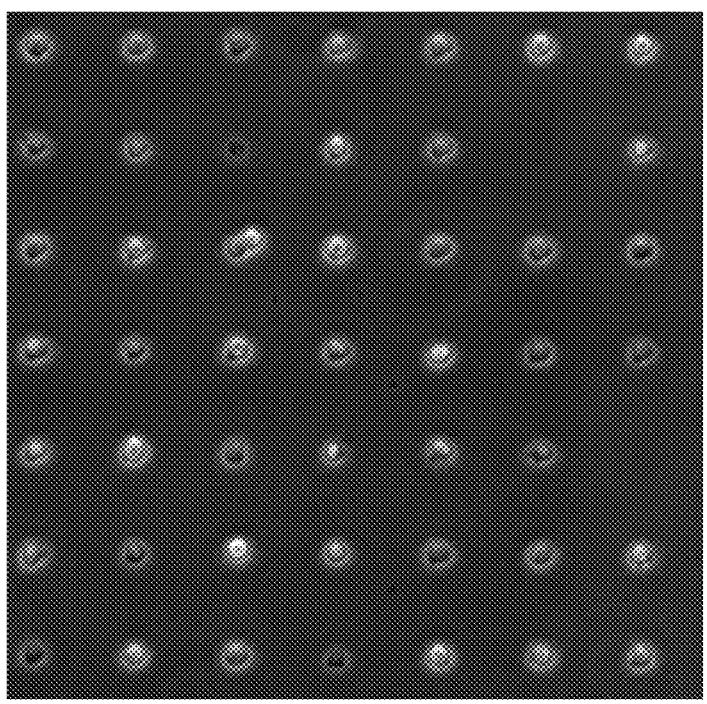
FIG. 32B
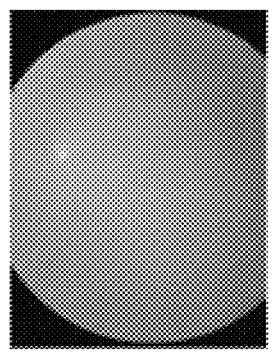
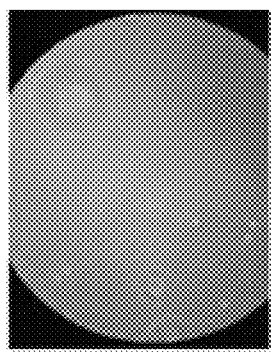
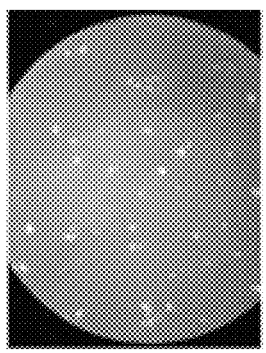
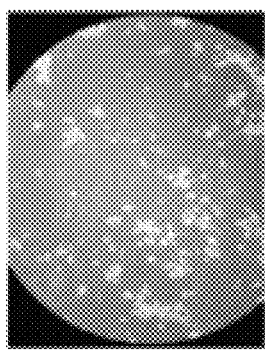
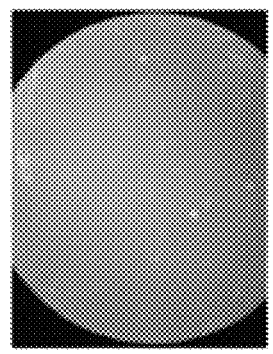
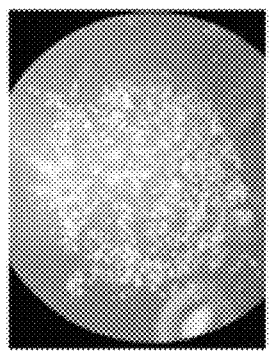
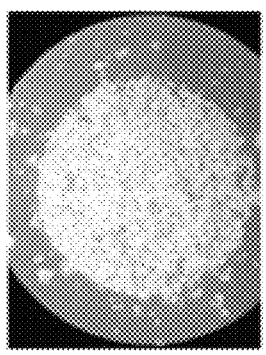
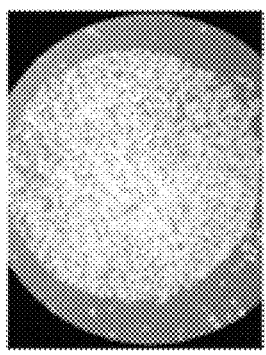
T = 0    T = 40    T = 60    T = 80

FIG. 33
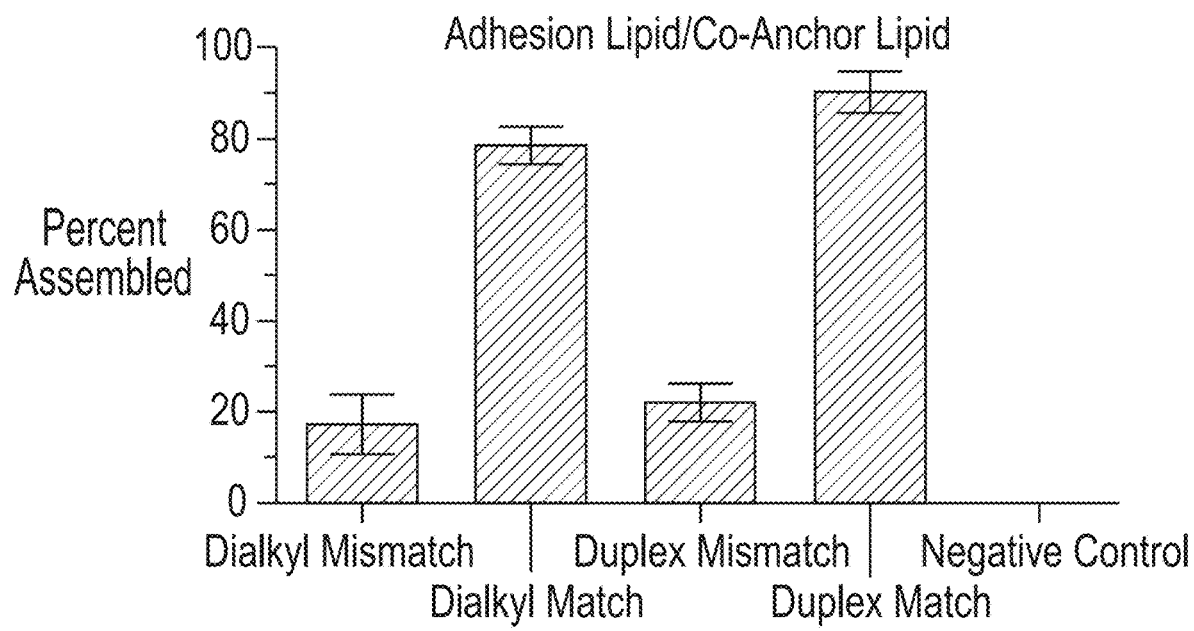

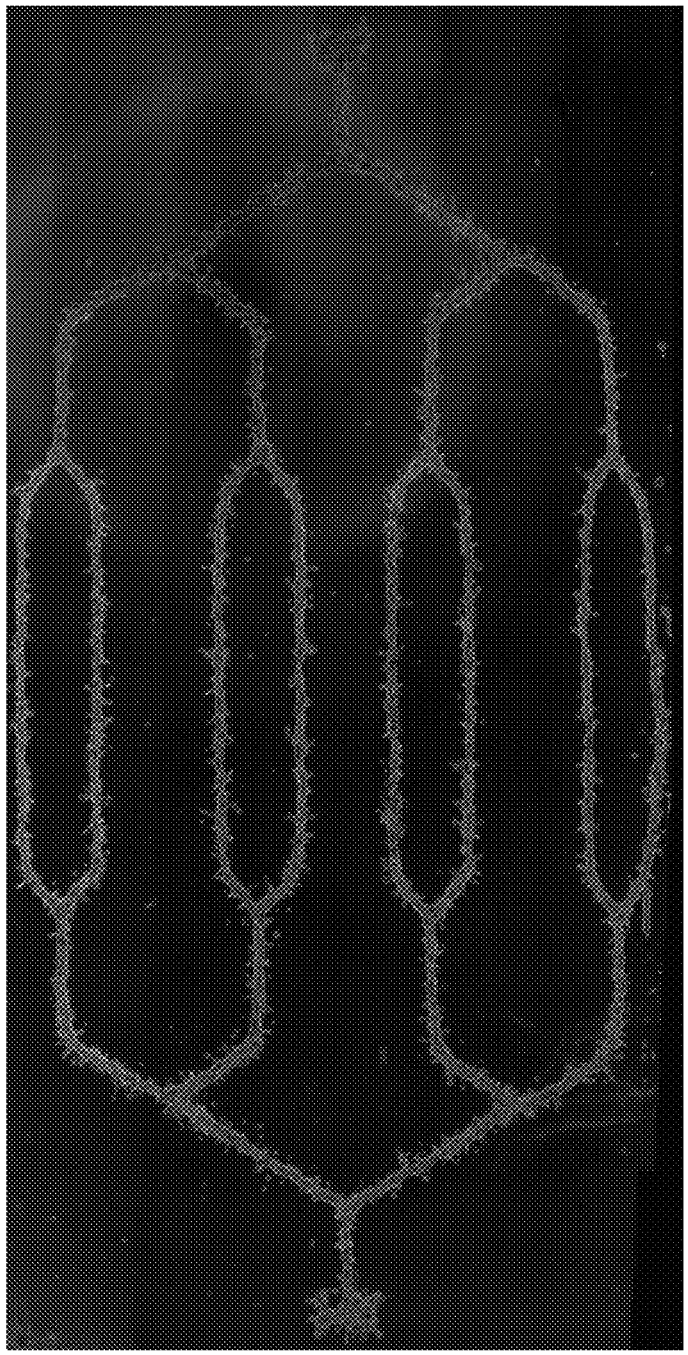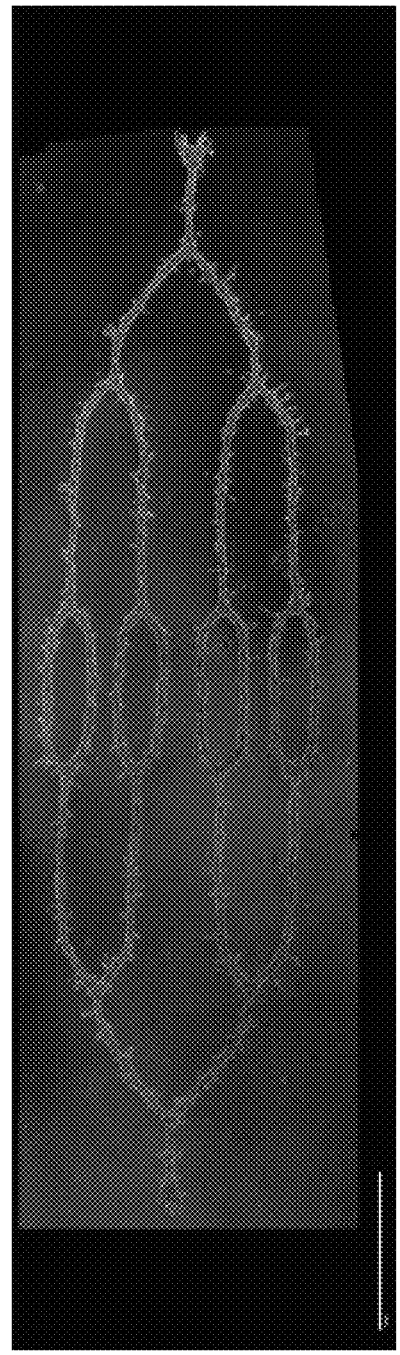
FIG. 39A
FIG. 39B

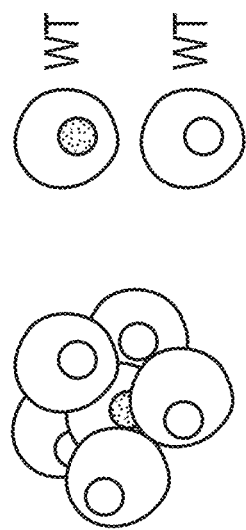
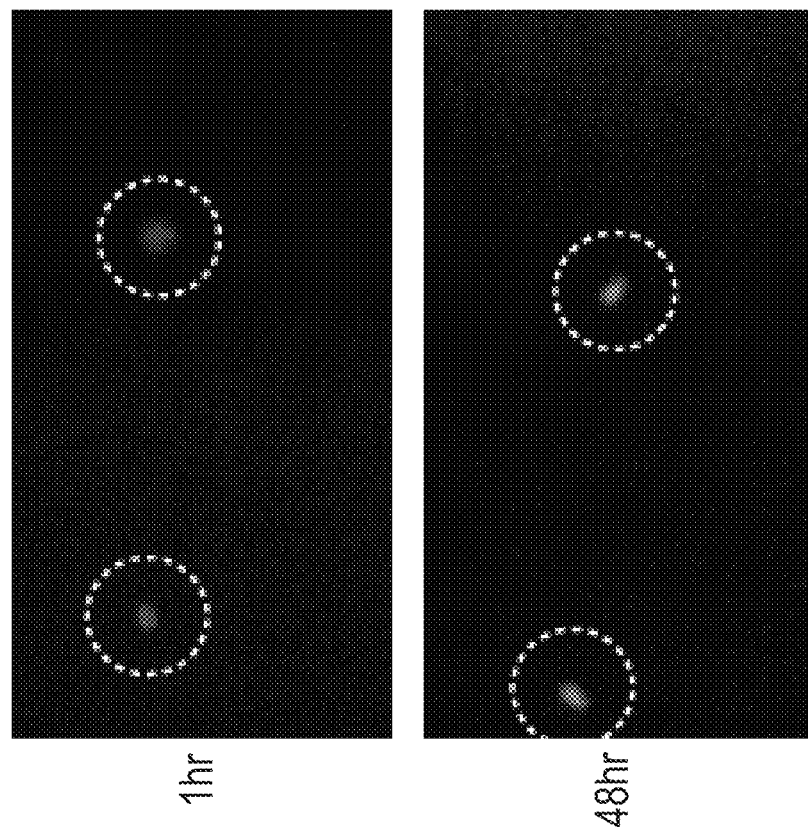
FIG. 40A
FIG. 40B

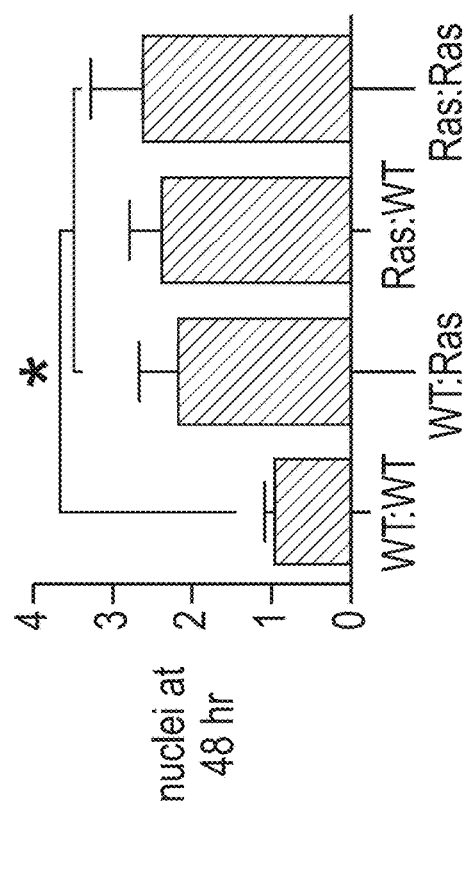
FIG. 40C
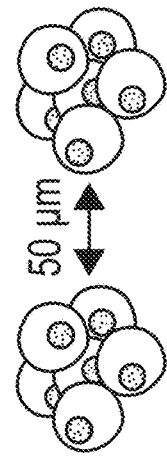
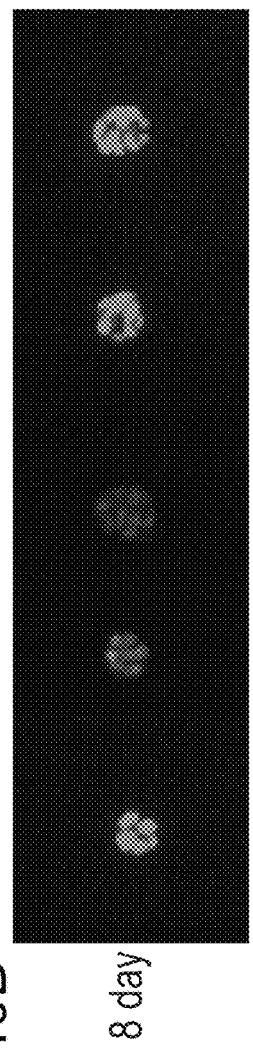
FIG. 40D
8 day
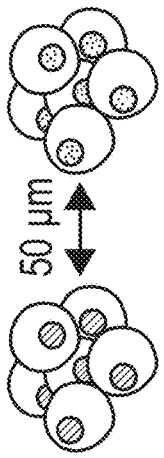
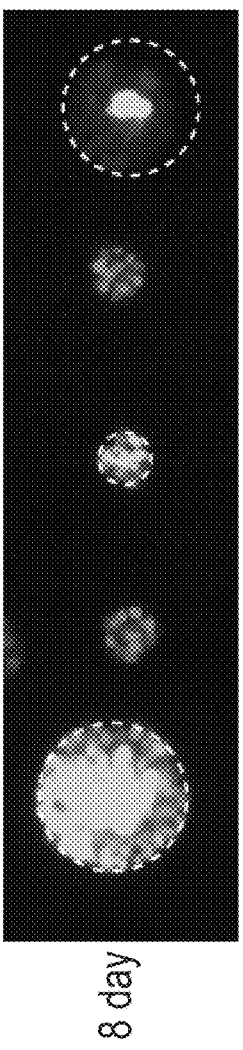
FIG. 40E
8 day

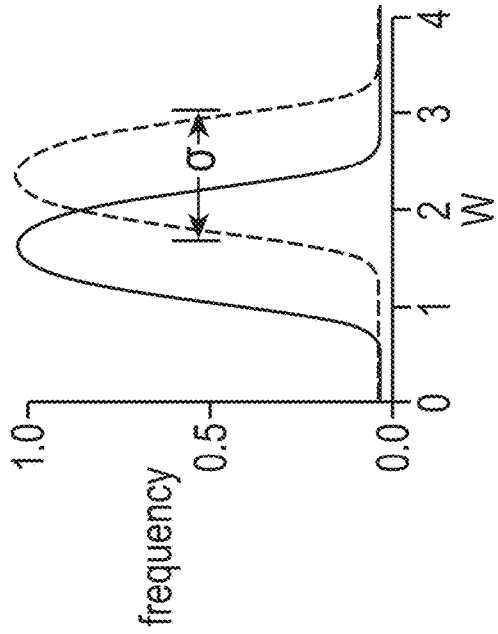
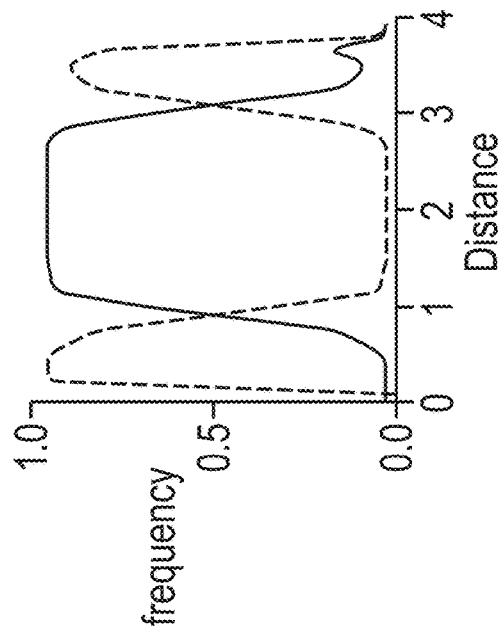
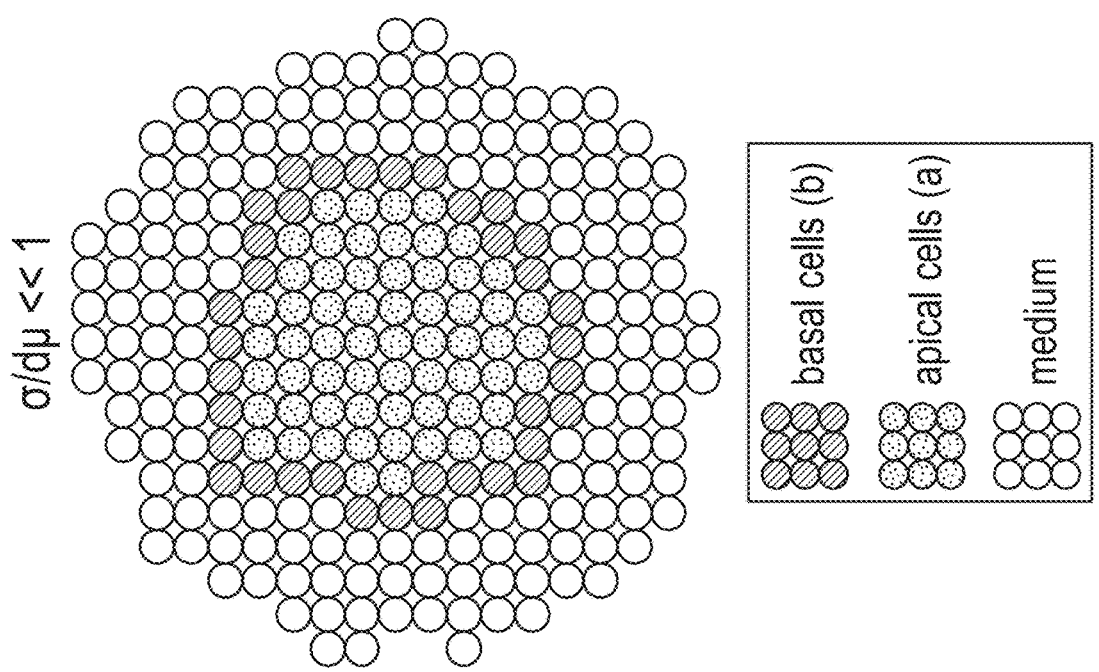

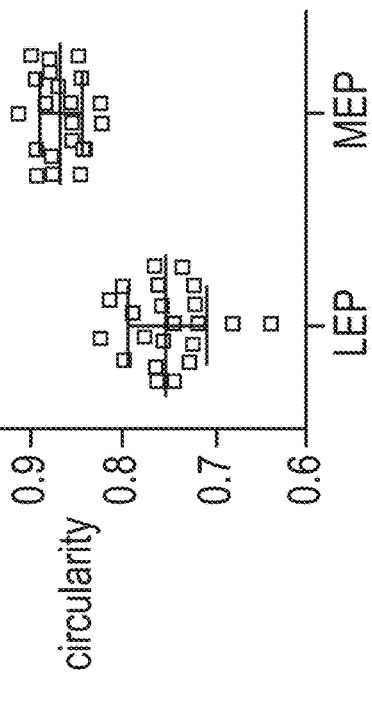
FIG. 47D
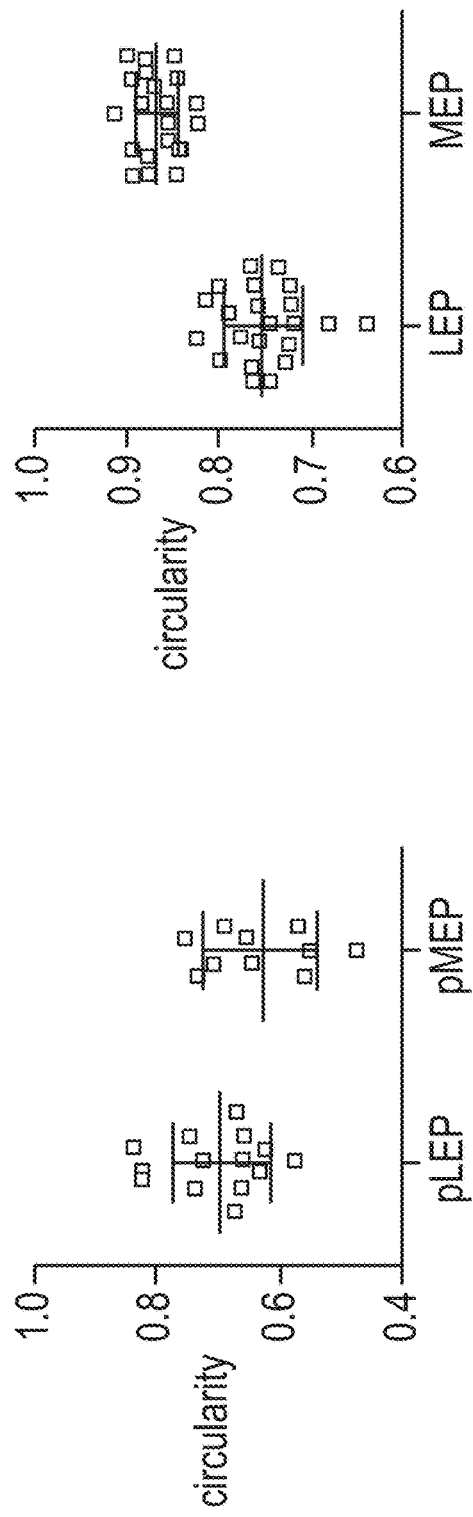
FIG. 47E
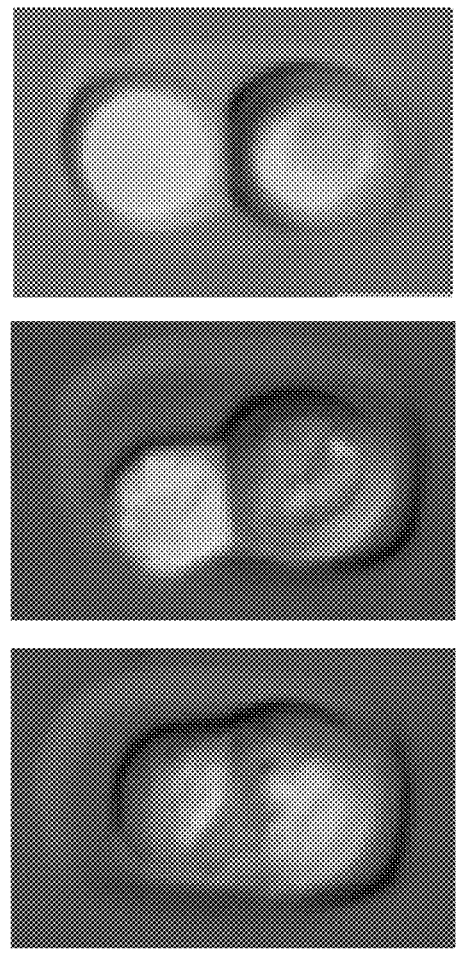
FIG. 47F
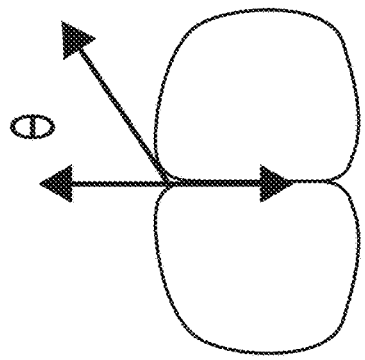

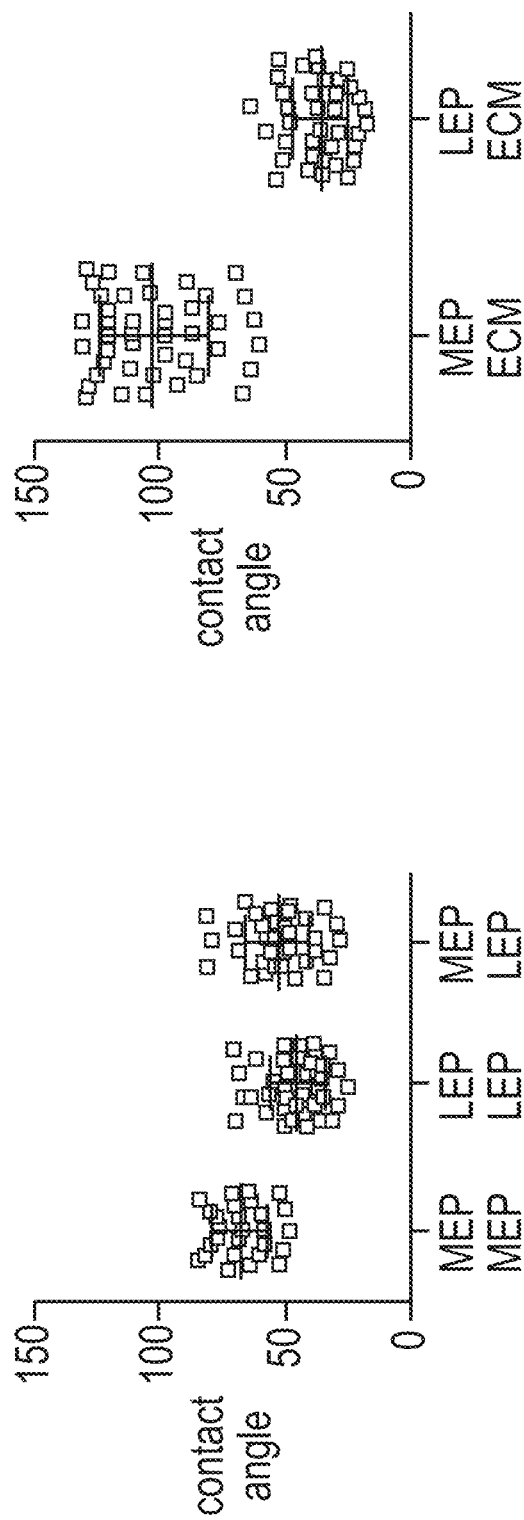
FIG. 47I
FIG. 47G
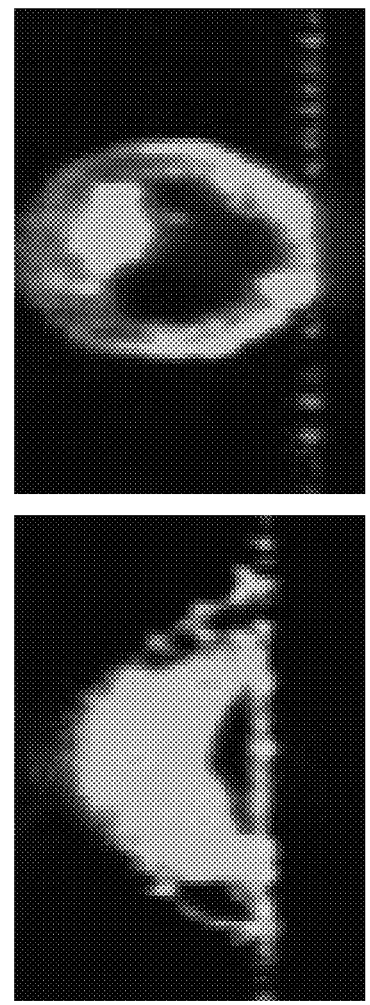
FIG. 47H

FIG. 48A
WT lrECM
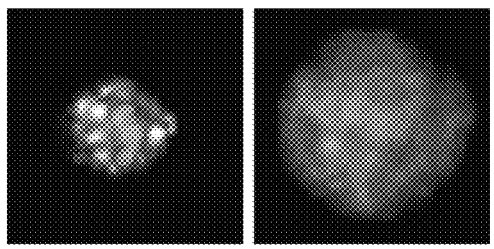
FIG. 48B
WT agarose
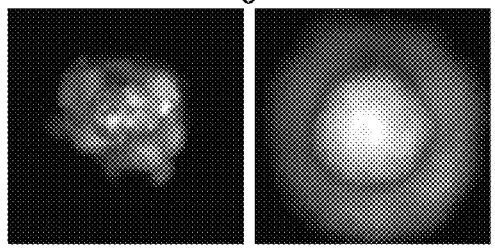
FIG. 48C
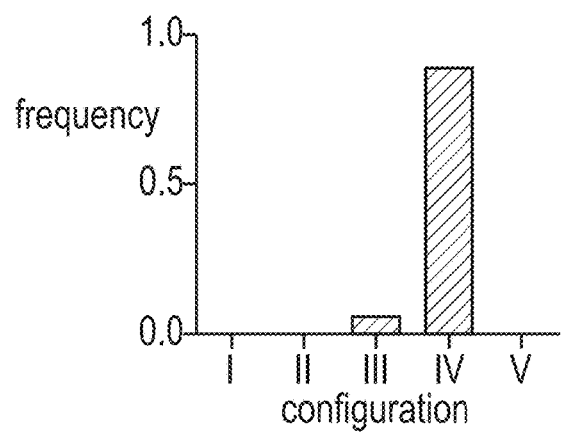
FIG. 48D
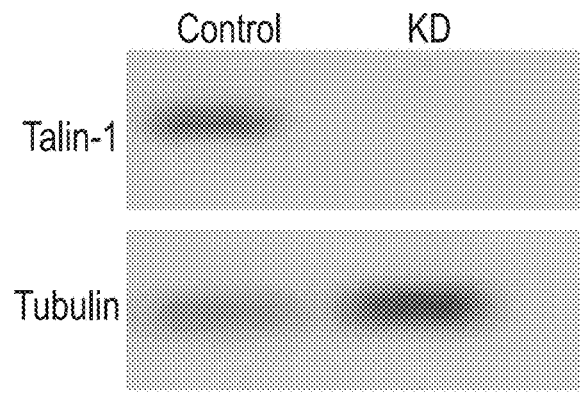
FIG. 48E
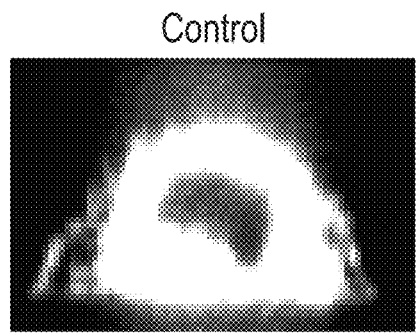
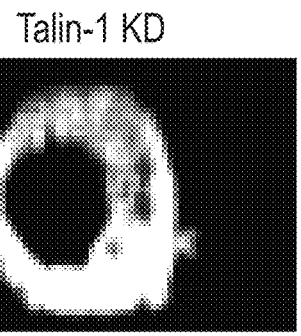

tain/matrigel

Control | P120 KD

Control | P120 KD

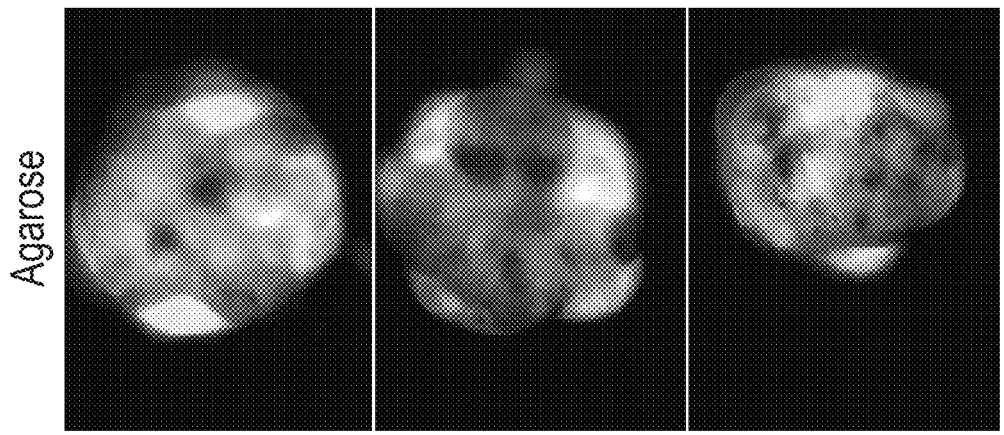
FIG. 50C Agarose
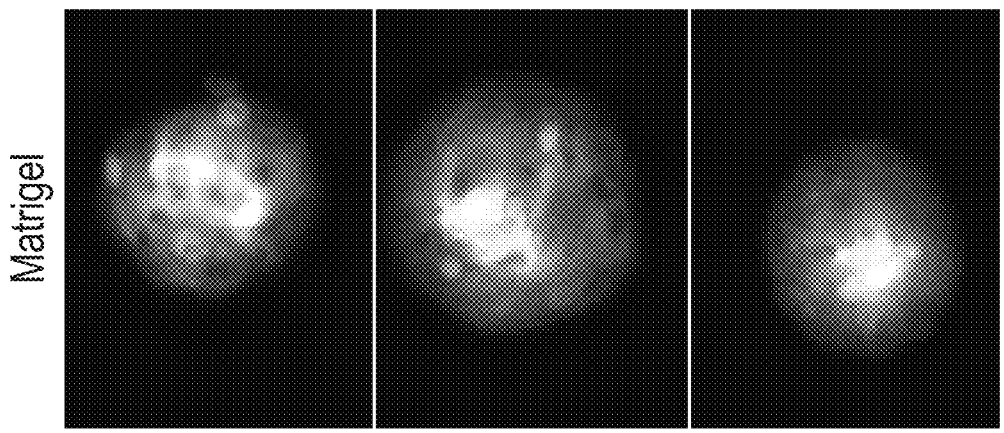
FIG. 50B Matrigel
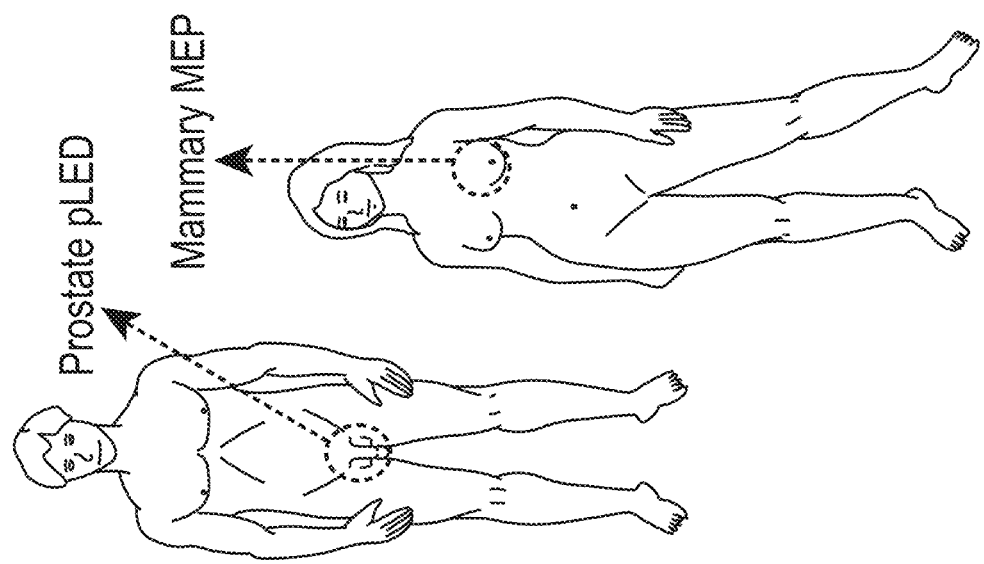
FIG. 50A

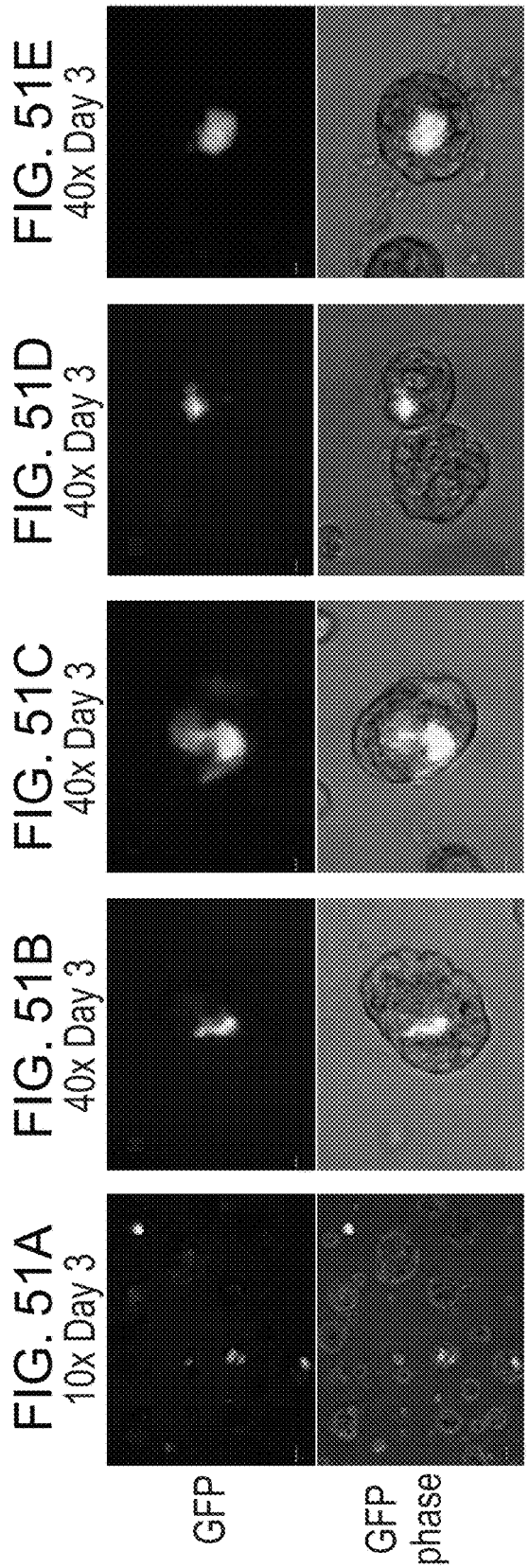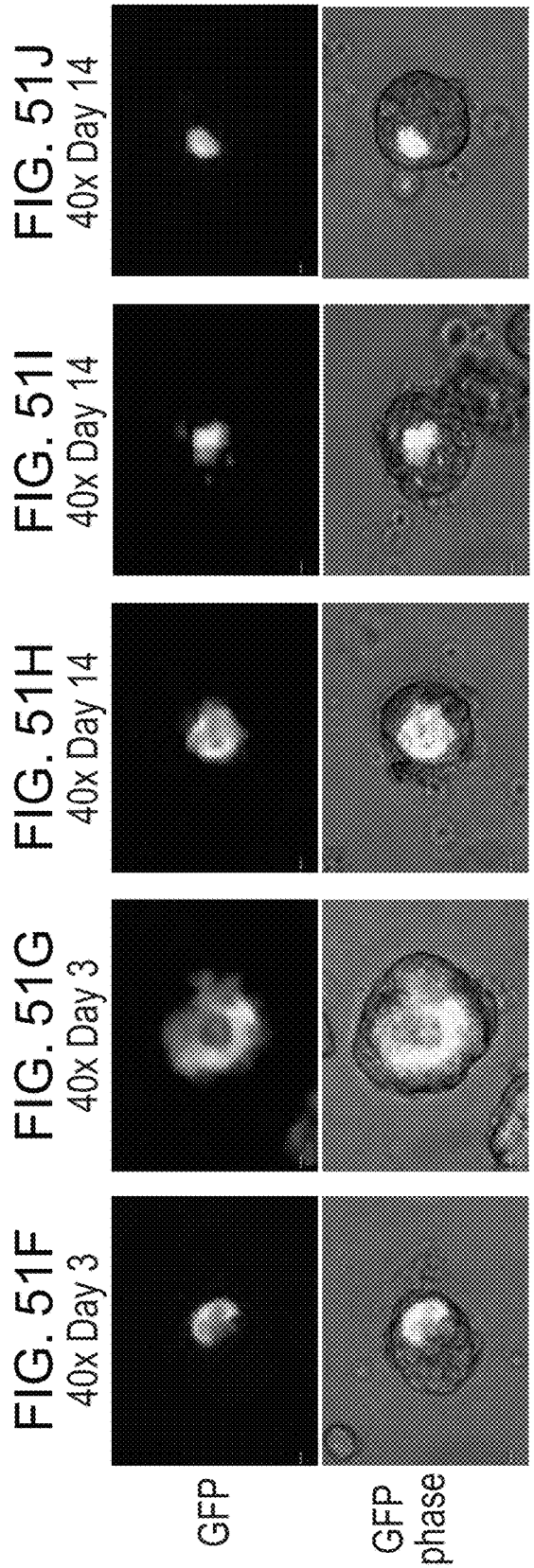

METHODS OF PATTERNING CELLS ON A SURFACE OF A SUBSTRATE AND PROGRAMMED ASSEMBLY OF THREE-DIMENSIONAL LIVING TISSUES

CROSS-REFERENCE TO RELATED APPLICATIONS

Pursuant to 35 U.S.C. § 119(e), this application claims priority to the filing date of U.S. Provisional Application Ser. No. 61/786,124 filed Mar. 14, 2013, and U.S. Provisional Application Ser. No. 61/722,694 filed Nov. 5, 2012, the disclosures of which are herein incorporated by reference in their entireties.

STATEMENT REGARDING FEDERALLY SPONSORED RESEARCH

This invention was made with government support under grant no. W81XWH-10-1-1023 awarded by the U.S. Army Medical Research and Materiel Command; and grant no. DGE-0648991 awarded by the National Science Foundation. The Government has certain rights in the invention.

INTRODUCTION

The human body contains some 10 trillion cells spanning over 210 differentiated cell types. Cells interact with materials and each other through adhesion molecules on their surfaces. These interactions serve to physically couple cells to their surroundings, and also alter cell behavior by triggering signaling cascades within the cytosol. There is considerable interest in understanding the mechanics of cell adhesion and in the development of methods to control cellular adhesion.

SUMMARY

The present disclosure provides methods of patterning cells on a surface of a substrate. The methods include disposing a pattern of nucleic acids on a surface of a substrate, and contacting the patterned nucleic acids under hybridization conditions with a first suspension of cells, where cells of the first suspension include cell surface-attached nucleic acids complementary to the patterned nucleic acids, and where the cell surface-attached nucleic acids hybridize to the patterned nucleic acids to pattern the cells on the surface of the substrate. Systems and kits for practicing the methods are also provided.

BRIEF DESCRIPTION OF THE DRAWINGS

The invention may be best understood from the following detailed description when read in conjunction with the accompanying drawings. Included in the drawings are the following figures:

FIG. 7, Panels A-C depict immunostaining of HMEC structures formed in 3D on top culture. Structures were extracted from matrigel, fixed, and stained with antibodies to K14 and K19 and counterstained with DAPI. Fluorescence images were collected using spinning disc confocal microscopy. Representative large (Panel A) and small (Panel B) structures at 20× show an outer layer of K14+/K19− MEP surrounding an inner layer of K14−/K19+ LEP. Panel C shows a 60× image of the small structure in a slightly different focal plane.

Figure 28A:
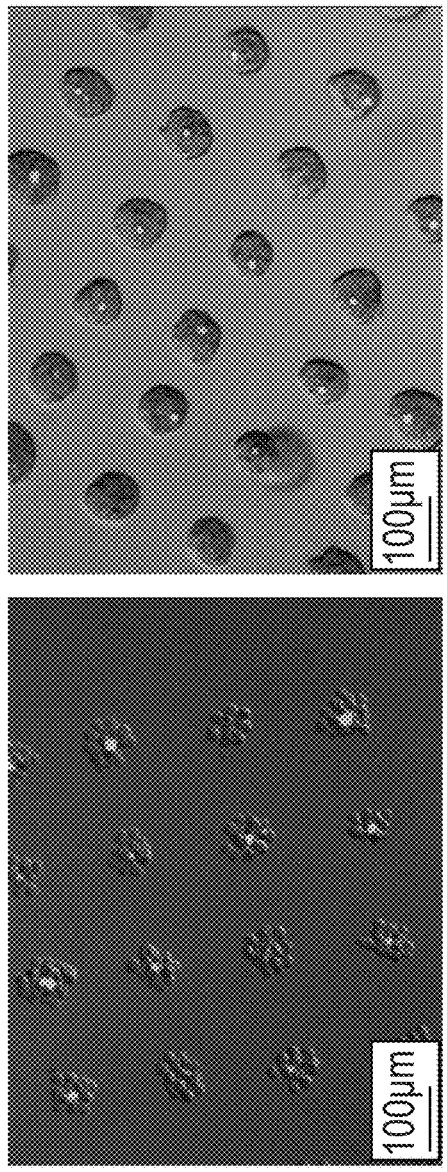
Figure 28B:
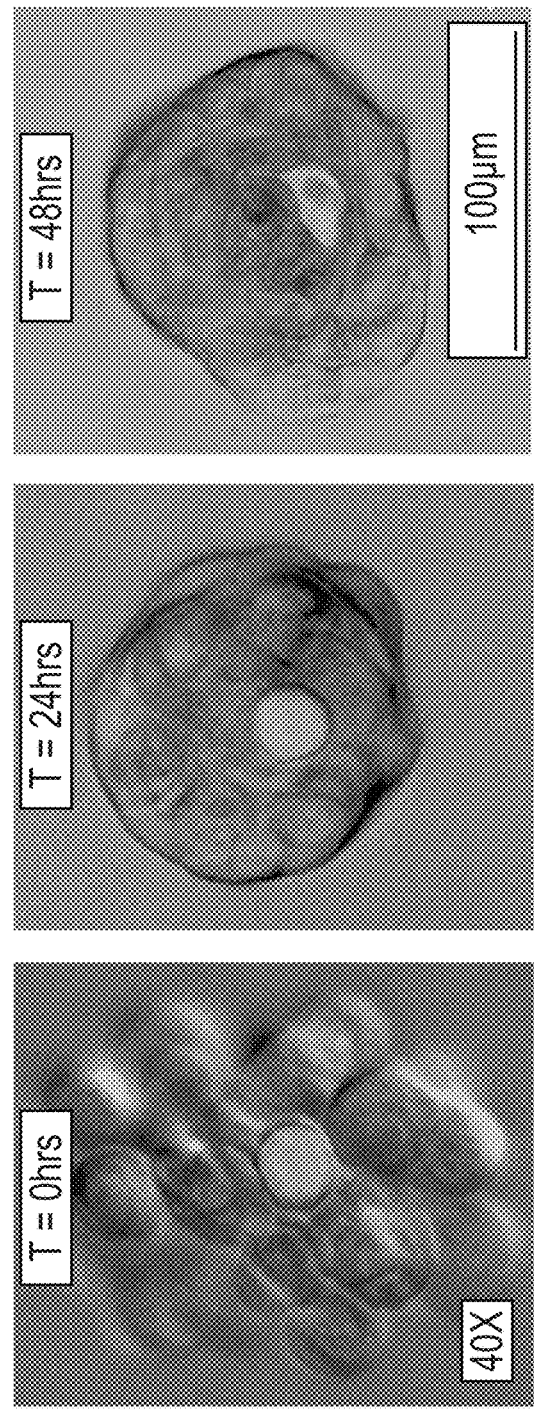

FIG. 28, Panels A-B show mosaic HMEC architectures with 1 LEP per cluster. Panel A: 10× view of HMEC clusters at time zero (left) and 24 hours later (right) enclosing 1 single LEP cell. As shown in Panel B, the position of the single cell within the tissue can be directly monitored as a function of time.

Figure 29C:
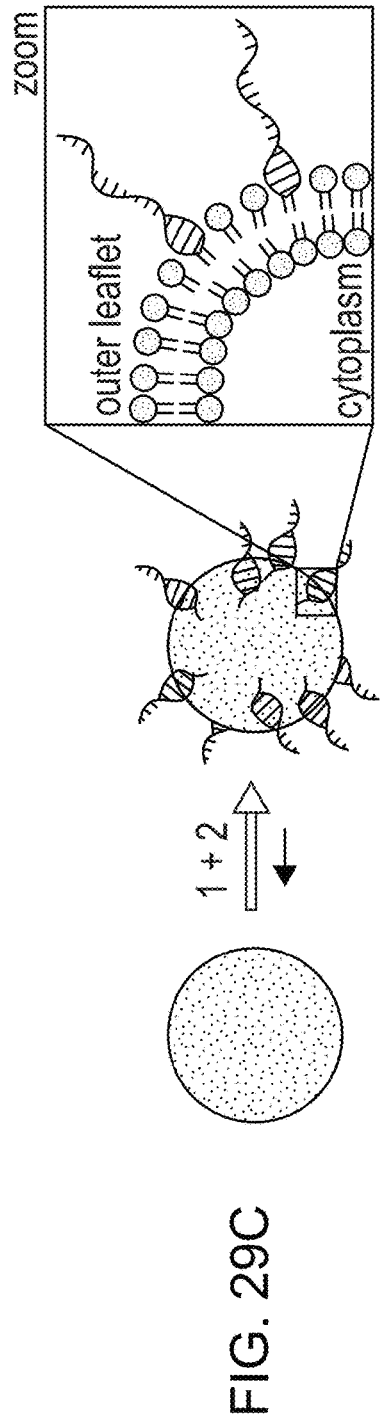

FIG. 29, Panels A-C show incorporation of lipid-modified oligonucleotides into cell membrane outer leaflets. Panel A: Two fatty acid modified oligonucleotides designed to hybridize in the lipid bilayer via a "lock region" and then present and adhesive "handle" region to neighboring cells and surfaces. Panels B-C: Hybridization of adhesion and co-anchor strand stabilizes lipid-modified oligonucleotides in the cells surface so they do not partition into the bulk medium. Panel D: Cell labeling efficiencies of various molecules relative to our previously reported dialkyl-lipid modified oligonucleotides.

Figure 30:
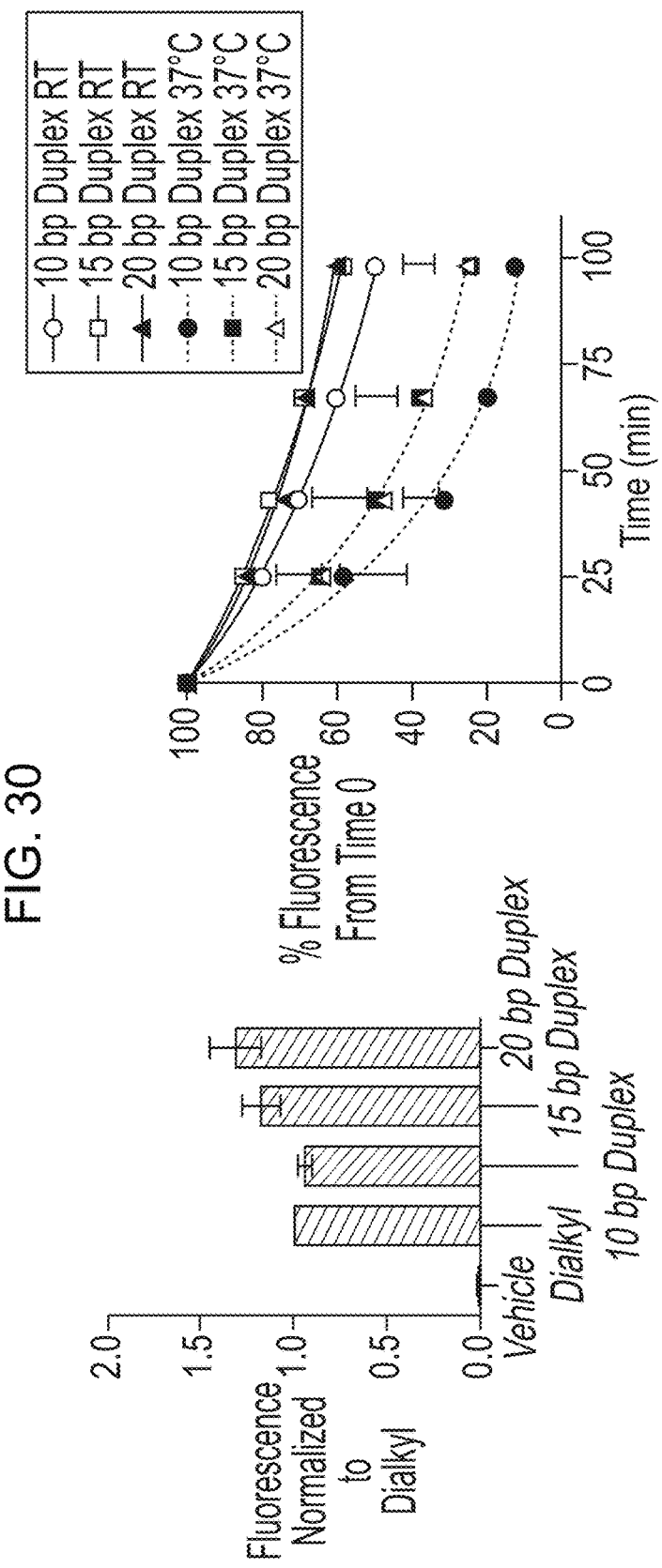
Figure 34A:
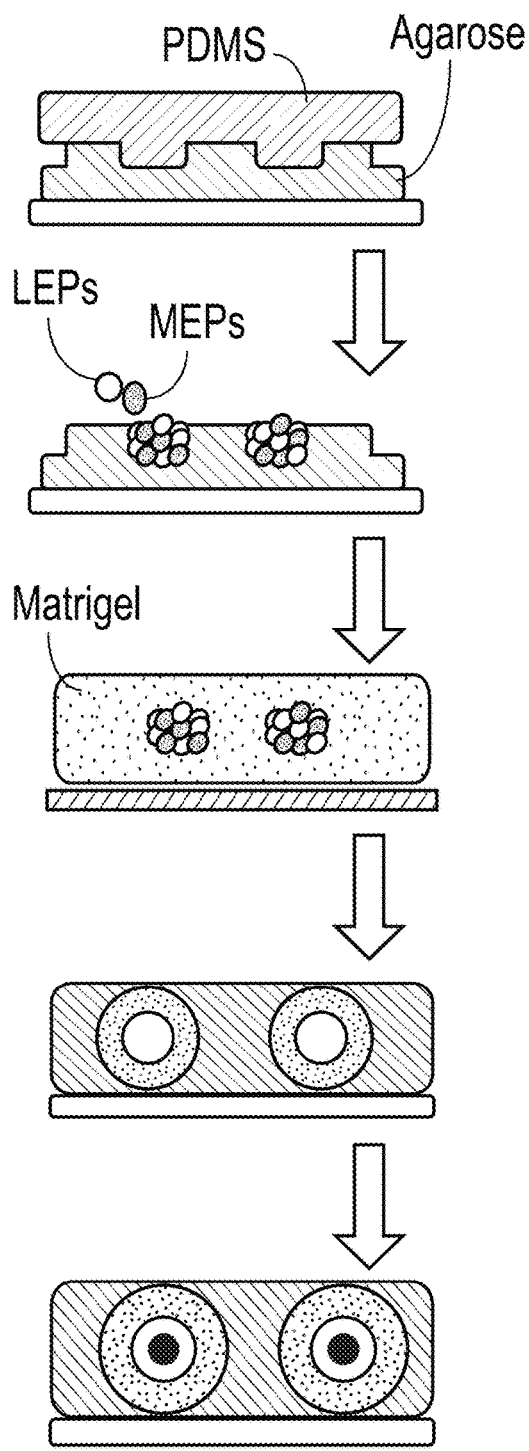
Figure 34B:
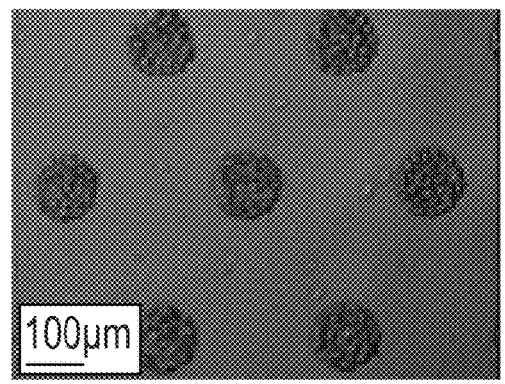
Figure 34C:
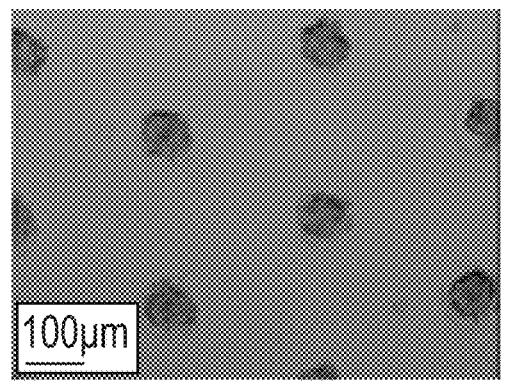
Figure 34D:
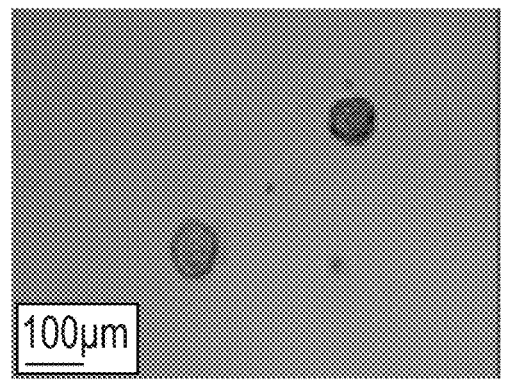
Figure 34E:
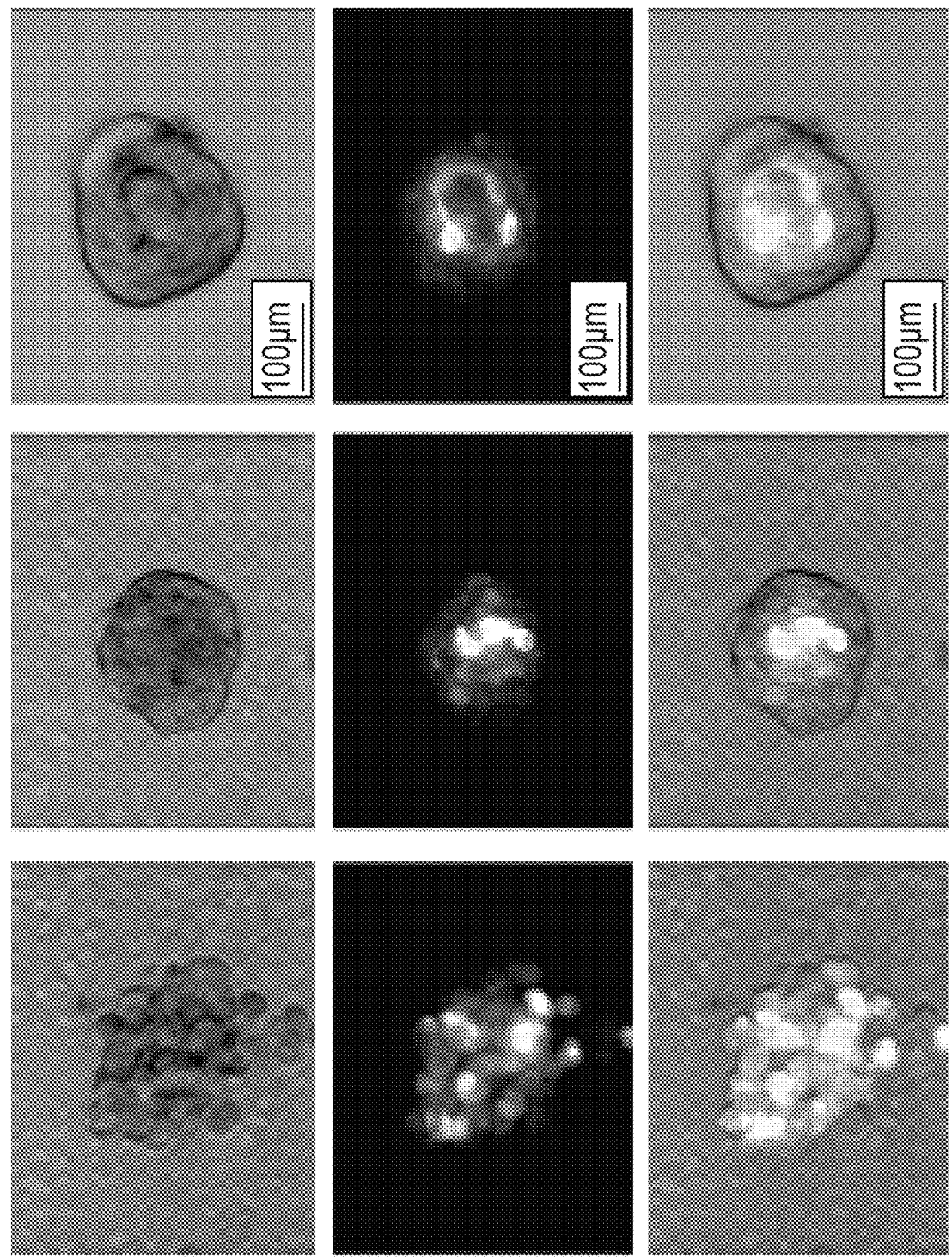

FIG. 30 depicts data showing cell labeling as a function of duplex formation. Left: Efficiency of membrane insertion as a function of lock-region depth. Right: Stability of oligonucleotides complexes in the cell membrane as a function of lock-region length and temperature.

FIG. 31 depicts data showing that cell surface labeling increases as the lipophilicity of the conjugated fatty acid anchor increases. Left: Cell-surface DNA concentration relative to the previously reported dialkyl strand immediately after cell labeling. Right: Cell-surface DNA concentration after 90 minute incubation in media.

FIG. 32A and FIG. 32B show surface adhesion of DNA-modified cells. FIG. 32A Top: total cell surface DNA measured for adhesions strands with the indicated polyT linker length. FIG. 32A Bottom: Surface adhesion efficiency of cells labeled with adhesive strands with the indicated polyT linker length. FIG. 32B left: representative images of the data used to calculate adhesion efficiency. FIG. 32B right: single cell microarrays prepared with mouse embryonic stem cells labeled with the C16/C24 adhesive strand combination.

FIG. 33 depicts DNA-programmed assembly data. Left: Efficiency of DNA-programmed assembly as judged by flow cytometry. Right: Representative image of a biased assembly with 1 green stained Jurkat surrounded by 5 red stained Jurkats.

FIG. 34, Panels A-E depict a method of preparing bilayered mammary epithelial tissues by micromolding and transfer to matrigel. Panel A: schemed for using agarose microwells to prepare controlled aggregates of HMEC. Panel B: HMEC in wells. Panel C: HMEC aggregates after 6-12 hours; Panel D: HMEC aggregates transferred to lrECM. Panel E: representative images of aggregates after matrigel culture showing correct organization and lumen formation.

Figure 35:
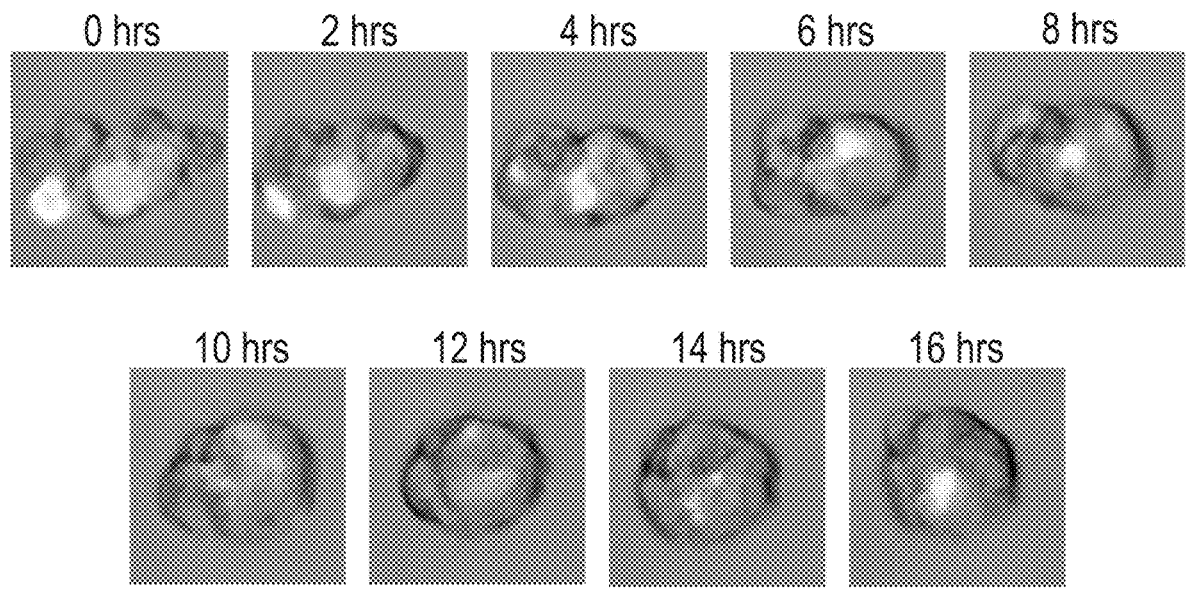
Figure 36A:
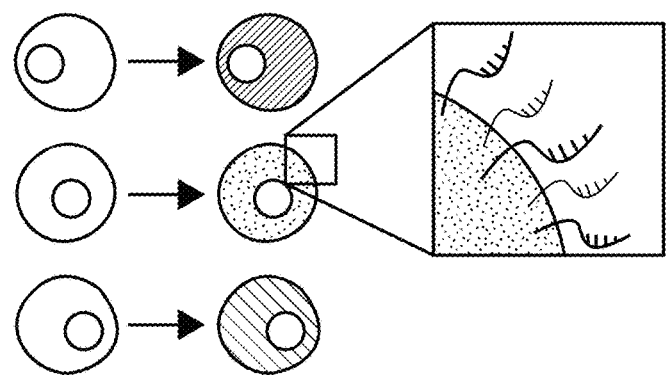
Figure 36B:
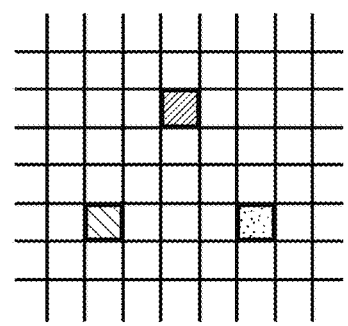
Figure 36C:
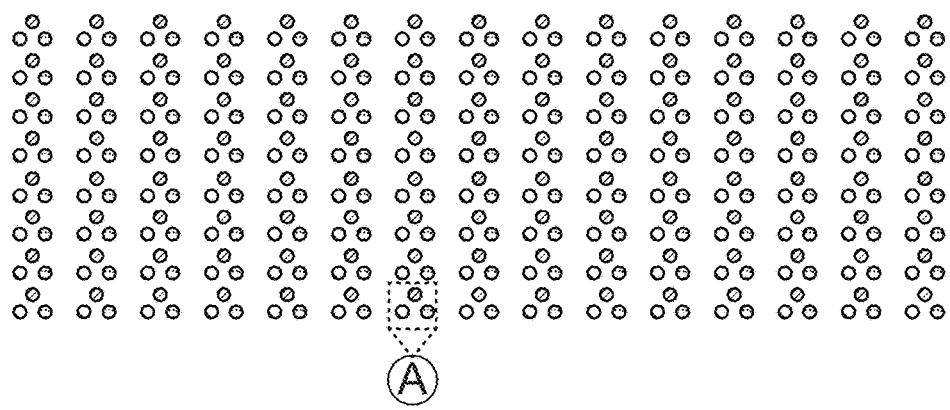
Figure 36D:
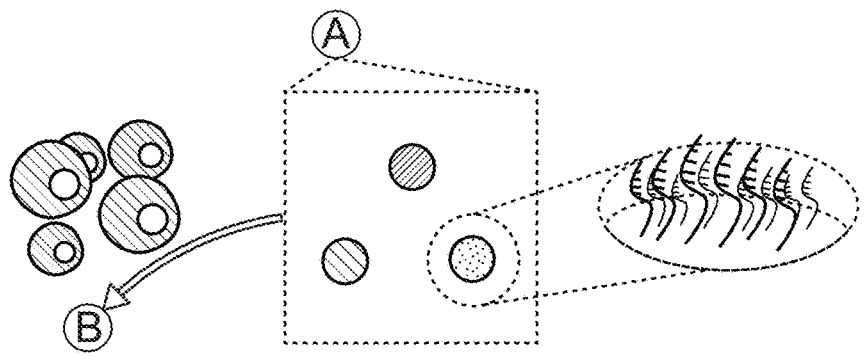
Figure 36E:
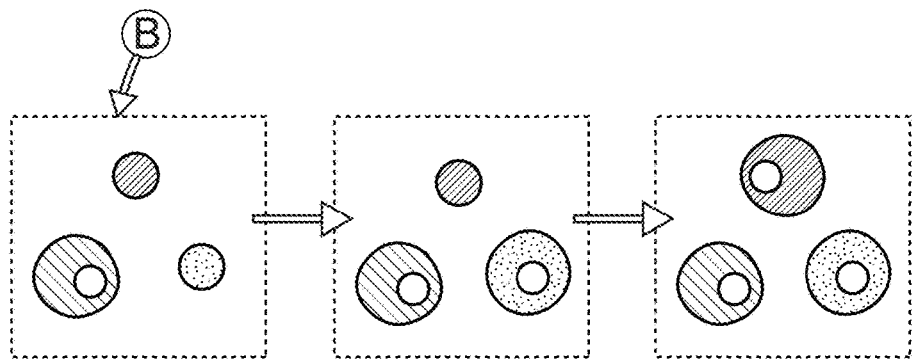
Figure 36F:
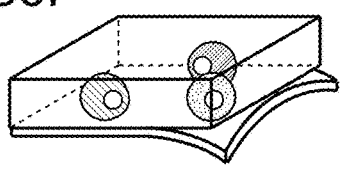
Figure 36G:
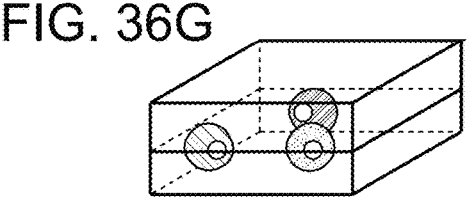

FIG. 35 shows time-lapse imaging of HMEC clusters self-organizing over a 16-hour period.

FIG. 36, Panels A-G depict a solid-phase assembly scheme according to one embodiment of the present disclosure. DNA is patterned on aldehyde-silanized surface using molecular writing. Seed cells are attached to pattern via DNA hybridization. Partner cells are assembled onto seed cells, creating microtissues. Microtissues are embedded in a matrix and released from the surface using DNase, allowing transfer of embedded cells to a 3D tissue culture context.

Figure 37:
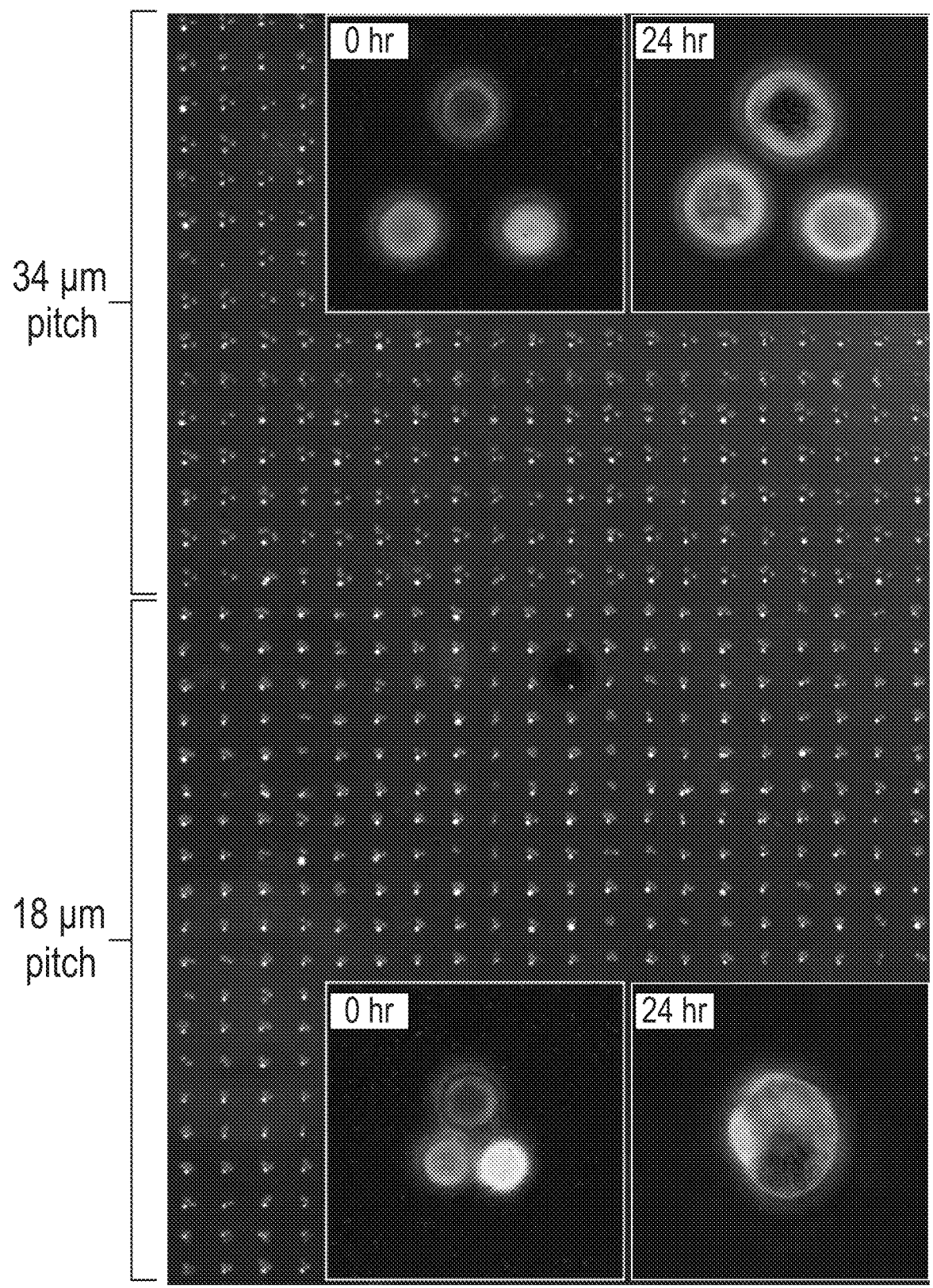

FIG. 37 shows solid-phase assembly of 3D tissue cultures. DNA is patterned on aldehyde-silanized surface using molecular writing. Seed cells are attached to pattern via DNA hybridization. Partner cells are assembled onto seed cells, creating microtissues. Microtissues are embedded in a matrix and released from the surface using DNase, allowing transfer of embedded cells to a 3D tissue culture context.

Figure 38A:
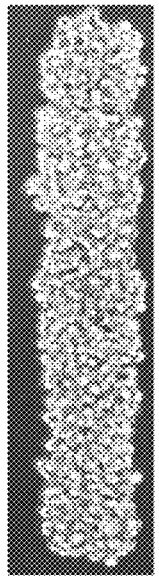
Figure 38B:
Figure 38C:
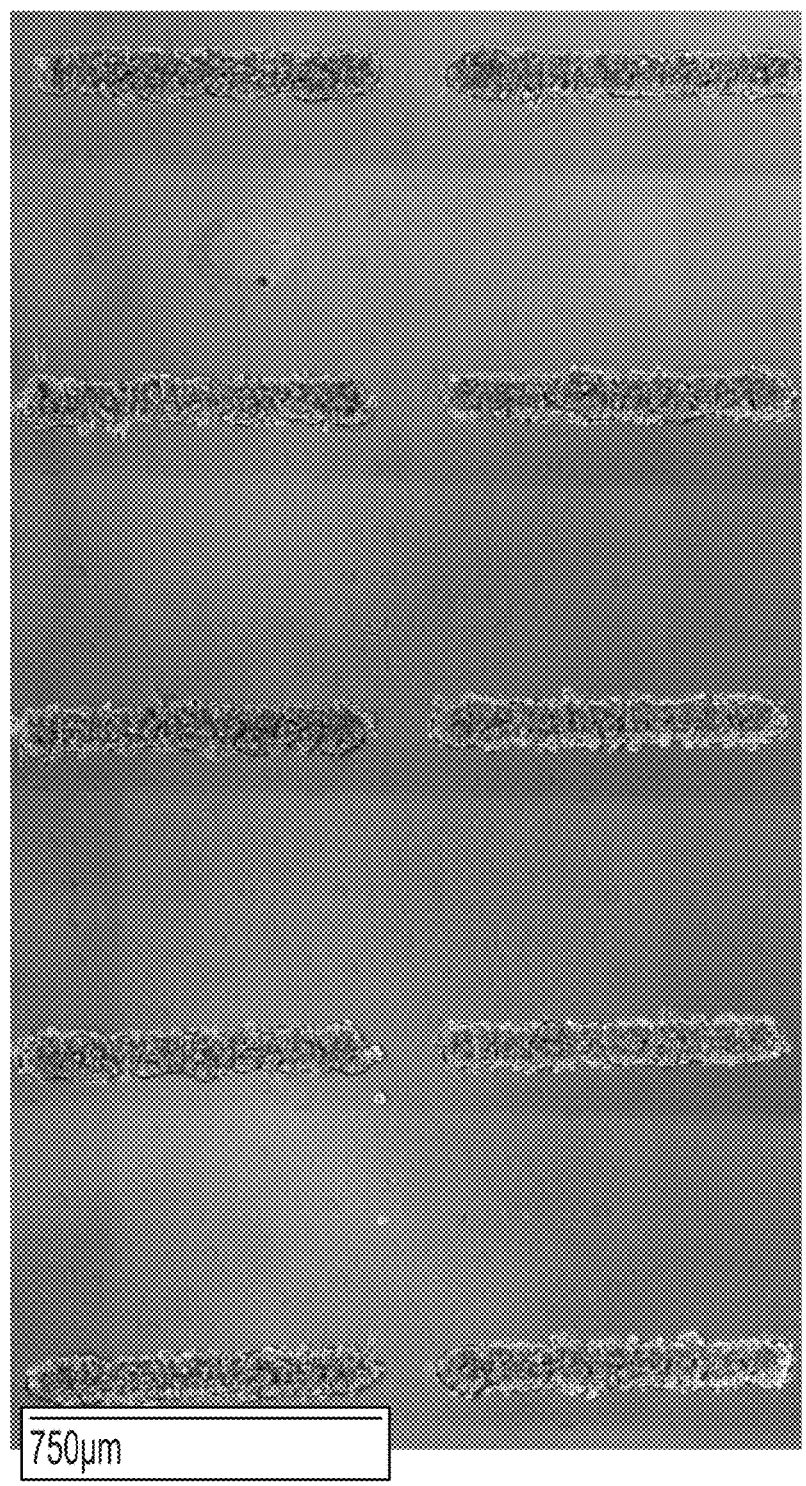

FIG. 38, Panels A-C depict assembly of epithelial tubular architectures.

FIG. 39, Panels A-B show the assembly of human umbilical cord vascular networks. Panel A: wide form factor. Panel B: narrow form factor. Scale bar=1 mm.

FIG. 40, Panels A-E provide data showing the effect of Ras transformed MCF10A cells on the growth of their normal neighbors. Tracking the growth of a single H2B-GFP expressing WT cell of 38 hours in a WT epithelial tissue (Panel A), or a Ras expressing epithelial tissue (Panel B). Quantification of 48 growth rate for single cells in different tissue contexts (Panel C). XX:YY=single cell genotype: epithelial genotype. 8 day growth of WT MCF10A tissues (Panel D) and WT MCF10A tissues growing 50 µm from Ras expressing tissues (Panel E).

Figure 41A:
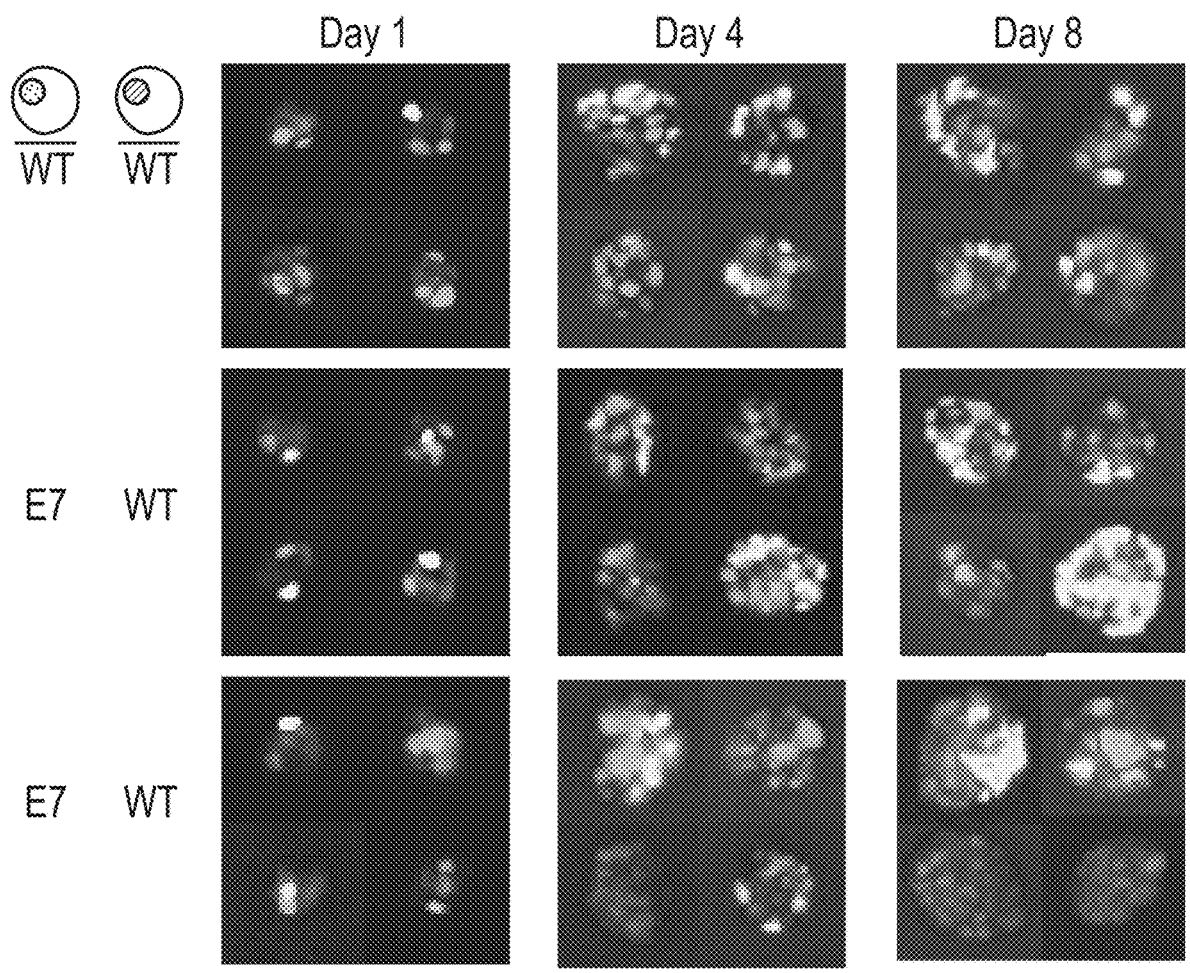
Figure 41B:
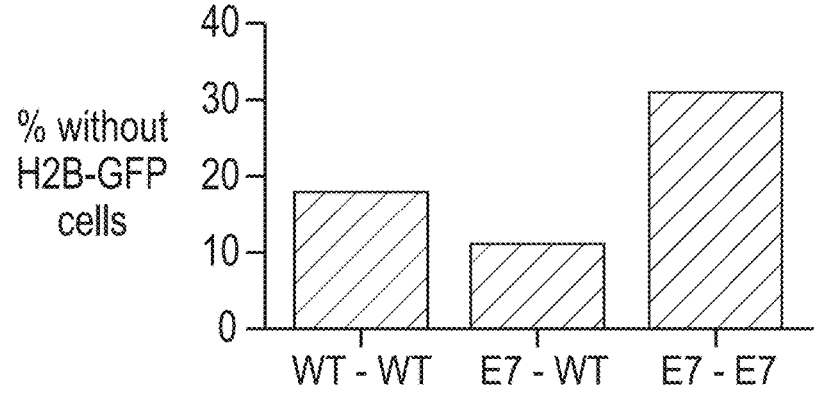

FIG. 41, Panels A-B provide data showing the effect of MCF10A cells on the growth of their E7 transformed neighbors. Panel A: Representative images of single WT or E7 expressing MCF10A cells growing within WT or E7 expressing acini after 1 day, 4 days, or 8 days in culture (on top of matrigel). Panel B: Fraction of acini that have lost their single H2BGFP expressing cell at day 8.

Figure 42:
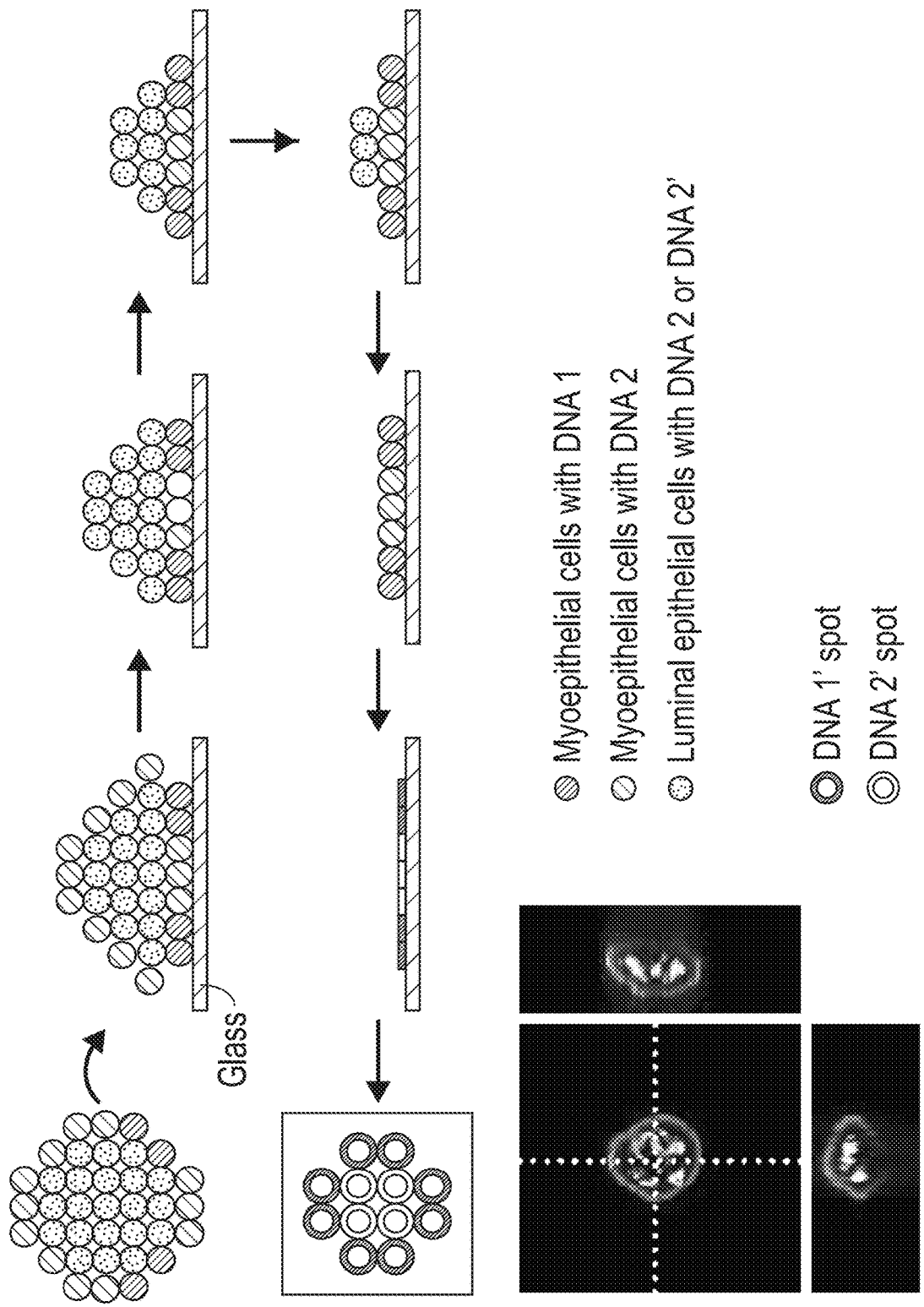
Figure 43A:
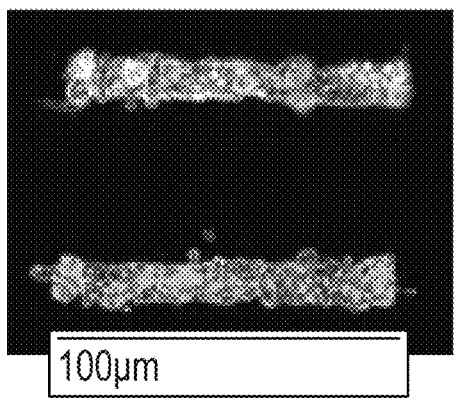
Figure 43B:
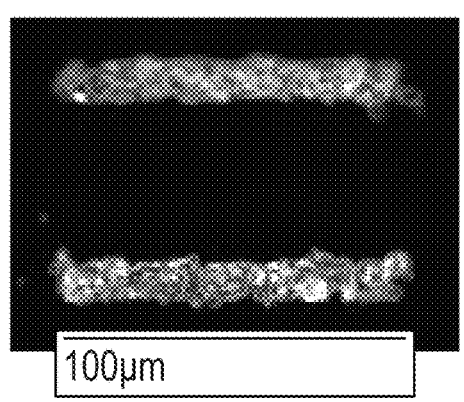
Figure 43C:
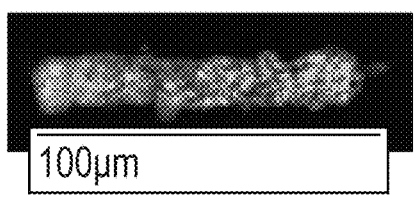
Figure 43D:
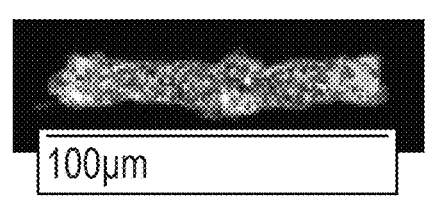
Figure 43E:
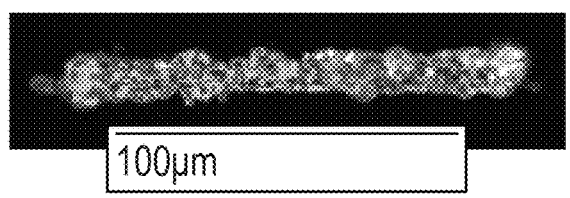
Figure 43F:

FIG. 42 shows multistep DNA-programmed assembly of epithelial spheroids with the topology of the human mammary gland. The scheme according to this embodiment shows a retrosynthetic analysis of the mammary gland. Starting from the upper left: A tissue with the topology of the human mammary gland and has been previously shown to spontaneously lumenize in laminin rich gels. Tissue surface tension causes a flattened tissue with the correct topology to round up in viscoelastic gels like lrECM. Three rounds to DNA programmed assembly generates the LEP core. A bulls-eye pattern of LEPs is prepared by two rounds of DNA-programmed assembly from a complementary pattern of DNA on glass. Bottom: K14 and K19 stained tissue less than 12 hours after transfer to lrECM.

FIG. 43, Panels A-F depict a 24-hour culture of MCF10A epithelial tubes constructed with DNA-programmed assembly with internal patterns of two cell types. A: homogeneous red and green tubes; B: placing a population of red cells at the ends or the middle of the tubes. C: gradients of cells. D: stripes of cells. E and F: longer tubes with red and green cells arranged at opposite ends or as a smooth gradient across the tube.

Figure 44:
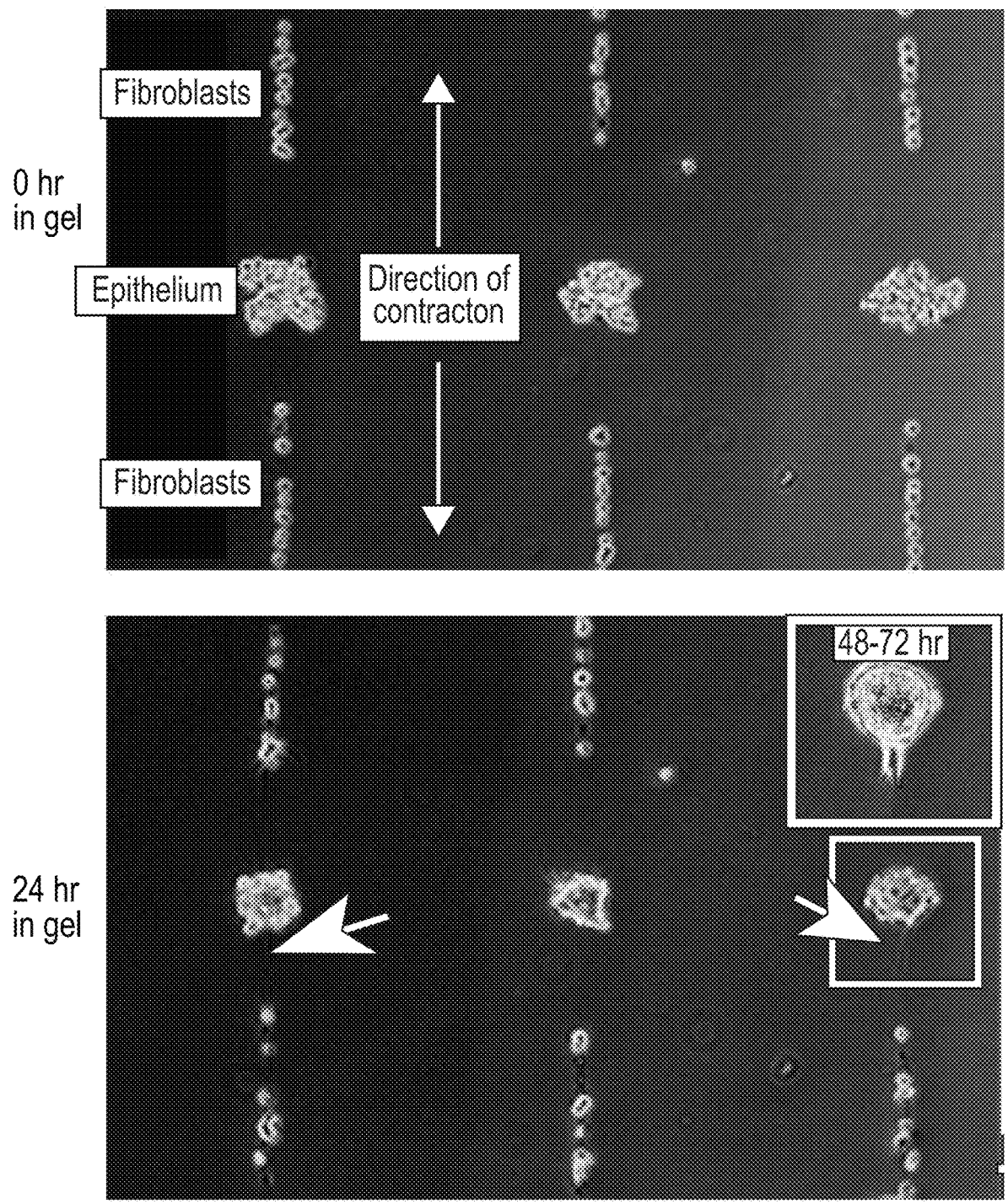
Figure 45A:
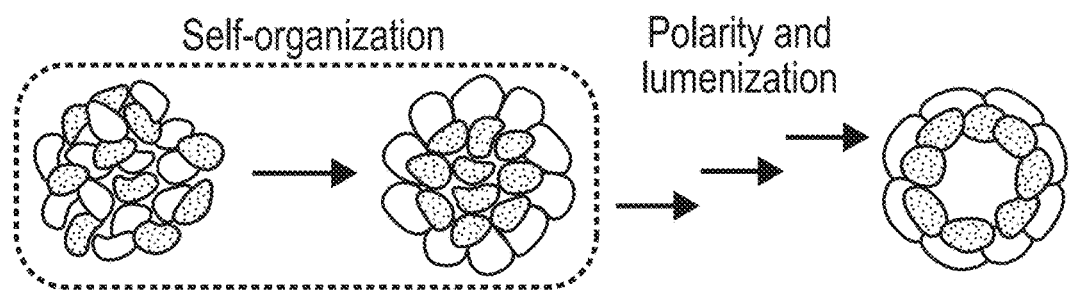
Figure 45B:
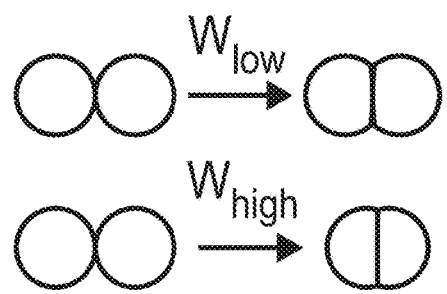
Figure 45C:
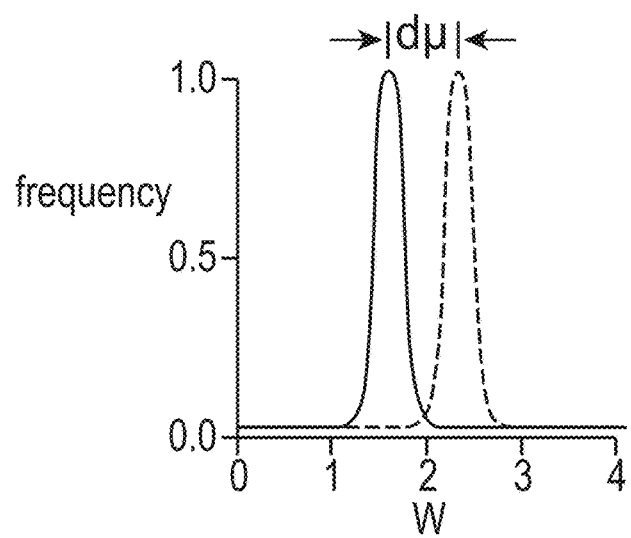
Figure 45H:
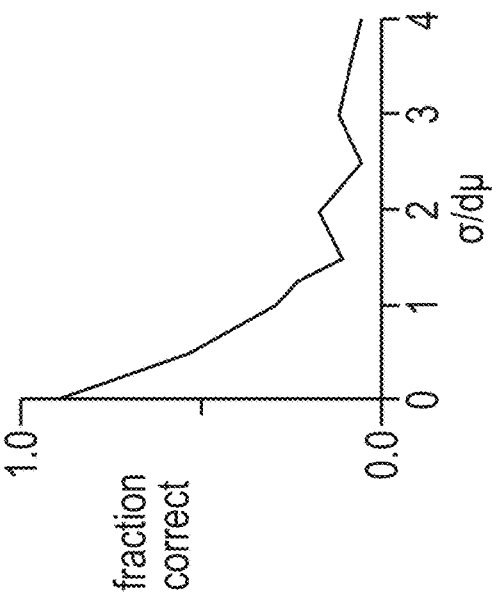
Figure 45I:
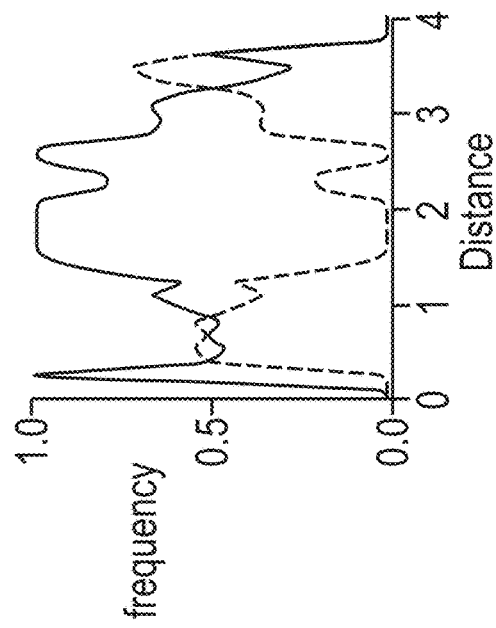
Figure 45G:
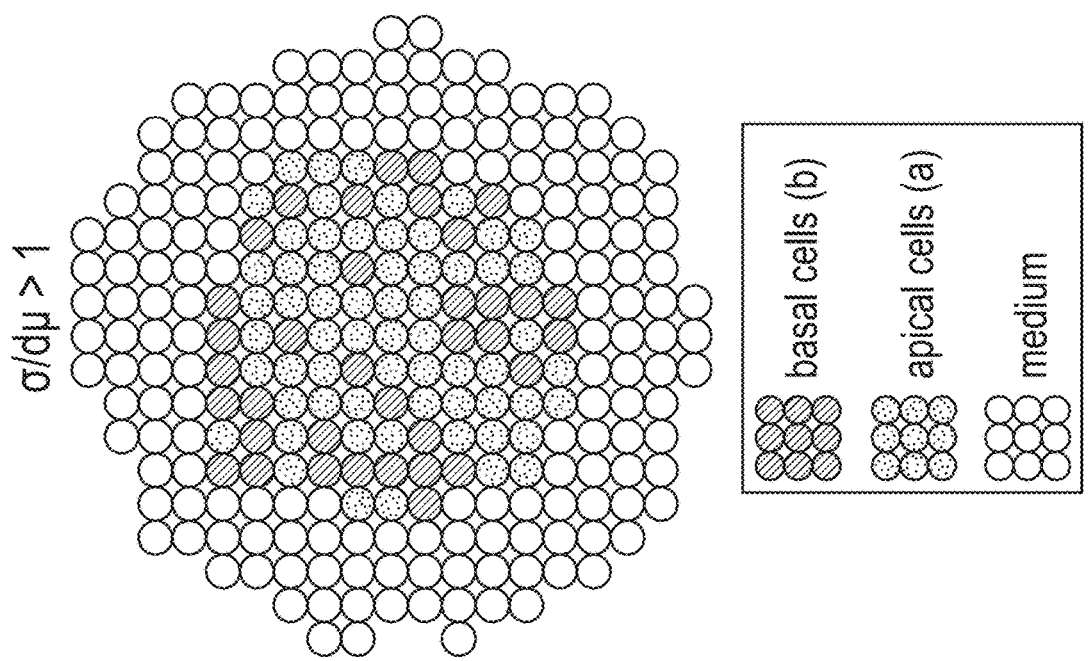
Figure 46B:
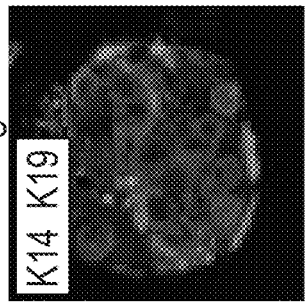
Figure 46C:
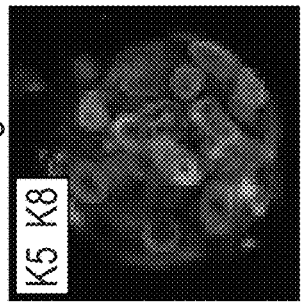
Figure 46A:
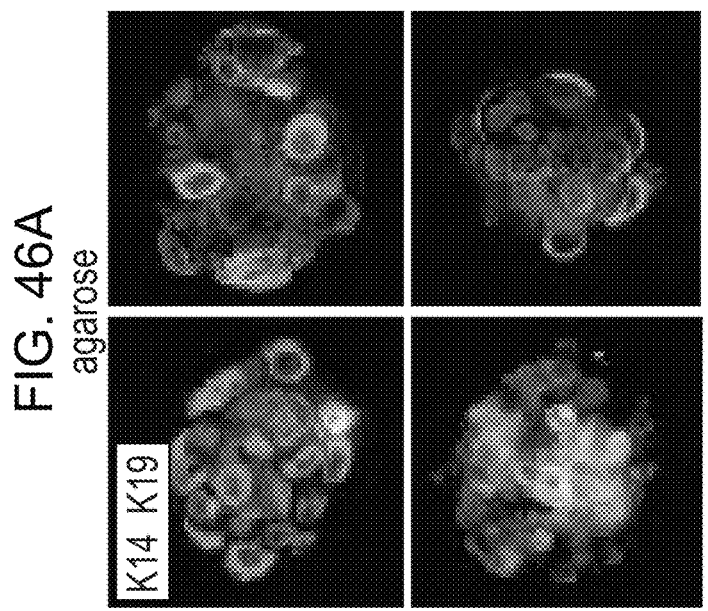
Figure 46D:
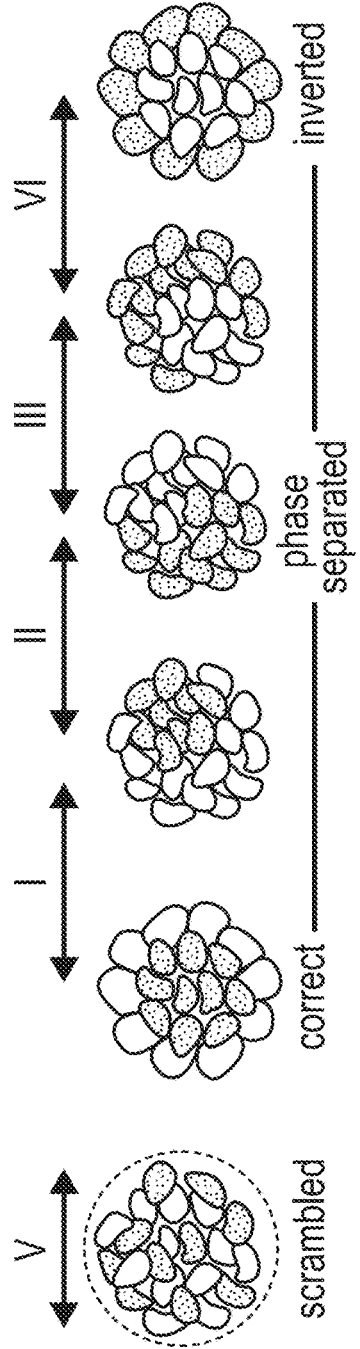
Figure 46E:
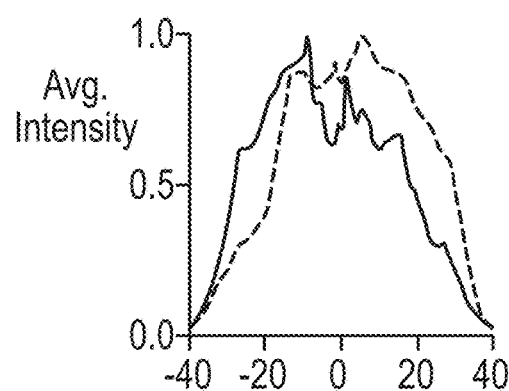
Figure 46F:
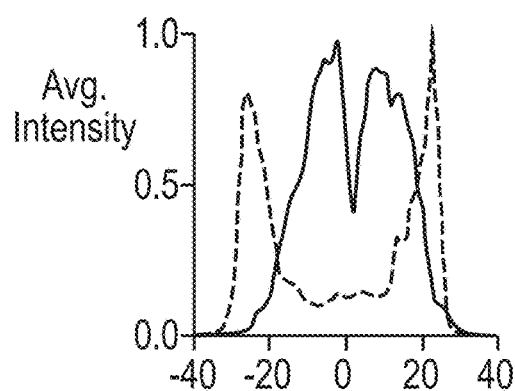
Figure 46G:
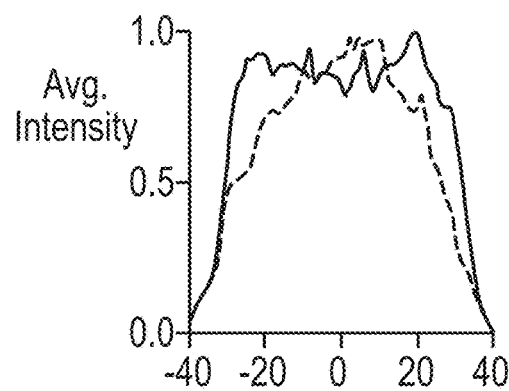
Figure 46H:
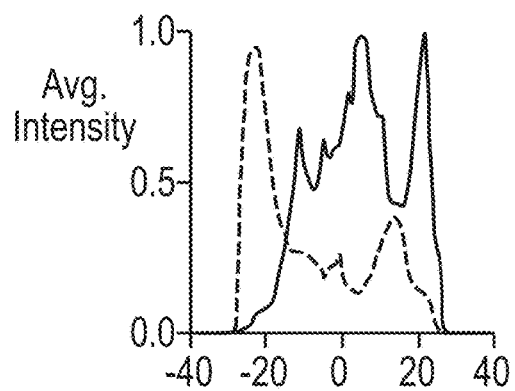
Figure 46I:
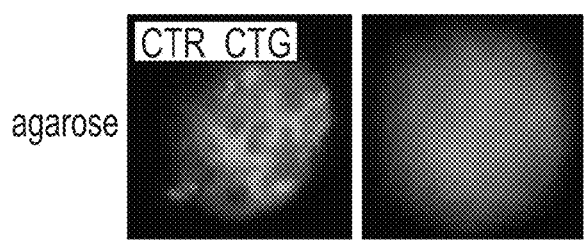
Figure 46J:
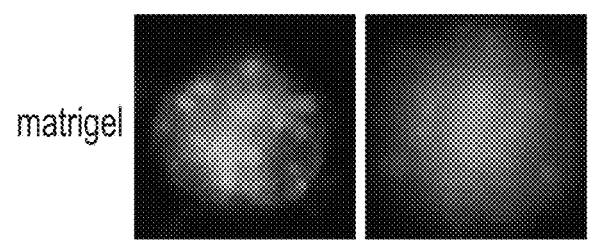
Figure 46K:
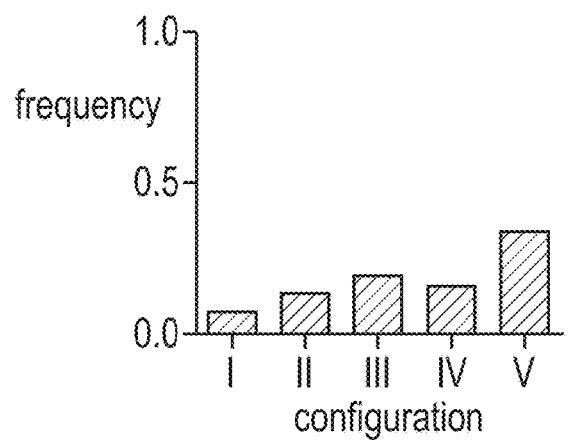
Figure 46L:
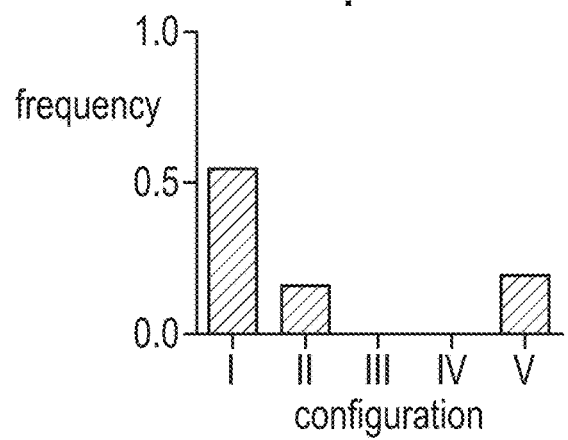
Figure 46M:
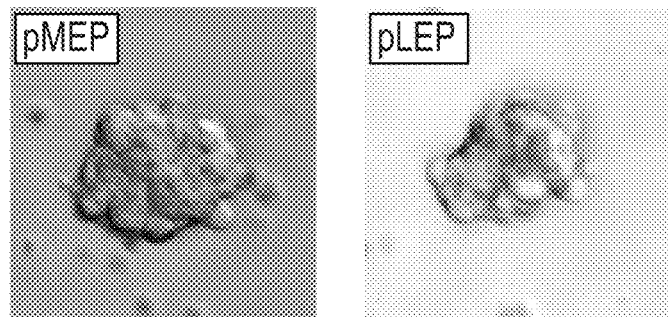
Figure 46N:
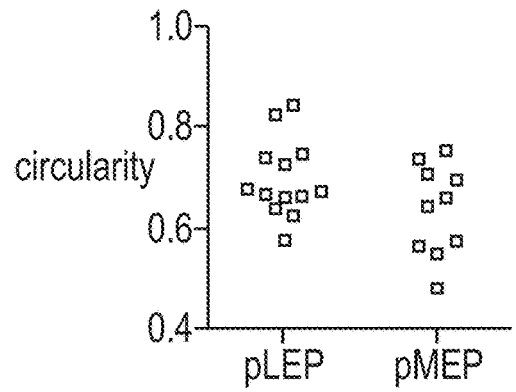
Figure 46O:
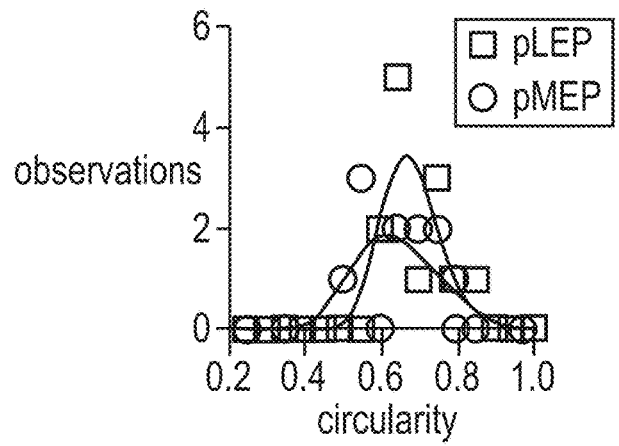

FIG. 44 provides images showing that fibroblast alignment induces directional invadopodia in nearby premalignant epithelial spheroids. (Top) Pattern of fibroblast and MCF10AT aggregates immediately after assembly and transfer to matrigel/collagen I gel. (Bottom) Same region of pattern after 24-hour culture. Arrowheads indicate putative invadopodia formation. Inset is representative of the fraction of tissues that invade along tracks made by invadopodia.

FIG. 45, Panels A-I schematically illustrate modeling the effect of cell-to-cell variability on the self-organization of the mammary gland. Panel A: Self-organization is a prerequisite for tissues to polarize and lumenize. Panel B: The preference for cells to expand cell-cell interfaces instead of cell-medium interfaces can be described by a parameter W. Panel C: Two populations of interacting cells with a low small variance in W relative to the difference in their mean W. Panel D: Predicted tissue architecture of for the distributions in Panel C. Panel E: Average radial distribution plot for 10 runs of the model. Panels F-H: Identical analysis shown in Panels C-D, but modeled using the distribution of W values shown in Panel F. Panel I: Plotting the fraction of correct cells against the ratio of variance to du demonstrates that cell-to-cell variability does not support robust and autonomous self-organization.

FIG. 46, Panels A-O schematically illustrate and provides data showing self-organization of primary human mammary and prostate epithelial cells. Panel A: Representative organizations of pHMEC after 24 hours in agarose wells. Panel B: Identical aggregates self-organize primarily into the correct architecture in Matrigel. Panel C: Primary prostate epithelial cells self-organized in Matrigel. Panel D: Roman numerals used to score the distributions of architectures from self-organization mammary and prostate epithelial cells. Panel E: Radial distribution profiles for pHMEC in agarose and Panel F matrigel. Panel G: Radial distribution plots for pHPEC in agarose and Panel H matrigel. Panel I: left: Representative images cell tracker green (CTG) stained LEP and cell tracker red (CTR) stained MEP in agarose; right: 30 superimposed images show the average radial distribution of red and green stain at after 24 hours in agarose wells. Panel J: same as Panel I, but in lrECM. Panel K: Quantitation of tissue configurations for pHMEC in agarose. Panel L: Quantitation of tissue configurations for pHMEC in matrigel. Panel M: Representative images of homogeneous primary MEP and LEP aggregates. Panel N: Quantitation of data in Panel M. Panel O: Alternative representation of data in Panel N showing the overlapping properties of primary LEP and MEP.

Figure 47A:
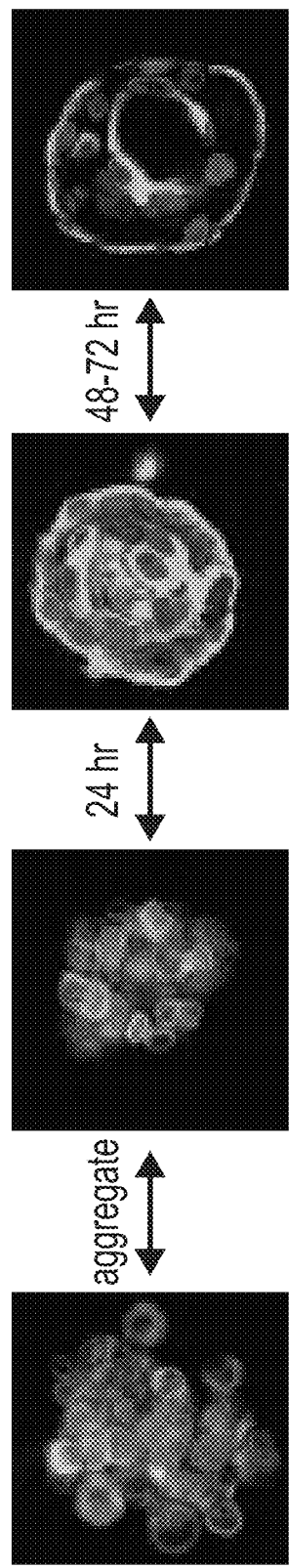
Figure 47C:
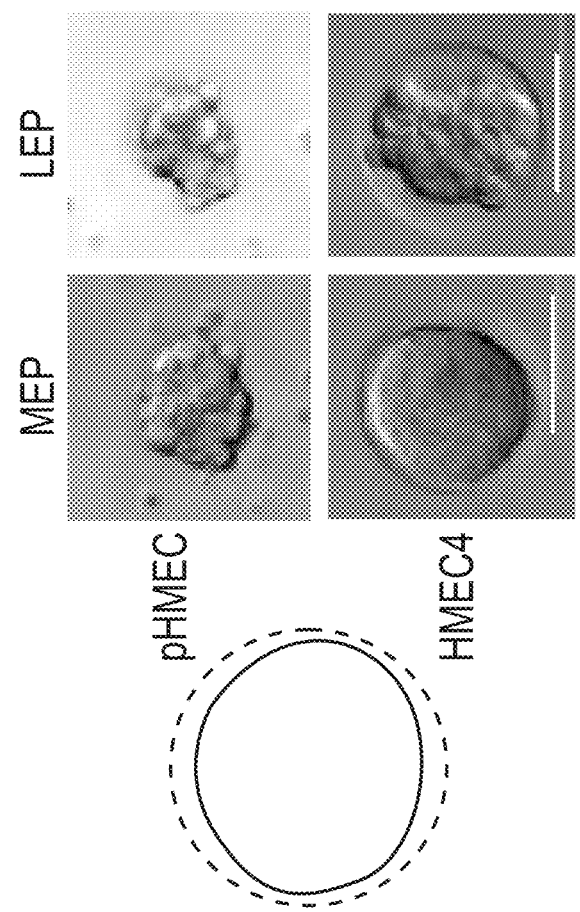
Figure 47B:
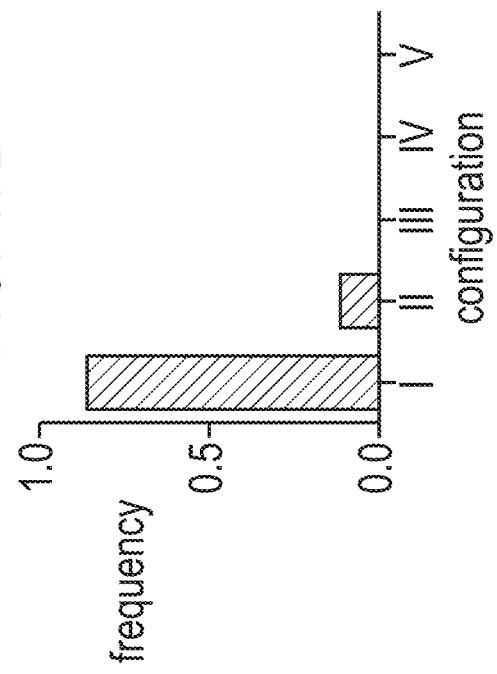
Figure 48F:
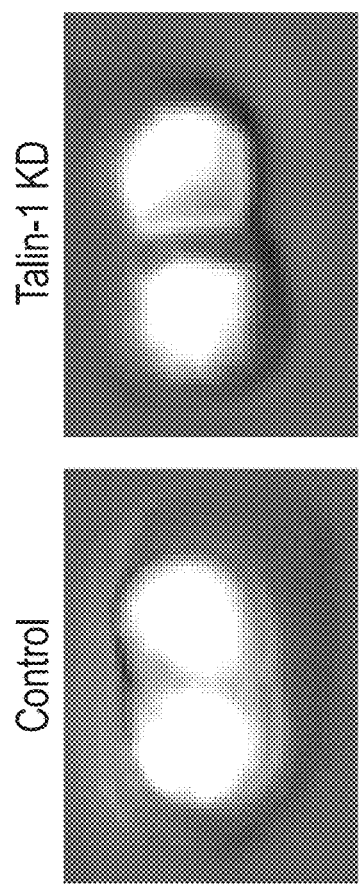
Figure 48G:
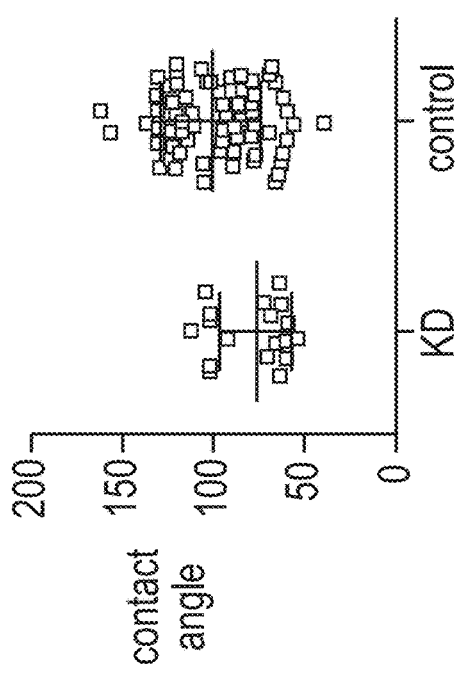
Figure 48H:
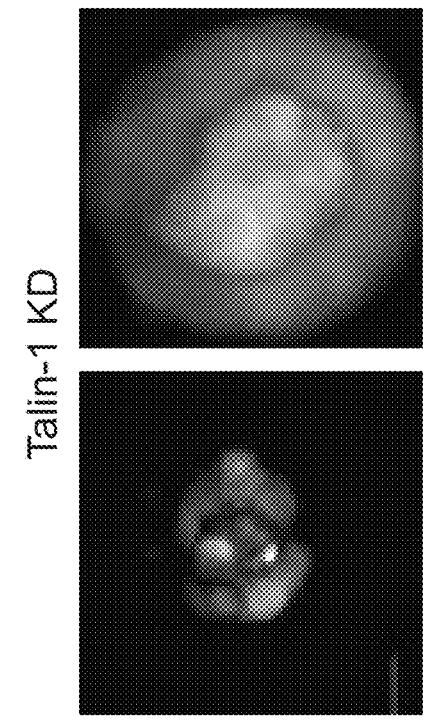
Figure 48I:
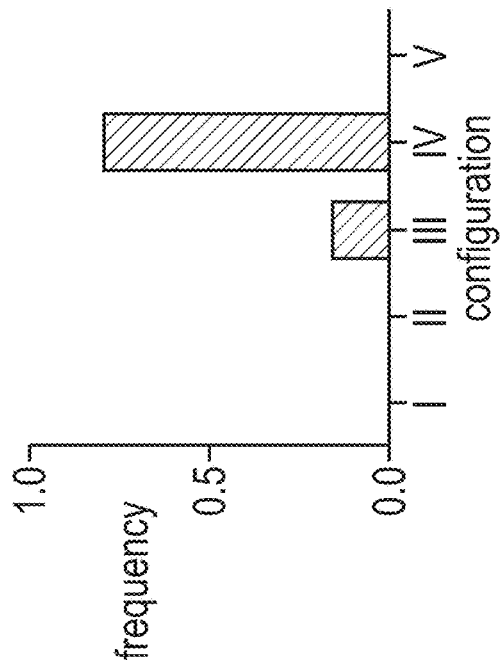
Figure 48J:
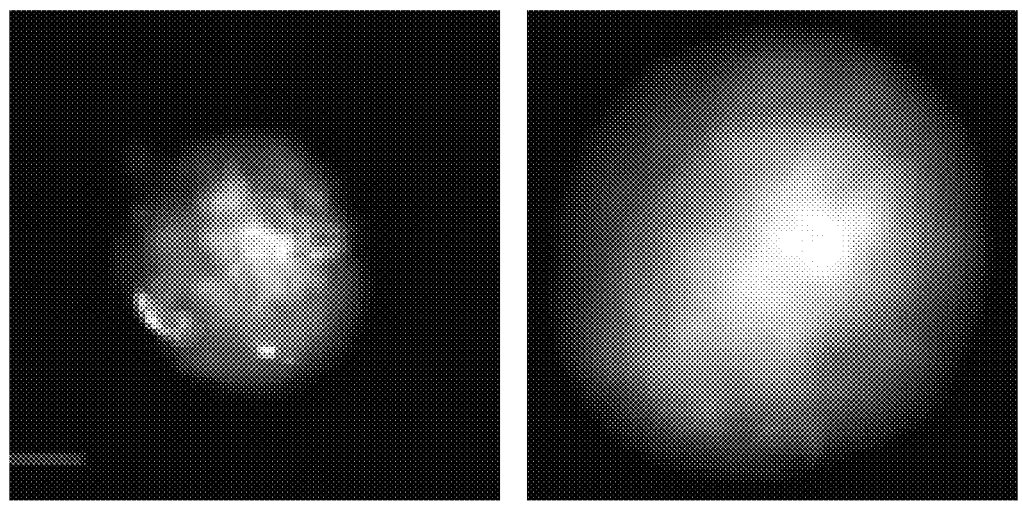
Figure 48K:
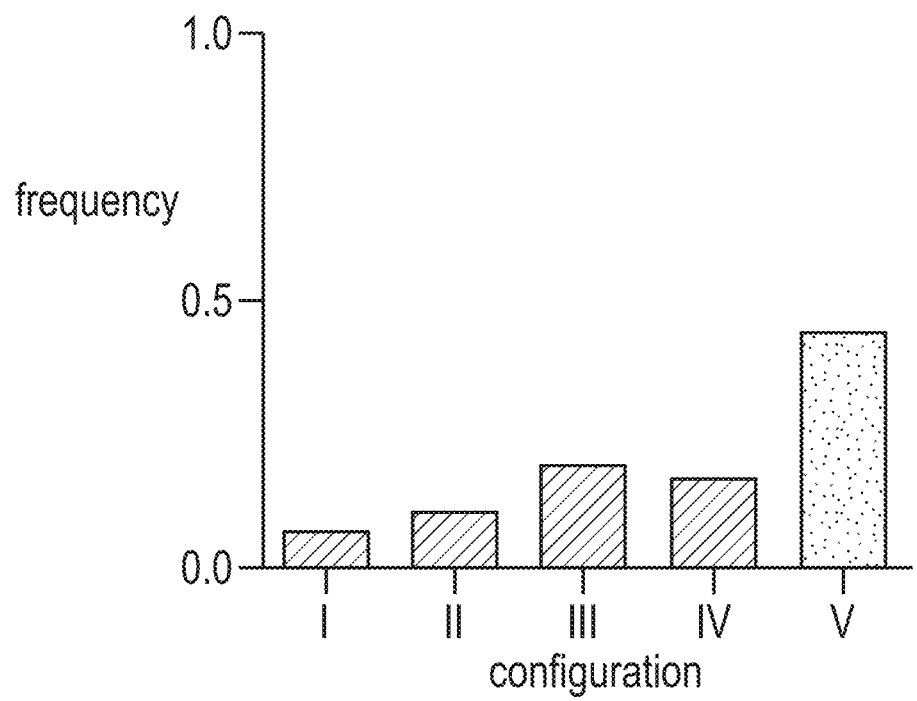
Figure 49A:
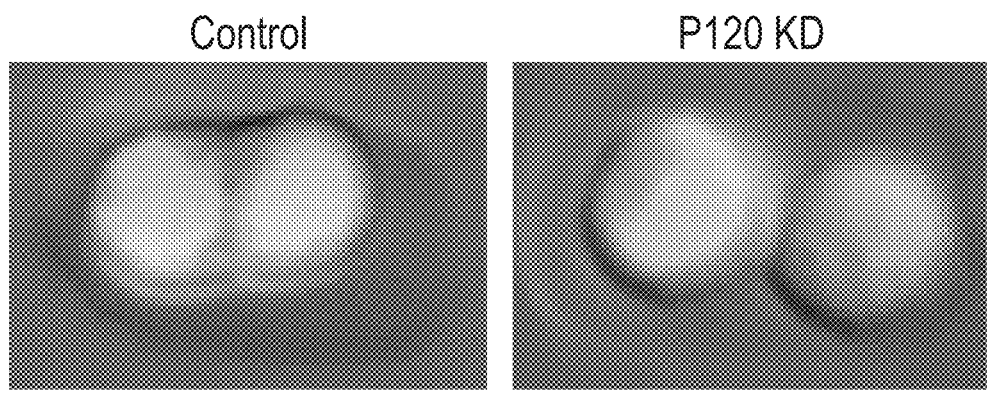
Figure 49B:
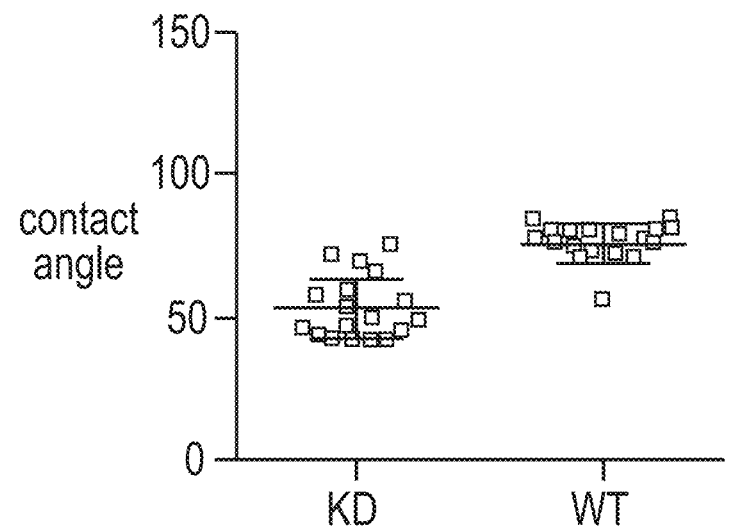
Figure 49C:
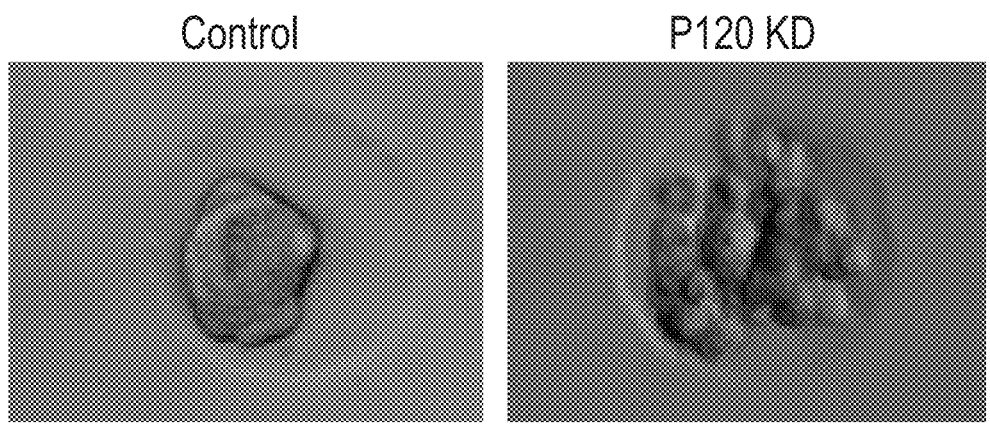
Figure 49D:
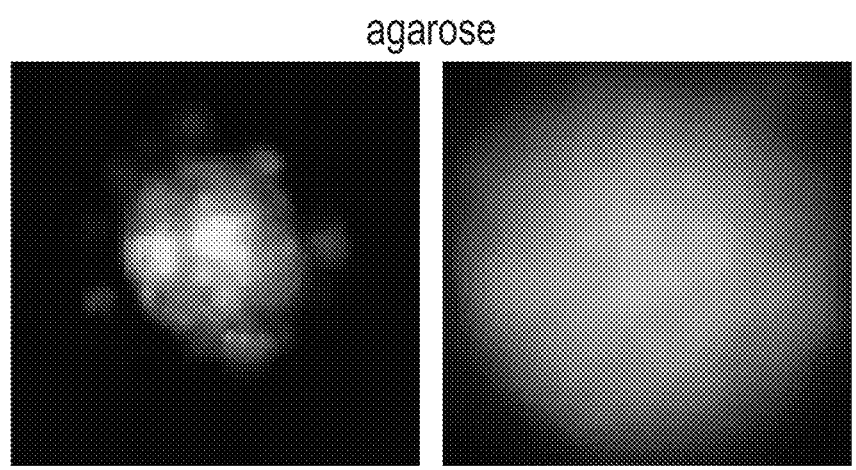
Figure 49E:
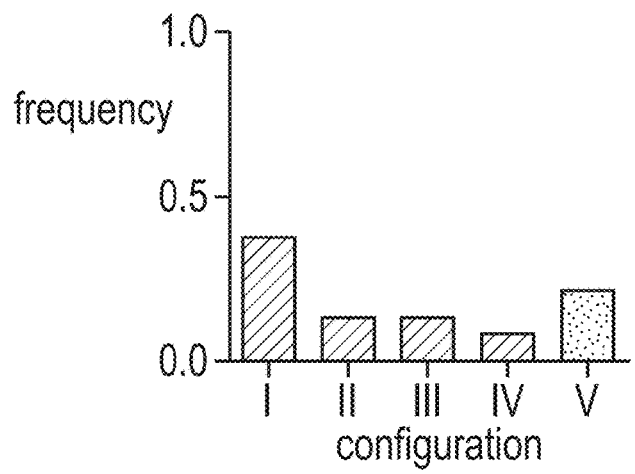
Figure 49F:
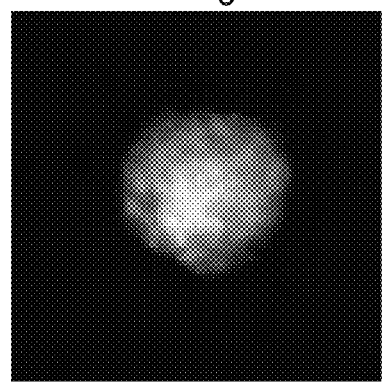
Figure 49G:
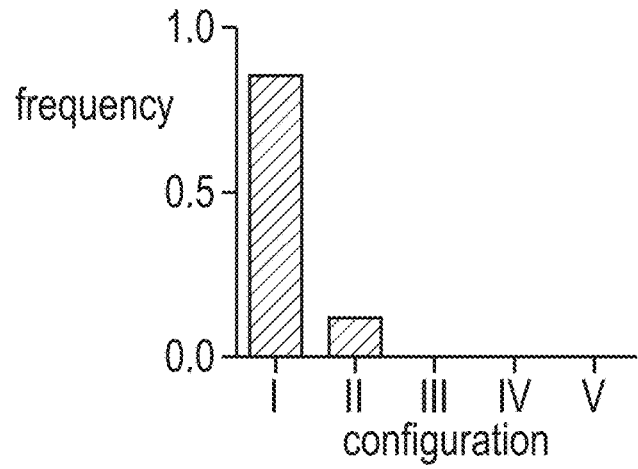

FIG. 47, Panels A-I show self-organization of fourth passage human mammary epithelial cells (HMEC4). Panel A: Compaction, self-organization, polarization and lumenization of HMEC4 in lrECM occurs over 72-96 hours. Panel B: Frequency of tissue configurations from self-organizing HMEC4 in lrECM. Panel C: Representative images of homogeneous aggregates of LEP and MEP purified from pHMEC and HMEC4 in agarose wells. Panel D: Circularity measurements for pHMEC. Panel E: Circularity measurements for HMEC4. Panel F: Images of homotypic and heterotypic cell doublets of HMEC4 used for contact angle measurements. Panel G: Quantitation of the images in Panel F. Panel H: Images of single MEP and LEP on matrigel-coated coverslips. Lines are quantum dots at the medium:matrigel interface. Panel I: Quantitation of images in Panel H.

FIG. 48, Panels A-K show catastrophic alterations to HMEC4 self-organization upon perturbations to MEP:ECM interactions. Panel A: Representative (left) and average intensity projections (right) of CTG-stained LEP and CTR-stained MEP self-organization in lrECM. Panel B: Final configuration of identical populations of LEP and MEP self-organizing in non-adhesive agarose microwells. Panel C: Frequency of configurations observed for HMEC4 in agarose microwells. Panel D: Western blot for Talin-1 in targeted and control siRNA treated cells. Panel E: X-Z projection of confocal images for control and Talin-1 KD MEPS spreading on matrigel coated glass surfaces. Panel F: Quantification of experiment shown in Panel E. Panel G: Representative images of control and Talin-1 KD MEP doublets in agarose microwells. Panel H: (left) Representative image of Talin-1 KD MEP self-organizing with WT LEP in agarose microwells; (right) average intensity projection of 30 experimental replicates. Panel I: quantitation of tissue configurations for the experiment described in Panel H. Panel J: (left) Representative image of Talin-1 KD MEP self organizing in lrECM; (right) average intensity projection of 30 experimental replicates. Panel K: Quantitation of tissue configurations for the experiment described in (J).

FIG. 49, Panels A-G depict data demonstrating that HMEC4 self-organization is robust to p120 KD in lrECM, but is altered in its absence. Panel A: Representative (left) control and (right) p120-KD MEP doublets. Panel B: Quantification of contact angle measurement from the experiment shown in Panel A. Panel C: Representative images of (left) control and (right) p120-KD MEP aggregates in agarose microwells. Panel D: (left) Representative image of p120 KD MEP self-organizing with WT LEP in agarose microwells; (right) average intensity projections of 30 experimental replicates. Panel E: Quantitation of tissue configurations from the experiment shown in Panel D. Panel F: Representative image of p120 KD MEP self-organizing with WT LEP in matrigel. Panel G: Quantification of the experiment shown in Panel F.

Figure 50D:
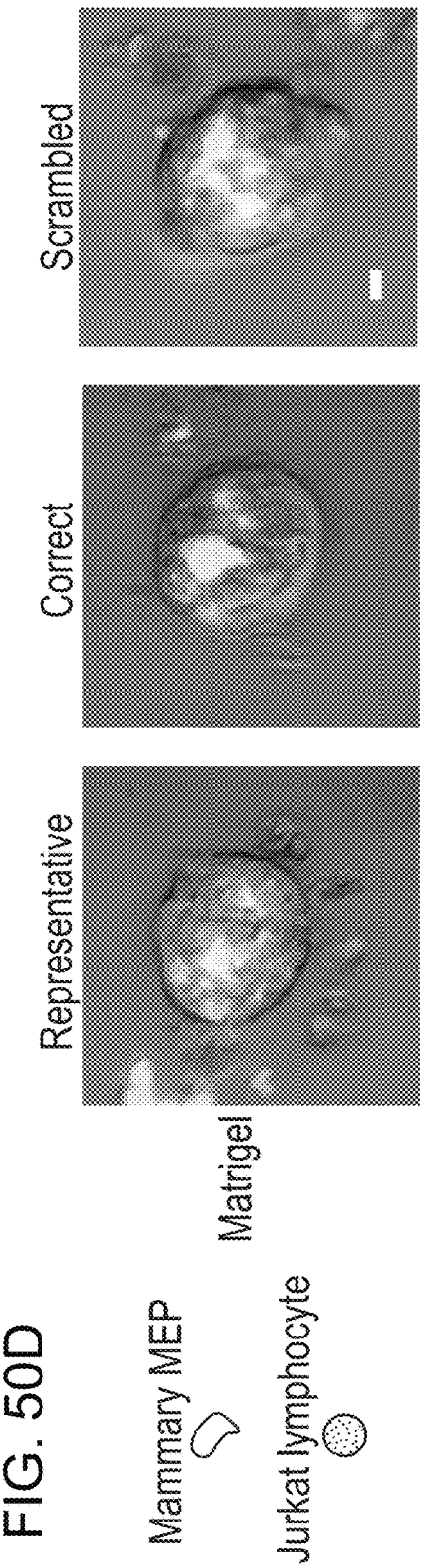
Figure 50E:
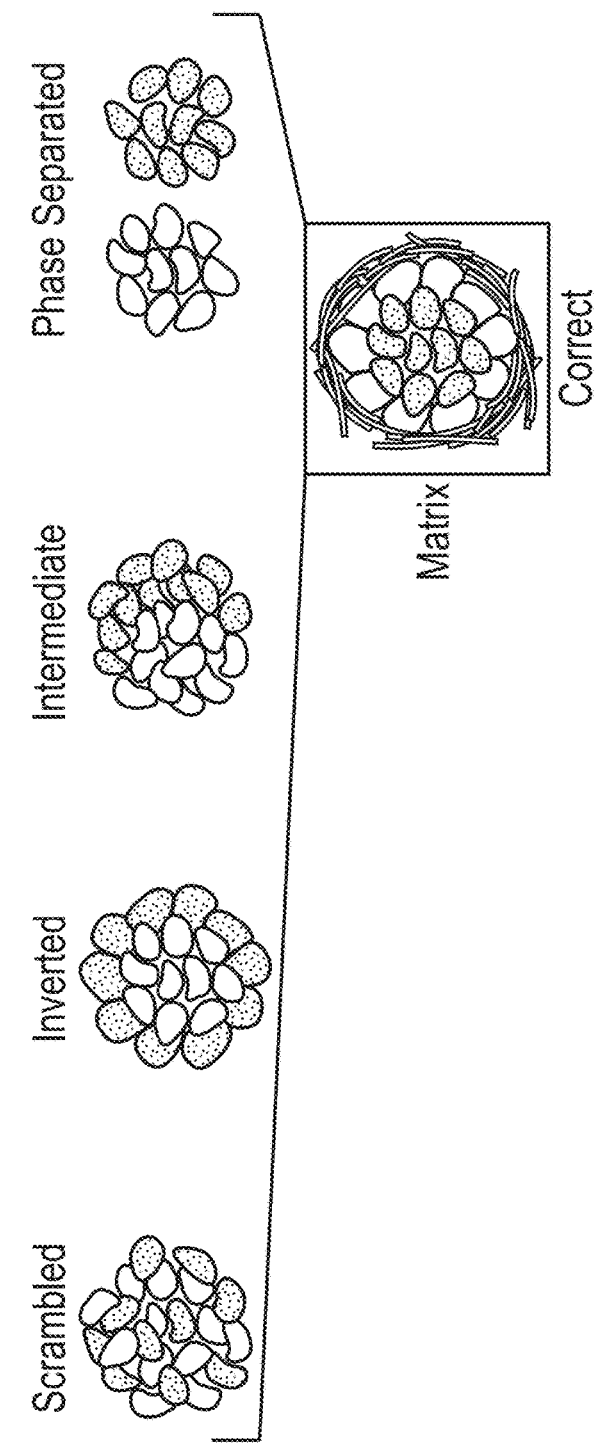

FIG. 50, Panels A-E depict probing the sufficiency of strong basal cell-ECM interactions for directing self-organization using non-interacting cell types. Panel A: MEPs were purified from HMEC4 and combined with luminal cells purified from human prostectomies for self-organization assays. Panel B: Representative images of self-organizing chimeric tissues at 24 hours in lrECM. Panel C: Representative images of self-organizing chimeric tissues at 24 hours in agarose microwells. Panel D: Representative images of assembled Jurkats and MEPs after 48 hours in culture. Panel E: Conceptual model illustrating the powerful impact that a dominant MEP-ECM interaction can have on glandular epithelial tissue architecture.

FIG. 51 provides images showing MEP self-organization and growth suppression of Myc and Cyclin-D1-CDK2 transformed LEP. (Panels A-F) By day 3, over 90% of aggregates containing an excess of GFP− and a few GFP+ cells had the GFP+ cells localized to the central region of the structure. (G) Aggregates with large numbers of GFP+ cells showed GFP− cells surrounding a core of GFP+ cells. (Panels H-J) At 14 days post seeding the aggregates showed very little additional growth of either the unstained cells or of the GFP+ oncogene-expressing cells. Scale bar for Panel A=50 μm. Scale bar for Panels B-J=10 μm.

Figure 52A:
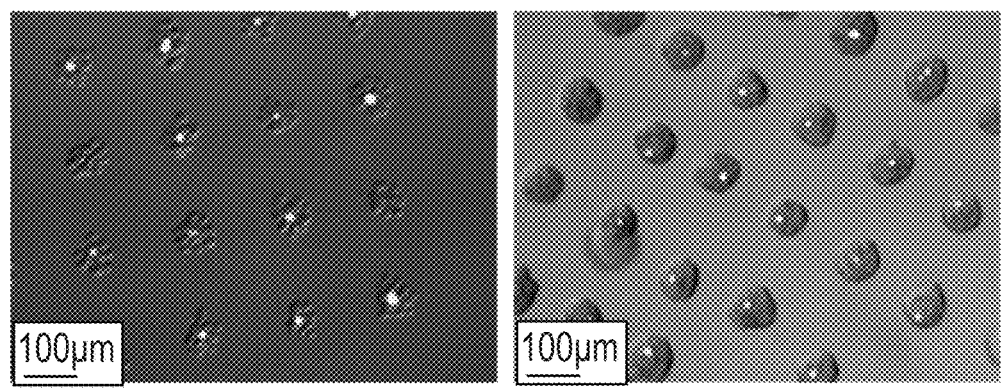
Figure 52B:
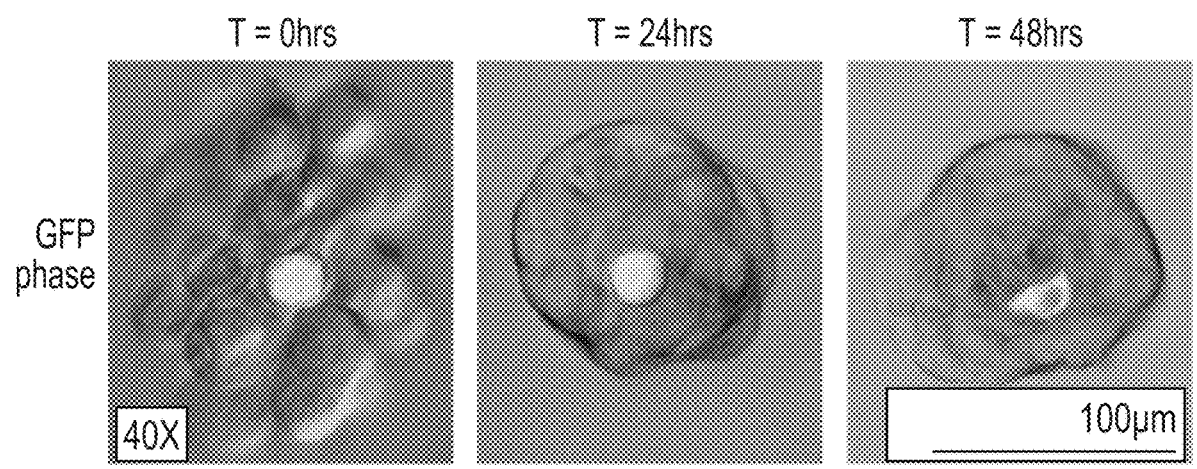
Figure 53A:
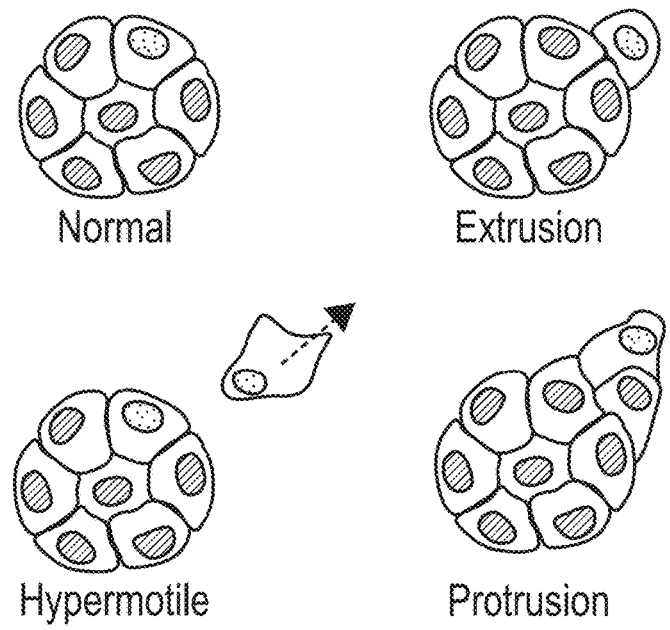
Figure 53B:
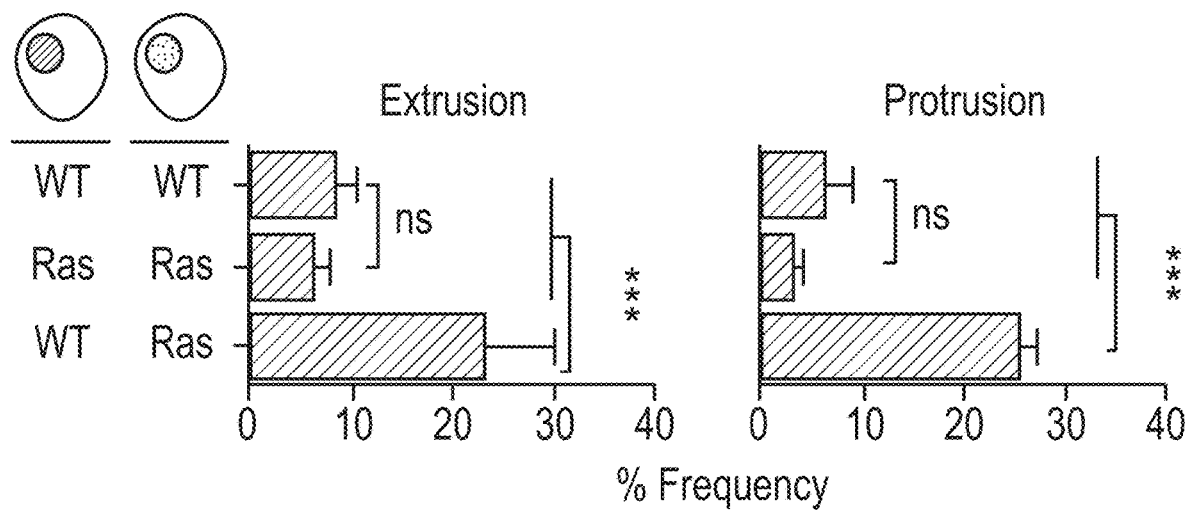
Figure 53C:
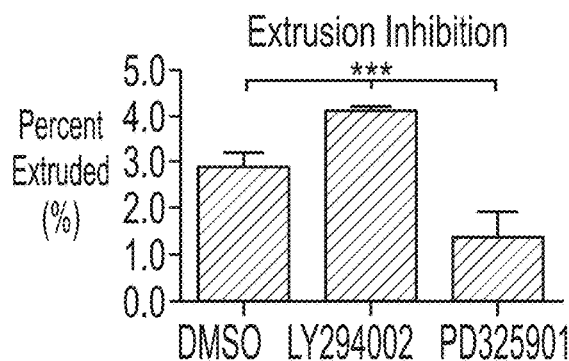
Figure 53D:
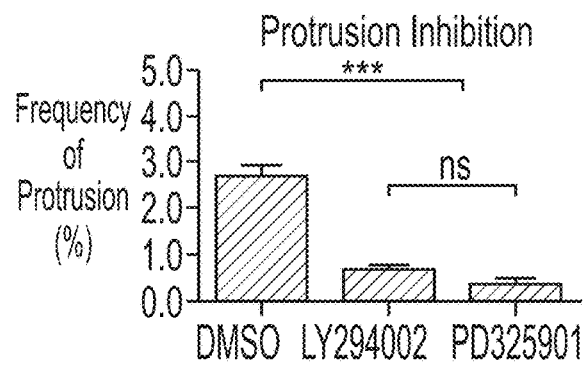
Figure 53E:
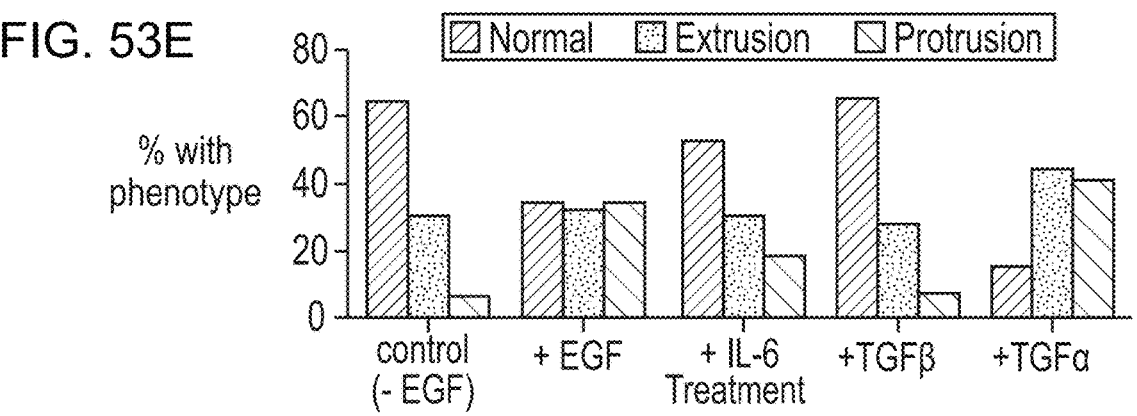
Figure 53F:
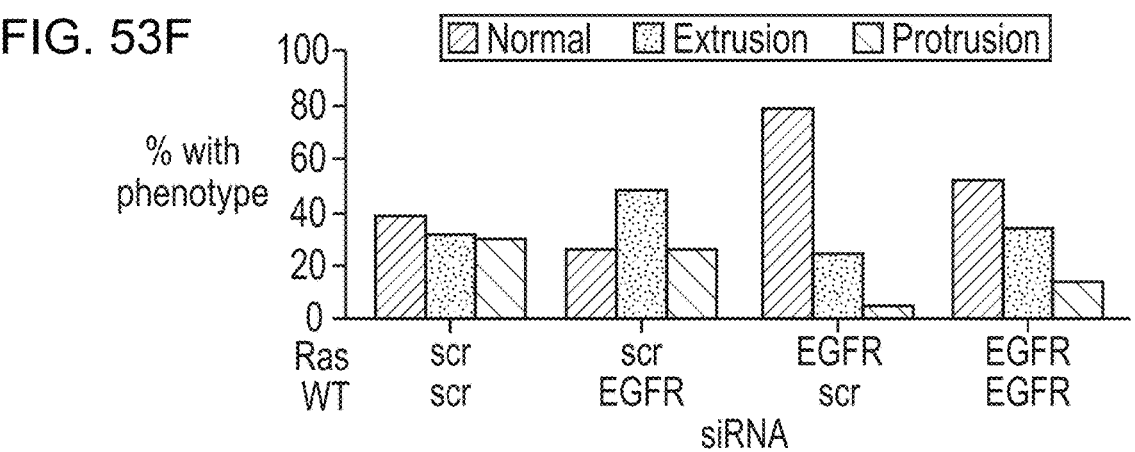

FIG. 52, Panels A-B show single fluorescently tagged LEP assembled with WT LAP and MEP by DNA-programmed assembly condense and sort into bilayered acini.

FIG. 53, Panels A-F depict an EGF-EGFR signaling axis that regulates multicellular protrusions in mammary epithelial heterogeneous for Ras expression. Panel A: Representation of observed phenotypes. Panel B: Frequency of extrusion and protrusions in mammary epithelial tissues of the indicated composition. Panel C: Effect of PI3K and MEK inhibition on the frequency of cell extrusion. Panel D: Effect PI3K and MEK inhibition on the frequency of multicellular protrusions. Panel E: Effect of cytokines and growth factors on the frequency of cell extrusions and protrusions. Panel F: Frequency of normal, extrusion and multicellular protrusion upon siRNA KD of EGFR in Ras, WT cells, or both.

DETAILED DESCRIPTION

The present disclosure provides methods of patterning cells on a surface of a substrate. The methods include disposing a pattern of nucleic acids on a surface of a substrate, and contacting the patterned nucleic acids under hybridization conditions with a first suspension of cells, where cells of the first suspension include cell surface-attached nucleic acids complementary to the patterned nucleic acids, and where the cell surface-attached nucleic acids hybridize to the patterned nucleic acids to pattern the cells on the surface of the substrate. Systems and kits for practicing the methods are also provided.

Before exemplary embodiments of the present invention are described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and exemplary methods and materials may now be described. Any and all publications mentioned herein are incorporated herein by reference to disclose and describe the methods and/or materials in connection with which the publications are cited. It is understood that the present disclosure supersedes any disclosure of an incorporated publication to the extent there is a contradiction.

It must be noted that as used herein and in the appended claims, the singular forms "a", "an", and "the" include plural referents unless the context clearly dictates otherwise. Thus, for example, reference to "a membrane anchored polynucleotide" includes a plurality of such membrane-anchored polynucleotides and reference to "the polynucleotide" includes reference to one or more polynucleotides, and so forth.

It is further noted that the claims may be drafted to exclude any element which may be optional. As such, this statement is intended to serve as antecedent basis for use of such exclusive terminology as "solely", "only" and the like in connection with the recitation of claim elements, or the use of a "negative" limitation.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed. To the extent such publications may set out definitions of a term that conflicts with the explicit or implicit definition of the present disclosure, the definition of the present disclosure controls.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

DEFINITIONS

The terms "surface-attached nucleic acid", "membrane-anchored polynucleotide," "lipid-DNA" and similar terms are to be broadly construed to include any oligonucleotide or polynucleotide that is attached by any means to a hydrophobic, lipophilic, or amphiphilic region that can be inserted into a membrane, regardless of whether the "membrane-anchored polynucleotide" or portion thereof is actually inserted into a membrane.

The term "membrane" or any similar term is used broadly and generically herein to refer to any lipid-containing membrane, cellular membrane, monolayer, bilayer, vesicle, liposome, lipid bilayer, etc., and the present invention is not meant to be limited to any particular membranes.

The particular use of terms "nucleic acid," "oligonucleotide," and "polynucleotide" should in no way be considered limiting and may be used interchangeably herein. "Oligonucleotide" is used when the relevant nucleic acid molecules typically comprise less than about 100 bases. "Polynucleotide" is used when the relevant nucleic acid molecules typically comprise more than about 100 bases. Both terms are used to denote DNA, RNA, modified or synthetic DNA or RNA (including but not limited to nucleic acids comprising synthetic and naturally-occurring base analogs, dideoxy or other sugars, thiols or other non-natural or natural polymer backbones), or other nucleobase containing polymers. Accordingly, the terms should not be construed to define or limit the length of the nucleic acids referred to and used herein.

Polynucleotides of the present disclosure may be single-stranded, double-stranded, triple-stranded, or include a combination of these conformations. Generally polynucleotides contain phosphodiester bonds, although in some cases, as outlined below, nucleic acid analogs are included that may have alternate backbones, comprising, for example, phosphoramide, phosphorothioate, phosphorodithioate, O-methylphophoroamidite linkages, and peptide nucleic acid backbones and linkages. Other analog nucleic acids include morpholinos, as well as those with positive backbones, non-ionic backbones, and non-ribose backbones. Nucleic acids containing one or more carbocyclic sugars are also included within the definition of nucleic acids. These modifications of the ribose-phosphate backbone may be done to facilitate the addition of additional moieties such as labels, or to increase the stability and half-life of such molecules in physiological environments.

The term "nucleic acid sequence" or "polynucleotide sequence" refers to a contiguous string of nucleotide bases and in particular contexts also refers to the particular placement of nucleotide bases in relation to each other as they appear in a polynucleotide.

The terms "complementary" or "complementarity" refer to polynucleotides (i.e., a sequence of nucleotides) related by base-pairing rules. For example, the sequence "5'-AGT-3'," is complementary to the sequence "5'-ACT-3". Complementarity may be "partial," in which only some of the nucleic acids' bases are matched according to the base pairing rules, or there may be "complete" or "total" complementarity between the nucleic acids. The degree of complementarity between nucleic acid strands affects the efficiency and strength of hybridization between nucleic acid strands under defined conditions.

As used herein, the terms "hybridize" and "hybridization" are used in reference to the pairing of complementary nucleic acids. Hybridization and the strength of hybridization (i.e., the strength of the association between the nucleic acids) is influenced by such factors as the degree of complementary between the nucleic acids, stringency of the conditions involved, and the $T_m$ of the formed hybrid. "Hybridization" methods involve the annealing of one nucleic acid to another, complementary nucleic acid, i.e., a nucleic acid having a complementary nucleotide sequence.

By "under hybridization conditions" is meant conditions permitting specific hybridization. The length of the complementary sequences, the secondary structure, and GC content affects the thermal melting point $T_m$ of the hybridization conditions necessary for obtaining specific hybridization of the target site to the target nucleic acid. Hybridization may be carried out under stringent conditions. The phrase "stringent hybridization conditions" refers to conditions under which a probe will hybridize to its target subsequence, typically in a complex mixture of nucleic acid, but to no other sequences at a detectable or significant level. Stringent conditions are sequence-dependent and will be different in different circumstances. Stringent conditions are those in which the salt concentration is less than about 1.0 M sodium ion, such as less than about 0.01 M, including from about 0.001 M to about 1.0 M sodium ion concentration (or other salts) at a pH between about 6 to about 8 and the temperature is in the range of about 20° C. to about 65° C. Stringent conditions may also be achieved with the addition of destabilizing agents, such as but not limited to formamide.

The terms "thermal melting point", "melting temperature" or "$T_m$" refer herein to the temperature (under defined ionic strength, pH, and nucleic acid concentration) at which 50% of probes complementary to a target hybridize to the target sequence at equilibrium (as the target sequences are present in excess, at $T_m$, 50% of the probes are occupied at equilibrium). In some cases, the term "$T_d$" is used to define the temperature at which at least half of a probe dissociates from a perfectly matched target nucleic acid.

The formation of a duplex molecule with all perfectly formed hydrogen-bonds between corresponding nucleotides is referred as "matched" or "perfectly matched", and duplexes with single or several pairs of nucleotides that do not correspond are referred to as "mismatched." Any combination of single-stranded RNA or DNA molecules can form duplex molecules (DNA:DNA, DNA:RNA, RNA:DNA, or RNA:RNA) under appropriate experimental conditions.

The phrase "selectively hybridizes" or "specifically hybridizes" refers to the binding, duplexing, or hybridizing of a molecule only to a particular nucleotide sequence under stringent hybridization conditions when that sequence is present in a complex mixture (e.g. total cellular or library DNA or RNA).

Those of ordinary skill in the art will readily recognize that alternative hybridization and wash conditions can be utilized to provide conditions of similar stringency and will recognize that the combination of parameters is much more important than the measure of any single parameter.

The term "fluorophore" refers to any molecular entity that is capable of absorbing energy of a first wavelength and re-emit energy at a different second wavelength. Exemplary fluorophores include, but are not limited to CAL Fluor Red 610 (FR610; Biosearch Technologies, Novato, Calif.), fluorescein isothiocyanate, fluorescein, rhodamine and rhodamine derivatives, coumarin and coumarin derivatives, cyanine and cyanine derivatives, Alexa Fluors (Molecular Probes, Eugene, Oreg.), DyLight Fluors (Thermo Fisher Scientific, Waltham, Mass.), and the like.

The term "bilayer" refers to a "sandwich-like" structure composed of amphiphilic lipid molecules (often phospholipids) that are arranged as two molecular layers with the hydrophobic tails on the inside and the polar head groups on the outside surfaces.

The term "monolayer" refers to a structure defined by a molecular layer of amphipathic molecules with the head groups enriched and substantially aligned on one side and hydrophobic groups enriched and substantially on the opposite side.

The term "physiological conditions" is meant to encompass those conditions compatible with living cells, e.g., predominantly aqueous conditions of a temperature, pH, salinity, etc. that are compatible with living cells.

The terms "therapeutic composition", "pharmaceutical composition", "cosmetic compositions", "therapeutic preparation", "pharmaceutical preparation" or "cosmetic preparation" are meant to encompass a composition suitable for application or administration to a subject, such as a mammal, especially a human. In general such composition is safe, usually sterile, and preferably free of contaminants that are capable of eliciting an undesirable response of the subject (e.g., the compound(s) in the composition is of an acceptable grade for a given end use). Compositions can be designed for application or administration to subjects or patients in need thereof via a number of different routes of administration including topical, oral, buccal, rectal, parenteral, subcutaneous, intravenous, intraperitoneal, intradermal, intratracheal, intrathecal, pulmonary, and the like. In some embodiments the composition is suitable for application or administration by a transdermal route. In other embodiments, the compositions are suitable for application or administration by a route other than transdermal administration.

As used herein, the terms "determining," "measuring," and "assessing," and "assaying" are used interchangeably and include both quantitative and qualitative determinations.

The term "substantially similar" as used in the context of nucleic acid or amino acid sequence identity refers to two or more sequences which have at least about 50%, at least about 60%, at least about 70%, at least about 75%, at least about 80%, at least about 85%, at least about 90%, at least about 95%, at least about 98%, at least about 99%, or 100% sequence identity.

As used herein "% sequence identity" is determined using the EMBOSS Pairwise Alignment Algorithms tool available from The European Bioinformatics Institute (EMBL-EBI), which is part of the European Molecular Biology Laboratory (EMBL). This tool is accessible at the website located by placing "www." in front of "ebi.ac.uk/Tools/emboss/align/". This tool utilizes the Needleman-Wunsch global alignment algorithm (Needleman, S. B. and Wunsch, C. D. (1970) J. Mol. Biol. 48, 443-453; Kruskal, J. B. (1983) An overview of sequence comparison In D. Sankoff and J. B. Kruskal, (ed.), Time warps, string edits and macromolecules: theory and practice of sequence comparison, pp. 1-44 Addison Wesley. Default settings are utilized which include Gap Open: 10.0 and Gap Extend 0.5. The default matrix "Blosum62" is utilized for amino acid sequences and the default matrix "DNAfull" is utilized for nucleic acid sequences.

Throughout the present disclosure, the nomenclature used to describe the "surface-attached nucleic acids" or "membrane-anchored polynucleotides" is as follows. First, conventional names are used for certain membrane-anchored portions of the compounds, such as dialkylphosphoglycieride, and monoalkylamide. Second, for the convenience of description, the following acronyms may be utilized: FACS, Fluorescence Activated Cell Sorting; DNA, Deoxyribonucleic Acids; DIFO, Difluorocyclooctyne; NHS, N-hydroxysuccinimide; PEG, polyethylene glycol; MFI; median fold fluorescence increase; dT, deoxythymidine; MEF, mouse embryonic fibroblast; PBS, phosphate buffered saline; TEAA, triethylammonium acetate; HPLC, high pressure liquid chromatography; P/I, phorbol-12-myristate-13-acetate (PMA) and ionomycin; FITC, fluoroscein isothiocyanate.

Methods

The present disclosure provides methods of patterning cells on a surface of a substrate. The methods include disposing a pattern of nucleic acids on a surface of a substrate, and contacting the patterned nucleic acids under hybridization conditions with a first suspension of cells, where cells of the first suspension include cell surface-attached nucleic acids complementary to the patterned nucleic acids, and where the cell surface-attached nucleic acids hybridize to the patterned nucleic acids to pattern the cells on the surface of the substrate. Systems and kits for practicing the methods are also provided. Various steps and aspects of the methods will now be described in greater detail below.

Figure 14:
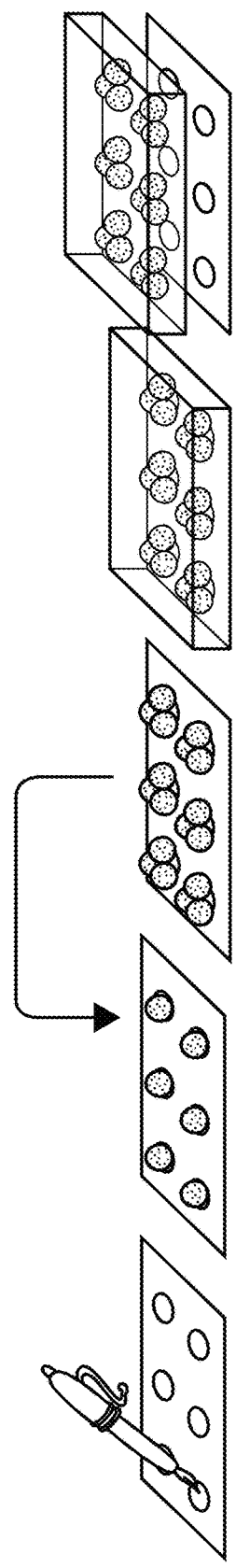
FIG. 14 is an illustration of a solid-phase assembly scheme. DNA is patterned on aldehyde-silanized surface using molecular writing. Seed cells (blue) are attached to pattern via DNA hybridization. Partner cells (green) are assembled onto seed cells, creating microtissues. Microtissues are embedded in a matrix and released from the surface using DNase, allowing transfer of embedded cells to a 3D tissue culture context.

Methods of the present disclosure include disposing a pattern of nucleic acids on a surface of a substrate. In certain aspects, the nucleic acids are disposed on the surface by transferring a liquid containing the nucleic acids in a pattern on the surface. One example approach is direct molecular writing, a 2D rapid prototyping tool that allows the transfer of a liquid "molecular ink" to a surface in any desired pattern. In certain aspects, disposing a pattern of nucleic acids on a surface of a substrate includes patterning amine-terminated oligonucleotides (e.g., by direct molecular writing) on aldehyde-coated glass surfaces via a reductive amination reaction. According to certain embodiments, the pattern of nucleic acids is disposed by molecular writing, where the liquid (or "ink") containing the nucleic acids includes the nucleic acids at a concentration of from 0.5 mM to 10 mM, such as from 1 mM to 5 mM. In certain aspects, the liquid for molecular writing includes the nucleic acids at a concentration of from 1 to 2 mM (e.g., 1.5 mM), 2 mM to 3 mM, or 3 mM to 4 mM. FIG. 14 is an illustration of a solid-phase assembly scheme, where DNA is patterned on aldehyde-silanized surface using molecular writing.

Figure 20:
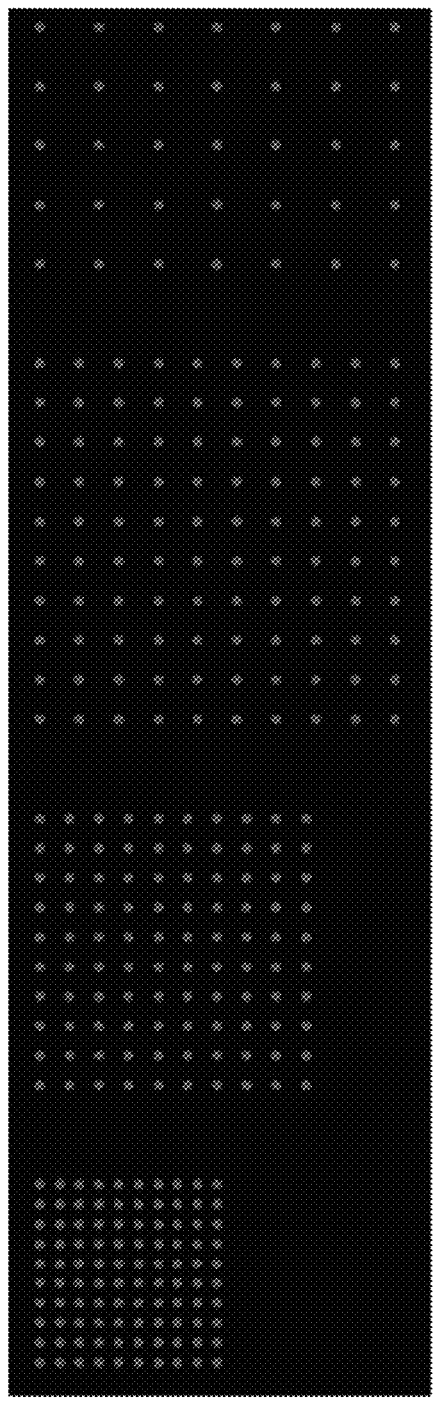
FIG. 20 is a schematic of homotypic single cell grids of multiple spacing. The largest grid has been truncated for the purpose of the figure.

The pattern of nucleic acids may be random, or the pattern may be pre-selected by a user. Pre-selecting the pattern may include creating an image (e.g., a bitmapped image) on a computer. Such a computer may be operably connected to a molecular writing device (e.g., a printer) and instruct the molecular writing device to dispose the pre-selected pattern on the surface of the substrate. The pattern may be any pattern desired by a practitioner of the subject methods. The pattern may be a one dimensional pattern (e.g., a single spot). Also of interest are two-dimensional patterns including, but not limited to, an array of two or more spots (an example of which is shown in FIG. 20), one or more lines (e.g., straight lines, curved lines, or combinations thereof), any shape of interest (circles, squares, triangles, etc., which shapes may be "solid" (e.g., filled in) or an outline of the shape), or any other two-dimensional pattern of interest (e.g., see FIGS. 13, 16, 17, etc.). According to certain embodiments, the pattern resembles the shape of a tissue or substructure thereof (e.g., the vasculature of a tissue) such that upon culturing cells attached to the pattern into 3D structures, the 3D cellular structures may form functional tissues or substructures thereof (which substructures may be combined and cultured into functional tissues if desired). An example of such patterns is shown, e.g., in FIG. 18.

In certain aspects, the pattern of nucleic acids includes a single population of nucleic acids having the same nucleotide sequence. In other aspects, the pattern may include two or more population of nucleic acids, where each population of nucleic acids includes a unique nucleotide sequence. That is, the nucleic acids of each population are capable of differentially hybridizing to populations of cells having different cell surface-attached nucleic acids (e.g., to target particular cell types to desired locations and/or in desired patterns on the substrate's surface). Populations of nucleic acids having unique nucleotide sequences may be co-localized on the surface (e.g., present in a single spot, each spot of an array of spots, etc.), or may be separately disposed at uniquely addressable locations on the surface of the substrate (e.g., an array of two or more spots, where each spot includes a single population of nucleic acids having the same nucleotide sequence).

The nucleic acids patterned on the surface of the substrate may be any type or combination of types of nucleic acids that find use in practicing the methods of the present disclosure. For example, the nucleic acids may be selected from DNA, RNA, PNA (peptide nucleic acids), LNA (locked nucleic acid), or any combination thereof. The nucleic acids may include one or more nucleotide analogs, modified, and/or labeled nucleotides useful, e.g., to facilitate detection of the patterned nucleic acids (e.g., via one or more fluorescently-labeled nucleotides), for enhanced hybridization to complementary cell surface-attached nucleic acids, to facilitate detachment of the patterned cells from the nucleic acids patterned on the surface (e.g., to facilitate transfer of the patterned cells to a different container, such as a tissue culture plate), and the like. In certain aspects, the nucleic acids patterned on the surface include one or more phosphorothioates nucleotides. For example, the nucleic acids may be oligonucleotides with phosphorothioate backbones, which exhibit enhanced stability (e.g., resistance to nuclease degradation) and other desirable properties in the context of the present disclosure.

In certain aspects, the nucleic acids patterned on the surface and/or the cell surface-attached nucleic acids complementary to the patterned nucleic acids are oligonucleotides. As used herein, an "oligonucleotide" is a single-stranded multimer of nucleotides from 2 to 500 nucleotides, e.g., 2 to 200 nucleotides. Oligonucleotides may be synthetic or may be made enzymatically, and, in some embodiments, are 10 to 50 nucleotides in length. According to certain embodiments, the oligonucleotides contain deoxyribonucleotide monomers (i.e., may be oligodeoxyribonucleotides or "DNA oligonucleotides"), ribonucleotide monomers (i.e., may be oligoribonucleotides or "RNA oligonucleotides"). Oligonucleotides may be 10 to 20, 21 to 30, 31 to 40, 41 to 50, 51 to 60, 61 to 70, 71 to 80, 80 to 100, 100 to 150 or 150 to 200, up to 500 or more nucleotides in length, for example.

The methods further include contacting the patterned nucleic acids under hybridization conditions with a first suspension of cells, where cells of the first suspension include cell surface-attached nucleic acids complementary to the patterned nucleic acids (or at least one population of nucleic acids therein, when the pattern includes two or more populations), and wherein the cell surface-attached nucleic acids hybridize to the patterned nucleic acids.

The contacting may be carried out using any cells of interest. In certain aspects, the methods are employed to generate cells useful for generating tissue substructures and/or "complete" tissues, where the cell type(s) is/are chosen as appropriate to produce the desired sub-structure and/or tissue. Cell types of interest include, but are not limited to, epithelial cells, endothelial cells, fibroblasts, lymphocytes, stem cells, and any combination thereof. Cell types according to certain aspects of the present disclosure are described elsewhere herein (e.g., in the Examples section). Alternatively, or additionally, the methods of the present disclosure may include introducing non-cellular material into the 2D or 3D cellular structure. Non-cellular materials of interest include, but are not limited to, nanoparticles, liposomes, hydrogels, shaped hydrogels, beads (e.g., gel beads), viruses, or any other non-cellular material of interest. In certain aspects, particles having an agent (e.g., a drug, cell signaling molecule, and/or the like) disposed on the surface thereof or embedded within the particles may be introduced into the 2D or 3D cellular structure, and the effect of the agent on a cell parameter (e.g., proliferation, differentiation, toxicity, bioavailability, metabolism, etc.) may be determined. Such agents may also be useful in generating the 2D or 3D cellular structures, e.g., by enhancing the proliferation, differentiation, or other cellular processes/characteristics which determine the final makeup of the structure.

According to certain embodiments, the surface of the substrate is passivated after disposing the pattern of nucleic acids on the surface, and prior to contacting the nucleic acids with the first suspension of cells. In embodiments where the surface was functionalized with aldehyde groups, e.g., for covalent binding of amine-terminated oligonucleotides via reductive amination, the aldehyde groups may be eliminated using a reducing agent, thereby rendering the surface less susceptible to non-specifically binding cells of the first suspension of cells (or any second or subsequent suspensions of cells). According to certain embodiments, after disposing the pattern of nucleic acids, the non-patterned portions of the surface are passivated with polytetrafluoroethylene or derivatives thereof to reduce or eliminate non-specific binding of cells to the surface. In certain aspects, after the contacting step (and any subsequent washing step(s)), the percentage of cells non-specifically attached to the surface is less than 20%, less than 15%, less than 10%, less than 5%, less than 2.5%, less than 1%, less than 0.5%, less than 0.25%, less than 0.1%, less than 0.05%, less than 0.01%, less than 0.05%, or less than 0.01%.

In certain aspects, the first suspension includes a single population of cells, where the single population is defined by being of a single cell type and/or having cell surface-attached nucleic acids of the same nucleotide sequence on their cell surface. In other aspects, the first suspension includes two or more populations of cells, where the two or more populations of cells are defined by being of unique/different cell types and/or having cell surface-attached nucleic acids of differing nucleotide sequence on their cell surface. According to certain embodiments, the pattern of nucleic acids includes two or more populations of nucleic acids having different nucleotide sequences, and the first suspension includes two or more populations of cells, where each population of cells includes surface-attached nucleic acids complementary to different populations of nucleic acids in the pattern. Such an embodiment finds use, e.g., where it is desirable to target different cell types to distinct locations on the surface of the substrate.

According to certain embodiments, the nucleic acids are patterned on the surface (e.g., by molecular writing) such that after the contacting step, the cells are attached to the surface at single cell resolution. By "single cell resolution" is meant that the cells specifically patterned on the surface (e.g., by specific binding to their orthogonal patterned nucleic acids) are physically separate from each other. That is, single cells may be patterned on the surface at non-overlapping locations on the surface, where a blank space on the surface exists between the single cells. Single cell resolution may be achieved, e.g., by high resolution disposal of the nucleic acids on the surface at suitable density on the surface, by selection of a suitable concentration of cells in the first suspension of cells, or the like.

The cell surface-attached nucleic acids may be attached to the surface of the cells by any convenient means. According to certain embodiments, the cell surface-attached nucleic acids are covalently linked to cell surface glycans via metabolic engineering and copper free click chemistry, where proteins may be modified by amine acylation. In certain aspects, the cell surface-attached nucleic acids include a lipid moiety attached (directly or indirectly) to a nucleic acid, which surface-attached nucleic acids are attached to the cells by insertion of the lipid moiety into the plasma membrane of the cells. When the cell surface-attached nucleic acids include a lipid moiety attached to a nucleic acid, a spacer may be present between the lipid moiety and the nucleic acid.

According to certain embodiments, the cell surface-attached nucleic acids are membrane-anchored polynucleotides. Examples of membrane-anchored polynucleotides are described in, e.g., Selden N S, et al. (2012) *J. Am. Chem. Soc.* 134, 765-768; and U.S. Patent Application Nos. 61/554,912 and PCT/US12/63092; the disclosures of each of which are incorporated herein by reference. The membrane-anchored polynucleotides generally include a membrane anchored region, and a polynucleotide. The polynucleotide has a membrane proximal end, and a membrane distal end. The polynucleotide may include a linker region and a membrane distal adhesion region. A linker region of a polynucleotide may include a contiguous stretch of at least about 20 nucleotides. A membrane distal adhesion region may include at least 10 nucleotides and be positioned distal to the linker region, wherein the linker region is not hybridizable to the membrane distal adhesion region.

The polynucleotide portion of a membrane-anchored polynucleotide may include DNA, e.g., single stranded DNA. In some embodiments, the polynucleotide may include RNA, PNA, LNA, or the like. In some embodiments, the polynucleotide may be single-stranded. Regardless of whether the 5' or 3' end of the polynucleotide is affixed closer to the membrane anchoring region, the end of the polynucleotide that is closer to the membrane anchoring region is considered to be the "membrane proximal end," whereas the other end of the polynucleotide is considered to be the "membrane distal end," unless the context clearly dictates otherwise. Moreover, if some A is "proximal" to some B, it is to be understood that A is closer to the membrane proximal end than is B. Similarly, if some A is "distal" to some B, it is to be understood that A is closer to the membrane distal end than is B.

The polynucleotide may include a linker region and a membrane distal adhesion region, where the linker region is closer to the membrane proximal end of the polynucleotide than is the membrane distal adhesion region. A polynucleotide may include a membrane proximal adhesion region, described in greater detail herein. The polynucleotide may be naturally occurring, or isolated from a naturally occurring source. In other embodiments, the polynucleotide may be synthesized or synthetic. In certain embodiments, the polynucleotide may be chimeric or heterologous. The polynucleotide may be attached to a membrane anchoring region at either its 5' end or 3' end, or attached at a position that is at neither end. In some embodiments, the polynucleotide is attached directly to the membrane anchoring region, such as by conjugation. When not directly attached to the membrane anchoring region, the polynucleotide may be separated from the membrane anchoring region by one or more atoms, most typically between one and 10 atoms, more typically between 1 and 8 atoms, more typically between 1 and 5 atoms. The polynucleotide may include adenine, guanine, cytosine, thymine, or uracil. Alternatively, or additionally, the polynucleotide may include other bases, including non-natural bases.

The polynucleotide may include a linker region, where the linker region includes a contiguous stretch of about 20 to about 3000 nucleotides. In certain embodiments, the linker region is separated from the membrane distal end of the polynucleotide by about 10 nucleotides or more. For example, the linker region may be separated from the membrane distal end of the polynucleotide by about 10 to 2000 nucleotides or more. In certain aspects, the polynucleotide includes a contiguous stretch of about 10 to 2000 nucleotides including only three types of bases. In some embodiments, the three bases are selected from A, C, T, and G. In certain embodiments, the three bases are A, C, and T.

According to certain embodiments, the polynucleotide region distal to the linker region and before the membrane distal end comprises a membrane distal adhesion region. The membrane distal adhesion region may hybridize to a polynucleotide, fluorophore, or pharmaceutical composition. The membrane distal adhesion region may hybridize to a polynucleotide present in another membrane anchored polynucleotide. Such hybridization may be between the membrane distal adhesion regions of the two membrane anchored polynucleotides. Such hybridization may be strict hybridization. In certain aspects, the sequence of the membrane distal adhesion region does not hybridize with any other region of the polynucleotide. The membrane distal adhesion region may include about 5 to about 3000 nucleotides. The membrane distal adhesion may include $(CAGT)_n$ and/or $(ACTG)_n$, where n is an integer equal to or greater than 1. In some embodiments, n is 1. In other embodiments, n is between 1 and 20. In certain embodiments, n is between 1 and 10, or more preferably between 1 and 5.

The region proximal to the linker region may include a membrane proximal adhesion region. In certain embodiments, the sequence of the membrane proximal adhesion region does not hybridize with any other region of the polynucleotide. In certain embodiments, the sequence of the membrane proximal adhesion region does not hybridize with any other region of the polynucleotide. In some embodiments, the membrane proximal adhesion region comprises $(CAGT)_n$ and/or $(ACTG)_n$, where n is an integer equal to or greater than 1. In other embodiments, the membrane proximal adhesion region comprises

GTAACGATCCAGCTGTCACT, (SEQ ID NO: 11)

GATCCAGCTGTCACT, (SEQ ID NO: 12)

AGCTGTCACT, (SEQ ID NO: 13)

AGTGACAGCTGGATCGTTAC, (SEQ ID NO: 5)

AGTGACAGCTGGATC, or (SEQ ID NO: 6)

AGTGACAGCT. (SEQ ID NO: 7)

The sequence of the polynucleotide may vary based upon the specific usage and desired properties for the membrane bound polynucleotide. In certain aspects, the polynucleotide includes a sequence selected from:

5'-GTAACGATCCAGCTGTCACT-$T_x$(CAGT)$_5$-3', (SEQ ID NO: 1)

5'-GATCCAGCTGTCACT-$T_x$(CAGT)$_5$-3', (SEQ ID NO: 2)

5'-AGCTGTCACT-$T_x$(CAGT)$_5$-3', (SEQ ID NO: 3)

5'-$T_{60}$(ACTG)$_5$-3', (SEQ ID NO: 4)

5'-AGTGACAGCTGGATCGTTAC-3', (SEQ ID NO: 5)

5'-AGTGACAGCTGGATC-3', (SEQ ID NO: 6)

5'-AGTGACAGCT-3', (SEQ ID NO: 7)

5'-$T_x$(CAGT)$_5$-3', (SEQ ID NO: 8)

5'-$T_x$(ACTG)$_5$-3', or (SEQ ID NO: 9)

5'-(CAGT)$_5$-3', (SEQ ID NO: 10)

where x = 0-100.

The polynucleotide selected from the above may be attached to the membrane anchoring region at the 5' end. In other embodiments, the polynucleotide selected above may be attached to the membrane anchoring region at the 3' end.

In certain aspects, the polynucleotide comprises a sequence that hybridizes to a sequence selected from:

5'-GTAACGATCCAGCTGTCACT-$T_x$(CAGT)$_5$-3', (SEQ ID NO: 1)

5'-GATCCAGCTGTCACT-$T_x$(CAGT)$_5$-3', (SEQ ID NO: 2)

5'-AGCTGTCACT-$T_x$(CAGT)$_5$-3', (SEQ ID NO: 3)

5'-$T_{60}$(ACTG)$_5$-3', (SEQ ID NO: 4)

5'-AGTGACAGCTGGATCGTTAC-3', (SEQ ID NO: 5)

```
                                              (SEQ ID NO: 6)
5'-AGTGACAGCTGGATC-3', (SEQ ID NO: 7)
5'-AGTGACAGCT-3', (SEQ ID NO: 8)
5'-T_x(CAGT)_5-3', (SEQ ID NO: 9)
5'-T_x(ACTG)_5-3',
or (SEQ ID NO: 10)
5'-(CAGT)_5-3',
where x = 0-100.
```

In still other embodiments, the polynucleotide sequence is selected so as to hybridize with a membrane distal adhesion region of another polynucleotide. This polynucleotide may be part of a membrane anchored polynucleotide, or may be attached or affixed to, for example, a fluorophore, pharmaceutical agent, nutriceutical agent, cosmeceutical agent, imaging agent, radiopharmaceutical, nuclear magnetic resonance contrast reagent, and the like.

Membrane anchored polynucleotides may contain a membrane anchoring region, which may include an alkyl chain comprising 12-22 carbons. In certain aspects, the membrane anchoring region is attached to a polynucleotide. According to certain embodiments, the membrane anchoring region is hydrophobic. In some embodiments, the membrane anchoring region is lipophilic. In certain aspects, the entire membrane anchoring region is hydrophobic. According to certain embodiments, the entire membrane anchoring region is lipophilic. In some embodiments, only a portion is lipophilic or hydrophobic. In certain aspects, the membrane anchoring region is amphiphilic. According to certain embodiments, the membrane anchoring region is such that it is energetically more favorable for the chain to be inserted into a membrane than be contained in solution (e.g. water). The membrane anchoring region may spontaneously insert into a lipid membrane.

The membrane anchoring region may insert into the membrane of a cell. In such embodiments, the polynucleotide attached to the membrane anchoring region may be on the extracellular side of the cell membrane. In certain embodiments, the polynucleotide will instead be on the intracellular side of the cell membrane. The membrane anchoring region may include a single alkyl chain. In other embodiments, the membrane anchoring region includes two alkyl chains. In certain aspects, the membrane anchoring region comprises more than two alkyl chains. Three or more alkyl chains may be included.

According to certain embodiments, the membrane anchoring region comprises an alkyl chain and an alkenyl, alkyl, aryl, or aralkyl chain. This alkenyl, alkyl, aryl, or aralkyl chain may comprise 12-22 carbon atoms. In some embodiments, the alkyl chain comprises about 12-22 carbon atoms, and the alkenyl, alkyl, aryl, or aralkyl chain comprises about 12-22 carbon atoms. In some embodiments, the chains share the same number of carbon atoms. In other embodiments, one chain has between about 1 and 10 fewer carbon atoms than the other chain. In some embodiments, one chain has about 1 fewer carbon atom than the other chain, about 2 fewer carbon atoms, about 3 fewer carbon atoms, about 4 fewer carbon atoms, about 5 fewer carbon atoms, about 6 fewer carbon atoms, about 7 fewer carbon atoms, about 8 fewer carbon atoms, about 9 fewer carbon atoms, or about 10 fewer carbon atoms. The membrane anchoring region may comprise more than one alkenyl, aryl, or aralkyl chain, with each chain comprising 12-22 carbon atoms.

In some embodiments, the membrane anchoring region may contain one or more unsaturated carbon bonds. In some embodiments, the unsaturated bonds are all contained within the same chain. In still other embodiments, the unsaturated bonds may be contained in more than one chain.

In certain embodiments, the membrane anchoring region comprises a dialkylphosphoglycieride, and the polynucleotide is conjugated to the dialkylphosphoglycieride. In some embodiments, each chain of the dialkylphosphoglycieride has the same number of carbon atoms with the other chain. In other embodiments, the number of carbon atoms is different between the two alkyl chains of the dialkylphosphoglycieride. In some embodiments, each chain has between 12 to 22 carbons. In some embodiments, each chain has about 12 carbon atoms, or about 14 carbon atoms, about 16 carbon atoms, about 18 carbon atoms, about 20 carbon atoms, or about 22 carbon atoms. In some embodiments, at least one chain has about 12 carbon atoms, about 14 carbon atoms, about 16 carbon atoms, about 18 carbon atoms, about 20 carbon atoms, or about 22 carbon atoms. In particular embodiments, the membrane anchoring region comprises $C_{16}$ dialkylphosphoglyceride.

The membrane anchoring region may comprise a monoalkylamide, and the polynucleotide may be conjugated to the monoalkylamide. In some embodiments, the monoalkylamide chain has between 12 to 22 carbon atoms. In some embodiments, the monoalkylamide chain has about 12 carbon atoms, or about 14 carbon atoms, about 16 carbon atoms, about 18 carbon atoms, about 20 carbon atoms, or about 22 carbon atoms. In certain embodiments, the monoalkylamide comprises about 16 or 18 carbon atoms.

In other embodiments, the membrane anchoring region and the polynucleotide are joined by a compound comprising a phosphate group. In other embodiments, the membrane anchoring region and the polynucleotide are joined by a compound comprising a urea group. In still other embodiments, the membrane anchoring region and the polynucleotide are joined by a compound comprising a sulfonyl group. In another embodiment, the membrane anchoring region and the polynucleotide are joined by a compound comprising a sulfonamido group.

In certain aspects, the methods of the present disclosure include contacting the pattern of cells on the surface under hybridization conditions with a second suspension of cells, where cells of the second suspension include cell surface-attached nucleic acids complementary to the cell surface-attached nucleic acids of the patterned cells, and where the cell surface-attached nucleic acids of cells of the second suspension hybridize to cell surface-attached nucleic acids of the cells patterned on the surface to form a three-dimensional pattern of cells. According to certain embodiments, the cells of the second suspension are selected from epithelial cells, endothelial cells, fibroblasts, lymphocytes, stem cells, or any combination thereof.

The methods of the present disclosure provide a two-dimensional (2D) pattern, e.g., at the level of the patterned nucleic acids and/or at the level of the patterned cells hybridized to the patterned nucleic acids. According to the present disclosure, this 2D pattern may be established such that it encodes a three-dimensional (3D) cellular structure having cells of a desired type at pre-selected locations (e.g., X-Y-Z coordinates) within the 3D structure. The 3D structure may be a tissue or sub-structure thereof, or a 3D structure capable of being cultured into a tissue or substructure thereof. Strategies for establishing a 2D pattern that encodes a desired 3D cellular structure are numerous. For example, a single population of nucleic acids having the same nucleotide sequence may be patterned on the surface, followed by contacting with cells having two or more different populations of cell surface attached nucleic acids, one of which specifically hybridizes to the patterned nucleic acids, and one or more which specifically hybridize to cell surface-attached nucleic acids of cells subsequently (or concurrently) contacted with the cells attached to the patterned nucleic acids. As such, the 3D cellular structure may be generated by the iterative addition of cells having cell surface-attached nucleic acids complementary to available cell surface-attached nucleic acids already present at encoded locations in the structure.

Alternatively, or additionally, the nucleic acids patterned on the surface may include two or more populations of the nucleic acids, each population having unique nucleotide sequences with respect to each other, where cells of the first suspension (which may include one, or two or more populations of cells) have cell surface-attached nucleic acids that specifically hybridize to only one population of the patterned nucleic acids. Accordingly, cells having particular features (e.g., being of a particular cell type and/or having a particular combination of different cell surface-attached nucleic acids) may be targeted to desired locations on the surface. Once these cells are attached to the surface, the 3D cellular structure may be generated by the iterative addition of cells having cell surface-attached nucleic acids complementary to available cell surface-attached nucleic acids already present at encoded locations in the structure.

The methods of the present disclosure may include introducing non-cellular material into the 2D or 3D cellular structure. Non-cellular materials of interest include, but are not limited to, nanoparticles, liposomes, hydrogels, shaped hydrogels, beads (e.g., gel beads), viruses, or any other non-cellular material of interest. In certain aspects, particles having an agent (e.g., a drug, cell signaling molecule, and/or the like) disposed on the surface thereof or embedded within the particles may be introduced into the 2D or 3D cellular structure, and the effect of the agent on a cell parameter (e.g., proliferation, differentiation, toxicity, bioavailability, metabolism, etc.) may be determined. Such agents may also be useful in generating the 2D or 3D cellular structures, e.g., by enhancing the proliferation, differentiation, or other cellular processes/characteristics which determine the final makeup of the structure.

Agents of interest include pharmaceutical agents (e.g., drugs), agents useful for studying biological processes (e.g., cell signaling agents), and/or any other agent of interest. Any of the 2D or 3D cellular structures generated using the methods of the present disclosure may be entirely composed of human cells, or alternatively, may be composed of a mixture of human and non-human cells.

The subject methods may include removing the patterned cells (e.g., a 2D or 3D cellular structure) from the surface. In certain aspects, the patterned cells are removed by embedding the cells in a matrix, and removing the matrix from the surface, where the patterning of the cells is retained in the matrix upon removal. Matrices of interest include but are not limited to extracellular matrices (ECM) such as Matrigel, collagen, fibrin, agarose, PEG-acrylate, and the like. The embedding may include filling a PDMS flow cell with liquid ECM containing high activity DNase, under conditions that maintain the gel in a liquid state (e.g. 4° C. for Matrigel). The flow cell is then shifted to physiological temperatures to simultaneously trigger the gel matrix to set, and to initiate enzymatic cleavage of the DNA strands between the cells and the glass substrate. The removal may include peeling the matrix containing the patterned cells off of the surface of the substrate.

In certain aspects, the methods include culturing the patterned cells. The patterned cells may be cultured under conditions such that the cells proliferate and/or form a desired tissue sub-structure or "complete" tissue. Embodiments of patterns and cell types, as well as example culture conditions useful for generating tissue sub-structures and tissues are described elsewhere herein (see, e.g., the Examples section). According to certain embodiments, the sub-structures and tissues are vascularized and connected to an external source of chemicals, e.g., chemicals that provide energy to the cells (e.g., glucose), signaling molecules (e.g., growth factors), or any other chemicals that enhance or facilitate culturing of the 2D or 3D cellular structure into the desired tissue or sub-structure thereof.

Substrates

Also provided by the present disclosure are substrates. In certain aspects, the substrates include a first population of nucleic acids disposed at an addressable location on a surface of the substrate, and a first population of cells that includes cell surface-attached nucleic acids complementary to the first population of nucleic acids, where the first population of cells is attached to the first population of nucleic acids by hybridization of the surface-attached nucleic acids to the first population of nucleic acids. The first population of cells may be of a cell type including, but not limited to, a cell type selected from epithelial cells, endothelial cells, fibroblasts, lymphocytes, stem cells, or any combination thereof.

Substrates of the present disclosure may further include a second population of nucleic acids disposed at an addressable location on the surface of the substrate, where the nucleotide sequences and addressable locations of the first and second populations of nucleic acids are different, and a second population of cells that includes cell surface-attached nucleic acids complementary to the second population of nucleic acids, where the second population of cells is attached to the second population of nucleic acids by hybridization of the surface-attached nucleic acids to the second population of nucleic acids. The second population of cells may include a cell type selected from epithelial cells, endothelial cells, fibroblasts, lymphocytes, stem cells, or any combination thereof. The second population of cells may be of a cell type including, but not limited to, a cell type selected from epithelial cells, endothelial cells, fibroblasts, lymphocytes, stem cells, or any combination thereof.

Substrates of the present disclosure may include any pattern or types of nucleic acids and/or cells as described elsewhere herein, and may be produced as described above with respect to the subject methods. Aspects of the substrates of the present disclosure include the population(s) of cells (e.g., attached to the substrate via a pattern of the population(s) of nucleic acids) embedded in a matrix. Matrices of interest include but are not limited to extracellular matrices (ECM) such as Matrigel, collagen, fibrin, agarose, PEG-acrylate, and the like. According to certain embodiments, the matrix may include a nuclease (e.g., DNase), e.g., to facilitate removal of the embedded 2D or 3D patterned cells from the substrate's surface, if desired (e.g., for transferring the patterned cells to a culture vessel, etc.).

Systems

The present disclosure also provided systems which find use, e.g., in practicing the subject methods. Systems of the present disclosure may include a computer operably connected to a nucleic acid disposing device, and any other useful components for carrying out the methods of the present disclosure. The computer may have an interface through which a user may pre-select a desired pattern of a population of nucleic acids (or two or more nucleic acid populations at uniquely addressable locations) to be disposed on a surface of a substrate. The computer has a memory and processing means, for storing and executing instructions to a nucleic acid disposing device (e.g., a direct molecular writing device) to dispose the pattern of nucleic acids on the surface of the substrate. The system may further include a fluidic system and flow cell (e.g., configured to hold the substrate or operably couplable to a substrate holder) for delivering nucleic acids, cell suspensions, matrices, and any other useful reagents to the surface of the substrate.

Kits

Also provided by the present disclosure are kits. The kits include one or more reagents useful in practicing the methods of the present disclosure. In certain aspects, the kits include patterning nucleic acids capable of being patterned on a surface of a substrate. In certain aspects, the patterning nucleic acids are modified nucleic acids, such as amine-terminated nucleic acids (e.g., amine-terminated oligonucleotides) which may be patterned on the aldehyde-coated glass surfaces via a reductive amination reaction. Reagents for coating surfaces with useful functional groups (e.g., aldehydes) to facilitate patterning of the nucleic acids may also be included in the kits. According to certain aspects, the subject kits include cell-labeling nucleic acids complementary to the patterning nucleic acids. Such cell-labeling nucleic acids may include a moiety (e.g., a lipid moiety) directly or indirectly linked (e.g., via a spacer) to the nucleic acid, where the moiety facilitates attachment of the cell-labeling nucleic acids to the surface of one or more cell populations of interest. The kits may include any other useful components, including matrix reagents for embedding 2D or 3D cellular patterns on the surface of a substrate, nucleases (e.g., DNase) for facilitating removal of embedded cellular patterns, reagents for culturing the cells into tissue substructures and/or tissues, etc. One or more components of the subject kits may be provided together (e.g., combined in a single container) or may be provided in separate containers. Kits of the present disclosure may also include instructions for patterning nucleic acids on a surface a substrate, labeling cells of interest with the cell-labeling nucleic acids, contacting the patterned nucleic acids with the labeled cells to pattern the cells on the surface (e.g., under hybridization conditions), embedding the patterned cells in a matrix, removing the matrix containing the patterned cells from the surface, culturing the cells into tissue substructures and/or tissues, or any other desired steps in practicing the methods of the present disclosure.

DNA Programmed Assembly

DNA programmed assembly is a method that can rebuild the local architecture of a 3D tissue from individual cells and is describe in, e.g., Liu J S, et al. (2012) *Trends Cell Biol.* pii: S0962-8924(12)00169-9; the disclosure of which is incorporated herein by reference. Aspects of DNA programmed assembly involve the temporary chemical remodeling of cellular adhesion with single stranded polynucleotide(s), such as a membrane-anchored polynucleotide. Because this is a fundamentally chemical approach, any cell type can be rendered selectively adhesive towards any other cell type or surface labeled with a complementary membrane-anchored polynucleotide.

In certain embodiments of DNA programmed assembly, two cell populations are chemically labeled with complementary membrane-anchored polynucleotides. When mixed under controlled conditions, populations of cells bearing complementary sequences of DNA on their surfaces rapidly self-assemble. The DNA is covalently linked to cell surface glycans via metabolic engineering and copper free click chemistry. Proteins are modified by amine acylation. In a preferred method, the lipid bilayer is modified non-covalently using lipid-conjugated oligonucleotides in just five minutes.

Suitable membrane-anchored polynucleotides for use in methods of the present disclosure are described in, for example, Selden N S, et al. (2012) *J. Am. Chem. Soc.* 134, 765-768; and U.S. Patent Application No. 61/554,912 and PCT/US12/63092; the disclosures of each of which are incorporated herein by reference. Briefly, membrane-anchored polynucleotides generally comprise a membrane anchored region, and a polynucleotide. The polynucleotide has a membrane proximal end, and a membrane distal end. The polynucleotide may comprise a linker region and a membrane distal adhesion region. A linker region of a polynucleotide may comprise a contiguous stretch of at least about 20 nucleotides. A membrane distal adhesion region may comprise at least 10 nucleotides and be positioned distal to the linker region, wherein the linker region is not hybridizable to the membrane distal adhesion region. Further characteristics and variations of membrane-anchored polynucleotides are described above.

Direct Molecular Writing

Direct molecular writing is a 2D rapid prototyping tool that allows the transfer of a liquid "molecular ink" to a surface in any desired pattern. Such approaches may also be referred to herein as "solid-phase assembly schemes."

FIG. 14 is an illustration of a solid-phase assembly scheme. In this example, DNA is patterned on aldehyde-silanized surface using molecular writing. Seed cells (blue) are attached to pattern via DNA hybridization. Partner cells (green) are assembled onto seed cells, creating microtissues. Microtissues are embedded in a matrix and released from the surface using DNase, allowing transfer of embedded cells to a 3D tissue culture context.

Appendix A further provides an illustration of a direct molecular writing scheme. A bitmapped image (e.g. an image created in Microsoft Paint or Adobe Photoshop) is translated by a molecular writing tool (e.g., a Bioforce nanoEnabler) into patterns of DNA spots and lines at a scale chosen by the user. The instrument has a practical resolution of about a micron. A 10,000-feature image is printed in less than three hours and the process requires no monitoring by the user. Multiple DNA sequences are printed on the same surface by changing the "ink" and realigning the instrument with the original pattern of spots.

To introduce DNA-labeled cells to the pattern, a polydomethylsiloxane (PDMS) flow cell may be prepared on the printed glass surface. A density of approximately one million cells per square centimeter is required to fill the pattern in five minutes. If more than one DNA sequence is used, the process is repeated to add the second and subsequent populations of cells. The number of cell types that can be patterned is only limited by the number of orthogonal DNA sequences printed by the user. The entire process, from conception to culturing of the pattern, takes less than a day.

Example 5 provides a further example of a direct molecular writing scheme. Using a molecular writing tool, ssDNA were patterned on chemically activated glass (FIG. 14). Reductive amination was utilized, wherein amine-modified DNA was covalently linking with an aldehyde-silanized glass surface using a selective reducing agent, sodium cyanoborohydride. This surface was passivated against cell adhesion by a combination of aldehyde reduction, hydrophobic silanization, and blocking with Pluronic F108. A flow cell was constructed over the patterned, passivated glass surface. Cells were labeled with complementary ssDNA and attached to the surface via DNA hybridization. These cells served as the scaffold for microtissue assembly via the hybridization of additional cells.

Assembled microtissues were embedded in a gel, such as 9 mg/mL Matrigel, containing DNase. The gel retained the structure of the microtissue while the DNase cleaved the linkages between the microtissue and the glass. After DNase action, the gel was peeled away from the glass, retaining the viable, patterned microtissues. This gel was transferred into growth medium for long-term observation of the microtissues.

Solid-phase programmed assembly offers the capability to combine top-down patterning with bottom-up assembly. Practically, this means that relatively simple patterns can be used to nucleate the assembly of more complicated microtissues. The capacity to do this is essential because the complexity of genuine tissues dwarfs the complexity achievable by patterning technology alone, and it allows for the production of 3D structures from 2D patterns.

Figure 15:
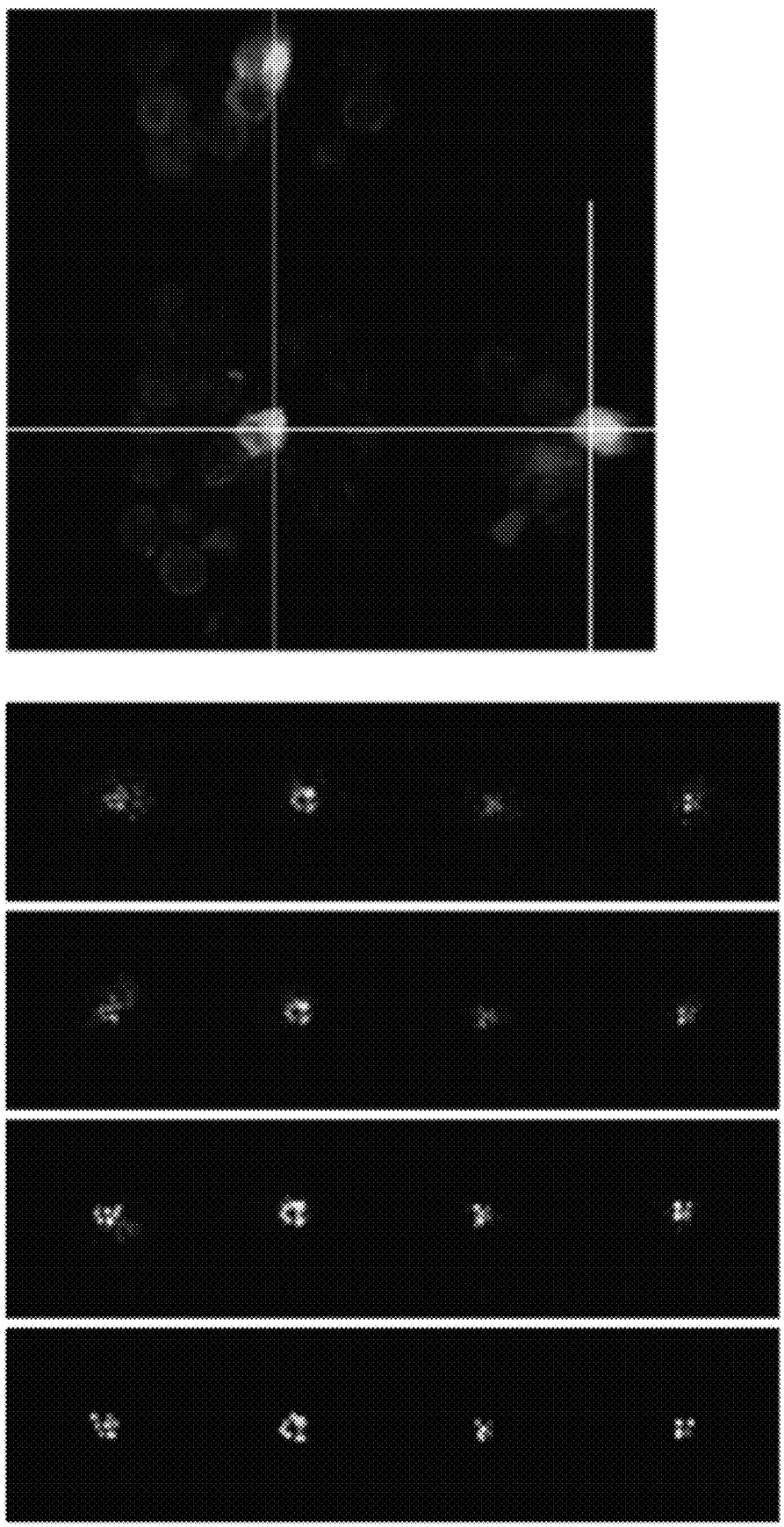
FIG. 15 shows synthesis of multistep assemblies. At left, a column of microtissues is tracked through four progressive steps of solid-phase assembly. At right, cross-sections of a single multistep assembly are visualized with confocal microscopy. Scale bars are 50 μm.

To demonstrate iterative assembly, four populations of DNA-labeled epithelial cells were color-coded (FIG. 15). The patterns were prepared and cells were labeled using the previously described methods (e.g., as described above). After the initial population of cells was patterned on the surface, successive cell populations were assembled, with each assembly step taking no more than five minutes. The growing microtissues were imaged after each round of assembly, and confocal sections were taken of the completed microtissues to verify their stratified composition.

Figure 16:
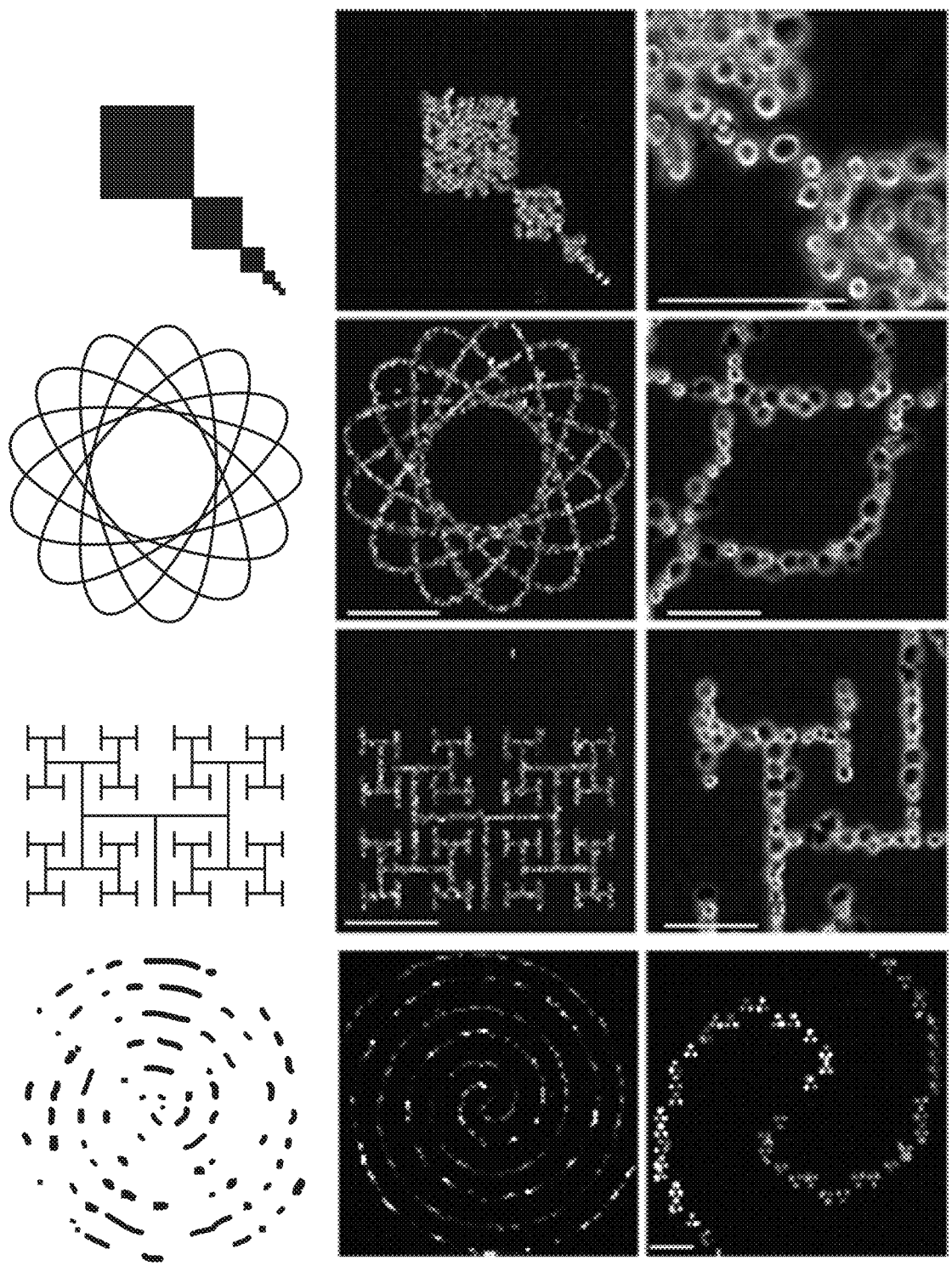
FIG. 16 illustrates the diversity of patterns achievable with direct writing. The left column shows bitmaps used as inputs for patterning. Center and right columns show patterns realized in mammalian cells. Center column scale bars are 400 μm and right column scale bars are 100 μm.
Figure 18:
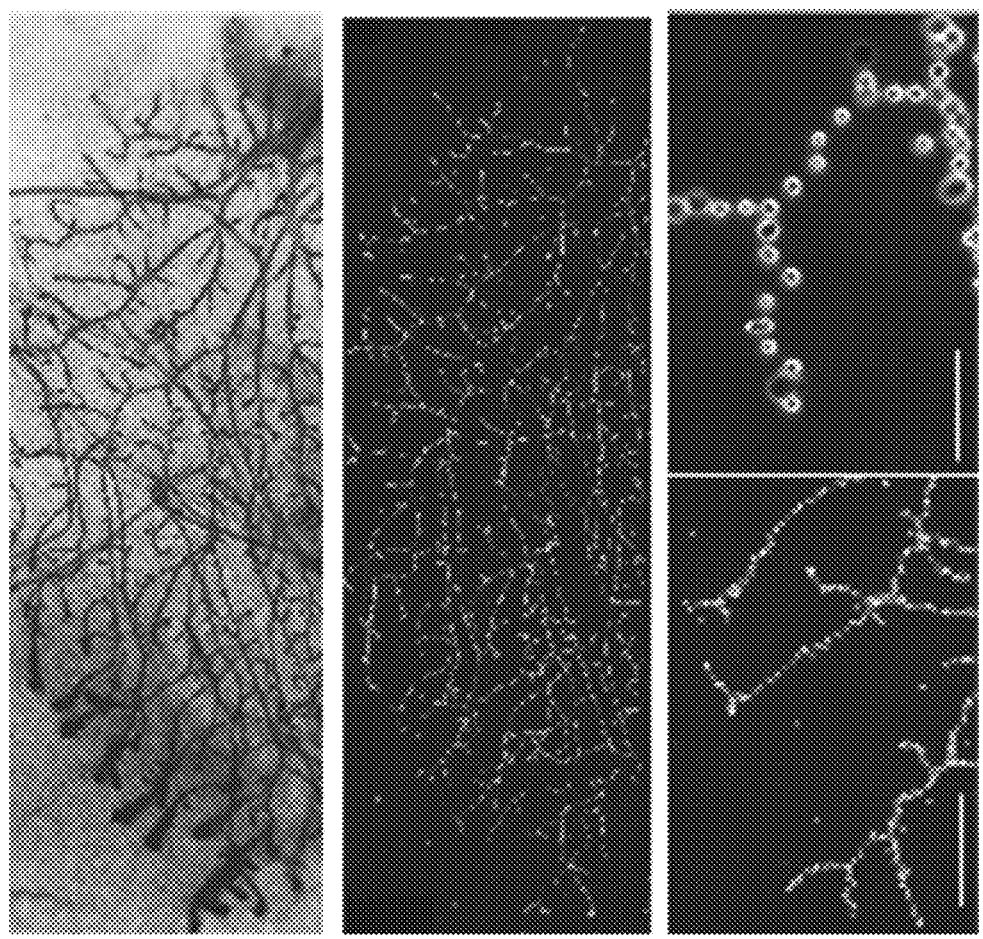
FIG. 18 shows large-scale patterning from a histological section. An image of a whole mouse mammary gland (at top) was converted into a binary bitmap and used as a template for solid-phase programmed assembly. The mammary gland model was built from MCF10As in a pattern spanning over a centimeter with single-cell resolution. Counterclockwise from top, scale bars are 1600 μm, 400 μm, and 100 μm.
Figure 17:
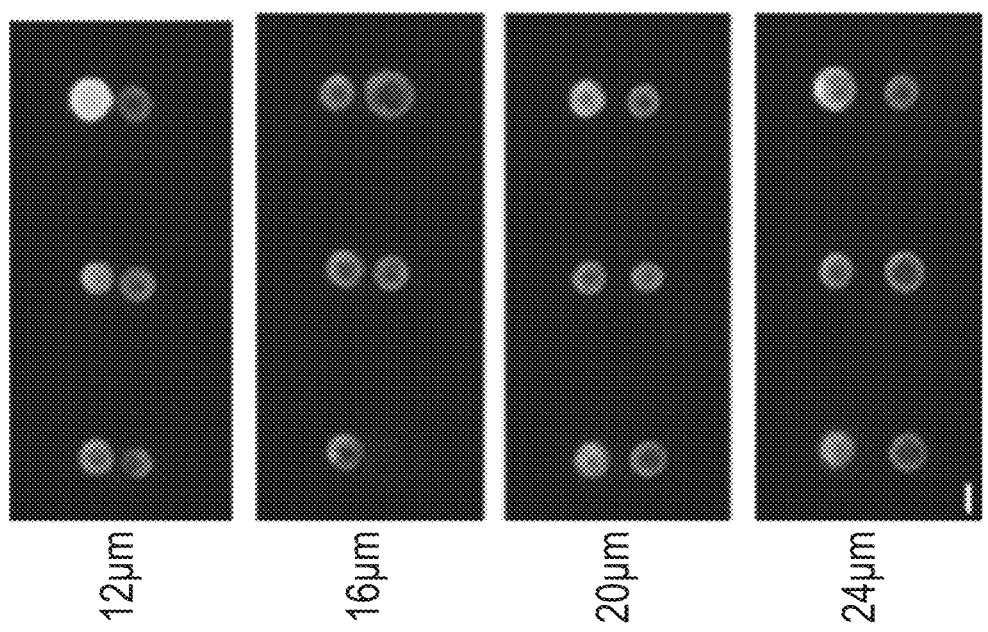
FIG. 17 shows high-resolution patterning of multiple cell types. Mammalian cells colored either green or red were patterned adjacent to one another with center-to-center spacing shown at right. Scale bar is 10 μm.

Direct writing of DNA was used to pattern mammalian cells in remarkable ways (FIG. 16). Patterning can be performed with single-cell resolution, and the position of any individual cell can be controlled to within a micron or two, much less than a cell's diameter (FIG. 17). Multiple DNA sequences were patterned to permit high-resolution patterning of multiple cell types simultaneously. Cells were organized in a variety of complicated, arbitrary patterns including hypotrochoids, spirals, and fractals that span distances from millimeters to centimeters. Furthermore, histological sections were used as templates for solid-phase programmed assembly, such that mammalian cells could be patterned as a genuine mammalian tissue (FIG. 18).

Utility

The methods, substrates, systems and kits of the present disclosure find use in a variety of different applications, including research, pre-clinical, and clinical applications. For example, the 2D and 3D cellular structures generated using the methods of the present disclosure can bring desired cell types into contact with each other, allowing the study of intercellular interactions (e.g., signaling and other interactions) that are critically important in biological processes such as cancer metastasis, stem cell differentiation, immune system function, and the like.

The methods, substrates, systems and kits also find use in pre-clinical applications. For example, 2D and 3D cellular structures generated using the methods of the present disclosure may be used to determine the effect of compounds, e.g., drug compounds, on cells within the structures, which structures are effectively replicates of tissues or sub-structures thereof found in the human body. As such, the present methods of the present invention find use in pre-clinical drug screening applications, where parameters such as toxicity, bioavailability, metabolism, and/or any other parameter of interest, may be established in a 3D physiologically-relevant cellular system prior to administration to a subject (e.g., a human patient).

Moreover, the methods, substrates, systems and kits find use in clinic applications. For example, the methods of the present disclosure are useful in regenerative medicine applications where it is desirable to generate 2D or 3D tissues or substructures thereof for purposes of providing such tissues or substructures thereof to a subject (e.g., a human patient) in need thereof, e.g., due to the subject lacking a functional corresponding tissue or tissue substructure.

EXAMPLES

As can be appreciated from the disclosure provided above, the present disclosure has a wide variety of applications. Accordingly, the following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Those of skill in the art will readily recognize a variety of noncritical parameters that could be changed or modified to yield essentially similar results. Thus, the following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, dimensions, etc.) but some experimental errors and deviations should be accounted for.

Example 1

Programmed Assembly of the Principal Cell Types of the Human Mammary Gland

A strategy of membrane-anchored polynucleotide assembly technique was employed, as described in Selden N S, et al. (2012) *J. Am. Chem. Soc.* 134, 765-768; Liu, J. S. et al. (2012) *Cell Reports* pii: S2211-1247(12)00278-1; and U.S. Patent Application No. 61/554,912 and PCT/US12/63092; the disclosures of each of which are incorporated herein by reference.

A sacrificial micromolding strategy for preparing wells from soft hydrogels for 3D culture of mammary epithelial cells was developed for assembling MEP (myoepithelial cells) and LEP (luminal epithelial cells) in microwells of different materials. This strategy aims to address the challenge of removing PDMS or silicon molds from the soft gels like matrigel. The strategy instead uses molds that simply dissolve once the gel is cast.

Figure 1:
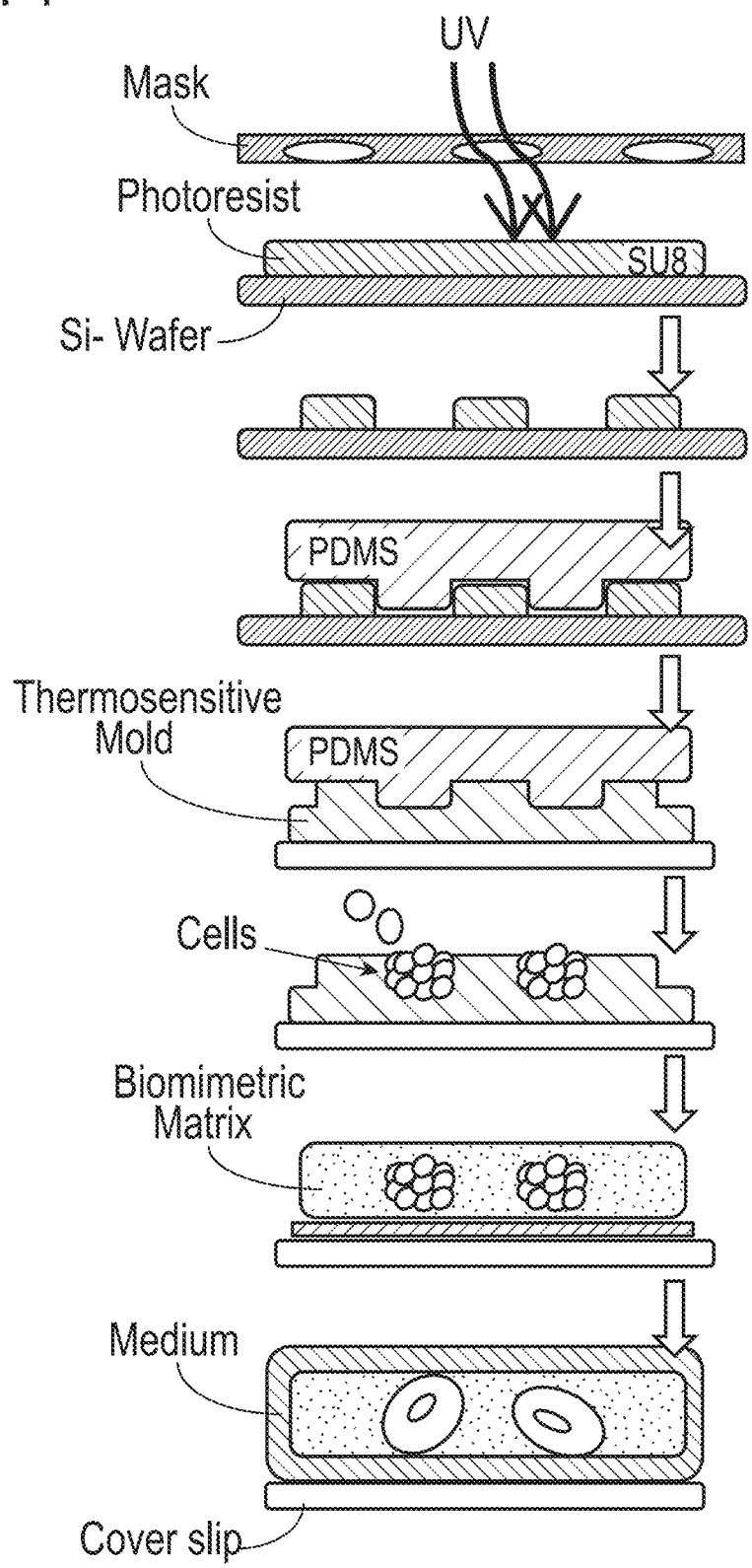
FIG. 1 is a scheme of sacrificial 3D micromolding. This microfabrication approach is carried out by patterning a silicon master with freestanding SU-8 features. The silicon master is then used to create PDMS micropillars that are used to micromold sacrificial microwells. Upon increasing the temperature from room temperature to 37° C., sacrificial molds are dissolved while a biomimetic matrix is allowed to set around the physically confined cell-clusters. 3D microtissues are then maintained in culture for subsequent self-organization studies.
Figure 2A:
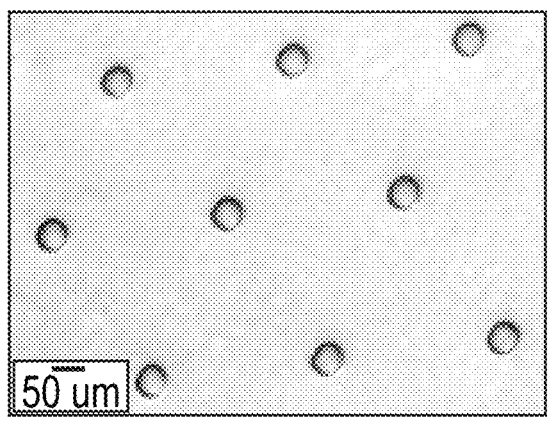
FIG. 2, Panels A-H depict the application of the sacrificial micromolding strategy to preparing epithelial spheroid of controlled size from various tissue types. Panel A: Empty gelatine wells are used to accommodate epithelial cells (Panel B). Panel C: Excess cells are then washed away and the "molded" cell-aggregates are transferred to Matrigel and maintained in culture for 4 days before immunofluorescence studies (Panels D-F). Panel G: a graphical representation of the transfer step. Panel H: sample time-lapse studies done using common epithelial cell lines. All scale bars are 50 µm.
Figure 2B:
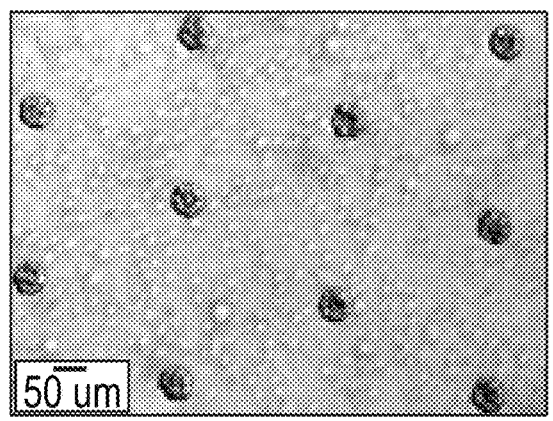
Figure 2C:
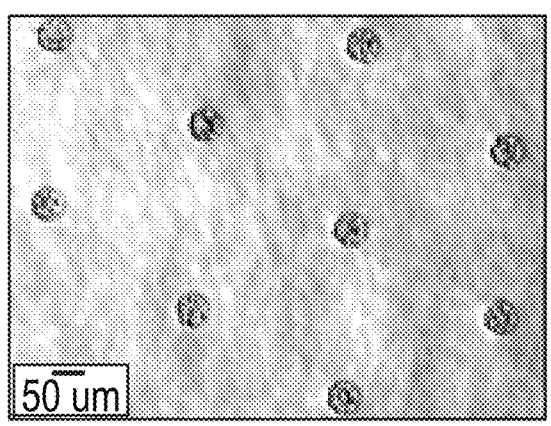
Figure 2D:
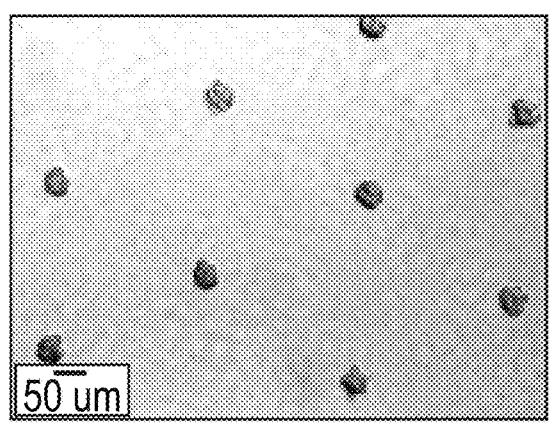
Figure 2E:
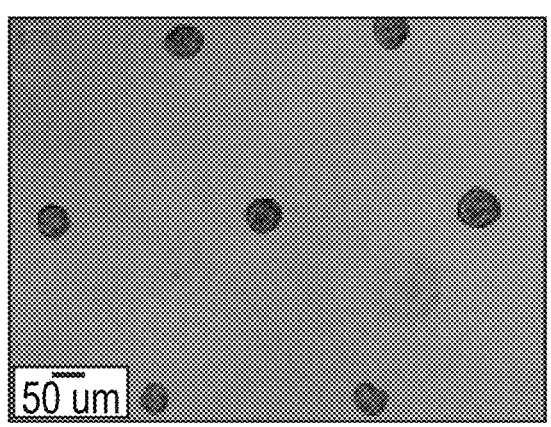
Figure 2F:
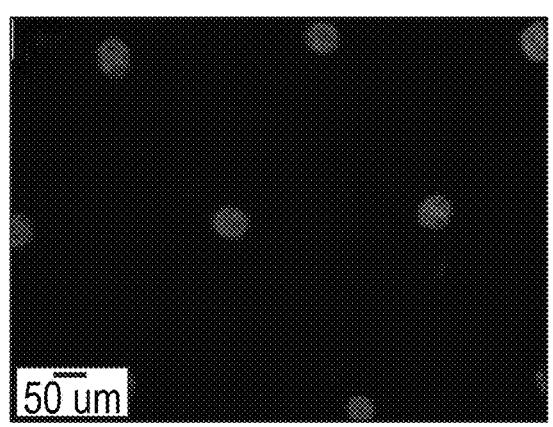
Figure 2G:
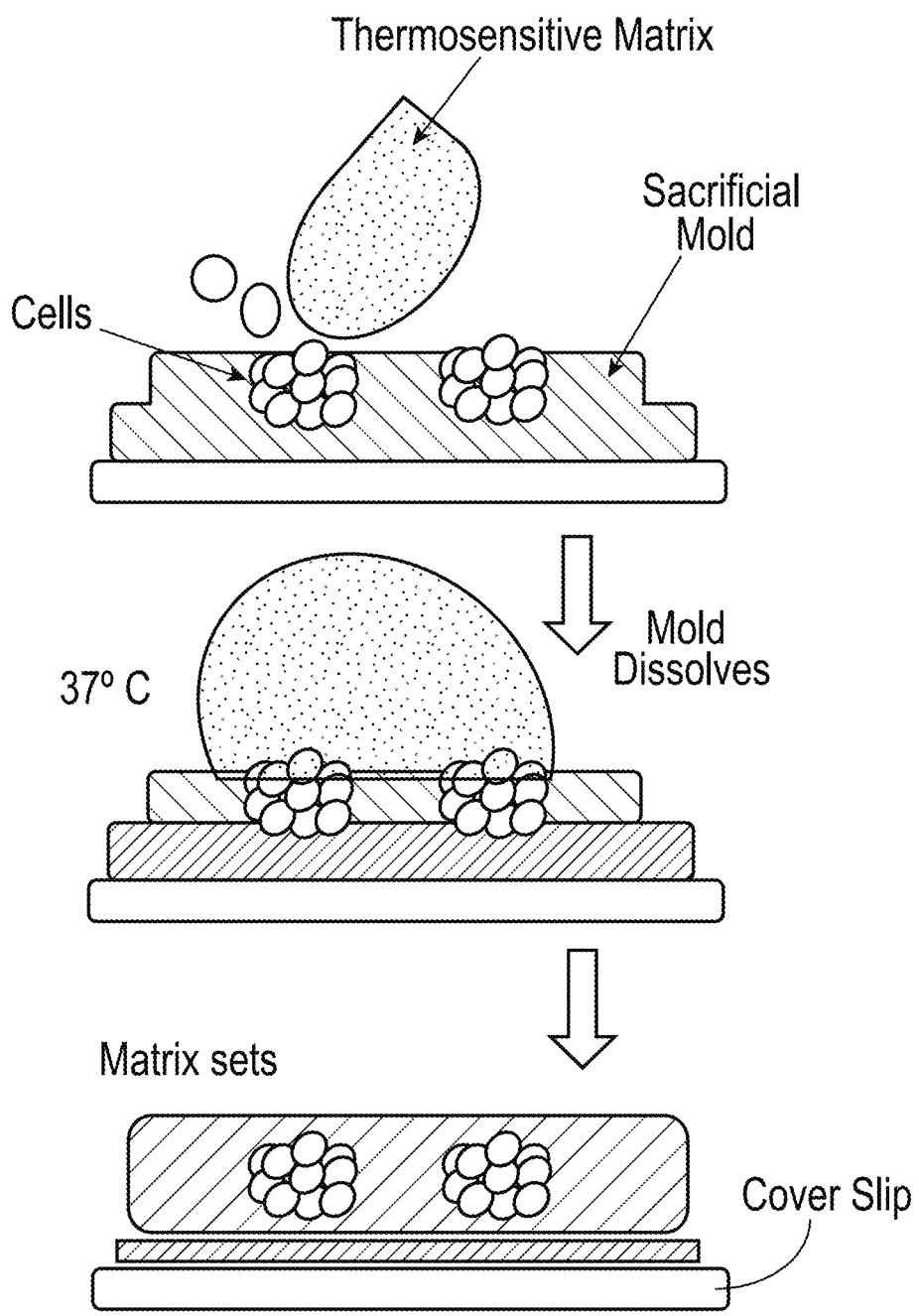
Figure 2H:
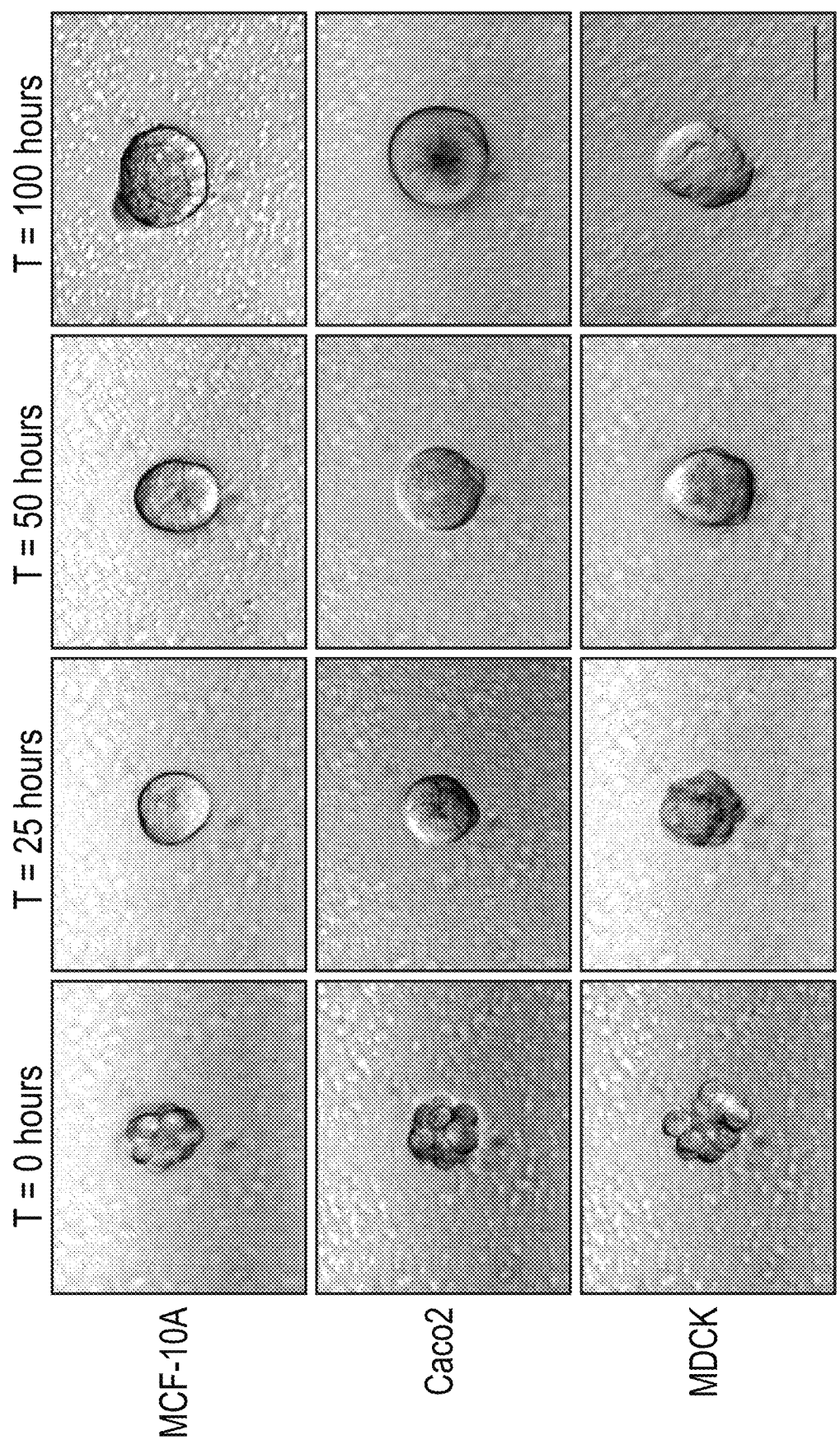

FIG. 1 provides a schematic summary of the sacrificial 3D micromolding strategy. These microfabrication approaches were carried out beginning with a silicon master. Using the Biomedical Micro- and Nano-Fabrication Center (BMNFC) at UCSF, freestanding SU-8 features (120 μm in diameter and 80 μm tall) on silicon wafers were fabricated using common photolithographic techniques. Briefly, SU-8 2035 (MicroCheM) was spun on the substrate at a velocity of 500 rpm for 10 seconds followed by a 1250 rpm spin for 30 seconds. The wafer was then soft-baked for 5 minutes at 65° C. and for 10 minutes at 95° C., UV-exposed with an exposure energy of 215mJ/cm2 (through a photo-mask designed in AutoCAD and purchased from Outputcity Co.), hard-baked for 5 minutes at 65° C. and for 10 minutes at 95° C., and developed in SU-8 developer (MicroCheM) for 20 minutes. The patterned substrate was finally washed with isopropanol/water and baked at 150° C. for 1 hour prior to measuring the pillar's height using a stylus-profilometer. The silicon master was used to create PDMS micropillars by pouring a Sylgard 184 silicone elastomer kit (Dow Corning) onto the patterned wafer using a base:crosslinker ratio of 10:1. After curing at room temperature overnight, the molded template was finally peeled off the substrate and used to imprint gelatin wells via micromolding a solution of 10% Gelatine (Knox) in 1×PBS.

As shown in FIG. 2, Panels A-H, empty gelatin wells were then used to accommodate epithelial cells by centrifuging a solution of one million cells/1 mL of medium. Excess cells were washed away and the "molded" cell-aggregates were transferred to Matrigel by taking advantage of the thermal properties of the sacrificial layer (i.e. gelatin) and the encapsulating biomimetic matrix (i.e. Matrigel). 3D microtissues were maintained in culture for 4 days before Immunofluorescence studies.

As shown in FIG. 2, Panels A-H, the sacrificial 3D micromolding strategy circumvents the time-consuming purification steps associated with a DNA-templated strategy. However, it only provides control of tissue size, and only minimal control for tissue composition is achievable. No control for initial cell-to-cell connectivity can be achieved using the technique. As excess cells that are not physically confined within the microwells are easily washed away, this method allows for the monitoring of the structure formation of established epithelial cell lines such as MCF10As, Caco2s and MDCKs. An additional advantage of using this physical confinement strategy is to reproduce results obtained via chemical strategies in order to rule out any side-effects of using DNA-mediated linkages between cells.

Figure 3A:
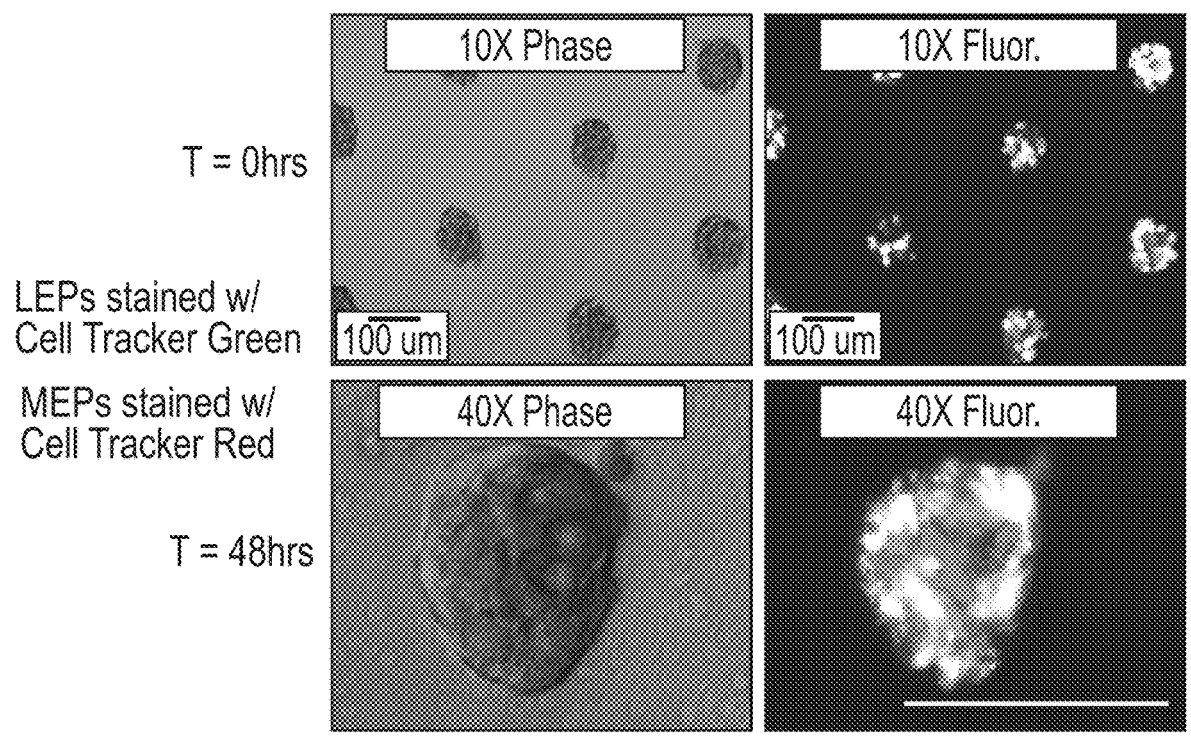
FIG. 3, Panels A-B show HMEC assembly via Sacrificial 3D Micromolding. When LEP and MEP cell aggregates are allowed to self-organize in Matrigel using the sacrificial 3D micromolding technique, a substantial fraction of microtissues exhibit proper bilayered organization as shown in Panel A. However, as shown in Panel B, an equal number of clusters branch and migrate towards adjacent HMEC spheroids. This phenomenon is referred to as "bridging" (white arrow). All scale bars are 100 µm.
Figure 3B:
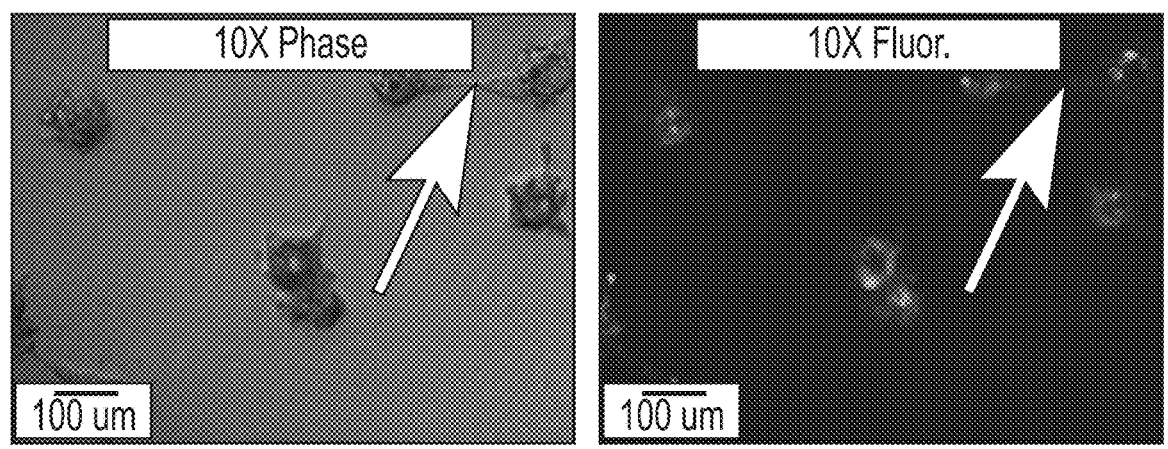

As shown in FIG. 3, Panel A, HMECs FACS sorted into Luminal and Myoepithelial cells can reach properly organized conformations exhibiting a LEP-core surrounded by a MEP-corona. Nevertheless, inhomogeneities in the encapsulating matrix can also give rise to interfacial phenomena that destabilize the architecture of the cell aggregates and promote migration or "bridging" between clusters (see FIG. 3, Panel B, arrows). On average, a 50% mix of well-defined clusters that maintain spherical morphology with proper positioning of MEPs and LEPs and distorted aggregates that loose proper architecture are qualitatively observed.

Example 2

Longitudinal Imaging Using Genetically Encoded Reporters and Immunofluorescent Staining for Lineage Specific Markers of Assembled Structures The capacity of human mammary epithelial cells (HMEC) to self-organize under basic culture conditions—sorted population cultured on top of a slab of matrigel—was investigated to establish whether the microscale and chemical manipulations were facilitating morphogenesis.

Figure 4A:
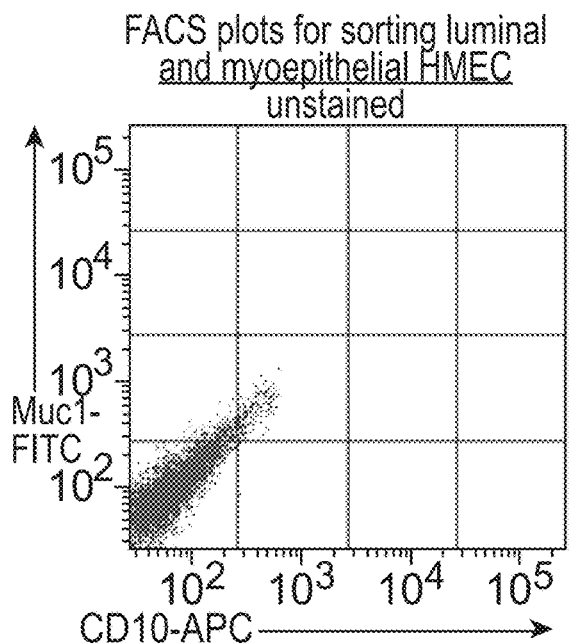
FIG. 4, Panels A-C show representative FACS plots for luminal and myoepithelial cells. Panel A: the FACS plot of unstained HMEC. Panel B: HMEC double stained for CD10 and Muc1. Panel C: the sorting gates used to isolate purified LEP and MEP populations. Gates were positioned to avoid weakly stained and double stained cells.
Figure 4B:
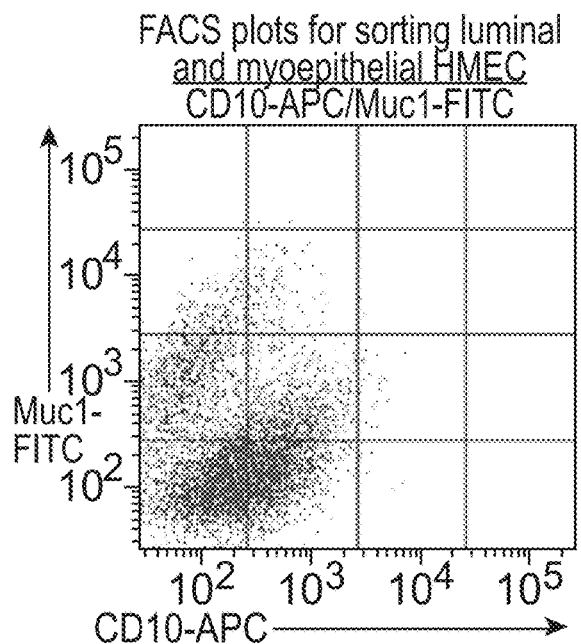
Figure 4C:
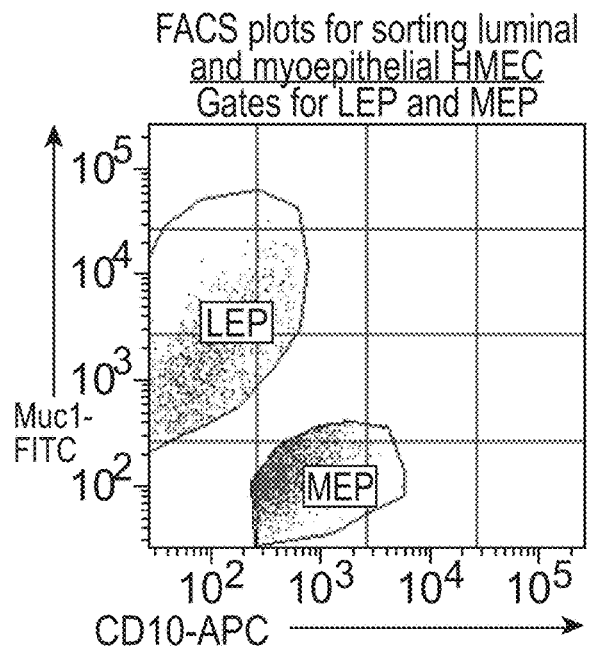
Figure 5:
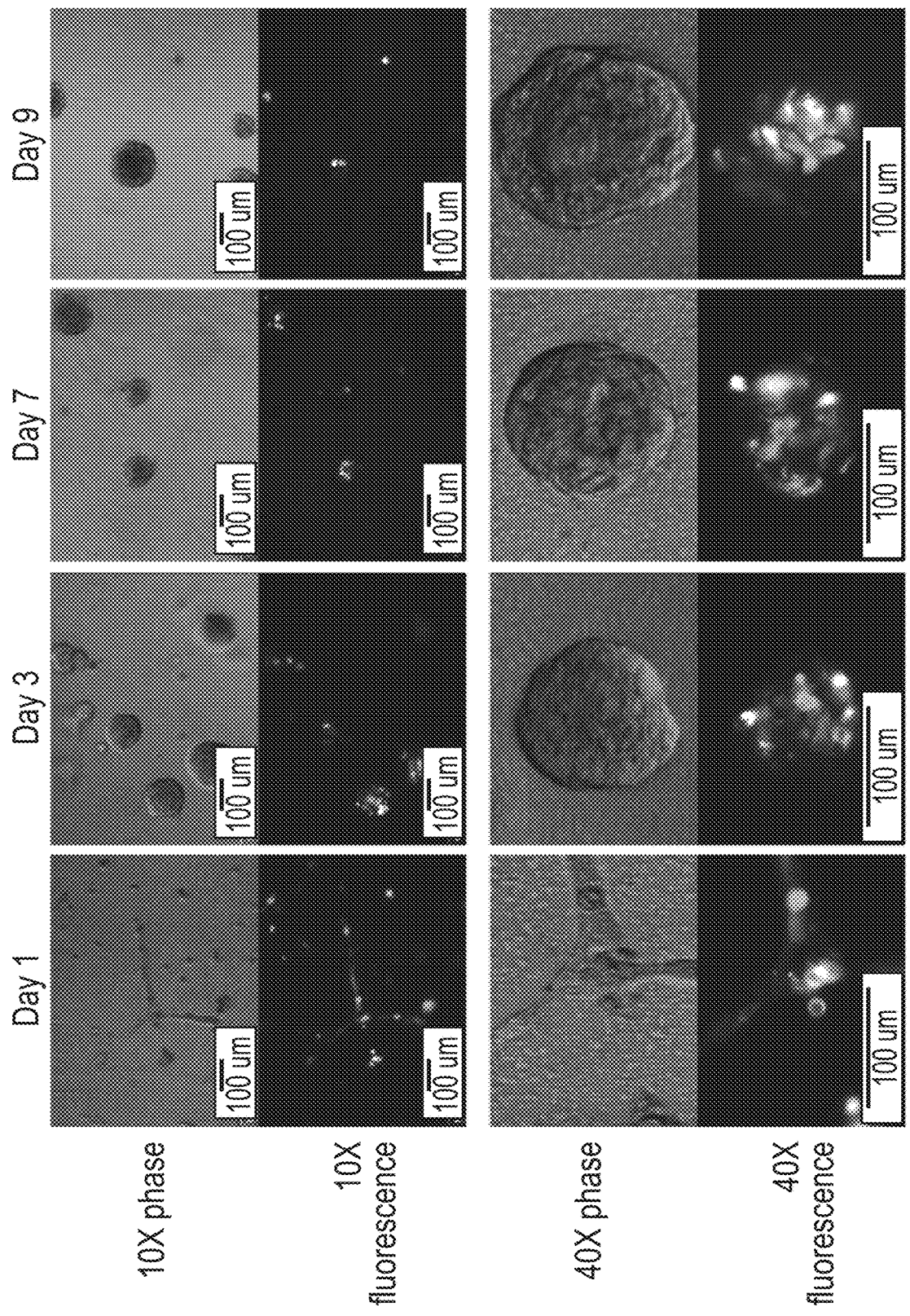
FIG. 5 shows a time series of HMEC structure assembly. Cell tracker labeled MEP and LEP were mixed at a 1:1 ratio and allowed to self-assemble on matrigel. Phase and matched fluorescence images at 10× and 40× magnification were collected at the indicated times. By 24 hours, individual cells migrated over the matigel to form clusters of cells. By day 3, cells were organized into structures with a center core of LEP surrounded by a layer of MEP. Correctly organized structures formed at greater than 80% efficiency and could remain stable for up to 11 days. Incorrect structure consisted mostly of cell clusters containing only one cell type or, rarely, clusters in which the MEP and LEP cells appeared to separating from each other.
Figure 6A:
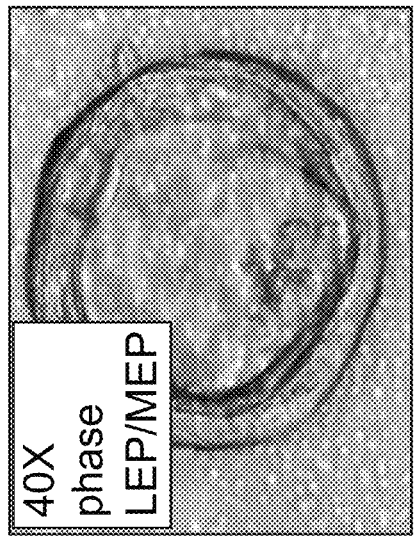
FIG. 6, Panels A-E show lumen formation in organized HMEC structures. In some experiments, organized HMEC 3D on top culture formed lumenized structures. Cell tracker labeled MEP and LEP were mixed at a 1:1 ratio and allowed to self-assemble on matrigel. Phase images of structures at 10× (Panel A), 20× (Panel B), and 40× (Panel C). Fluorescence images of one structure at 20× (Panel D) and 40× (Panel E) show LEP and MEP have formed a properly organized acinar structure. When lumenized structures formed in an experiment, the efficiency was over 70%.
Figure 6B:
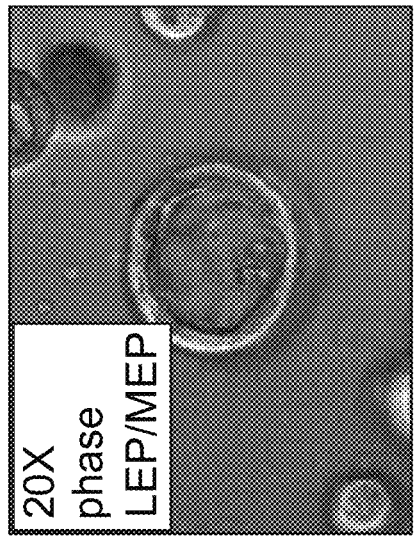
Figure 6C:
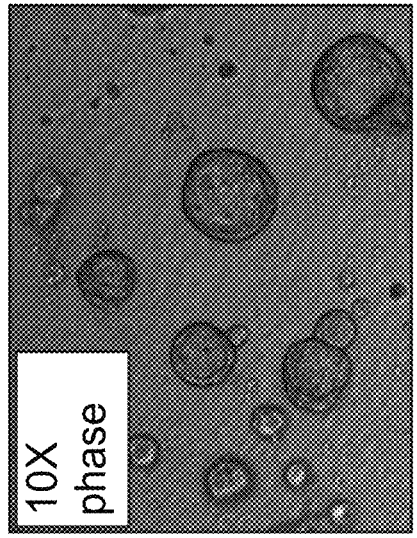
Figure 6E:
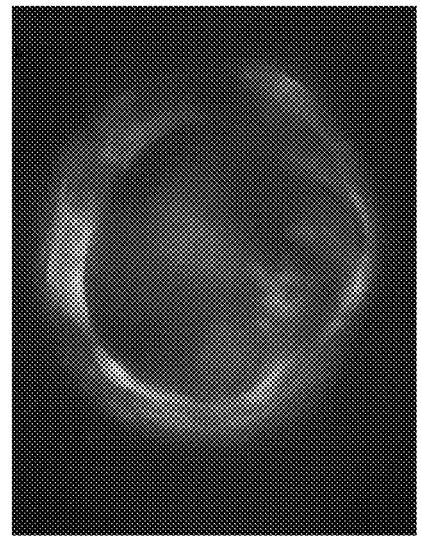
Figure 6D:
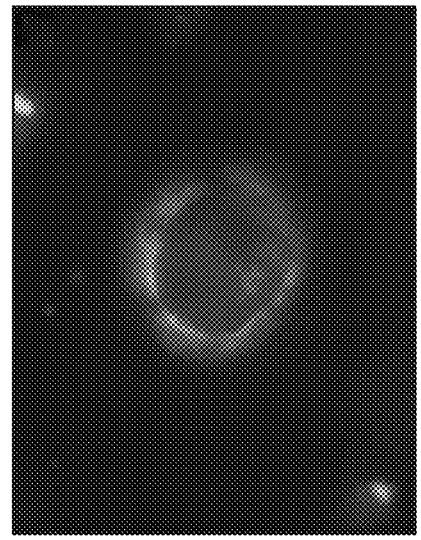

Finite lifespan HMEC were FACS sorted into luminal (LEP) and myoepithelial (MEP) populations based on expression of the lineage specific cell surface markers Muc1 and CD10 (FIG. 4, Panels A-C). HMEC were cultured in M87A medium supplemented with 0.1 nM oxytocin until just confluent and lifted by treatment with PBS-EDTA followed by a trypsin pulse. Cells were stained with FITC conjugated anti-Muc1 and APC conjugated anti-CD10 and sorted using a BD FacsAria2. LEP were defined as Muc1+ CD10− and MEP are Muc1− CD10+. Purified LEP and MEP were labeled with cell tracker green and red respectively, mixed in a 1:1 ratio, and seeded on top of a layer of matrigel in 8 well chamber slides at 20,000 cells per well. Cells were fed with M87A medium supplemented with 5% matrigel. Cultures were imaged by phase and fluorescence microscopy over 10-12 days to monitor assembly of organized structures (FIG. 5). Immunofluorescence analysis was performed after releasing structures from the matrigel and fixing with 4% paraformaldehyde (FIG. 6, Panels A-E). Structures were immunostained with antibodies against keratin 14 (K14, MEP) and keratin 19 (K19, LEP). Stained structures were counterstained with DAPI and imaged (FIG. 7, Panels A-C). These experiments revealed that HMEC have the capacity to self organize when cultured on top of matrigel and form lumen.

Example 3

Measurement of Levels of E-Cadherin Expression on Luminal and Myoepithelial Cell Lines HMEC self-organize in non-adherent agarose well, forming organized aggregates with exactly inverted organization to the normal mammary gland: with MEP on the inside of aggregates and LEP on the outside. To address the question of why LEPs and MEPs self-organize in distinct conformations depending on microenvironment, quantitative PCR (qPCR) was performed to detect the mRNA of cell-cell and cell-ECM adhesion proteins that have been previously implicated in the positioning of luminal and myoepithelial cells in the human mammary gland.

Briefly, 3 different batches of 240L HMECs were FACS-sorted (using Muc1 and CALLA) into LEP and MEP populations (on 3 different days). Immediately after sorting, RNA was isolated from the 2 cell populations, converted to cDNA, mixed with QIAGEN's RT2 PCR master mix, and aliquoted across 2 SA-Biosciences PCR arrays (PAHS-146Z for cell-cell adhesion molecules and PAHS-013 for cell-ECM adhesion molecules); the target concentration of RNA loaded into each array was 2 ug. The plates were then run on a ABI Vii7A RT-PCR instrument. Positive and negative controls established successful PCR amplification with no genomic DNA contamination. Identical threshold values for all MEP (n=3) and LEP (n=3) plates were used in order to extract raw Cts (cycle thresholds) from the RT-PCR instrument. These raw Ct values were then used to calculate fold-changes using the $\Delta\Delta Ct$ method. To normalize the data, the average of the arithmetic means of 3 housekeeping genes was used: GAPDH, ACTB, and HPRT1. To interpret the data, the LEP population was used as the "control" (i.e. over or under expression of MEP genes w.r.t LEPs). Any gene that showed up after cycle 35 was ignored in analysis.

Figure 8A:
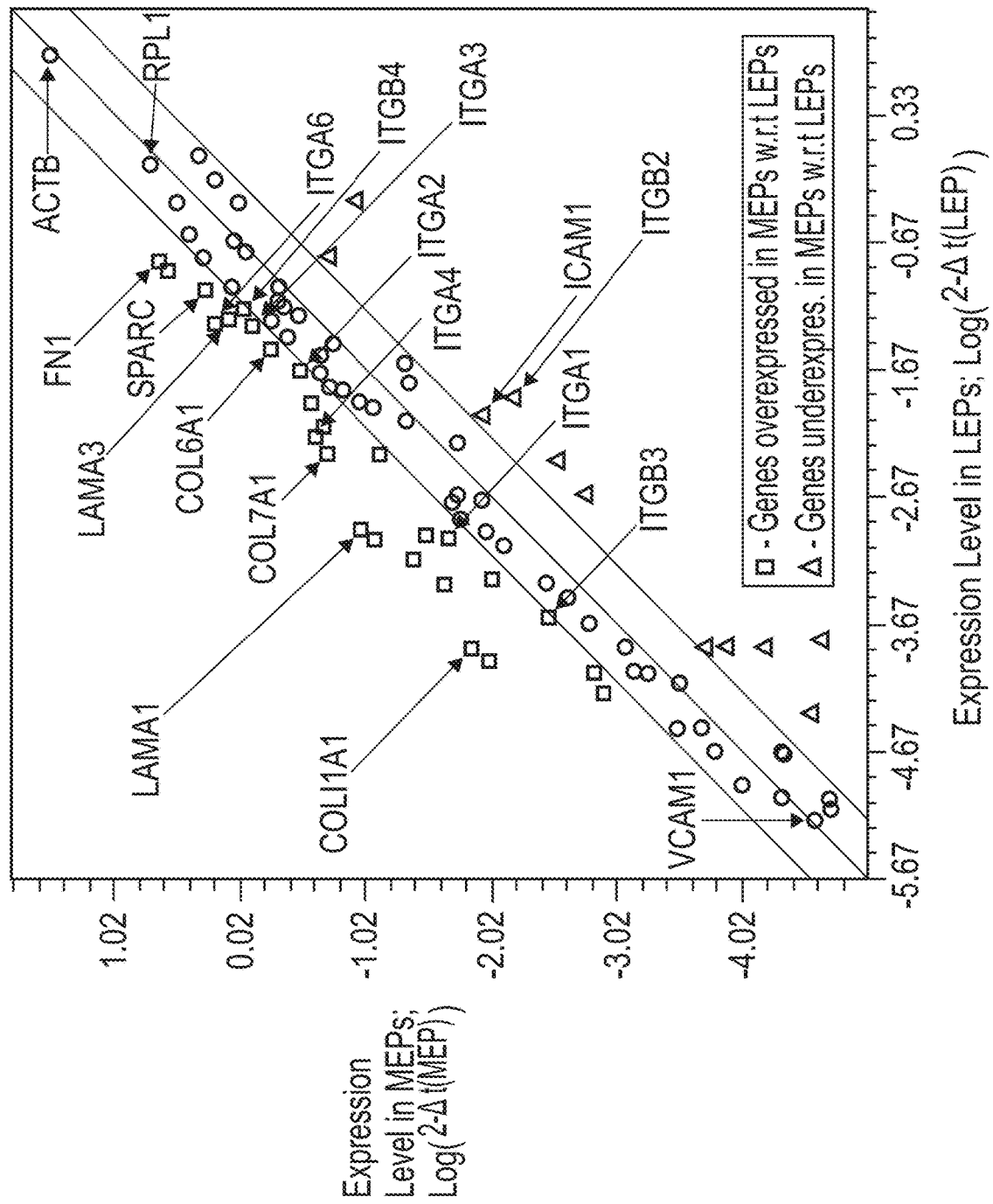
FIG. 8, Panels A-C show qPCR screening of cell-ECM adhesion molecules. Panel A: scatter plot that allows graphical visualization of avg. fold-changes while looking at the genes' relative expression levels for MEPs vs LEPs. Panel B: Volcano plot displaying statistical significance versus avg. fold-change on the y- and x-axes, respectively. Panel C: table summarizing the gene, avg. fold regulation, and P-value (based on a Student's t-test of the replicate $2^{(-\Delta Ct)}$ values) for the most significant hits emerged from the cell-ECM qPCR screening.
Figure 9B:
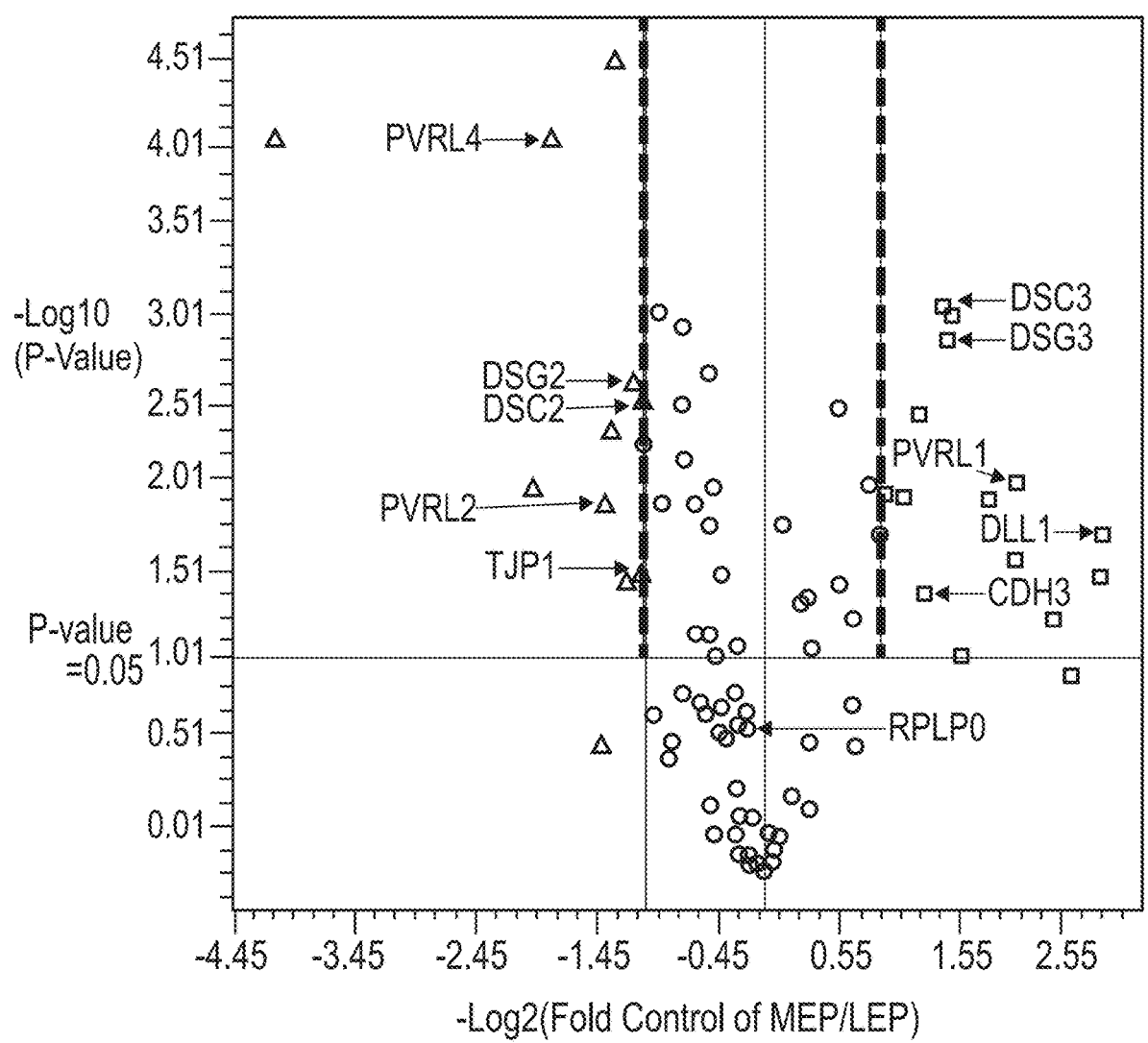
FIG. 9, Panels A-C show qPCR screening of cell-cell adhesion molecules. Panel A: scatter plot that allows graphical visualization of avg. fold-changes while looking at the genes' relative expression levels for MEPs vs LEPs. Panel B: Volcano plot displaying statistical significance versus avg. fold-change on the y- and x-axes, respectively. Panel C: table summarizing the gene, avg. fold regulation, and P-value (based on a Student's t-test of the replicate $2^{(-\Delta t)}$ values) for the most significant hits emerged from the cell-ECM qPCR screening.
Figure 10A:
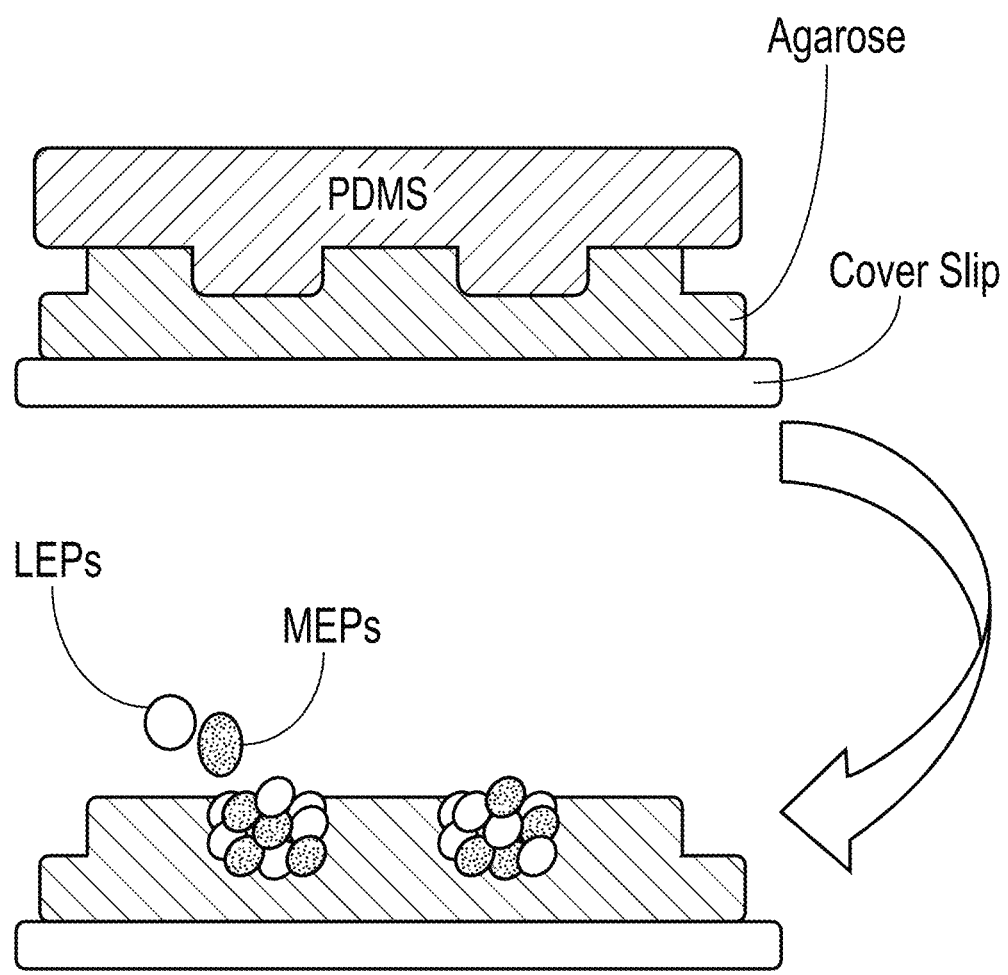
FIG. 10, Panels A-F show HMEC self-organization in non-adhesive microwells. Panel A: HMEC sorted into luminal and myoepithelial lineages are allowed to self-organize in non-adherent microwells microfabricated as schematically shown. Cell-dye tracking (Panel B) or immunohistochemistry (Panel C) for cellular (i.e., K14 for MEPs and K19 for LEPs) markers reveal the formation of an inverted structure with MEPs in the core and LEPs in the periphery of the cluster. Panel D: Confocal orthogonal rendering (Z-stack) of a representative clusters in 3D (XY, YZ, and XZ planes). Panel E: The average intensity K14 and K19 signal for 10 representative clusters. Panel F: Quantification of keratin signal as a function of radial distance obtained by radially re-slicing the average intensity images shown in Panel E. In Panel B, the scale bars are 100 μm for the 10× magnification images and 50 μm for the 40× magnification images. In Panel C, the scale bar is 50 μm.
Figure 10E:
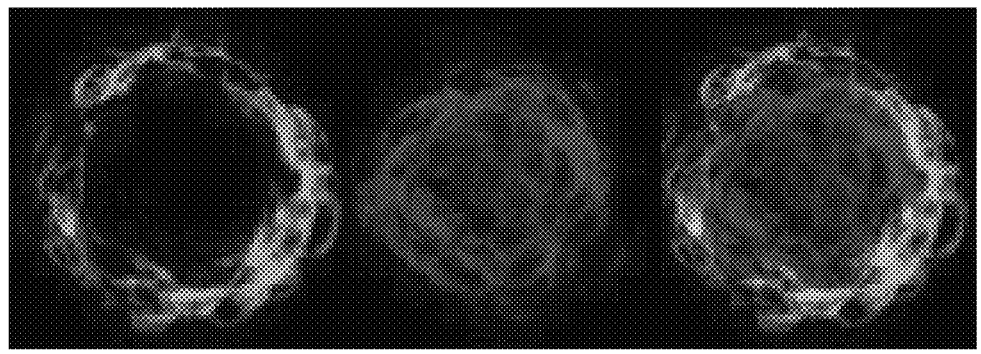
Figure 10D:
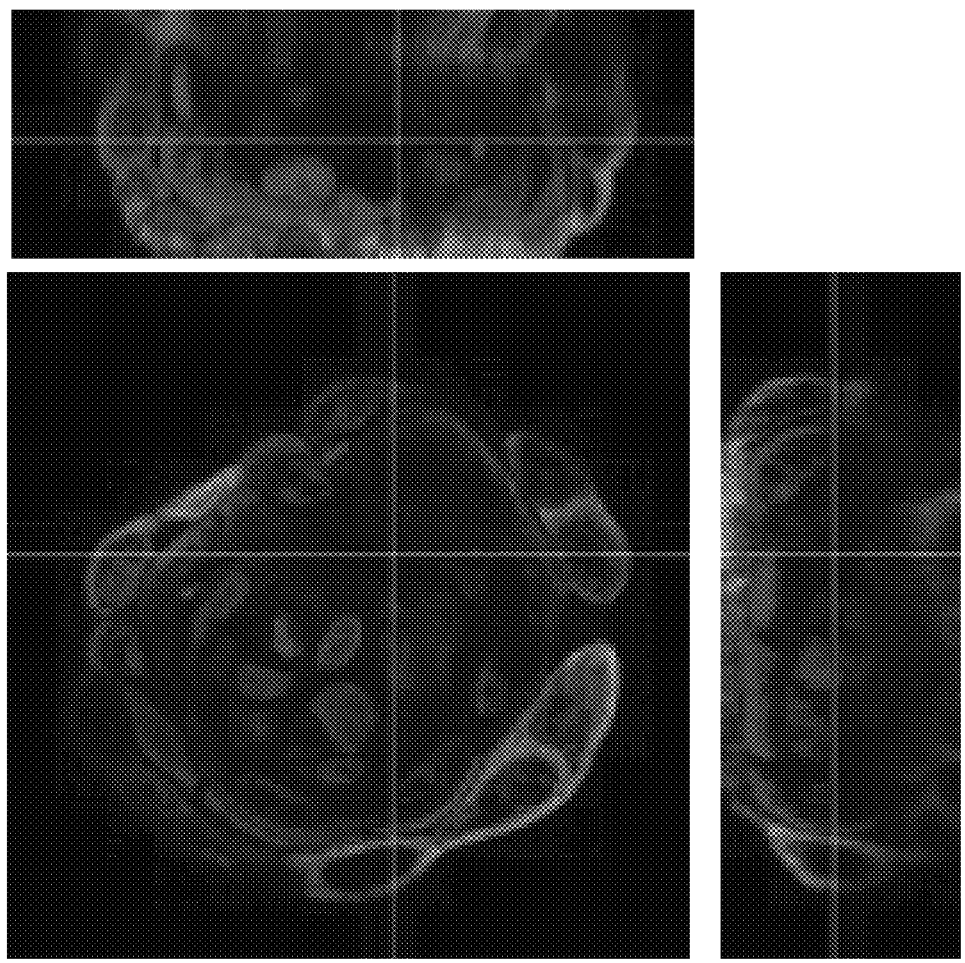
Figure 10F:
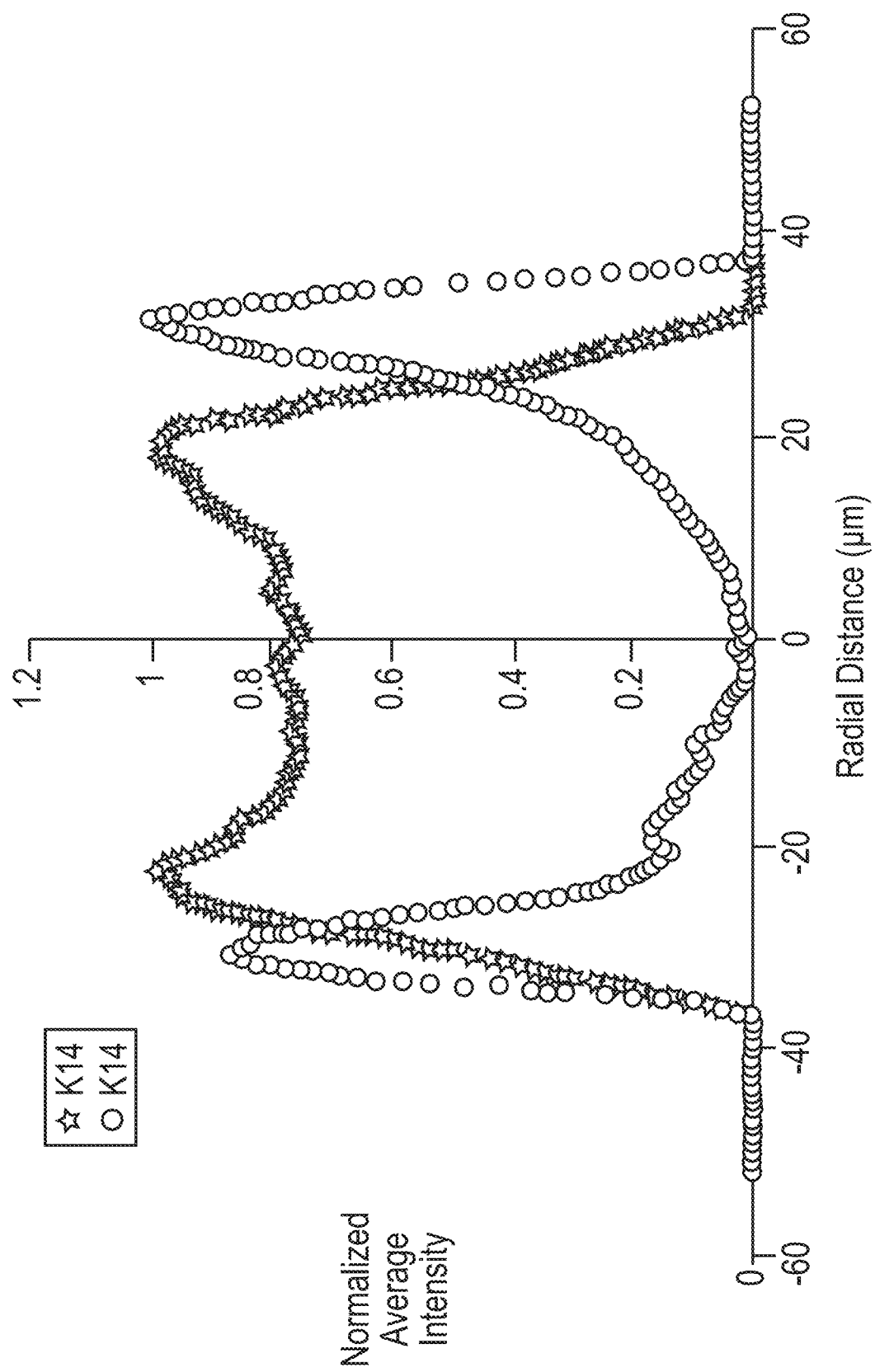

FIG. 8, Panels A-C and FIG. 9, Panels A-C summarize the data with (1) a scatter plot that allows graphical visualization of average fold-changes while looking at the genes' relative expression levels for MEPs vs LEPs, (2) a volcano plot displaying statistical significance versus average fold-change on the y- and x-axes, respectively, and (3) a table summarizing the gene, average fold regulation, and P-value (based on a Student's t-test of the replicate $2^{(-\Delta Ct)}$ values) for the most significant hits emerged from the cell-cell and cell-ECM PCR screenings.

MEPs appeared to overexpress P-cadherin, Desmoglein3, Desmocollin3, Fibronectin1, Laminin 1, Laminin 3, and several Collagen types. LEPs exhibited higher levels of mRNA for Desmoglein2 and Desmocollin2, while substantially lower levels for virtually all ECM secreted proteins. E-CAD was not found to be over or under expressed at the transcriptional level.

Example 4

Development of a Functional Assay for LEP and MEP Cell-Positioning

In order to identify, in a high-throughput manner, the effect of the microenvironment on the positioning of LEPs and MEPs a microwell assay was optimized. As previously described, all microwells were fabricated beginning with a silicon master patterned according to common photolithography techniques. The silicon master was then used to create PDMS micropillars that are peeled off the substrate and used to imprint non-adherent wells via micromolding a solution of 3% agarose in 1×PBS. Agarose was chosen as the non-adherent material of choice to represent "inert environments" because it was the cheapest among 2 other hydrogels (i.e. Polyethylene Glycol and Polyacrylamide) that (1) showed non-adhesive properties towards luminal and myoepithelial cells, (2) could be easily micromolded around previously fabricated PDMS microfeatures, (3) reproduced the self-organization of a bilayered cell-cluster with MEPs in the core and LEPs in the periphery (FIG. 10, Panels A-F) and (4) could be easily functionalized with ECM proteins of choice in order to probe the effect of adhesive microenviornments on the positioning of LEPs and MEPs.

Figure 11:
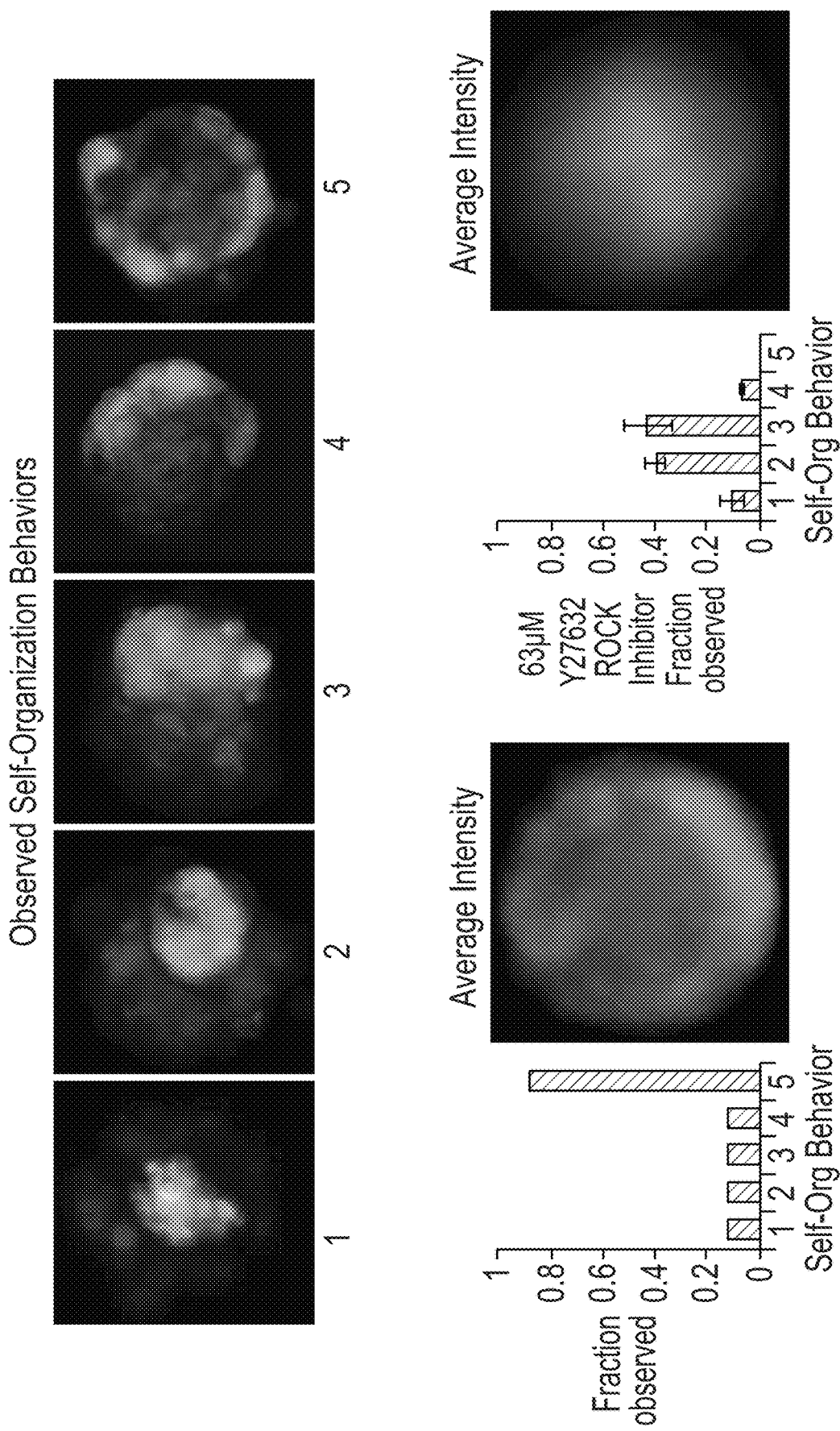
FIG. 11, Panels A-B illustrate self-organization in the presence of ROCK inhibitor. When HMEC sorted into luminal and myoepithelial lineages are allowed to self-organize in non-adherent microwells 5 possible conformations are observed (Panel A). If the drug is the ROCK inhibitor Y27632 considerably more of conformations 1-3 are observed, consistent with altered cell contractility and adhesion (Panel B).
Figure 12A:
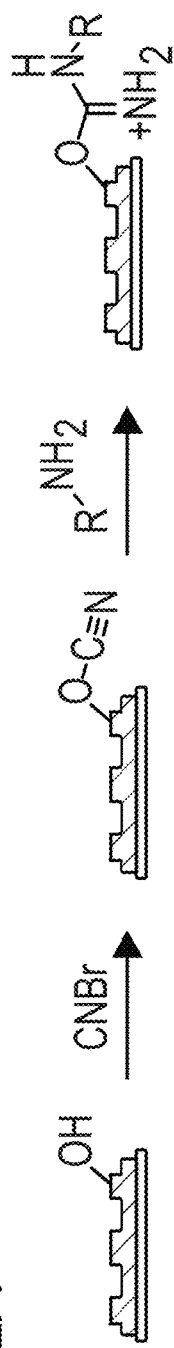
FIG. 12, Panels A-B show collagen coated agarose wells direct self-organization of HMEC clusters with a LEP core and a MEP periphery. Panel A: Schematic representation of the method adopted to functionalize agarose wells using cyanogen bromide. Panel B: Fluorescent microscopy images of HMEC clusters 24 hours after cell-sorting. Control wells were treated with cyanogen bromide but neutralized with ethanolamine after agarose activation. Test wells were either treated with bovine serum albumin (BSA) or Rat Tail collagen 1 (CollI). All scale bars are 100 μm.
Figure 12B:
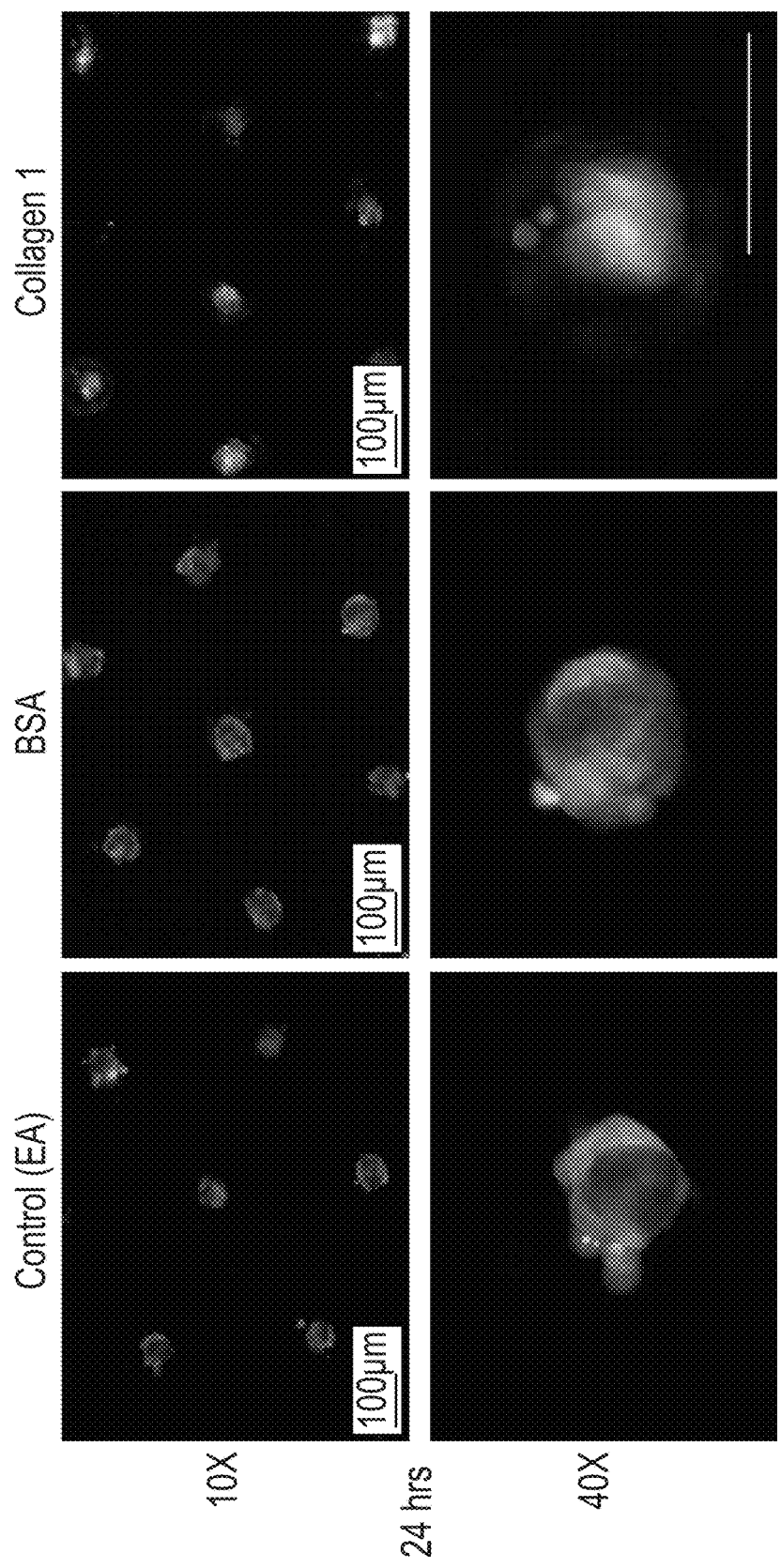

To load the wells with traceable LEP and MEP lineages, HMECs were FACS-sorted and separately stained with 54 of either DiI (Invitrogen red membrane dye) for MEPs and 5 µL of DiO (Invitrogen green membrane dye) for LEPs. The cells were then incubated for 10 minutes at 37° C., pelleted again, and resuspended in medium at a concentration of 1 million cells/mL. The cells were then mixed at target ratio of 1 MEP:1 LEP and centrifuged into the wells at 160×g for 4 minutes. Excess cells were washed away with medium and the remaining clusters, which were physically confined in the non-adhesive agarose microwells, were monitored for self-organization by video microscopy. When using soluble molecular inhibitors as pertubations to this process, the ML87A medium was doped with a defined concentration of drug as shown in FIG. 11, Panels A-B. If trying to perturb self-organization by modifying the chemical composition of the microenvironment, the microwells were functionalized as shown in FIG. 12, Panels A-B.

To functionalize the molds (i.e. agarose wells) they were washed 2 times with 0.1 M sodium carbonate at pH 8.5 (coupling buffer) and resuspended in 2M sodium carbonate (activation buffer). Cyanate ester groups were then formed by adding 5M cyanogen bromide in acetonitrile for ~2 mins at Room Temp. These activated molds were subsequently washed with 1mL of ice-cold deionized water and 1 mL of coupling buffer. Finally, wells were treated with either 2 mg/mL BSA, 0.5 mg/mL protein, or no protein in coupling buffer overnight at 4° C. The day after ligand coupling via isourea bond formation, the wells were given a fresh solution of protein in PBS for another incubation period of 24 hours at Room Temp. On the day of the experiment, residual reactive groups were blocked by treating the wells with 50 mM ethanolamine (pH 9.0) for 1 hour prior to copious washing with PBS for several hours at RT.

Figure 13A:
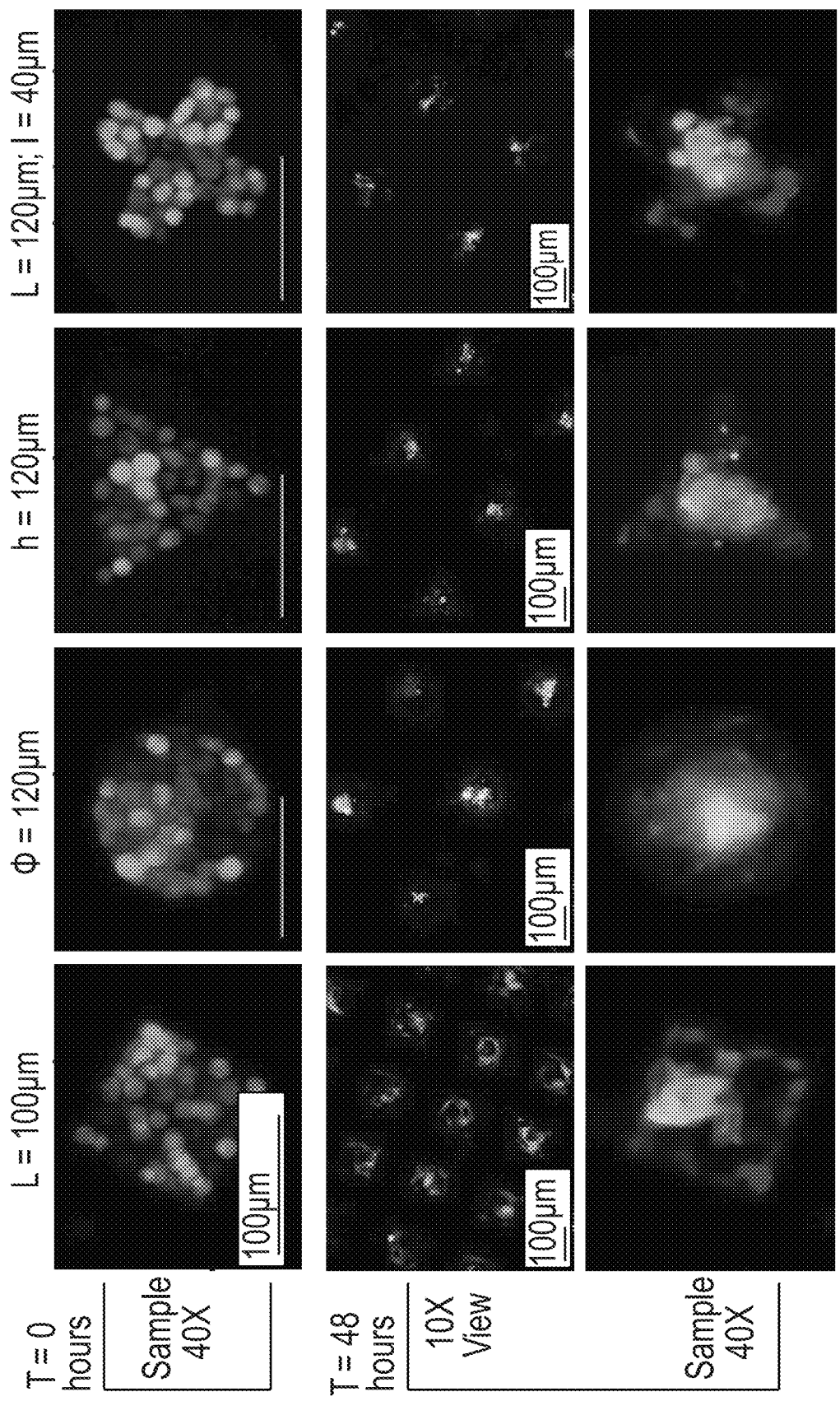
FIG. 13A and FIG. 13B show HMEC Self-Organization in PDMS wells. When HMECs sorted into luminal and myoepithelial lineages are allowed to self-organize in PDMS microwells, the cells organize correctly. However, as the cells conform to the geometry of the well, it can be concluded that the cells are subject to extrinsic signals emerging from their interaction with the walls of the PDMS well. All scale bars are 100 μm.
Figure 13B:
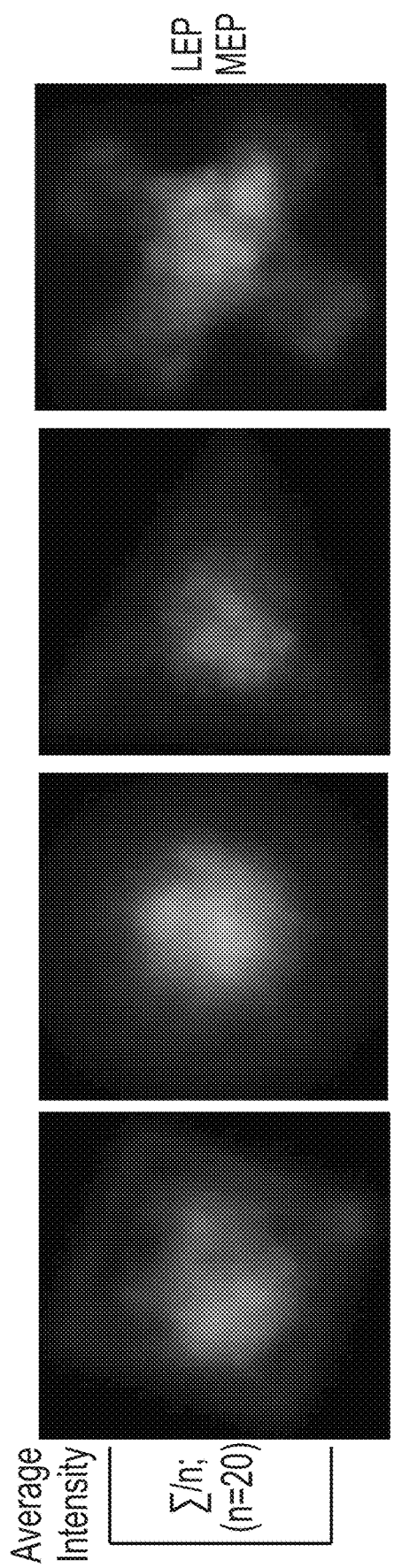

Chanson et al. (*PNAS* 2011 Feb. 22; 108(8):3264-9; the disclosure of which is incorporated herein by reference) described that when 240L HMECs are sorted into luminal and myopeithelial lineages and recombined at a ratio of 1 LEP:1 MEP into PDMS wells, these cells reconstitute bilayered structures with a LEP core and a MEP corona. With the intent of exploring the possibility that these cells could also form a bilayered luminized acinus that better mimic the human mammary gland than current established 3D in vitro models (i.e. immortalized MCF10As and S1s), the work of Chanson was repeated and it was noticed that LEPs and MEPs organized properly but that they extensively interacted with the walls of the PDMS well (FIG. 13A and FIG. 13B). Furthermore, the HMECs lost their 3D organizational architecture after 2 days in culture, and typically did not maintain tight apposition between LEP and MEP cell membranes.

As shown in FIG. 10, Panels A-F, when these same cells are places in non-adherent microwells, they organize with an inverted architecture: MEPs surrounded by LEPs. Therefore, these results suggested that microenvironmental signals extrinsic to HMECs play a significant role in dictating cellular self-organization of luminal and myoepithelial cells. In other words, if the cells' intrinsic properties were sufficient to dictate structure formation, the chemistry of the microwell should not perturb their self-organization. To test whether cell-ECM interactions can dominate over cell-cell interactions in dictating self-organization of HMEC, non-adhesive agarose microwells were methodically functionalized with an adhesive ECM protein and showed that by changing the chemical composition of the well one can controllably dictate the positioning of LEPs and MEPs in vitro (FIG. 12, Panels A-B). Collagen 1 was identified as an ECM protein of interest that can restore the inverted self-organization observed in non-adhesive wells (FIG. 12, Panels A-B) into properly organized architectures of bilayered HMECs. The small drug ROCK inhibitor Y27632 was shown to affect structure formation (see FIG. 11, Panels A-B). This indicated that although cell adhesion molecules play a fundamental role in determining the architecture of HMECs, the cytoskeleton's ability to contract, remodel, and stabilize cell-cell as well as cell-ECM adhesions is also important.

Example 5

A Solid-Phase Strategy for Preparing Multistep Tissues Composed of Human Mammary Epithelial Cells Using a molecular writing tool, ssDNA were patterned on chemically activated glass (FIG. 14). Reductive amination was utilized, wherein amine-modified DNA was covalently linking with an aldehyde-silanized glass surface using a selective reducing agent, sodium cyanoborohydride. This surface was passivated against cell adhesion by a combination of aldehyde reduction, hydrophobic silanization, and blocking with Pluronic F108. A flow cell was constructed over the patterned, passivated glass surface. Cells were labeled with complementary ssDNA and attached to the surface via DNA hybridization. These cells served as the scaffold for microtissue assembly via the hybridization of additional cells.

Assembled microtissues were embedded in a gel, such as 9 mg/mL Matrigel, containing DNase. The gel retained the structure of the microtissue while the DNase cleaved the linkages between the microtissue and the glass. After DNase action, the gel was peeled away from the glass, retaining the viable, patterned microtissues. This gel was transferred into growth medium for long-term observation of the microtissues.

Solid-phase programmed assembly offers the capability to combine top-down patterning with bottom-up assembly. Practically, this means that relatively simple patterns can be used to nucleate the assembly of more complicated microtissues. The capacity to do this is essential because the complexity of genuine tissues dwarfs the complexity achievable by patterning technology alone, and it allows for the production of 3D structures from 2D patterns.

To demonstrate iterative assembly, four populations of DNA-labeled epithelial cells were color-coded (FIG. 15). The patterns were prepared and cells were labeled using the previously described methods (e.g., as described above). After the initial population of cells was patterned on the surface, successive cell populations were assembled, with each assembly step taking no more than five minutes. The growing microtissues were imaged after each round of assembly, and confocal sections were taken of the completed microtissues to verify their stratified composition.

Direct writing of DNA was used to pattern mammalian cells in remarkable ways (FIG. 16). Patterning can be performed with single-cell resolution, and the position of any individual cell can be controlled to within a micron or two, much less than a cell's diameter (FIG. 17). Multiple DNA sequences were patterned to permit high-resolution patterning of multiple cell types simultaneously. Cells were organized in a variety of complicated, arbitrary patterns including hypotrochoids, spirals, and fractals that span distances from millimeters to centimeters. Furthermore, histological sections were used as templates for solid-phase programmed assembly, such that mammalian cells could be patterned as a genuine mammalian tissue (FIG. 18).

Example 6

Assembly of Cell Lines into Multistep Tissues

Figure 19A:
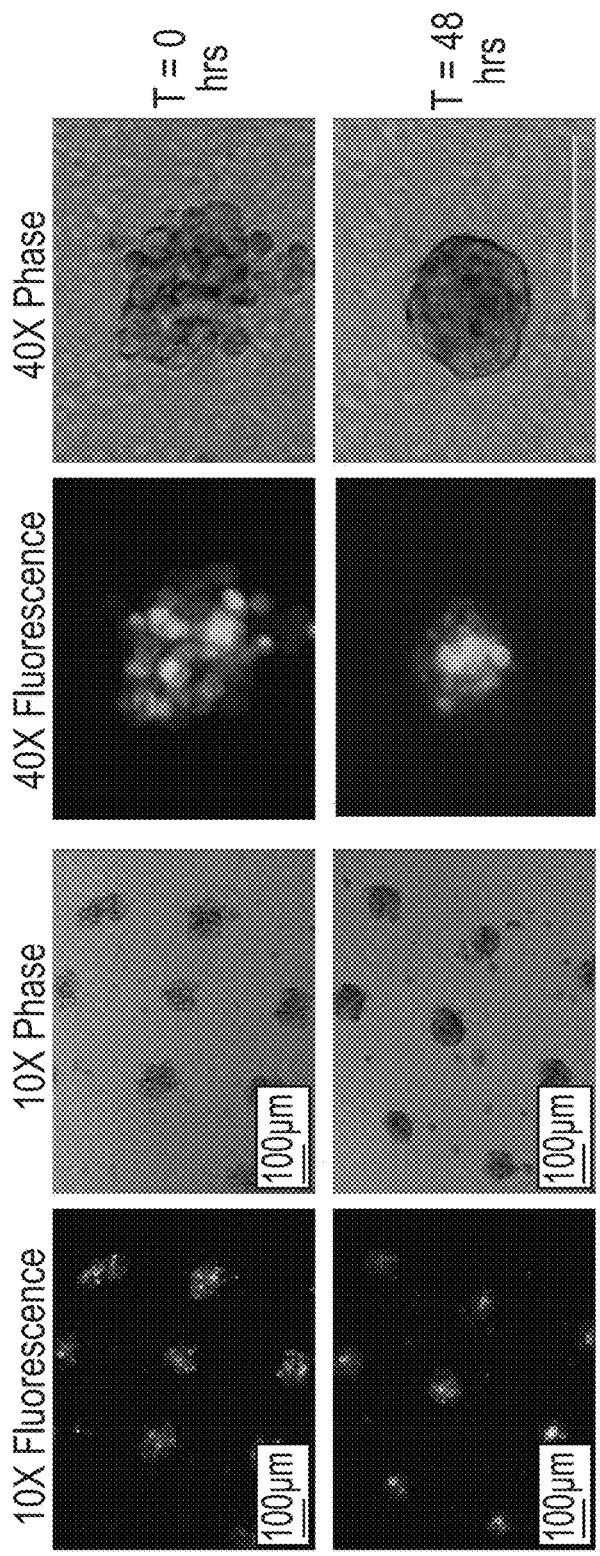
FIG. 19, Panels A-E show HMEC self-organization in matrigel. When HMECs sorted into luminal and myoepithelial lineages are assembled using the solid-phase strategies of the present disclosure, lineage specific dye (Panel A) or cell-type specific (Panel B) (i.e., K14 for MEPs and K 19 for LEP5) markers reveal the formation of a properly organized structure with LEPs in the core and MEPs in the periphery (approx. 90%). Panel C: Confocal orthogonal rendering (Z-stack) of a representative clusters in 3D (XY, YZ, and XZ planes). Panel D: Average intensity K14 and K19 signals for 10 representative clusters. Panel E: Quantification of keratin signal as a function of radial distance obtained by radially reslicing the average intensity images shown in Panel E. In Panel A, the scale bars are 100 μm. In Panel B, the scale bar is 50 μm.
Figure 19B:
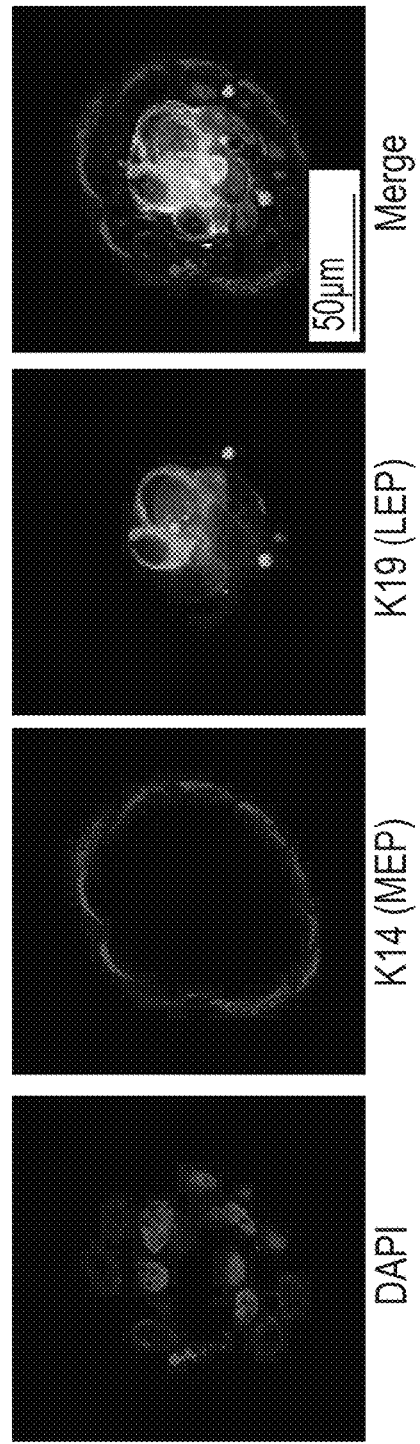
Figure 19E:
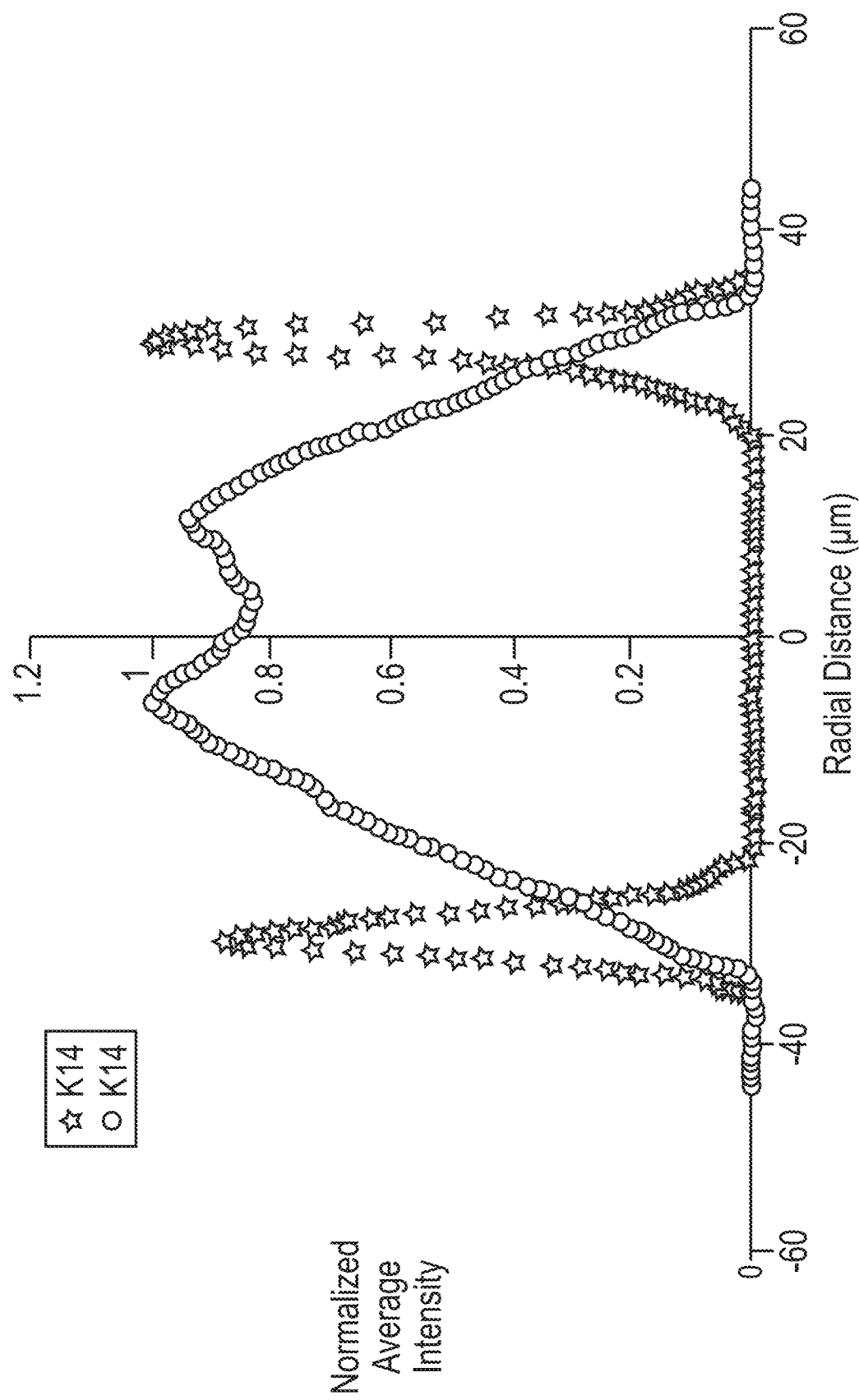

As shown in FIG. 19, Panels A-E, the solid-phase strategy not only reproduced the proper organization of LEPs and MEPs previously observed using the Sacrificial 3D Micromolding strategy but also improved the yield of cell-clusters that maintained spherical and proper organization to approximately 90%. In addition, this method allows for the encapsulation of these clusters closer to glass cover-slips thereby bypassing technical difficulties related to imaging.

Example 7

Quantification of the Ability of Myoepithelial Cell Lines to Modulate the Rate of Proliferation of Both Non-Tumorigenic and Tumorigenic Luminal Epithelial Cell Lines Via Direct Cell-Cell Contact in 3D To understand the ability of myoepithelial cell lines to modulate the rate of proliferation of neighboring non-tumorigenic and tumorigenic luminal epithelial cell lines, proof of principle experiments were performed using the non-tumorigenic MCF-10A mammary epithelial cell line and the tumorigenic MCF-10AT mammary epithelial cell line.

The solid-phase strategy (e.g., as described above) was implemented in the design of homotypic and heterotypic patterns of MCF-10A and MCF-10AT cells such that each individual cell is placed at varying distances from neighboring cells.

Paracrine Signaling of MCF-10A and MCF-10AT Cells

Two general types of experimental setups were used to distinguish between communication via soluble factors across a distance and communication via direct cell-cell contact. Towards the study of communication between cells at a distance, the solid-phase strategy (e.g., as described above) was used to pattern individual MCF-10A cells in grids of one hundred cells with distances of 60, 90, 120, and 180 microns between each individual MCF-10AT cell (FIG. 20).

Figure 21:
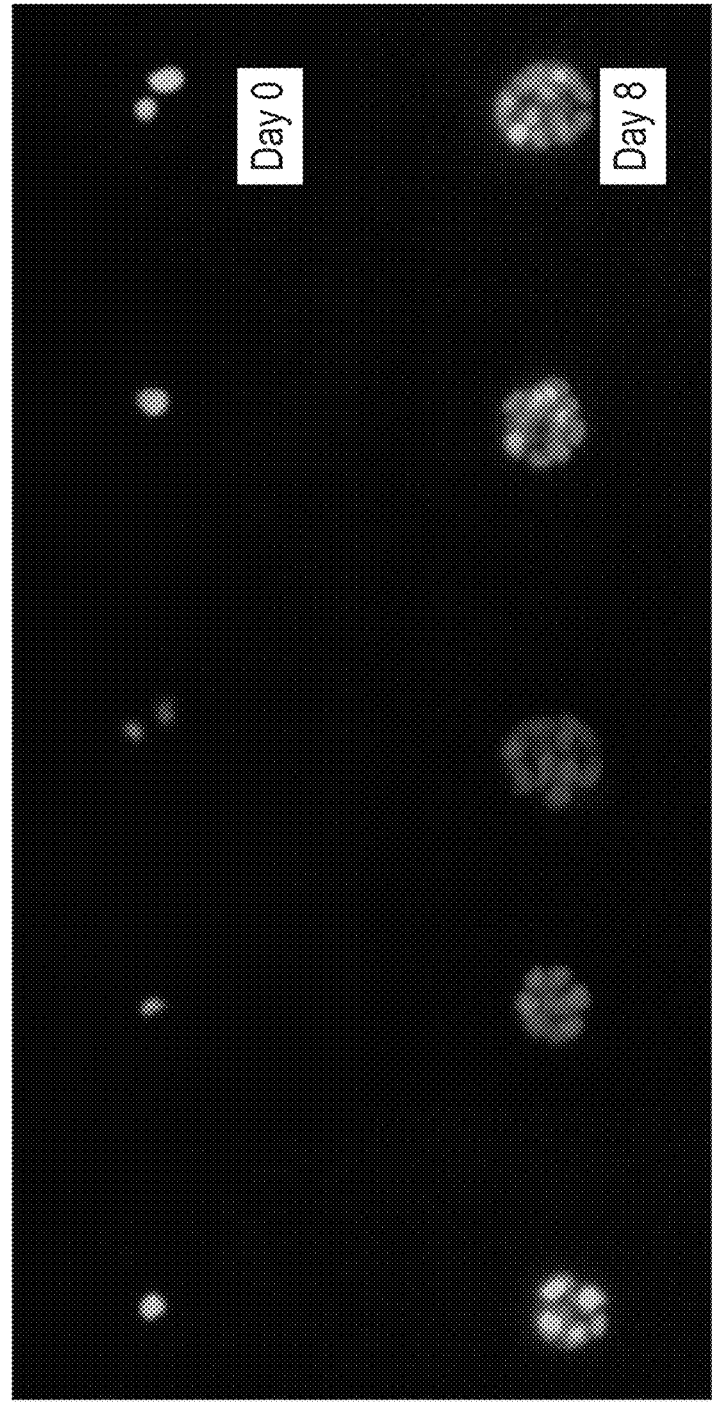
FIG. 21 illustrates a single-cell pattern of MCF-10A cells. Growth of MCF-10A tissues are unaffected by the proximity of neighboring MCF-10A tissues.

The effect of distance between neighboring tissues on tissue growth was assayed to look for a signature of pro-growth paracrine circuit. MCF-10A cells were patterned in grids of one hundred cells with distances of 60, 90, 120, and 180 microns between each individual MCF-10AT cell and then fully embedded in the middle of a Matrigel matrix that was approximately 600 microns thick. Individual cells were mostly not in direct contact, and cells that are directly touching were not measured. These patterns were then grown in 3D culture for 8 days (FIG. 21).

Figure 22:
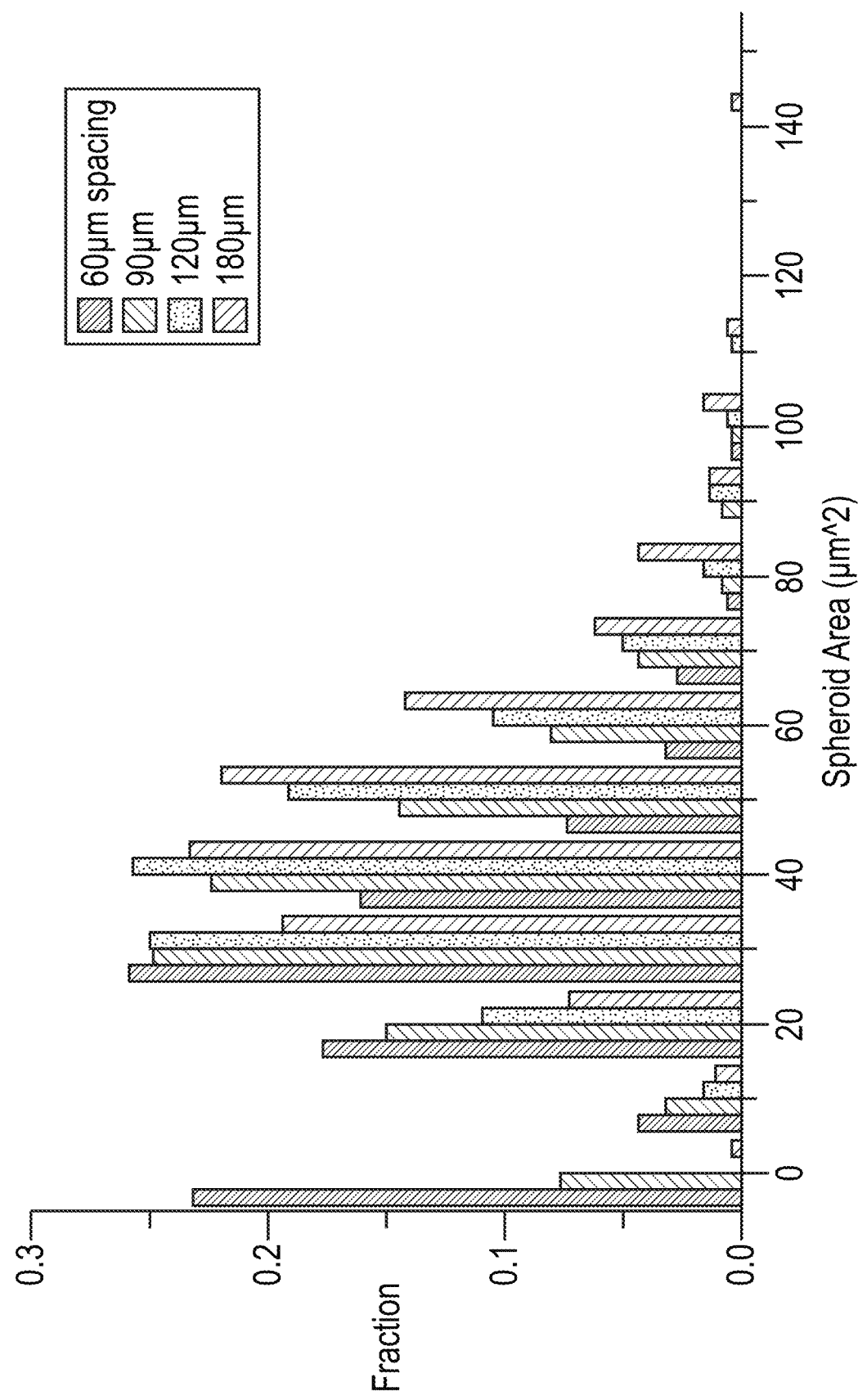
FIG. 22 shows the distribution of MCF-10A tissue growth in grids of varied spacing. Growth of MCF-10A tissues are unaffected by the proximity of neighboring MCF-10A tissues.

To assay for change in growth, images of the single cell patterns were taken at the start of the experiment and after 2, 4, and 8 days. These images were processed to measure the size of each individual tissue by determining the area of a cross section of each tissue. The areas were determined individually for each grid of tissues at a given spacing, and then averaged. The mean of tissue cross sections for a given spacing was then compared to the other grids of different spacing such that growth of tissues can be compared when the tissues were separated by distances of 60, 90, 120, and 180 microns. The distribution of areas of MCF-10A spheroids when grown at 60, 90, 120, and 180 microns from neighbors are shown in FIG. 22.

Figure 23:
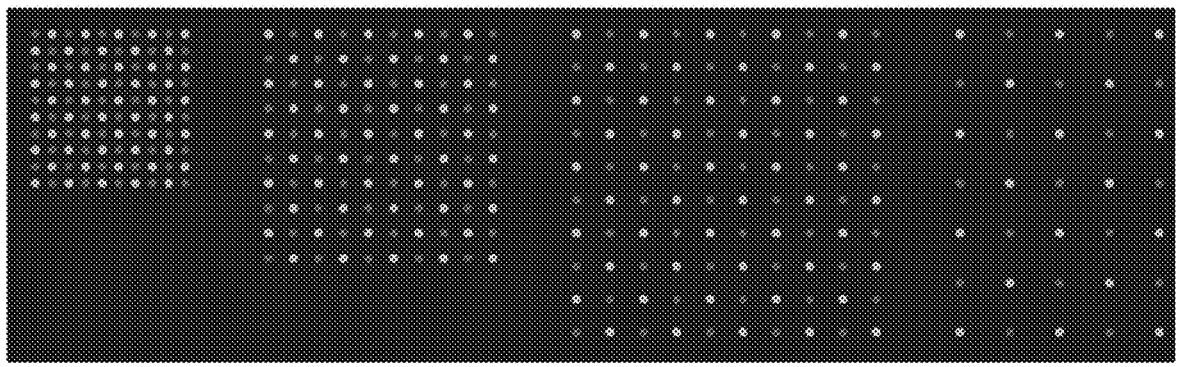
FIG. 23 is a schematic of heterotypic single cell grids of multiple spacing. Purple circles represent MCF-10A cells and green circles represent MCF-10AT cells. The largest grid has been truncated for the purpose of the figure.

The effects of the tumorigenic MCF-10AT cell line on the growth of MCF-10A tissues was explored. The same experimental setup as described above was used, with the addition of interspersed MCF-10AT within each grid of a given spacing (FIG. 23).

Figure 24:
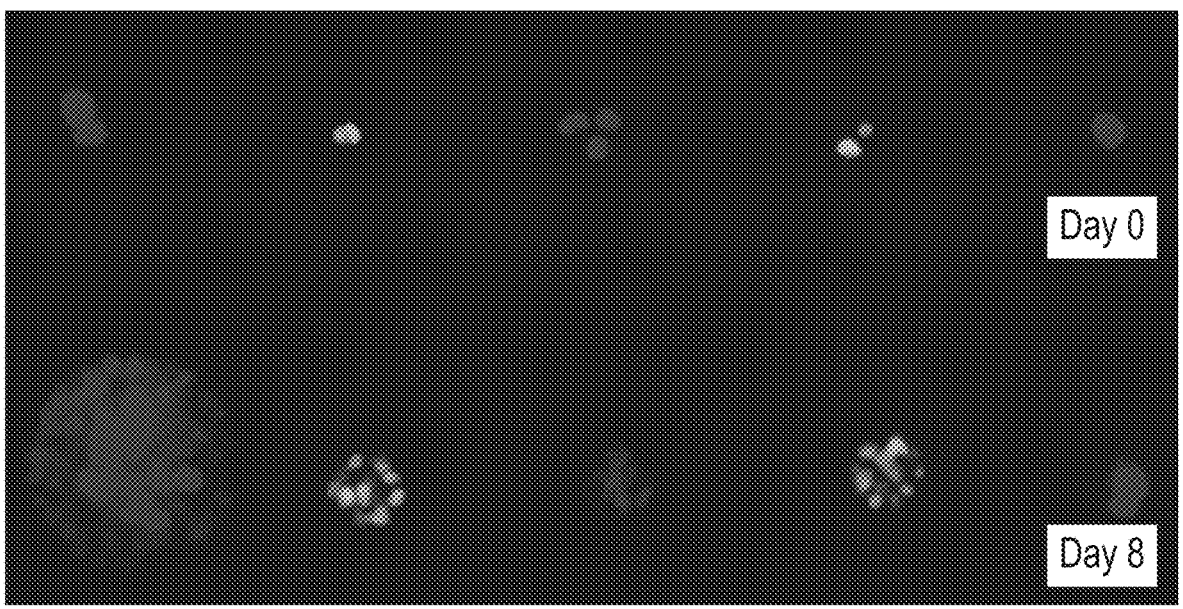
FIG. 24 shows the single-cell heterotypic pattern of MCF-10A and MCF-10AT cells. Growth of MCF-10A tissues are unaffected by the proximity of neighboring MCF-10AT tissues. MCF-10AT tissue growth shows a wide range of heterogeneity.

Surprisingly, MCF-10A tissue growth did not seem to be affected by the neighboring MCF-10AT tissues. This result was especially interesting in light of the large distribution in MCF-10AT tissue sizes that surround the MCF-10A tissues; MCF-10A tissues seemed to grow uniformly regardless of the size of neighboring MCF-10AT tissues (FIG. 24).

Direct Cell-Cell Contact of MCF-10A and MCF-10AT Cells

Figure 25:
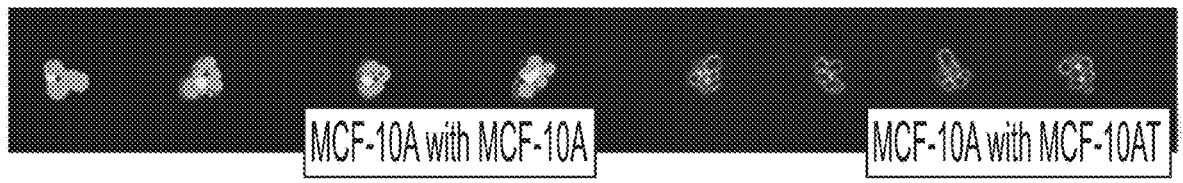
FIG. 25 contains images of assemblies of either MCF10A or MCF10AT on top of single MCF-10A seed cells. Only the seed cells have been marked with fluorescent nuclei to track the proliferation of a single cell within the tissue.

In order to observe communication between cells via direct cell-cell contact, the solid-phase strategy (e.g., as described above) was employed to create arrays MCF-10A and MCF-10AT cell assemblies of homogeneous and heterogeneous composition (FIG. 25).

Each assembly was composed of a single seed cell with a fluorescently-marked nucleus, and immediately surrounded by a layer of the same or different cell type. The DNA that bound the assemblies together forced direct cell-cell contact between the cells within an assembly. Every possible combination of MCF-10A and MCF-10AT assemblies was patterned and observed: MCF-10A seed cell with MCF-10A assembly, MCF-10A seed cell with MCF-10AT assembly, MCF-10AT seed cell with MCF-10A assembly, MCF-10AT seed cell with MCF-10AT assembly.

Figure 26:
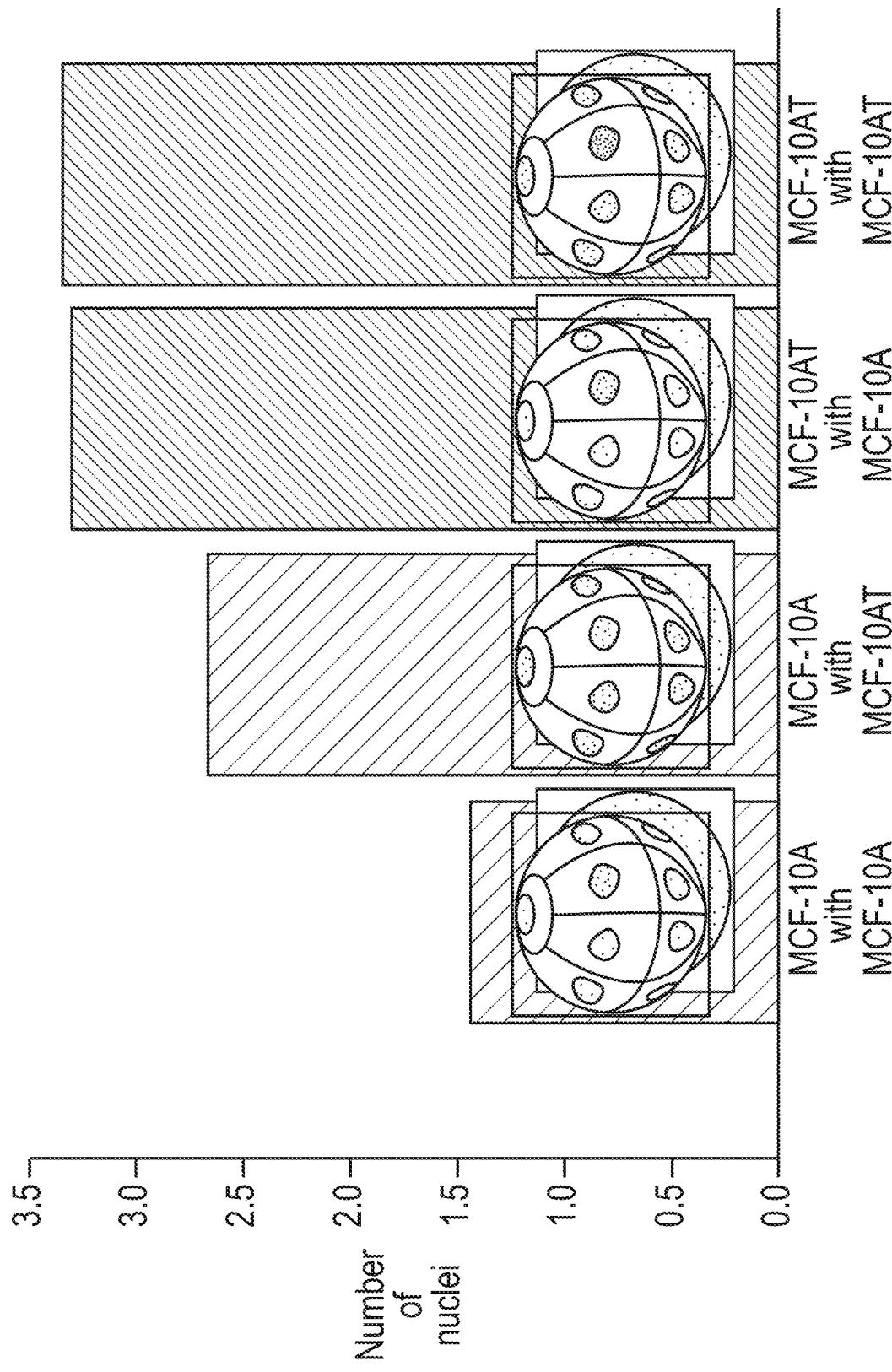
FIG. 26 is a graph showing proliferation of single seed cell after 48 hours. MCF-10A cells are colored with green nuclei and MCF-10AT cells are colored with red nuclei.

To understand the ability of the MCF-10AT cell line to modulate the rate of proliferation of MCF-10A cells and vice versa, arrays of 800 MCF-10A and MCF-10AT homogenous and heterogeneous assemblies spaced were embedded in Matrigel of approximately 600 micron thickness and grown in 3D culture for 96 hours. Each assembly was spaced 150 microns apart to minimize any possible contact that might occur due to outgrowth of the assembly tissues. Images of the array of assemblies were obtained using phase contrast and epifluorescence microscopy immediately after embedding, after 48 hours, and after 96 hours. For each assembled tissue that began with a single seed cell with a fluorescently-marked nucleus, the number of fluorescently marked nuclei within the tissue after 48 hours was determined as an assay for proliferation. Nuclei counts after 96 hours were inaccurate due to excess proliferation as well as outgrowth of the tissue in the z plane. The data summarized in FIG. 24 shows that MCF-10AT proliferation was largely unaffected by direct cell-cell contact with other MCF-10AT or MCF-10A cells whereas MCF-10A cell proliferation was influenced by direct cell-cell contact with MCF-10AT cells (FIG. 26).

Example 8

Development of an Assay for Cell Polarity in Mixed Heterotypic Cultures

Figure 27C:
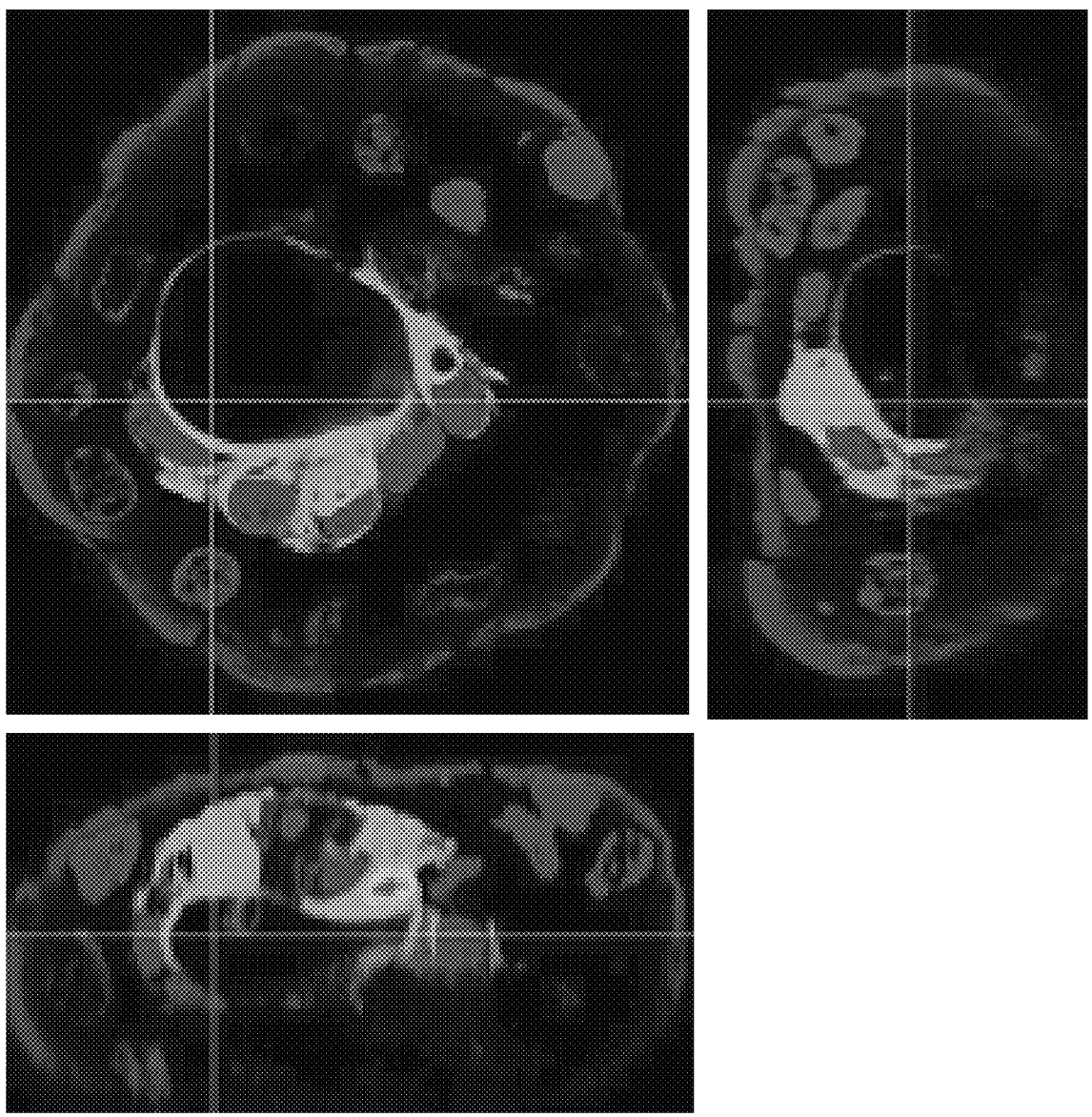
FIG. 27, Panels A-D show HMECs can reconstitute bilayered acini. When HMECs sorted into luminal and myoepithelial lineages are cultured in Matrigel for 4 days, immunohistochemistry for lineage (i.e., K14 for MEPs and K19 for LEP5) (Panels A, B, and C) and polarity (Panel D) markers reveal that these cells can reconstitute a microtissue that resembles the bilayered acinus found in vivo (approx. 50% of clusters). Panel B: average intensity K14 and K19 signals for 10 representative clusters with the quantification of keratin signal as a function of radial distance obtained by reslicing the average intensity images shown. Panel C: a confocal orthogonal rendering (Z-stack) of hollow clusters in 3D (XY, YZ, and XZ planes). All scale bars are 50 µm.
Figure 27D:
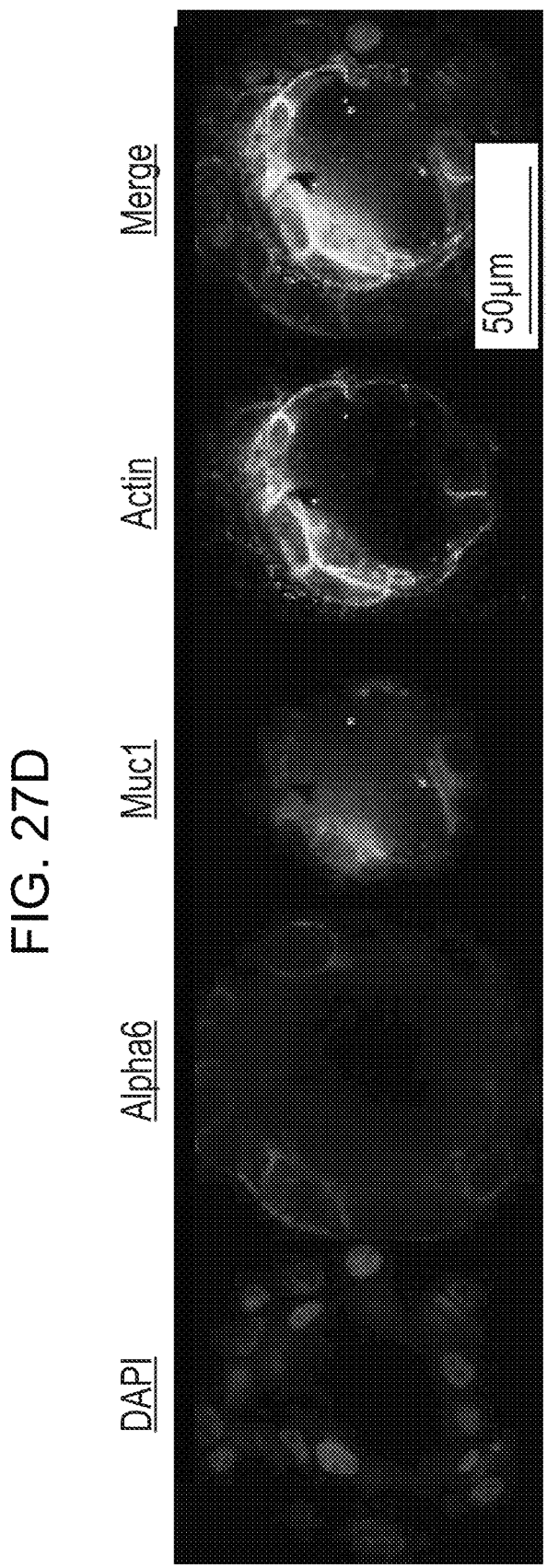

Polarity and lumen formation in the bilayered acini prepared by programmed assembly from HMEC was investigated. When FACS sorted HMECs were cultured in Matrigel for 4 days, approximately 50% of clusters were capable of maintaining proper organization and lumenizing. As shown in FIG. 27, Panels A-D, polarity markers such as Alpha 6 Integrin (baso-lateral), Mucin1 (apical), and Desmoglein2 (desmosomal) reflected the architecture found in vivo.

Example 9

Introduce Minority Populations of Tumor-Derived Luminal Epithelial Cell Lines into Multistep Structures As shown in FIG. 28, Panels A-B, the strategies described above can be adopted in order to reproducibly assemble HMEC-clusters with single cell resolution of a minority population with distinct phenotype.

Example 10

Establish Conditions for Efficient Assembly of High Viability Representative Tumorigenic and Non-Tumorigenic Human Mammary Luminal and Myoepithelial Cells Cells adhere to each other and their surroundings through the combined action of numerous adhesion molecules expressed on their surfaces. Controlling cell adhesion is challenging due to the overlapping affinity of common adhesion molecules such as integrins and cadherin for their numerous binding partners. Moreover, many adhesion molecules are also components of transmembrane signaling complexes whose activities are altered upon cell-cell or cell-matrix engagement. Therefore, simultaneously controlling cell-adhesion without inappropriately activating intracellular signaling pathways can be challenging. These observations have motivated the development of chemical means to target cells to specific physical sites independent of the native cellular adhesion machinery. These chemical technologies have applications in the preparation of synthetic tissues, immunotherapies, nanotechnology, and synthetic biology. Furthermore, the ability to selectively bind lymphocytes and other non-adherent cells to a surface without altering their intracellular milieu is useful for cell biology applications and diagnostics.

Among chemical adhesion molecules, single stranded DNA (ssDNA) is a particularly attractive candidate because it is selectively biodegradable, easy to synthesize and functionalize, has specific adhesive properties determined by Watson-Crick base-pairing, and has well defined structural and physical properties. In addition, judiciously chosen nucleic acids sequences do not cross-react with cell surface molecules or the innate immune system, and form duplexes rapidly and robustly under physiological conditions. For these and other reasons, several approaches for functionalizing cell surfaces with ssDNA have been described. Lipid-modified oligonucleotides, in particular, provide a simple and rapid method for introducing ssDNA sequences to cell surfaces. Optimization of lipid chain length led to reagents that efficiently modify cell surfaces and directed cell-cell and cell-surface adhesion. However, we also found that these lipid-modified oligonucleotides underwent slow equilibrium with the surrounding cell media, leading to gradual loss of the ssDNA from the cell surface and exchange of orthogonal sequences between neighboring cells. One potential solution to this problem was to increase the length of the alkyl chains and concomitantly, lipophilicity of the lipids, leading to stabilization of the lipid-DNA in cell surfaces. However, we found that the efficiency of partitioning lipid DNA into cell surfaces from the bulk solution was sensitive to alkyl chain length. This may be a consequence of a competing aggregation reaction of the more hydrophobic molecules in the surrounding cell media.

Due to the sensitivity of membrane insertion by DNA-modified dialkylglycerols to lipid chain length, we sought an alternative strategy to optimize the incorporation efficiency and stability of lipid-DNA conjugates to cell surfaces. We used 5'-cholesterol-modified ssDNA molecules that spontaneously insert into the outer leaflet of synthetic liposome membranes. These molecules have only limited stability once incorporated into lipid bilayers. Introduction of a second cholesterol-modified oligonucleotide as a co-anchor strand, designed to hybridize to the first adhesive strand proximal to the liposome surface, increases the net hydrophobicity of the hybridized complex, and trap the doubly modified duplex in the membrane.

We translated this general strategy from liposomes to mammalian cell surfaces and found that a co-anchor strand led to substantially more efficient cell-surface labeling compared to oligonucleotides bearing only a single cholesterol moiety. To measure the extent of DNA incorporation to cell surfaces, we incubated labeled cells with FAM-conjugated ssDNA which was complementary to the 'handle region' of the adhesion strand (FIG. 29). After washing with PBS, the resulting fluorescent signal was measured using flow cytometry, allowing us to quantify the amount of DNA retained in the cell membrane compared to our previously published dialkylglyceride oligonucleotide.

The locked dicholesterol oligonucleotides mediated efficient incorporation into cell surfaces when compared to dialkyl-modified oligonucleotides. However, cholesterol modified oligonucleotides did not offer a straightforward path towards additional optimization due to the synthetic complexity of modifying the sterol scaffolds. Therefore, we turned to saturated fatty acids as synthetically tractable hydrophobic anchors that are easily conjugated to the 3' or 5' end of amine-modified oligonucleotides using dehydrating reagents such as carbodiimides.

Similar to cholesterol modified oligonucleotides, a 100 bp ssDNA bearing a 5'-stearic acid (C18) amide (adhesion strand) did not yield significant fluorescent signal when incubated with Jurkat cells, presumably because the majority of the membrane-bound DNA-conjugate is lost due spontaneous re-equilibration with the media during washing of the cells to remove excess reagent. However, addition of a second, complimentary 20 bp oligonucleotide (co-anchor strand) with a 3' palmitic acid amide (C16) dramatically increased the cellular fluorescence to near that of the dialkylglyceride and cholesterol controls. Cellular fluorescence was dose-dependent and occurred without a change in cell viability within the range of 0.5 to 5 µM (not shown). Moreover, for fatty acids with more hydrophobicity, pre-hybridizing the co-anchor and adhesive strand, thereby generating the non-covalent complex prior to membrane insertion, also reduced cell surface incorporation considerably. These data are consistent with a model wherein lipid-modified oligonucleotides partition into the cell membrane as single strands, then hybridize within the membrane to generate a more lipophilic anchor region that stabilizes the bivalent complex in the cell surface. Thus, separating the lipophilicity of the DNA anchors onto separate molecules allows rapid insertion of monoacylated oligonucleotide but greatly slows the rate of re-equilibration into the surrounding medium by becoming a diacylated oligonucleotide in the membrane after Watson-Crick base pairing (FIG. 29).

Having demonstrated that Watson-Crick base-pairing between two FA-linked oligonucleotides stabilize the duplex at the cell membrane, we investigated how the number of base pairs forming a duplex in the lock region and the lipophilicity of the fatty acids used affected the insertion and stability of oligonucleotides. To investigate the requirements of the co-anchor duplex length on cell-surface stability, we prepared a short series of complimentary palmitic acid-modified DNA oligomers, CA1-CA3, which could form duplexes of 10, 15, and 20 base pairs with the adhesion strand. The theoretical Tm for the 10, 15, and 20 bp duplexes were 31.3, 47.4, and 54.4° C., respectively. The 15 and 20mers inserted into cell membranes with greater efficiency than the 10mer strands (FIG. 30). To confirm that duplex formation stabilized FA-modified oligonucleotides in the cells surface, rather that promoting their more rapid insertion we monitored total DNA at the cells surface over a 90 minute time course by hybridizing the adhesion strand with a complementary sequence bearing a fluorescein functionality. At 25° C., below the Tm all the oligonucleotides, the rate of decay was enhanced for the 10mer anchor strand, but similar for the 15 and 20 bp strands. However, at 37° C. the differences in the labeling efficiency became more pronounced, with the 20mer anchor strand providing significantly enhanced stability. The increase in cell surface stability with increasing duplex length is consistent with our proposed model, but could also be explained by differences in the rates of endocytosis at 25 and 37° C. To test this second hypothesis, we took advantage of the decreased fluorescence of fluorescein at the low pH of the endocytic compartment. We repeated a subset of these experiments using an oligonucleotide conjugated to Alexafluor488, a fluorophore with more stable fluorescence across the pH range of 4-8. We found a similar rate of decay of cell surface fluorescence, indicating that signal loss at elevated temperatures was due to partitioning out of the cell surface rather than endocytosis.

We hypothesized that increasing the lipophilicity of the FA anchors would reduce the partitioning of modified oligonucleotides into the surrounding culture medium, thereby increasing the total concentration of oligonucleotide maintained in the outer leaflet of the cell membrane. To test this idea we synthesized a series of 5'-amine modified adhesion strands conjugated at their 5' end to FAs with 16 to 24 methylene units. After incubating these oligonucleotides with cells, we added a 20 bp co-anchor strand conjugated to palmitic acid (C16). Increasing the length, and therefore lipophilicity, of the FA linked to the adhesion strand greatly enhanced the efficiency of labeling, providing an improvement over both the dialkyl control and cholesterol linked oligomers (FIG. 31). Consistent with these observations, we found that the kinetics of oligonucleotide loss from the cell surface after 90 minutes at 37° C. was reduced for adhesion strands incorporating more hydrophobic FAs (FIG. 31). Of the molecules tested in this panel, we found that a lignoceric (C24) FA on the adhesion strand, and a palmitic (C16) FA on the co-anchor strand provided the highest and most consistent labeling. Validating the notion that sequential addition of an adhesion and co-anchor strand minimizes aggregation in solution while maximizing stability in the membrane, pre-hybridizing the two molecules prior to addition to cells significantly reduced membrane incorporation. Although further optimization of FA length would yield additional gains in cell surface DNA incorporation, we selected this molecule for further testing to evaluate its ability to mediate cell-cell and cell-surface adhesion.

We previously demonstrated that Jurkat cells bearing a DNA-linked 16-carbon dialkylglyceride provided robust adhesion to surfaces bearing complementary oligonucleotides when incorporating a 40-80 polyT spacer between the lipophilic membrane anchor and the handle region. Presumably, the spacer allows the adhesion handle to extend above the cellular glycocalyx where it is more accessible for interactions with apposing surfaces. We tested the efficiency of surface adhesion of membrane-anchored oligonucleotides using the co-anchor strategy and found a similar trend. Even with high numbers of cell surface oligonucleotides (FIG. 32A), we found little to no surface adhesion for oligonucleotides incorporating fewer than 40 thymine nucleotides between the duplex region and the beginning of the adhesion handle. In contrast, membrane anchored oligonucleotides with more than 40 spacer nucleotides mediated efficient adhesion between Jurkat cells and aldehyde coated glass slides bearing complementary DNA sequences. We did not observe significant increases in adhesion when linker lengths were extended from 60 to 80 nucleotides (FIG. 32B). These oligonucleotides also mediated efficient adhesion between cells and complementary spots of DNA with the diameter of a single cell, allowing the efficient preparation of single cell microarrays of mouse embryonic stem cells (FIG. 32B). Based on these results, we selected a 60 poly-thymine linker for additional testing.

In addition to directing the adhesion between cells and surfaces, membrane anchored oligonucleotides can also direct the adhesion between two populations of cells. To demonstrate that the co-anchor strategy provides robust adhesion between complementarily labeled populations of cells, we labeled Jurkat cells with either red or green cell tracker dyes (Invitrogen) and labeled the each population with one of two complementary adhesion strands. We initiated programmed assembly by mixing them at a 1:60 ratio and analyzed the efficiency of assembly by monitoring the fraction of green cells attached to red cells using flow cytometry. We observed nearly quantitative assembly using the C16/C24 coanchor/adhesion strand and significant improvement relative to the C16 dialkyl modified oligonucleotides we previously reported. Only low levels of assembly were observed with mismatched controls (FIG. 33).

We also used the co-anchor strategy to prepare 3D microtissues mosaic for fluorescent protein expression. Assembled tissues were purified by Fluorescence Activated Cell Sorting (FACS) and cultured for 48 hours in laminin rich ExtraCellular Matirx (lrECM, matrigel). Consistent with our previous reports, these small microtissues quickly condensed into spherical and polarized tissues.

In conclusion, we report a more synthetically accessible and tuneable method for directing the adhesion of cells to surfaces or other cells. This strategy involves the synthesis of amine-modified oligonucleotides and subsequent coupling to saturated fatty acids on the solid phase. Though the system can be further optimized, current oligonucleotides show significant improvement over previous molecules in terms of total cell surface incorporation, stability in the membrane, synthetic ease, and adhesivity. These features facilitate efficient binding of cells to surfaces as well as cell-cell assembly without significant losses of cell viability. The structure-activity relationships for membrane insertion and stability revealed in this study are likely relevant to other hydrophobic modification to oligonucleotides used to increase the association between nucleic acids and cells.

Example 11

Optimize Conditions for the Purification of Homo- and Heterotypic Structures by Fluorescence Activated Cell Sorting (FACS)

In some cases, the precision offered by our DNA-based programmed assembly strategy might be unnecessary for generating tissues where we care only about controlling tissue size. We are therefore exploring microscale engineering approaches for assembling MEP (myoepithelial cells) and LEP (luminal epithelial cells) in microwells of different materials. We have explored sacrificial micromolding as a strategy for preparing wells from soft hydrogels for 3D culture of mammary epithelial cells. This strategy aims to address the challenge of removing PDMS or silicon molds from the soft gels like matrigel. We explored an even simpler approach—casting aggregates in agarose microwells then transferring the aggregates to matrigel for culture.

Photolithography and Micromolding.

Using the Biomedical Micro- and Nano-Fabrication Center (BMNFC) at UCSF, freestanding SU-8 features (120 µm in diameter and 80 µm tall) on silicon wafers were fabricated using common photolithographic techniques. Briefly, SU-8 2035 (MicroCheM) was spun on the substrate at a velocity of 500 rpm for 10 seconds followed by a 1250 rpm spin for 30 seconds. The wafer was then soft-baked for 5 minutes at 65° C. and for 10 minutes at 95° C., UV-exposed in contact printing with an exposure energy of 215mJ/cm2 (through a photo-mask we designed in AutoCAD and purchased from Outputcity Co.), hard-baked for 5 minutes at 65° C. and for 10 minutes at 95° C., and developed in SU-8 developer (MicroCheM) for at least 20 minutes. The patterned substrate was finally washed with isopropanol/water and baked at 150° C. for 1 hour prior to measuring pillar's height using a stylus-profilometer. The silicon master was used to create PDMS micropillars by pouring a Sylgard 184 silicone elastomer kit (Dow Corning) onto the patterned wafer using a base:crosslinker ratio of 10:1. After curing at room temperature overnight, the molded template was finally peeled off the substrate and used to imprint agarose wells via micromolding a solution of 3% agarose in 1×PBS (w/v).

Isolation of luminal (LEP) and myoepithelial (MEP) cells from HMEC4 Before isolating the two lineages by Fluorescent-Activated Cell Sorting (FACS), human mammary epithelial cells at passage 4 (HMEC4) were established and maintained in M87A medium according to previously reported methods. To lift the cells from the dish, a 10 cm dish is rinsed with PBS-EDTA and incubated with PBS-EDTA (Calcium and Magnesium free) at 37 C until cells are rounded and some are floating off the surface. The PBS-EDTA is then transferred to a collection tube and 1.0 ml of 0.05% trypsin is added to the flask and incubated for 30-60 seconds at 37° C. The flask is then tapped sharply to dislodge cells and the cells are collected in additional PBS plus soybean trypsin inhibitor.

Cells are then counted and pelleted at 160×g for 4 minutes. Pelleted cells are washed once more with PBS and resuspended in growth medium at 10^7/ml. Fluorescently tagged antibodies for CD10 (CD10-APC) and CD227 (CD227-FITC) are added to the cells and they are incubated for 30 minutes on ice. Labeled cells are washed 3× with PBS to remove unbound antibody and resuspended in FACS buffer (PBS/2% BSA/1mM EDTA). Cells are then sorted on a BD FACSAria II controlled by FacsDiva software. While LEPs are defined as CD227+/CD10−(Muc1+/Calla−) cells, MEPs are defined as CD227−/CD10+(Muc1−/Calla+) cells.

Cell Staining Using Cytosolic Dyes.

Sorted LEPs or MEPs were suspended in 10 mL of PBS and incubated with either 1uL of either Cell Tracker Green (CTG, Invitrogen) for LEPs or 1uL of Cell Tracker Red (CTR, Invitrogen) for MEPs for 5 minutes at 37° C., palleted, and resuspended at a concentration of 1 million/mL in M87A.

Loading Cells in Microwells and Transferring Cell-Clusters to Matrigel.

Homotypic or heterotypic populations of stained or unstained cells are centrifuged into the wells at 160×g for 4 minutes. Excess cells are then washed away with medium and the remaining physically confined cell-aggregates are finally monitored for self-organization patterns by time lapse microscopy or immunohistochemistry. For monitoring self-organization patterns in matrigel, cell-aggregates are allowed to compact into scrambled cell-clusters (at least 5 hours for HMEC4 and at least 1 day for Primary Epithelia) before carefully resuspending the clusters in 15 mL of PBS, centrifuging at 160×g for 4 minutes, discarding the excess volume, and depositing as many clusters as possible onto a thin layer of solid Matrigel. After allowing the clusters to deposit onto the gel for 10 minutes, an additional layer of liquid matrigel is overlaid on top and allowed to set for at least 20 minutes at 37° C. before adding M87A medium.

Example 12

Establish Protocols for Longitudinal Imaging Using Genetically Encoded Reporters and Immunofluorescent Staining for Lineage Specific Markers of Assembled Structures in Reconstituted Basement Membrane (Matrigel) and Collagen Gels We have used live cell imaging to monitor how MEP and LEP self-organize as random populations on top of a slab of matrigel. We have applied our various assembly strategies to monitor LEPs and MEPs as they self-organize while fully embedded in matrigel.

Finite lifespan HMEC were FACS sorted into luminal (LEP) and myoepithelial (MEP) populations based on expression of the lineage specific cell surface markers Muc1 and CD10. HMEC were cultured in M87A medium supplemented with 0.1 nM oxytocin until just confluent and lifted by treatment with PBS-EDTA followed by a trypsin pulse. Purified LEP and MEP were labeled with cell tracker green and red respectively, and assembled using a programmed assembly strategy. Cells were fed with M87A medium. Cultures were imaged by phase contrast and fluorescence microscopy every 30 minutes to monitor self-organization (FIG. 35).

Example 13

Develop a Multistep Synthetic Scheme for Assembling Collections of Cells into Small Heterotypic Tissues with the Connectivity of the Human Mammary Gland We have made the intriguing observation that E-cadherin expression level differences between LEPs and MEPs do not determine the ultimate architecture of human mammary epithelial tissues.

We found that E-cadherin is overexpressed at the protein level on luminal epithelial cells, but that E-cad transcripts are seen at similar levels in MEPs and LEPs. P-cadherin, in contrast is overexpressed in the MEP lineage, both at the protein and mRNA levels Explore a Solid-Phase Strategy as an Alternative Means of Preparing Multistep Tissues Composed of Human Mammary Epithelial Cell We improved a solid phase approach for templating tissue assembly. We significantly extended the functionality of this method to build a variety of tissue architectures relevant to the human mammary gland. Those are described briefly here.

Using a molecular writing tool, we pattern ssDNA on chemically activated glass (FIG. 36). Covalent linkage of amine-modified DNA with an aldehyde-silanized glass surface occurs using a selective reducing agent, sodium cyanoborohydride. The resulting surface is passivated against cell adhesion using a combination of aldehyde reduction, hydrophobic silanization, and blocking with Pluronic F108. A flow cell is constructed over the patterned, passivated glass surface. Cells are labeled with complementary ssDNA and attached to the surface via DNA hybridization. These cells serve as the scaffold for microtissue assembly via the hybridization of additional cells.

Assembled microtissues are embedded in a gel, such as 9 mg/mL Matrigel, containing DNase. The gel retains the structure of the microtissue while the DNase cleaves the linkages between the microtissue and the glass. After DNase action, the gel can be peeled away from the glass, retaining the viable, patterned microtissues. This gel can be transferred into growth medium for long-term observation of the microtissues.

Solid-phase programmed assembly offers the capability to combine top-down patterning with bottom-up assembly. Practically, this means that we can use relatively simple patterns to nucleate the assembly of more complicated microtissues. The capacity to do this is essential because the complexity of genuine tissues dwarfs the complexity achievable by patterning technology alone, and it allows us to produce 3D structures from 2D patterns. We have demonstrated this basic capability. Further, we have substantially improved the diversity and complexity of 3D tissues that can be faithfully constructed using solid-phase programmed assembly. The outline of this technique is included below:

The functional properties of tissues arise through a multiplicity of interactions between cells and their surrounding microenvironment. Interactions occur in the context of specific tissue structures that serve to organize the flow of chemical, electrical and mechanical information between cells. Defining relationships between these tissue structures and their function is a major goal of developmental biology and a requirement for successful application of tissue engineering to regenerative medicine. However, connecting structure to function can be difficult because tissues are complex, containing numerous cell types arranged into three-dimensional structures that are difficult to control a priori. Therefore, means of reconstructing complex tissue architecture, across multiple length scales, and from simpler building blocks will facilitate this goal.

Reconstruction of tissue architecture from individual cells poses several challenges from a synthetic perspective. First, the local microenvironment of each cell must be defined with sufficient detail so that the tissue's own homeostatic mechanisms can finish the job. Since the fundamental length scale of tissues is that of a single cell, this requires means of rebuilding tissue architecture with single cell resolution. When such fine resolution is required, bottom-up (self-assembly) methods provide superior resolution without compromising scalability and speed. Second, the function of many tissues requires the combined interactions of cells locally with other populations over larger distances spanning hundreds of microns to millimeters. These long-range interactions are difficult to control using self-assembly, but are more easily manipulated using top-down, printing or microfabrication methods. To simultaneously address these challenges to synthesizing tissue at high resolution, combining self-assembly with top-down patterning approaches would be advantageous.

We envisioned such a strategy for rapidly prototyping multiscale 3D tissue cultures beginning with cellular "zip-codes"—patterns of DNA sequences directly printed on a solid surface at the resolution of a single cell (FIG. 36). When combined with recently described methods for introducing synthetic oligonucleotides to cell surfaces, the DNA "zip codes" program the self-assembly of a pattern of cells onto the substrate. Additional rounds of programmed assembly then construct tissue architecture into the third dimension and proceed through step-wise addition of cell types bearing the appropriate DNA sequences on their surfaces. Each cell type's x, y, and z position is encoded by its order of addition to the assembling tissue, and its cell-surface DNA sequence. Upon completion of tissue assembly, transfer of the resulting 3D cellular pattern to physiologically relevant extracellular matrices (ECM) results in a structured tissue of unprecedented detail and complexity.

To implement this strategy, we prepared a simple bitmap image of a cellular pattern with Microsoft Paint designed to control the local architecture of three cell types with 10 µm resolution. The image consisted of repeating triangular subunits, 34 µm on the side, and with vertices corresponding to 3 distinct DNA sequences (FIG. 37). We rendered this pattern in 8 µm DNA spots by direct molecular writing using a Bioforce NanoeNabler. The NanoeNabler prints features with the requisite fidelity at a frequency of 1-10 Hz. Therefore, a 10,000 feature pattern requires several tens of minutes to several hours to print, depending on its complexity. To assemble a simple 3D tissue culture, we constructed a PDMS flow cell above the DNA pattern and passivated the surface to non-specific adhesion by treatment with a hydrophobic silane and then pluronic F108. Subsequent addition of human mammary epithelial cells bearing cell surface DNA sequences complementary to one of the triangle vertices led to rapid cell adhesion to the corresponding DNA "zip-code" on the glass surface. Washing with PBS rapidly removed all non-adherent cells, allowing the addition of a second and then third population of cells bearing the appropriate cell-surface DNA sequence to complete the cellular pattern. Self-assembly occurs quickly, and multiple rounds of assembly and washing are easily accomplished in a period of minutes. To release the pattern for culture in 3D, we then filled the flow cell with liquid matrigel containing high activity DNase. Setting of the gel occurred concurrent to DNA cleavage by the nuclease. Removal of the cell pattern and subsequent matrix underlay resulted in a fully embedded 3D cell pattern containing three unique cellular features with precisely defined spatial positions. Image analysis revealed that the pattern had the expected average center-to-center spacing of 34 m that was retained with high fidelity after 24 hours of tissue culture.

To further demonstrate a spatial resolution below that of a single cell, we changed the average spacing of vertices to 18 μm. This configuration places neighboring cells in direct contact, rather than separated by a thin film of lrECM. Consequently, these patterns condense into small epithelial tissues with exactly 1 red, 1 green, and 1 blue cell after transfer to lrECM and 24 hour culture (FIG. 37). Thus, direct molecular writing of DNA, when coupled with DNA-programmed assembly and transfer to ECM, allows the reconstruction of tissues with precisely defined compositions, while also allowing the identity of neighboring tissues to be controlled with cellular resolution.

As a purely chemical method, we found that this rapid tissue prototyping technique is generalizable to multiple cell types and extracellular matrix compositions. For example, we successfully patterned square grids of neurons, epithelial cells, fibroblasts, endothelial cells, and lymphocytes with high resolution and yield. Similarly, we successfully transferred cellular patterns of MCF10A cells to gels of diverse chemistries, including laminin rich extracellular matrix (lrECM, or matrigel), lrECM/collagen mixtures, agarose, and fibrin. In principle, any biocompatible liquid pre-polymer that can be set around live cells is compatible with this method.

Printing single cells for 3D culture at high resolution provides a foundation for the programmed assembly of more physiologically relevant cell dense tissues that would be extraordinarily time consuming to print one cell at a time. Printed cells retain their cell surface DNA, which provides a substrate for subsequent steps of DNA-programmed assembly to reconstruct the surrounding tissue into the third dimension. For example, we assembled populations of MCF10A cells above single cells, or groups of exactly three cells to make small epithelial spheroids for 3D culture. Similar to our previous findings, these assembled aggregates rapidly polarize once transferred to Matrigel, positioning the basal adhesion machinery next to a laminin rich basement membrane. In addition to spheroids assembled above single or small groups of cells, we extended this general strategy to assemble duct-like tissue architectures above lines of printed cells. For example, a line of MCF10AT cells was elaborated through 4 rounds of programmed assembly and then transferred to a matrigel/collagen mixture where they condensed into cylindrical tissues resembling epithelial ducts (FIG. 38). The same strategy can be applied to components of the stroma such as vasculature. We reconstructed a contiguous centimeter of a 3D culture endothelial (FIG. 39).

These spatially patterned cell-dense tissues provide quantitative control over cell number and composition of each tissue and over large distances. Therefore, they provide a useful framework for quantitatively studying cell-cell and cell-tissue interactions within and between neighboring tissues. In the human breast, malignant, premalignant, and normal cells often grow within tight proximity at the margins of carcinomas but it is unclear whether these cells communicate autonomously with one another across the intervening ECM. We used this rapid tissue prototyping technique to build structured co-cultures to measure how premalignant MCF10AT cells affect the growth of WT MCF10A cells when within the same tissue, or when separated by only 10-50 μm of matrigel. We tracked the growth of single WT or Ras H2B-GFP expressing cells when placed within or next to tissues of the same or different type (FIG. 40). Interestingly, we found that WT cells did not significantly affect the growth of MCF10AT cells over the 48 hours of the assay when compared to homogeneous tissues. However the converse was not true—MCF10AT cells significantly increased the growth of WT cells when combined in the same tissue. We also found that a thin membrane of lrECM separating WT and MCF10AT tissues was sufficient to completely block this effect, as single MCF10A cells did significantly change their growth when MCF10AT tissues were growing at a center-center distance of 120 μm (~50 μm edge-to-edge). Thus, these results would indicate that epithelial tissue compartmentalization provides an effective strategy to block the autocrine/paracrine pro-growth effects of premalignant lesions of the type mimicked by MCF10AT cells.

These data contrast with similar experiments conducted with E7 expressing MCF10A cells. E7 cells grow more quickly than WT cells but similar to MCF10AT cells, still form growth arrested and hollow acini after 16 days in matrigel. We grew E7 and WT cells together and found that WT cells actually enhance the growth of E7 expressing cells over 8 days, while E7 expressing cells decrease the survival of their E7 expressing neighbors (FIG. 41).

The specificity and addressability of DNA-hybridization, when combined with the ability to control the order of addition of cells to the assembling tissue, also provides an unprecedented means of controlling the position of cells in the x, y, and z direction simultaneously. For example, many epithelial tissues have a closed topology consisting of an outer layer of a basal cell type, surrounding a central core of a luminal cell type that would be impossible to prepare without x, y and z control. This organization is epitomized by the human prostate, salivary, apocrine, and mammary glands. In the latter tissue an outer layer of myoepithelial cells (MEP) surrounds and inner layer of luminal epithelial cells (LEP). By combining the logic of DNA-hybridization with the controlled order of addition of cells, we reconstructed this key 3D tissue architecture from limited lifespan human mammary epithelial cells. We first printed a bull's-eye pattern of two DNA sequences on a solid support, and then prepared two populations of MEPs labeled with corresponding complementary sequences (FIG. 42). Step-wise addition rendered the DNA pattern in MEP. We next prepared two populations of LEP bearing cell-surface oligonucleotides corresponding to the sequences used to assembly the core of the bull's-eye. Three rounds of DNA-programmed assembly alternating between the two labeled LEP populations prepared the core of the mammary epithelial tissue. A final round of DNA-programmed assembly coated the outer layer with MEP prior to release into matrigel with DNase. Confocal microscopy revealed the resulting tissues had the correct 3D architecture after transfer and that it was retained after 24 and 48 hours in culture.

This general strategy also allows for the assembly of extended, tube-like epithelial architectures that incorporate subpopulations of cells with unique signaling status at precise locations. Distinct subpopulations of epithelial cell may emerge within tissues as a consequence of spatial heterogeneities in microenvironment—for example through chemical or mechanical gradients. We simulated these spatial patterns by preparing 3D tubular epithelial structures incorporating differentially stained red and green mammary epithelial cells. DNA-logic allows the placement of these cells at any position within a tubular structure. In a single experiment we prepared homogeneous epithelial tubes, as well as tubes incorporating subpopulations at the ends, the middle, as stripes, or as random or structured gradients across the length of the tube. In all cases, the chemically adhered cell tubes condensed rapidly in matrigel/collagen mixtures into 3D cylindrical structures after 24 hours in culture. Together, these experiments demonstrate that programmed assembly from surfaces enables the assembly of tissue culture architecture comprising multiple cell types, at high resolution, and across three dimensions. Thus these rapid tissue prototyping tools provide a powerful toolkit for dissecting the relationship between tissue structure and function in 3D tissue culture.

To demonstrate how rapid tissue prototyping can be used to build structure/function relationships in 3D culture, we investigated how tissue architecture constrains epithelial/stromal interactions between a premalignant mammary epithelial spheroid and non-transformed fibroblasts. Fibroblasts are critical components of the chemical and mechanical epithelial microenvironment, secreting a number of soluble paracrine factors and remodeling the collagen rich ECM. As a consequence, their individual properties, as well as their arrangement in three-dimensional space, can have profound consequences on the behavior of nearby epithelial tissues, inducing their outgrowth during morphogenesis, or invasion during tumor progression. The ability of fibroblasts to contract the ECM surrounding epithelial tissue has gained particular attention. For example, fibroblasts contract 3D collagen gels. Similarly, tumor associated fibroblasts have been shown to potentiate the outgrowth of premalignant epithelial spheroids in collagen rich gels by aligning collagen. In Wnt-1 driven mouse mammary tumors collagen is similarly aligned at the margin of invasive, but not non-invasive tumors. Thus, we hypothesized that fields of fibroblasts perpendicularly aligned to the edge of a premalignant epithelial tissue would enhance collagen alignment and potentiate epithelial cell invasion and dissemination (FIG. 44).

To test this idea we prepared large aggregates of premalignant MCF10AT flanked by lines of single fibroblasts oriented perpendicularly to the spheroid edge.

Computational modeling using the COMSOL multiphysics software package indicated that this arrangement would generate directional tension fields in the proximity of nearby epithelial spheroids. The entire pattern was embedded in lrECM containing 2 mg/ml collagen-I. Within 24 hours in culture, we observed the appearance of features in the gel between fibroblasts and the epithelial aggregates that, at higher magnification and contrast, revealed extensions of the cell membrane—possibly invadipodia—extending from the aggregate surface towards the line of fibroblasts. These features became more prominent over the subsequent 48 hours such that approximately 50% of the tissues manifested these features, while fewer than 10% of tissue showed these features in the absence of fibroblasts. In fact, by 48-72 hours, 25% of the tissues began to invade the surrounding ECM, always in the direction of the nearby fibroblasts lines. This 3D tissue rapid prototyping tool will be the foundation for future studies to relate the structure of cellular networks to their function.

Example 14

Assembly of Appropriate Cell Lines into Multistep Tissues

Since the physical organization of luminal and myoepithelial cells into a bilayered architecture is a prerequisite for normal glandular function and the suppression of disease, we have deeply analyzed the factors that influence the proper organization of the mammary gland. We have performed the detailed characterization of the physical rules guiding the self-organization of luminal and myoepithelial cells into specific physical location in the mammary gland. Our findings have been extraordinarily interesting. Briefly, we've found that the gland has evolved a remarkable strategy to render LEP/MEP self-organization robust to all kinds of perturbations or cell-to-cell variability. This finding is remarkable, since previously it was believed that self-organization occurred according to the rules of Malcolm Steinberg's differential adhesion hypothesis. Our findings are included below:

Morphogenesis is a multistep process that derives from a hierarchy of cellular interactions that cascade to form a specific three-dimensional tissue architecture. However, a prerequisite of all steps of morphogenesis is the need for cells to achieve the correct physical position within a tissue. The capacity of two or more populations of interacting cells to autonomously self-organize is therefore a fundamental property of metazoan tissues that contributes to structure formation during development, tissue breakdown during cancer progression, and the reconstitution of engineered functional tissues in vitro. Most models of autonomous tissue self-organization require that the interacting populations of cells have clear differences in physical properties—for example motility, contractility, cohesivity, or interfacial tension—that drive each cell type to unique physical location relative to their neighbors. However, many populations of cells can be heterogeneous in these properties, blurring the differences that are necessary to drive self-organization robustly towards a single tissue configuration. The extent to which such heterogeneity can actually impair self-organization in human tissues and other organisms has not been investigated. Consequently, little is known about control strategies used by tissues to render self-organization robust to perturbations and variability in cell physical properties.

To identify strategies of self-organization that are robust to perturbations or cell-to-cell variability, we chose as a model system glandular epithelial organs such as the submandibular, prostate, and mammary glands. These tissues possess two clearly defined epithelial compartments, consisting of a basal population surrounding luminal cells, both of which are encased in extracellular matrix. This basic three-dimensional architecture is retained during morphogenesis, normal tissue function and homeostasis, and even the early stages of malignant disease. Such conservation of tissue architecture through time and space suggests a robust underlying program for structure formation and maintenance. Consistent with this notion, several of these tissues have been shown to self-assemble in biomimetic microenvironments, and mammary epithelial cells have been shown to self-organize by differences in interfacial tension. However, a hallmark of these tissues is also their heterogeneity. For example, the luminal population of the mammary gland has well documented heterogeneity in processes likely to affect self-organization, such as signaling pathway activation, expression of cytoskeletal polymers and adhesion molecules, and numerous other markers of differentiation. How this heterogeneity affects the ability of luminal and basal cells to autonomously self-organize is unclear.

To build an intuition for how heterogeneity affects self-organization, we implemented a computational model that evaluates the impact of heterogeneity on the autonomous self-organization of two interacting cellular populations into a bilayered architecture based on each cell type's preference for different types of neighbors (FIG. 45). When the model is programmed with neighbor preferences drawn from narrow distributions following the rule aa>ab>bb, self-organization is efficient. However, when preferences for each cell type are drawn from populations with identical average properties but with higher variance, we observed a loss of robust self-organization similar to what would be expected from changing the mean properties of each population. In general we found that as the ratio of sigma:du increased, the efficiency of self-organization dropped.

We next tested the capacity of primary human luminal and basal epithelial cells to autonomously self-organize (FIG. 46). We prepared purified populations of luminal (LEP) and myoepithelial (MEP or basal) cells from reduction mammoplasty tissue by fluorescence activated cell sorting (FACS) according to lineage specific luminal (Muc1) and basal (Cala) cell surface markers. Purified cells were reconstituted at a 50:50 ratio in inert 120 μm agarose microwells to initiate self-organization. After 24-48 hours, aggregates were fixed and stained for keratin-14 (basal) and 19 (luminal) expression to visualize their final configuration. In stark contrast to previous reports, we did not observe a single predominant three-dimensional organization of the reconstituted epithelial spheroids. Rather, a spectrum of organizations were observed, including correct, inverted, phase separated, and scrambled architectures. Similar results were obtained using purified populations of healthy basal and luminal cells from human prostatectomies. Average intensity maps from 20-30 aggregates revealed no enrichment for luminal or basal cells at internal or peripheral positions in either tissue type.

We next repeated the assay, but analyzed the capacity of each tissue type to self-organize as aggregates fully embedded in laminin-rich extra cellular matrix (lrECM, Matrigel). In contrast to agarose, epithelial spheroids in lrECM underwent a dramatic reorganization, with the majority possessing the correct three-dimensional organization after 48 hours—having a core of luminal cell surrounded by a cortex of basal cells. Average intensity maps from 20-30 aggregates revealed clear enrichment for the basal population around the periphery of the spheroids, with enrichment for the luminal population in the core. Similar results were obtained using epithelia isolated from human prostates. One explanation for this dramatic shift in tissue configuration is that epithelial cells have been reported to up-regulate basal markers when in contact with lrECM. To exclude this possibility, we altered the assay, using primary luminal and basal cells first treated with live cell fluorescent green and red dyes, respectively, and counted the distributions of tissue configurations using wide field fluorescent microscopy. Again, we found a pronounced enrichment for tissues identical or similar to the correct configuration in matrigel, while we found little preference for any specific configuration in agarose. Taken together these observations suggest that the properties of the ECM can influence the outcome of self-organization.

Given that mammary epithelial cells had previously been shown to self-organize through a process involving cell adhesion molecules, and given the differential interaction between pHMEC and matrigel coated surfaces, we hypothesized that a physical interaction between basal cells and the surrounding ECM provides a dominant directional cue to MEPs, driving self-organization towards a single correct configuration despite heterogeneity in the strength of cell-cell interactions within the luminal and basal lineages.

To explore this hypothesis in greater detail, we expanded primary human mammary epithelial cells through four passages creating a more homogeneous and renewable cell system that additionally enables targeted genetic manipulations and single cell biophysical analysis. The common extracellular microenvironment retains lineage specific markers yet renders each lineage more homogeneous with respect to other markers of differentiation relative to primary tissue. Fourth passage HMEC retain the capacity to self-organize in matrigel, forming the correct architecture greater with over 90% efficiency. Properly organized aggregates further go on to form bilayered lumenized structures after an additional 72-hours in lrECM.

Since changes in interfacial tension are believed to drive self-organization in the mammary gland, we first used this cell system to characterize difference in interfacial tension among homotypic aggregates. Large differences in interfacial tension between cell-cell and cell-medium interfaces have been shown to result in aggregates with more circular cross sections, expanding cell-cell interfaces to as to minimize cell-medium interfaces. Comparing the ratio of the circumference of basal and luminal cell aggregates to that of a circle revealed that basal cells were significantly more circular than luminal cells, and thus, release more significantly more interfacial tension upon forming cell-cell contacts (FIG. 47). In contrast, comparison of circularity of primary luminal and basal cell aggregates showed little difference in the circularity of homotypic aggregates, yet large tissue-to-tissue variability.

We extended this analysis to the single cell-level and measured the relative pairwise interaction preferences of luminal and basal cells. To do so, we measured the contact angle between homo and heterotypic cell pairs after several hours in small non-adherent microwells. The magnitude of the contact angle is related to the size of the interface buried at the cell-cell junction. Previous AFM measurements revealed the cortical tension in LEP and MEP HMEC4 culture fall into a similar range. Thus, contact angle provides a measure of the surface tension released upon cell-cell contact formation, and thus, the relative preference for forming different cell-cell interfaces. Consistent with the circularity measurements, we reproducibly found that basal cells formed the largest cell-cell interface, and thus had the larger contact angle, followed by the heterotypic basal-luminal cell interactions, and finally the luminal-luminal interaction. Although the differences in these values were statistically significant, they were not large.

We additionally measured the contact angle between luminal cells, basal cells, and the underlying ECM. We coated glass coverslips with lrECM and then a thin film of quantum dots to mark the matrix/liquid interface. Luminal and basal cells were then allowed to adhere and spread on the interface and the contact angle measure in the x/z and y/z directions using confocal microscopy. Consistent with the predictions of the model, the cell-ECM contact angle for basal cells was pronounced, several fold larger than the cell-cell contact angle. Moreover, luminal cells hardly interacted with the ECM, having an average contact angle near the lower limit of detection for the assay. Together, these data are consistent with the hypothesis that a release of interfacial tension between MEPs and the ECM is the dominant interaction directing self-organization of mammary gland and other bilayered epithelial tissues.

To further explore the implications of this hypothesis, we elaborated the computational model to include the measured preferences of HMEC4 for forming homo and heterotypic cell-cell interfaces, along with a surrounding ECM. We represented ECM as a third population of non-motile cells surrounding the tissue. Including this third population of non-motile cells gives rise to two new W values between each cell type and the external ECM. We modeled self-organization using the measured interaction preferences (W) for HMEC4:

MEP/ECM>>MEP/MEP>MEP/LEP>LEP/LEP and LEP/ECM=0.

This course-grained model reproduced the self-organizing behavior of HMEC4, despite the higher W of the MEP:MEP interaction relative to the LEP:LEP interaction. The model was also consistent with our results using primary cells, predicting robust self-organization even upon increasing cell-to-cell variability in LEP:LEP and MEP:MEP W to well beyond what triggered breakdown in the absence of ECM.

Further exploration of parameter space around those measured for HMEC4 revealed a striking sensitivity to perturbations to the MEP:ECM interaction, with an equally striking robustness to perturbations to individual cell-cell interactions. To test sensitivity to self-organization to a sharp reduction in MEP:ECM interaction, we directed HMEC4 self-organization in non-adhesive agarose microwells. Unlike pHMEC, MEP and LEP isolated from HMEC4 cultures have more homogeneous properties, possessing clear differences in interfacial tension with the media, with MEP exhibiting significantly higher interfacial tension. Thus, loss of MEP-ECM adhesion would be predicted to result in the efficient formation of an inverted architecture, rather than a distribution of architectures as observed in pHMEC. Remarkably, purified populations of LEP and MEP cells isolated from HMEC4 self-organized into the expected inverted architecture in over 90% of aggregates. The inverted architecture was not a consequence of a particular chemical feature of agarose, as identical results were obtained in microwells formed from other non-fouling materials such as PEG-diacrylate or polyacrylamide.

To further confirm that the inverted tissue architecture was a consequence of a loss of integrin association the ECM, we sought additional perturbations that would block MEP-ECM interactions. MEP express a palette of integrins, and we found that KD of single integrin subunits expressed by MEP such as alpha-6 or Beta-1 did not have a pronounced effect on MEP-ECM contact angle or self-organization. However, we hypothesized that knock-down of Talin-1, a key adapter protein that facilitates the coupling of actin cytoskeleton with the full family integrin receptors, would decouple cell contractility from adhesion with the ECM.

Thus, cells lacking Talin-1 should be incapable of spreading and contracting against the ECM. To test this idea we used pooled siRNA to KD Talin-1, and confirmed KD by western blot. Talin-1 KD did not significantly affect MEP:MEP cell contact angle, although it did slightly decrease basal cell circularity. However, Talin-1 KD significantly decreased MEP:ECM contact angle to a level that approached that of the MEP:MEP contact angle (FIG. 48). Like WT MEPs, Talin-1 KD MEPs self-organized alongside WT LEPs into an inverted architecture in agarose microwells, confirming that the Talin-1 KD did not significantly perturb the MEP-MEP or MEP-LEP interactions. Unlike WT MEPs, however, Talin-1 KD MEPs did not self-organize efficiently with WT LEPs in lrECM. Instead, we observed a striking loss of tissue architecture, with a significant enrichment of disorganized and inverted configurations relative to correctly organized WT tissues.

These data clearly demonstrate that a strong MEP-ECM interaction is necessary for correct self-organization in lrECM, and is dispensable for achieving the predicted inverted architecture in agarose. However, the model predicts that a strong MEP/ECM interaction also renders self-organization robust to a variety of perturbations that would otherwise lead to transitions among tissue architecture in agarose. For example, interfacial tension at the MEP/MEP interfaces is significantly lower than at the LEP-LEP interface, explaining the inverted architecture of the tissue in agarose microwells. The model predicts that self-organization is robust to perturbations to this interaction in lrECM, but that the same perturbation would lead to a transition from an inverted to a correct architecture in agarose. Because MEP express both P- and E-cadherin, and because E-cadherin mediates both LEP-LEP and MEP-LEP adhesion, we targeted p120-catenin for knock-down as it is a key stabilizer of all cadherin-based adhesions. MEP aggregate circularity was markedly reduced upon p120 KD, as was homotypic MEP:MEP cell contact angle (FIG. 49). However, MEP-ECM contact angle was not significantly affected by p120 KD. Despite a significant loss in the stability of MEP-MEP interfaces, MEPs bearing a p120 KD self-assembled robustly in lrECM with WT luminal cells. However, in agarose, p120 KD MEPs underwent a transition towards a correct, rather than inverted architecture.

We next performed the same set of experiments, but directed knock-down of p120 catenin in the luminal, rather than myoepithelial population. Knock-down led to a decrease in LEP aggregate circularity. However, our less sensitive contact angle assay was not able to measure a significant change upon p120 KD, possibly because the WT contact angle was already at the lower limit of detection in this assay. Consistent with the model, self-organization of WT MEP and p120 KD LEP was not significantly effected in lrECM. Moreover, self-organization of the same cells in agarose led to the predicted inverted architecture given the already weak LEP-LEP interaction.

As a more stringent test of our model, we asked whether strong basal cell/ECM adhesion coupled to weak luminal/ECM adhesion was sufficient to direct self-organization in lrECM, even among cell types that would not normally be expected to interact in vivo. To answer this question, we first purified populations of basal HMEC4 and directed their self-assembly with luminal pPMEC in both lrECM and agarose (FIG. 50). Remarkably, self-organization was efficient in lrECM, but led to the predicted inverted architecture in agarose due to the strong MEP-MEP interaction observed among HMEC4. s an even more stringent test of the model, we replace the pPMEC in the assay with completely non-adhesive Jurkat lymphocytes. These cells do not have detectable physical associations in culture and are derived from a completely different tissue type. Remarkably, MEP from HMEC4 self-organized with Jurkat into a correct three dimensional architecture, albeit with slower kinetics and efficiency than with LEP. Together, these data provide strong support that a strong and exclusive interaction between MEP and the surrounding ECM is sufficient to direct the self-organization of the mammary gland.

Example 15

Define the Relative Roles of Contact-Dependent and Independent Processes on the Tumor Suppressor Properties of Myoepithelial Cell Lines in Three-Dimensional Culture We explored the ability of HMEC4 MEP to self-organize and envelope LEP transformed with cMyc and a CyclinD1-CDK2 fusion:

Generation of Oncogene-Expressing Luminal HMEC.

Luminal HMEC were isolated by FACS as CD227+ CD10− cells and seeded into wells of a 24 well plate. Two days after seeding, the cells were infected with a lentivirus expressing a constitutive cyclinD1 cdk2 fusion protein and GFP. The cells were then infected with a c-myc expressing retrovirus and selected with hygromycin. Cells were expanded and sorted by FACS for GFP+ expression to isolate the cyclinD1:myc expressing cells.

3D on Top Assemblies of Unstained Luminal and Myoepithelial Cells with GFP+ Oncogene-Expressing Luminal Cells.

Luminal (CD227+ CD10−), myoepithelial (CD227− CD10+), and oncogene expressing luminal HMEC (GFP+) were assembled and seeded onto a matrigel coated chamber slide with 5% matrigel in M87A medium. Cells were incubated at 37° C. to allow aggregation and organization to occur. Aggregates were imaged at days 3 and 14.

In addition, we have investigated polarity and lumen formation in the bilayered acini we prepared by programmed assembly from HMEC. We have looked more deeply into the ability of luminal and myoepithelial cells to achieve the appropriate relative position in the current reporting period.

Example 16

Assess the Role of Focal Disruption of Myoepithelial Cell Function on the Proliferation, Apoptosis, and Polarity of Luminal Epithelial Cell Lines in Bilayered Acini In Vitro We have explored more deeply the paracrine circuits in tissues where cell-to-cell variability in Ras activation trigger invasive behavior. We found that the single Ras expressing mammary epithelial cells growing alongside WT mammary epithelial cells triggered emergent behaviors: cell extrusions, multicellular protrusions led by single Ras expressing cells, single hypermotile cells, all occurring alongside seemingly normal tissues. Importantly, tissues homogeneous for Ras expressing cells, or tissues composed of a majority of Ras expressing cells with a minority of WT cells, did not manifest these phenotypes appreciably. These results indicated that cell-to-cell variability in Ras activity is a potent inducer of malignant behaviors at the multicellular level.

Cell extrusions, multicellular extrusions, and single hypermotile cells were emergent properties of heterogeneous tissues—they were not properties of the Ras expressing cells on their own. We therefore sought to identify the mechanism at the multicellular level that gave rise to these behaviors. Treatment of small molecule inhibitors revealed that motile protrusions were dependent of MEK and PI3K activity, while extrusions depended only on MEK activity. Analysis of the microenvironmental conditions contributing to these behaviors revealed a unique sensitivity of the protrusive behavior to EGF concentrations: removal of EGF blocked multicellular protrusions and EGF withdrawal could be rescued with added TGFalpha. Moreover, cell extrusions were unaffected by these conditions. These data led us focus on EGFR signaling as part of a key axis directing multicellular protrusions in tissue heterogeneous for Ras activity. However, we were unable to identify where EGFR activity was necessary for initiating multicellular protrusions: in Ras cells, WT cells, or both. To identify the cell where EGFR activity was necessary to initiate multicellular protrusions, we performed siRNA knockdown of EGFR in WT, Ras cells, or both cell types within assembled microtissues (FIG. 53). We observed a marked reduction in multicellular protrusions only when EGFR was KD in Ras cells.

We therefore hypothesize that PI3K activity in Ras cells is a consequence of the combined action of RasV12 on a phosphorylated EGFR scaffold.

To summarize select findings above: EGF/EGFR signaling was identified as an autocrine signaling axis that is necessary for dissemination of single cells and the collective invasion of groups of cells in tissues with heterogeneity in Ras activation; it was demonstrated that MEP-ECM interactions are the primary driver in the hierarchy of interactions that control mammary gland tissue organization; it was demonstrated that the same rules likely apply to the prostate, salivary, and apocrine sweat glands; it was demonstrated that normal MEPs retain the capacity to drive the self-organization of CyclinD1 and Myc transformed LEPs; conditions to insert a single genetically distinct cell in into a bilayered human mammary acinus were identified; data was gathered suggesting a mechanism by which changes in the physical and chemical properties of the microenvironment can drive tissue reorganization; a powerful 3D patterning technology for preparing large-scale tissues from human mammary epithelial and stromal cells was developed that allows 10 μm resolution for the positioning of each individual cell in tissue spanning areas greater than one square centimeter; a new strategy was developed that renders all cell types, including stem cells, to adhesive remodeling with single stranded DNA; and a microwell strategy for assembling aggregates of HMEC LEP and MEP for long term culture in matrigel was developed.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims. It is also to be understood that the terminology used herein is for the purpose of describing particular embodiments only, and is not intended to be limiting, since the scope of the present invention will be limited only by the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. A method of generating a pattern of cells, comprising:
    disposing a two dimensional (2D) pattern of nucleic acids on a surface of a substrate;
    contacting the patterned nucleic acids under hybridization conditions with a first suspension of cells, wherein cells of the first suspension comprise cell surface-attached nucleic acids complementary to the patterned nucleic acids, wherein the hybridization conditions are sufficient for specific hybridization between the cell surface-attached nucleic acids and the patterned nucleic acids and wherein the cell surface-attached nucleic acids hybridize to the patterned nucleic acids to pattern the cells on the surface of the substrate; and
    removing the pattern of cells by:
        covering the pattern of cells with a liquid biocompatible matrix comprising a nuclease under conditions that maintain the biocompatible matrix in a liquid state; and
        incubating the cells in the biocompatible matrix under physiological temperature to simultaneously trigger setting of the biocompatible matrix around the cells and cleavage of the nucleic acids by the nuclease; and
        removing the matrix from the surface, wherein the pattern of cells is retained in the matrix upon removal.

2. The method according to claim 1, wherein the pattern of nucleic acids comprises a single population of nucleic acids having the same nucleotide sequence.

3. The method according to claim 1, wherein the pattern of nucleic acids comprises two or more population of nucleic acids, wherein each population of nucleic acids comprises a unique nucleotide sequence.

4. The method according to claim 3, wherein the nucleic acids of each population are uniquely addressable on the surface of the substrate.

5. The method according to claim 3, wherein the first suspension of cells comprises two or more populations of cells, wherein each population of cells comprises surface-attached nucleic acids complementary to one of the populations of nucleic acids in the pattern.

6. The method according to claim 5, wherein each population of cells of the first suspension comprises a unique cell type.

7. The method according to claim 1, wherein the cells of the first suspension are of a cell type selected from the group consisting of: epithelial cells, endothelial cells, fibroblasts, and lymphocytes.

8. The method according to claim 1, comprising contacting the pattern of cells on the surface under hybridization conditions with a second suspension of cells, wherein cells of the second suspension comprise cell surface-attached nucleic acids complementary to the cell surface-attached nucleic acids of the patterned cells, and wherein the cell surface-attached nucleic acids of cells of the second suspension hybridize to cell surface-attached nucleic acids of the cells patterned on the surface to form a three-dimensional pattern of cells.

9. The method according to claim 8, wherein the cells of the second suspension are of a cell type selected from the group consisting of: epithelial cells, endothelial cells, fibroblasts, and lymphocytes.

10. The method according to claim 1, wherein the disposing comprises printing a liquid comprising the nucleic acids on the substrate.

11. The method according to claim 1, wherein the pattern of nucleic acids is pre-selected by a user.

12. The method according to claim 11, wherein the user pre-selects the pattern of nucleic acids by creating an image of the pattern on a computer.

13. The method according to claim 1, wherein the nucleic acids are oligonucleotides.

14. The method according to claim 1, wherein the cell surface-attached nucleic acids comprise a lipid moiety attached to a nucleic acid, and wherein the cell surface-attached nucleic acids are attached to the cells by insertion of the lipid moiety into the plasma membrane of the cells.

15. The method according to claim 14, wherein the cell surface-attached nucleic acids comprise a spacer between the lipid moiety and the nucleic acid.

16. The method according to claim 1, comprising contacting the cells on the surface with a non-cellular material selected from nanoparticles, liposomes, hydrogels, shaped hydrogels, beads, hydrogel beads, and viruses.

17. The method according to claim 16, wherein the non-cellular material comprises a pharmaceutical agent or a cell signaling agent disposed on the surface of the non-cellular material or embedded within the non-cellular material.

18. The method of claim 1, wherein the cells are mammalian cells.

19. The method of claim 1, wherein the biocompatible matrix comprises extracellular matrix (ECM).

20. The method of claim 7, wherein the cells are mammalian cells.

* * * * *

```
                        SEQUENCE LISTING

<160> NUMBER OF SEQ ID NOS: 13

<210> SEQ ID NO 1
<211> LENGTH: 140
<212> TYPE: DNA
<213> ORGANISM: Artificial sequence
<220> FEATURE:
<223> OTHER INFORMATION: Synthetic nucleic acid sequence
<220> FEATURE:
<221> NAME/KEY: misc_feature
<222> LOCATION: (21)..(120)
<223> OTHER INFORMATION: The "t" at these positions can be present or
      absent such that this region can have anywhere from 0-100
      nucleotides.

<400> SEQUENCE: 1
gtaacgatcc agctgtcact tttttttttt tttttttttt tttttttttt tttttttttt     60
tttttttttt tttttttttt tttttttttt tttttttttt tttttttttt tttttttttt    120
cagtcagtca gtcagtcagt                                                140

<210> SEQ ID NO 2
<211> LENGTH: 135
<212> TYPE: DNA
<213> ORGANISM: Artificial sequence
<220> FEATURE:
<223> OTHER INFORMATION: Synthetic nucleic acid sequence
<220> FEATURE:
<221> NAME/KEY: misc_feature
<222> LOCATION: (16)..(115)
<223> OTHER INFORMATION: The "t" at these positions can be present or
      absent such that this region can have anywhere from 0-100
      nucleotides.

<400> SEQUENCE: 2
gatccagctg tcacttttt tttttttttt tttttttttt tttttttttt tttttttttt      60
tttttttttt tttttttttt tttttttttt tttttttttt tttttttttt tttttcagtc    120
agtcagtcag tcagt                                                     135

<210> SEQ ID NO 3
<211> LENGTH: 130
<212> TYPE: DNA
<213> ORGANISM: Artificial sequence
<220> FEATURE:
<223> OTHER INFORMATION: Synthetic nucleic acid sequence
<220> FEATURE:
<221> NAME/KEY: misc_feature
<222> LOCATION: (11)..(110)
<223> OTHER INFORMATION: The "t" at these positions can be present or
      absent such that this region can have anywhere from 0-100
      nucleotides.

<400> SEQUENCE: 3
agctgtcact tttttttttt tttttttttt tttttttttt tttttttttt tttttttttt     60
tttttttttt tttttttttt tttttttttt tttttttttt tttttttttt cagtcagtca    120
gtcagtcagt                                                           130

<210> SEQ ID NO 4
<211> LENGTH: 80
<212> TYPE: DNA
```

```
<213> ORGANISM: Artificial sequence
<220> FEATURE:
<223> OTHER INFORMATION: Synthetic nucleic acid sequence

<400> SEQUENCE: 4
tttttttttt tttttttttt tttttttttt tttttttttt tttttttttt tttttttttt    60
actgactgac tgactgactg                                                 80

<210> SEQ ID NO 5
<211> LENGTH: 20
<212> TYPE: DNA
<213> ORGANISM: Artificial sequence
<220> FEATURE:
<223> OTHER INFORMATION: Synthetic nucleic acid sequence

<400> SEQUENCE: 5
agtgacagct ggatcgttac                                                 20

<210> SEQ ID NO 6
<211> LENGTH: 15
<212> TYPE: DNA
<213> ORGANISM: Artificial sequence
<220> FEATURE:
<223> OTHER INFORMATION: Synthetic nucleic acid sequence

<400> SEQUENCE: 6
agtgacagct ggatc                                                      15

<210> SEQ ID NO 7
<211> LENGTH: 10
<212> TYPE: DNA
<213> ORGANISM: Artificial sequence
<220> FEATURE:
<223> OTHER INFORMATION: Synthetic nucleic acid sequence

<400> SEQUENCE: 7
agtgacagct                                                            10

<210> SEQ ID NO 8
<211> LENGTH: 120
<212> TYPE: DNA
<213> ORGANISM: Artificial sequence
<220> FEATURE:
<223> OTHER INFORMATION: Synthetic nucleic acid sequence
<220> FEATURE:
<221> NAME/KEY: misc_feature
<222> LOCATION: (1)..(100)
<223> OTHER INFORMATION: The "t" at these positions can be present or
      absent such that this region can have anywhere from 0-100
      nucleotides.

<400> SEQUENCE: 8
tttttttttt tttttttttt tttttttttt tttttttttt tttttttttt tttttttttt    60
tttttttttt tttttttttt tttttttttt tttttttttt cagtcagtca gtcagtcagt   120

<210> SEQ ID NO 9
<211> LENGTH: 120
<212> TYPE: DNA
<213> ORGANISM: Artificial sequence
<220> FEATURE:
<223> OTHER INFORMATION: Synthetic nucleic acid sequence
<220> FEATURE:
<221> NAME/KEY: misc_feature
<222> LOCATION: (1)..(100)
<223> OTHER INFORMATION: The "t" at these positions can be present or
      absent such that this region can have anywhere from 0-100
      nucleotides.
```

```
<400> SEQUENCE: 9
tttttttttt tttttttttt tttttttttt tttttttttt tttttttttt tttttttttt        60
tttttttttt tttttttttt tttttttttt tttttttttt actgactgac tgactgactg       120

<210> SEQ ID NO 10
<211> LENGTH: 20
<212> TYPE: DNA
<213> ORGANISM: Artificial sequence
<220> FEATURE:
<223> OTHER INFORMATION: Synthetic nucleic acid sequence

<400> SEQUENCE: 10
cagtcagtca gtcagtcagt                                                    20

<210> SEQ ID NO 11
<211> LENGTH: 20
<212> TYPE: DNA
<213> ORGANISM: Artificial sequence
<220> FEATURE:
<223> OTHER INFORMATION: Synthetic nucleic acid sequence

<400> SEQUENCE: 11
gtaacgatcc agctgtcact                                                    20

<210> SEQ ID NO 12
<211> LENGTH: 15
<212> TYPE: DNA
<213> ORGANISM: Artificial sequence
<220> FEATURE:
<223> OTHER INFORMATION: Synthetic nucleic acid sequence

<400> SEQUENCE: 12
gatccagctg tcact                                                         15

<210> SEQ ID NO 13
<211> LENGTH: 10
<212> TYPE: DNA
<213> ORGANISM: Artificial sequence
<220> FEATURE:
<223> OTHER INFORMATION: Synthetic nucleic acid sequence

<400> SEQUENCE: 13
agctgtcact                                                               10
```